(12) United States Patent
Mazzolini et al.

(10) Patent No.: US 11,173,180 B2
(45) Date of Patent: Nov. 16, 2021

(54) COMPOSITIONS AND METHODS FOR INCREASING MESENCHYMAL STROMAL CELL MIGRATION TO TUMORS

(71) Applicants: Consejo Nacional de Investigaciones Cientificas y Tecnicas (CONICET), Caba (AR); Asociacion Civil De Estudios Superiores, Pilar (AR); INIS BIOTECH LLC, Milford, DE (US)

(72) Inventors: Guillermo Daniel Mazzolini, Garin (AR); Mariana Gabriela Garcia, Munro (AR); Juan Bayo, Belen de Escobar (AR)

(73) Assignee: Consejo National de Investigaciones Cientificas y Tecnicas (CONICET), Buenos Aires (AR)

( * ) Notice: Subject to any disclaimer, the term of this patent is extended or adjusted under 35 U.S.C. 154(b) by 509 days.

(21) Appl. No.: 15/892,680

(22) Filed: Feb. 9, 2018

(65) Prior Publication Data
US 2019/0022143 A1    Jan. 24, 2019

Related U.S. Application Data

(63) Continuation of application No. 14/916,963, filed as application No. PCT/US2014/054389 on Sep. 5, 2014, now abandoned.

(60) Provisional application No. 61/874,852, filed on Sep. 6, 2013.

(51) Int. Cl.
*A61K 35/28*    (2015.01)
*C12N 5/077*    (2010.01)
*C12N 5/0775*    (2010.01)

(52) U.S. Cl.
CPC ............ *A61K 35/28* (2013.01); *C12N 5/0668* (2013.01); *C12N 5/0669* (2013.01); *C12N 2501/20* (2013.01); *C12N 2501/40* (2013.01); *C12N 2501/998* (2013.01); *C12N 2502/99* (2013.01)

(58) Field of Classification Search
CPC .... A61K 35/28; C12N 5/0669; C12N 5/0668; C12N 2502/99; A61P 35/00
See application file for complete search history.

(56) References Cited

U.S. PATENT DOCUMENTS

| | | | |
|---|---|---|---|
| 4,683,195 | A | 7/1987 | Mullis et al. |
| 5,849,287 | A | 12/1998 | Greenberger et al. |
| 9,180,166 | B2 | 11/2015 | Arinzeh et al. |
| 2004/0258669 | A1 | 12/2004 | Dzau et al. |
| 2010/0047217 | A1 | 2/2010 | Refaeli et al. |
| 2010/0247577 | A1 | 9/2010 | Foussat et al. |
| 2011/0038844 | A1 | 2/2011 | Foussat et al. |
| 2011/0256061 | A1 | 10/2011 | Lundgren-Akerlund |
| 2013/0171115 | A1 | 7/2013 | Li et al. |

FOREIGN PATENT DOCUMENTS

| | | |
|---|---|---|
| WO | WO-2007035843 A2 | 3/2007 |
| WO | WO-2009050282 A1 | 4/2009 |
| WO | WO-2013158962 A1 | 10/2013 |

OTHER PUBLICATIONS

Altschul, S.F., et al., "Basic Local Alignment Search Tool," Journal of Molecular Biology 215(3):403-410, Academic Press, England (1990).
Araki, K., et al., "Phosphoglucose Isomerase/Autocrine Motility Factor Promotes Melanoma Cell Migration through ERK Activation Dependent on Autocrine Production of Interleukin-8," The Journal of Biological Chemistry 284(47):32305-32311, American Society for Biochemistry and Molecular Biology, United States (2009).
Baumann, M., et al., "The Diagnostic Validity of the Serum Tumor Marker Phosphohexose Isomerase (PHI) in Patients with Gastrointestinal, Kidney, and Breast Cancer," Cancer Investigation 8(3-4):351-356, Marcel Dekker Inc., United States (1990).
Bayo, J., et al., "Human Umbilical Cord Perivascular Cells Exhibited Enhanced Migration Capacity Towards Hepatocellular Carcinoma in Comparison with Bone Marrow Mesenchymal Stromal Cells: A Role for Autocrine Motility Factor Receptor," BioMed Research International 2014:Article ID 837420, Hindawi Publishing Corporation, United States (2014).
Bayo, J., et al., "Increased Migration of Human Mesenchymal Stromal Cells by Autocrine Motility Factor (AMF) Resulted in Enhanced Recruitment Towards Hepatocellular Carcinoma," PLoS One 9(4):e95171, Public Library of Science, United States (2014).
Bayo, J., et al., "The Therapeutic Potential of Bone Marrow-derived Mesenchymal Stromal Cells on Hepatocellular Carcinoma," Liver International 34(3):330-342, Wiley-Blackwell, United States (2014).
Bernardo, M.E., et al., "Mesenchymal Stromal Cells," Annals of the New York Academy of Sciences 1176:101-117, New York Academy of Sciences, United States (2009).
Chong, P.P., et al., "Human Peripheral Blood Derived Mesenchymal Stem Cells Demonstrate Similar Characteristics and Chondrogenic Differentiation Potential to Bone Marrow Derived Mesenchymal Stem Cells," Journal of Orthopaedic Research 30(4):634-642, Wiley, United States (2012).
Dai, L.J., et al., "Potential Implications of Mesenchymal Stem Cells in Cancer Therapy," Cancer Letters 305(1):8-20, Elsevier Science, Ireland (2011).
De Lope, C.R., et al., "Management of HCC," Journal of Hepatology 56 Suppl 1:S75-S87, Elsevier, Netherlands (2012).

(Continued)

*Primary Examiner* — Hong Sang
(74) *Attorney, Agent, or Firm* — Sterne, Kessler, Goldstein & Fox P.L.L.C.

(57) ABSTRACT

The present application is directed to compositions and methods for treating a subject with cancer and/or increasing migration of a mesenchymal stromal cells (MSCs) stimulated with a recombinant autocrine motility factor (rAMF) to a tumor or a tumor cell, e.g. hepatocellular carcinoma (HCC). In addition, methods for increasing adhesion of MSCs to endothelial cells with rAMF are disclosed. In some embodiments, the MSCs comprise a therapeutic agent, e.g., an anti-tumor agent.

19 Claims, 11 Drawing Sheets
Specification includes a Sequence Listing.

(56) References Cited

OTHER PUBLICATIONS

Dobashi, Y., et al., "Differential Expression and Pathological Significance of Autocrine Motility Factor/glucose-6-phosphate Isomerase Expression in Human Lung Carcinomas," The Journal of Pathology 210(4):431-440, John Wiley and Sons, England (2006).

Dominici, M., et al., "Minimal Criteria for Defining Multipotent Mesenchymal Stromal Cells. The International Society for Cellular Therapy Position Statement," Cytotherapy 8(4):315-317, ICST, England (2006).

Dwyer, R.M., et al., "Advances in Mesenchymal Stem Cell-mediated Gene Therapy for Cancer," Stem Cell Research and Therapy 1(3):25, BioMed Central Ltd., UAE (2010).

Ferenci, P., et al., "World Gastroenterology Organisation Guideline. Hepatocellular Carcinoma (HCC): A Global Perspective," Journal of Gastrointestinal and Liver Diseases 19(3):311-317 (2010).

Gao, H., et al., "Activation of Signal Transducers and Activators of Transcription 3 and Focal Adhesion Kinase by Stromal Cell-derived Factor 1 is Required for Migration of Human Mesenchymal Stem Cells in Response to Tumor Cell-conditioned Medium," Stem Cells 27(4):857-865, AlphaMed Press, United States (2009).

Gao, Y., et al., "Human Mesenchymal Stem Cells Overexpressing Pigment Epithelium-derived Factor Inhibit Hepatocellular Carcinoma in Nude Mice," Oncogene 29(19):2784-2794, Nature Publishing Group, England (2010).

Garcia, M.G., et al., "Hepatocellular Carcinoma Cells and their Fibrotic Microenvironment Modulate Bone Marrow-derived Mesenchymal Stromal Cell Migration in Vitro and in Vivo," Molecular Pharmaceutics 8(5):1538-1548, American Chemical Society, United States (2011).

Gregory, C.A., et al., "Adult Bone Marrow Stem/progenitor Cells (MSCs) are Preconditioned by Microenvironmental "Niches" in Culture: A Two-stage Hypothesis for Regulation of MSC Fate," Science's STKE : Signal Transduction Knowledge Environment 2005(294):pe37, American Chemical Society, United States (2005).

Higgins, D.G., and Sharp, P.M., "Fast and Sensitive Multiple Sequence Alignments on a Microcomputer," Computer Applications in the Biosciences 5(2):151-153, Oxford University Press, United Kingdom (1989).

Higuchi, R., "Using PCR to Engineer DNA", in PCR Technology: Principles and Applications for DNA Amplification, Erlich, H., ed., Stockton Press, Chapter 6, pp. 61-70 (1989).

Hutchison, C.A., et al., "A Complete Library of Point Substitution Mutations in the Glucocorticoid Response Element of Mouse Mammary Tumor Virus," Proceedings of the National Academy of Sciences USA 83(3):710-714, National Academy of Sciences, United States (1986).

Hutchison, C.A., et al., "Mutagenesis at a Specific Position in a DNA Sequence," The Journal of Biological Chemistry 253(18):6551-6560, American Society for Biochemistry and Molecular Biology, United States (1978).

International Search Report and Written Opinion for International Application No. PCT/US2014/054389, ISA/US, Alexandria, Virginia, United States, dated Dec. 22, 2014, 9 pages.

Kalwitz, G., et al., "Gene Expression Profile of Adult Human Bone Marrow-derived Mesenchymal Stem Cells Stimulated by the Chemokine CXCL7," The International Journal of Biochemistry and Cell Biology 41(3):649-658, Elsevier, Netherlands (2009).

Khuri, F.R., et al., "A Controlled Trial of Intratumoral ONYX-015, a Selectively-replicating Adenovirus, in Combination with Cisplatin and 5-Fluorouracil in Patients with Recurrent Head and Neck Cancer," Nature Medicine 6(8):879-885, Nature Publishing Company, United States (2000).

Le, P.U., et al., "Caveolin-1 Is a Negative Regulator of Caveolae-mediated Endocytosis to the Endoplasmic Reticulum," The Journal of Biological Chemistry 277(5):3371-3379, American Society for Biochemistry and Molecular Biology, United States (2002).

Liotta, L.A., et al., "Tumor Cell Autocrine Motility Factor," Proceedings of the National Academy of Sciences USA 83(10):3302-3306, National Academy of Sciences, United States (1986).

Livak, K.J., and Schmittgen, T.D., "Analysis of Relative Gene Expression Data Using Real-Time Quantitative PCR and the $2^{-\Delta \Delta C}$ Method" Methods 25(4):402-408, Elsevier Science, United States (2001).

Lopez, M.V., et al., "A Tumor-stroma Targeted Oncolytic Adenovirus Replicated in Human Ovary Cancer Samples and Inhibited Growth of Disseminated Solid Tumors in Mice," Molecular Therapy 20(12):2222-2233, The American Society of Gene & Cell Therapy, United States (2012).

Nakashima, H., et al., "Directing Systemic Oncolytic Viral Delivery to Tumors via Carrier Cells," Cytokine and Growth Factor Reviews 21(2-3):119-126, Elsevier Science, England (2010).

Niess, H., et al., "Selective Targeting of Genetically Engineered Mesenchymal Stem Cells to Tumor Stroma Microenvironments Using Tissue-specific Suicide Gene Expression Suppresses Growth of Hepatocellular Carcinoma," Annals of Surgery 254(5):767-774, Lippincott Williams and Wilkins, United States (2011).

Ogata, R., et al., "Increased Expression of Membrane Type 1 Matrix Metalloproteinase and Matrix Metalloproteinase-2 with Tumor Dedifferentiation in Hepatocellular Carcinomas," Human Pathology 30(4):443-450, W B Saunders, United States (1999).

Oliphant, A.R., et al., "Cloning of Random-sequence Oligodeoxynucleotides," Gene 44(2-3):177-183, Elsevier Science Publishers B.V., Netherlands (1986).

Pochampally, R.R., et al., "Serum Deprivation of Human Marrow Stromal Cells (hMSCs) Selects for a Subpopulation of Early Progenitor Cells with Enhanced Expression of OCT-4 and Other Embryonic Genes," Blood 103(5):1647-1652, American Society of Hematology, United States (2004).

Ponte, A.L., et al., "The in vitro Migration Capacity of Human Bone Marrow Mesenchymal Stem Cells: Comparison of Chemokine and Growth Factor Chemotactic Activities," Stem Cells 25(7):1737-1745, American Society of Hematology, United States (2007).

Prockop, D.J., and Oh, J.Y., "Medical Therapies with Adult Stem/Progenitor Cells (MSCs): A Backward Journey from Dramatic Results in Vivo to the Cellular and Molecular Explanations," Journal of Cellular Biochemistry 113(5):1460-1469, Wiley-Liss, United States (2012).

Ries, C., et al., "MMP-2, MT1-MMP, and TIMP-2 are Essential for the Invasive Capacity of Human Mesenchymal Stem Cells: Differential Regulation by Inflammatory Cytokines," Blood 109(9):4055-4063, American Society of Hematology, United States (2007).

Sarugaser, R., et al., "Human Umbilical Cord Perivascular (HUCPV) Cells: A Source of Mesenchymal Progenitors," Stem Cells 23(2):220-229, AlphaMed Press, United States (2005).

Shimizu, K., et al., "The Autocrine Motility Factor Receptor Gene Encodes a Novel Type of Seven Transmembrane Protein," FEBS Letters 456(2):295-300, Federation of European Biochemical Societies., England (1999).

Silletti, S., et al., "Purification of B16-F1 Melanoma Autocrine Motility Factor and Its Receptor," Cancer Research 51(13):3507-3511, American Association for Cancer Research, United States (1991).

Tapper, J., et al., "Changes in Gene Expression During Progression of Ovarian Carcinoma," Cancer Genetics and Cytogenetics 128(1):1-6, ElsevierScience Inc., Netherlands (2001).

Torimura, T., et al., "Autocrine Motility Factor Enhances Hepatoma Cell Invasion Across the Basement Membrane through Activation of Beta1 Integrins," Hepatology 34(1):62-71, Wiley, United States (2001).

Torsvik, A., and Bjerkvig, R., "Mesenchymal Stem Cell Signaling in Cancer Progression," Cancer Treatment Reviews 39(2):180-188, Elsevier, Netherlands (2013).

Tsutsumi, S., et al., "Overexpression of the Autocrine Motility Factor/Phosphoglucose Isomerase Induces Transformation and Survival of NIH-3T3 Fibroblasts," Cancer Research 63(1):242-249, American Association for Cancer Research, United States (2003).

Viale, D.L., et al., "Therapeutic Improvement of a Stroma-targeted CRAd by Incorporating Motives Responsive to the Melanoma

(56) References Cited

OTHER PUBLICATIONS

Microenvironment," The Journal of Investigative Dermatology 133(11):2576-2584, Elsevier, United States (2013).

Wakao, S., et al., "Multilineage-differentiating Stress-enduring (Muse) Cells are a Primary Source of Induced Pluripotent Stem Cells in Human Fibroblasts," Proceedings of the National Academy of Sciences USA 108(24):9875-9880, National Academy of Sciences, United States (2011).

Watanabe, H., et al., "Purification of Human Tumor Cell Autocrine Motility Factor and Molecular Cloning of its Receptor," The Journal of Biological Chemistry 266(20):13442-13448, American Society for Biochemistry and Molecular Biology, United States (1991).

Watanabe, H., et al., "Tumor Cell Autocrine Motility Factor is the Neuroleukin/Phosphohexose Isomerase Polypeptide," Cancer Research 56(13):2960-2963, American Association for Cancer Research, United States (1996).

Welinder, C., and Ekblad, L., "Coomassie Staining as Loading Control in Western Blot Analysis," Journal of Proteome Research 10(3):1416-1419, American Chemical Society, United States (2011).

Yanagawa, T., et al., "Overexpression of Autocrine Motility Factor in Metastatic Tumor Cells: Possible Association with Augmented Expression of KIF3A and GDI-beta," Laboratory Investigation 84(4):513-522, Nature Publishing Group, United States (2004).

Yu, F.L., et al., "Induction of Hepatoma Cells Migration by Phosphoglucose Isomerase/Autocrine Motility Factor through the Upregulation of Matrix Metalloproteinase-3," Biochemical and Biophysical Research Communications 314(1):76-82, Elsevier, United States (2004).

Zoller, M.J., and Smith, M., "Oligonucleotide-directed Mutagenesis: A Simple Method Using Two Oligonucleotide Primers and a Single-stranded DNA Template," DNA 3(6):479-488, Mary Ann Liebert, United States (1984).

Zuk, P.A., et al., "Multilineage Cells from Human Adipose Tissue: Implications for Cell-based Therapies," Tissue Engineering 7(2):211-228, Mary Ann Liebert, Inc., United States (2001).

Fairbank, M., et al., "The complex biology of autocrine motility factor/phosphoglucose isomerase (AMF/PGI) and its receptor, the gp78/AMFR E3 ubiquitin ligase," *Molecular Biosystems* 5(8):793-801, Royal Society of Chemistry, England (2009).

Shah, K. et al., "Mesenchymal Stem Cells engineered for Cancer Therapy," *Advanced Drug Delivery Reviews* 64: 739-748, Elsevier, B.V., The Netherlands (2012).

Park et al., "Cytokine secretion profiling of human mesenchymal stem cells by antibody array," International Journal of Stem cells 2(1):59-68, Korean Society for Stem Cell Research, South Korea (2009).

FIG. 1A-B
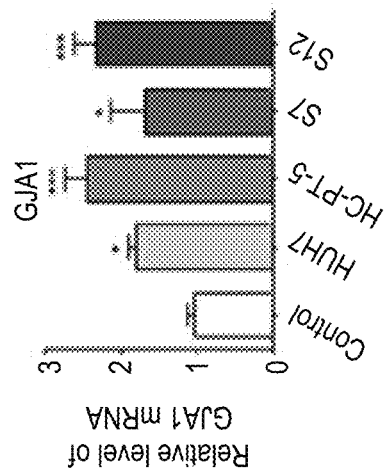
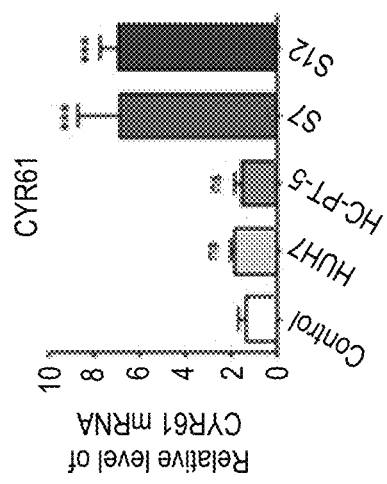
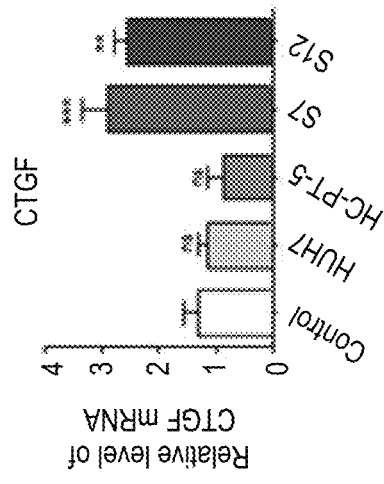
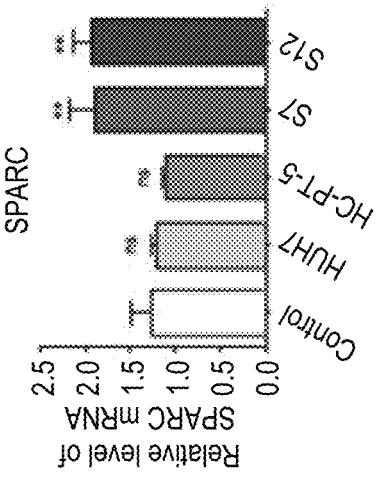
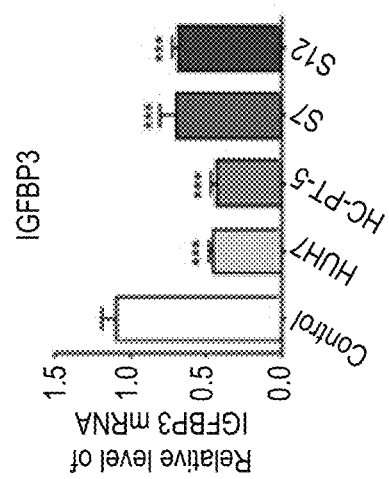
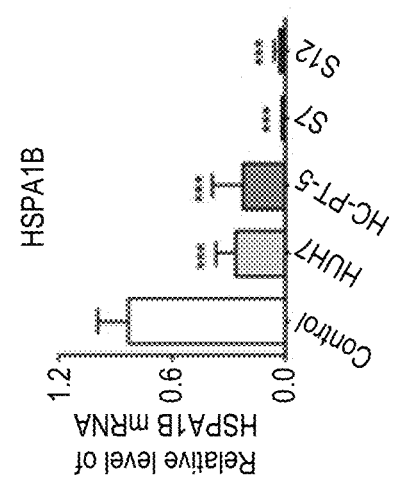
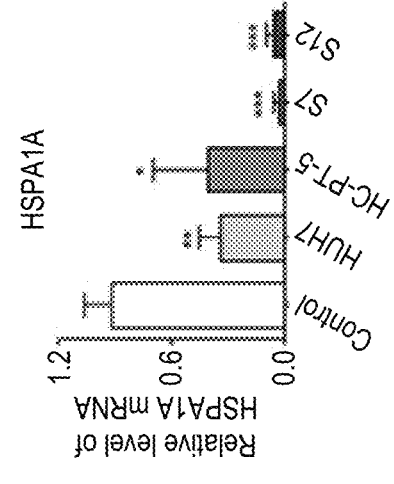

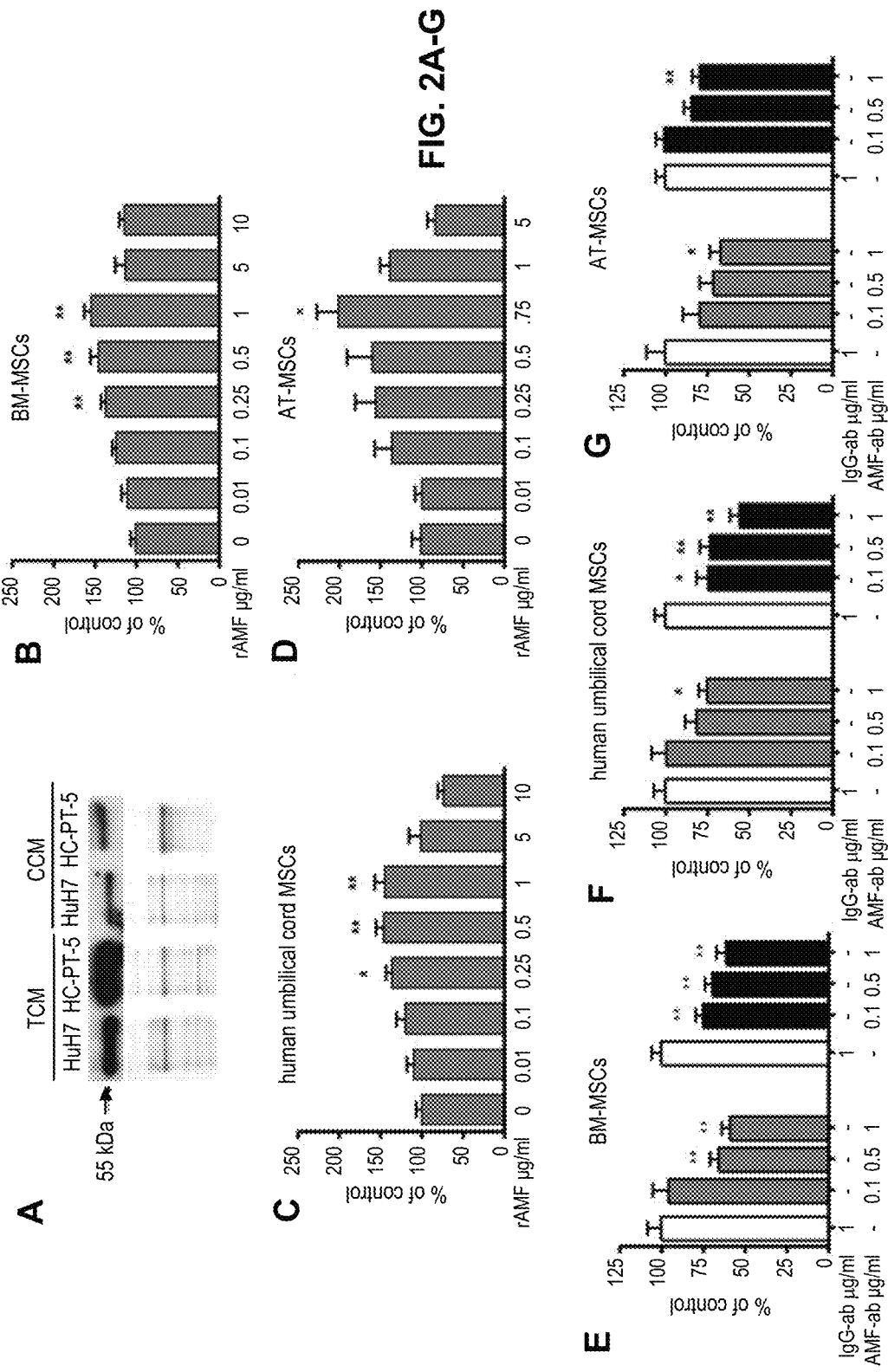
FIG. 2A-G

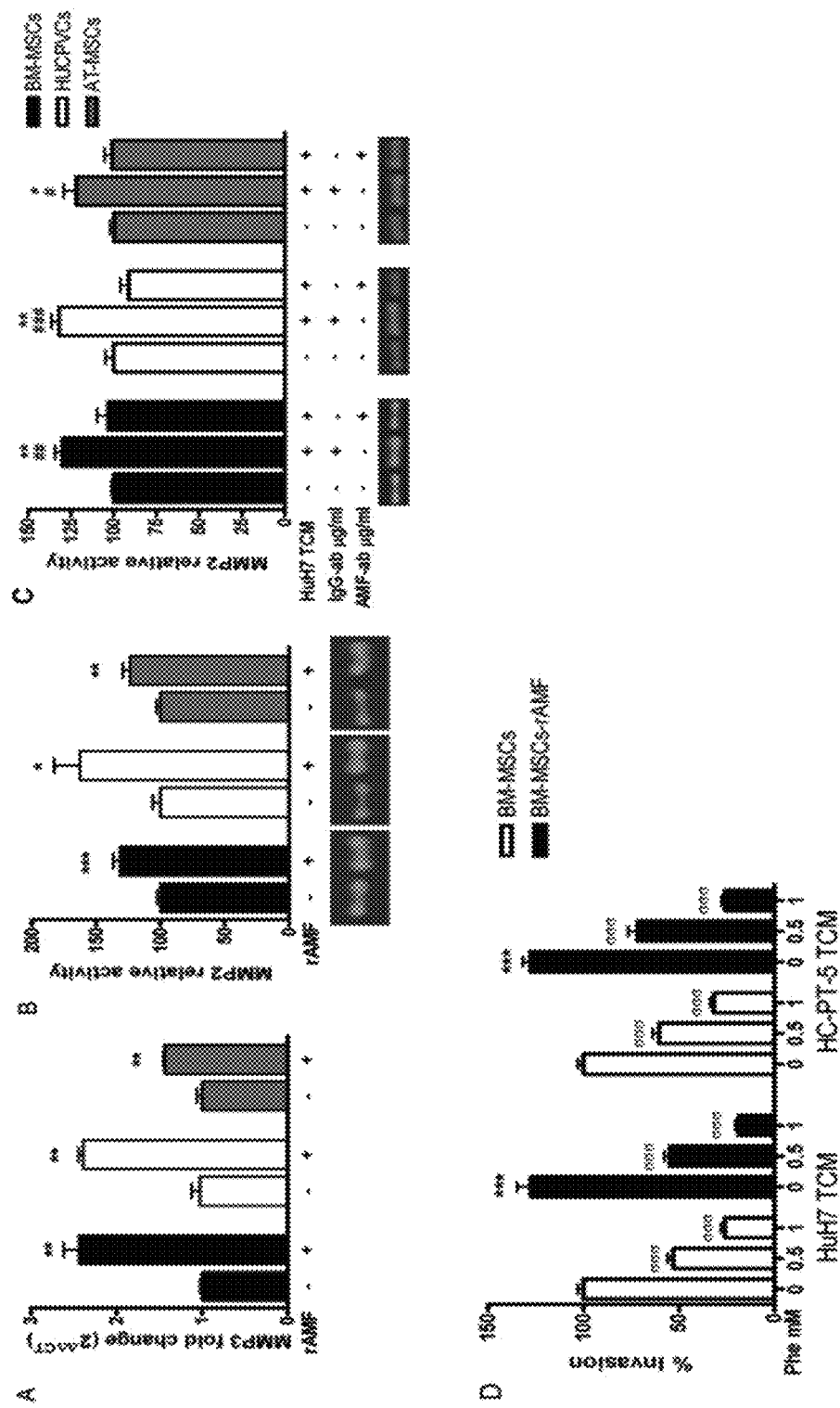
FIG. 3A-D

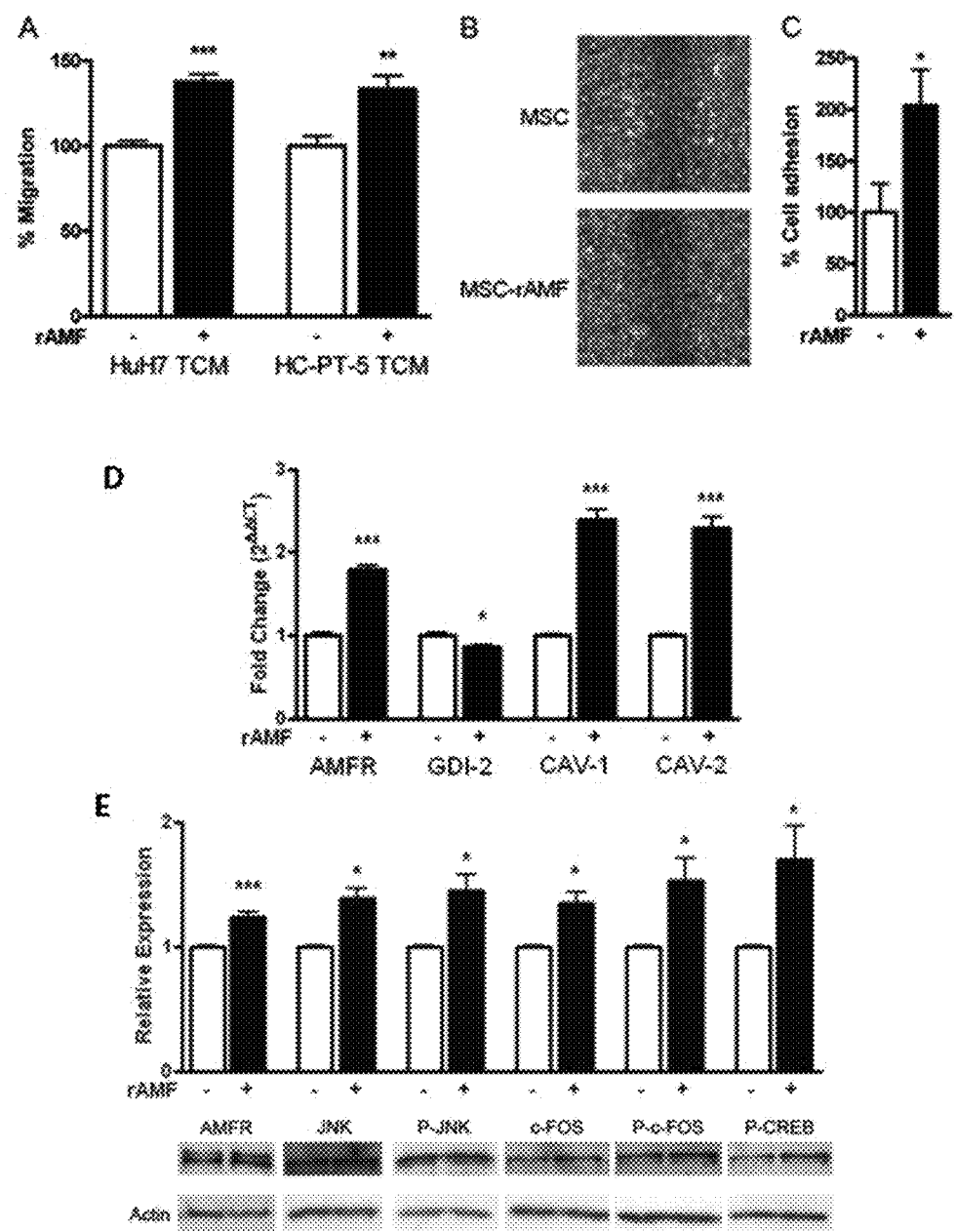
FIG. 4A-E

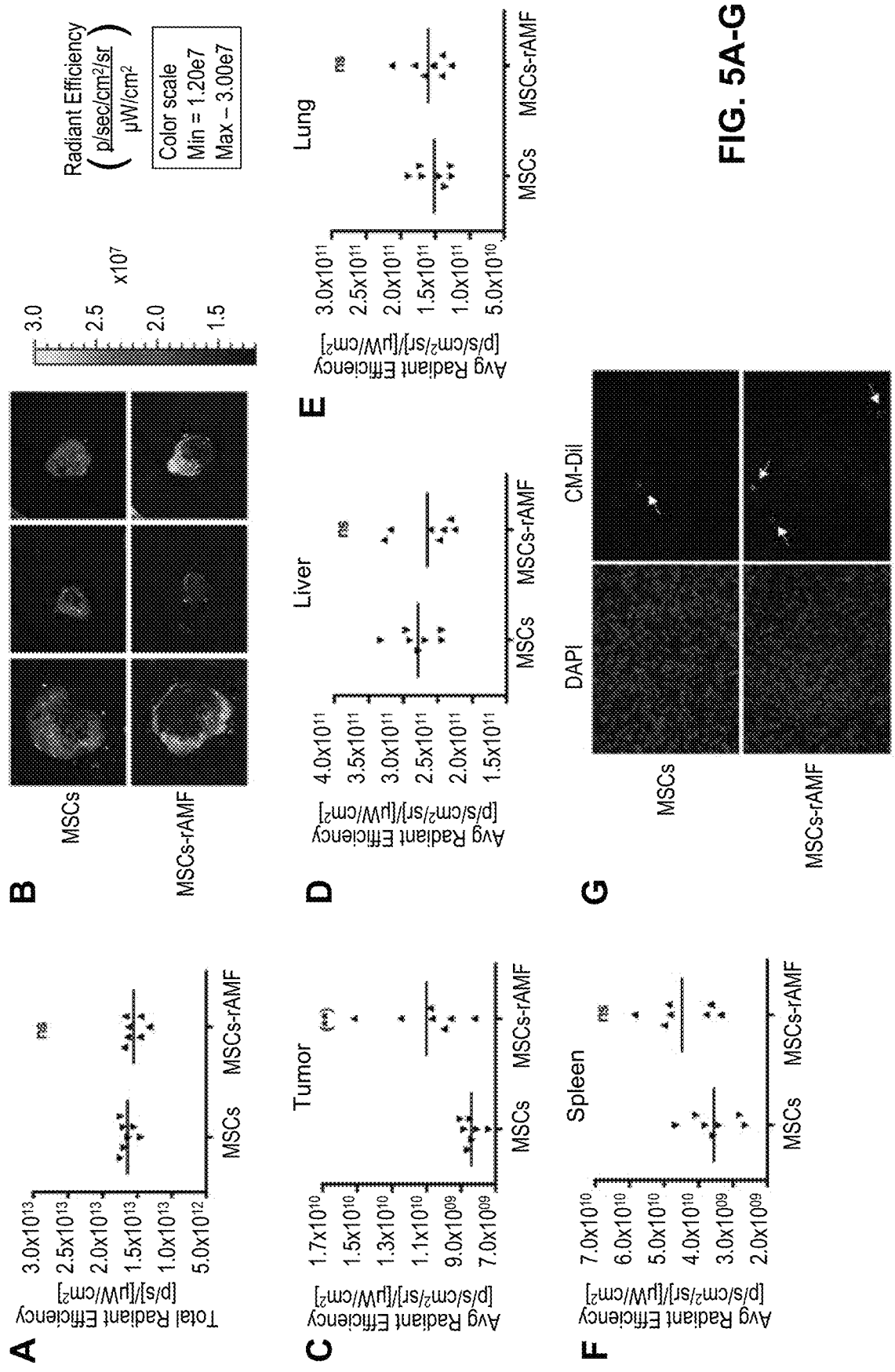
FIG. 5A-G

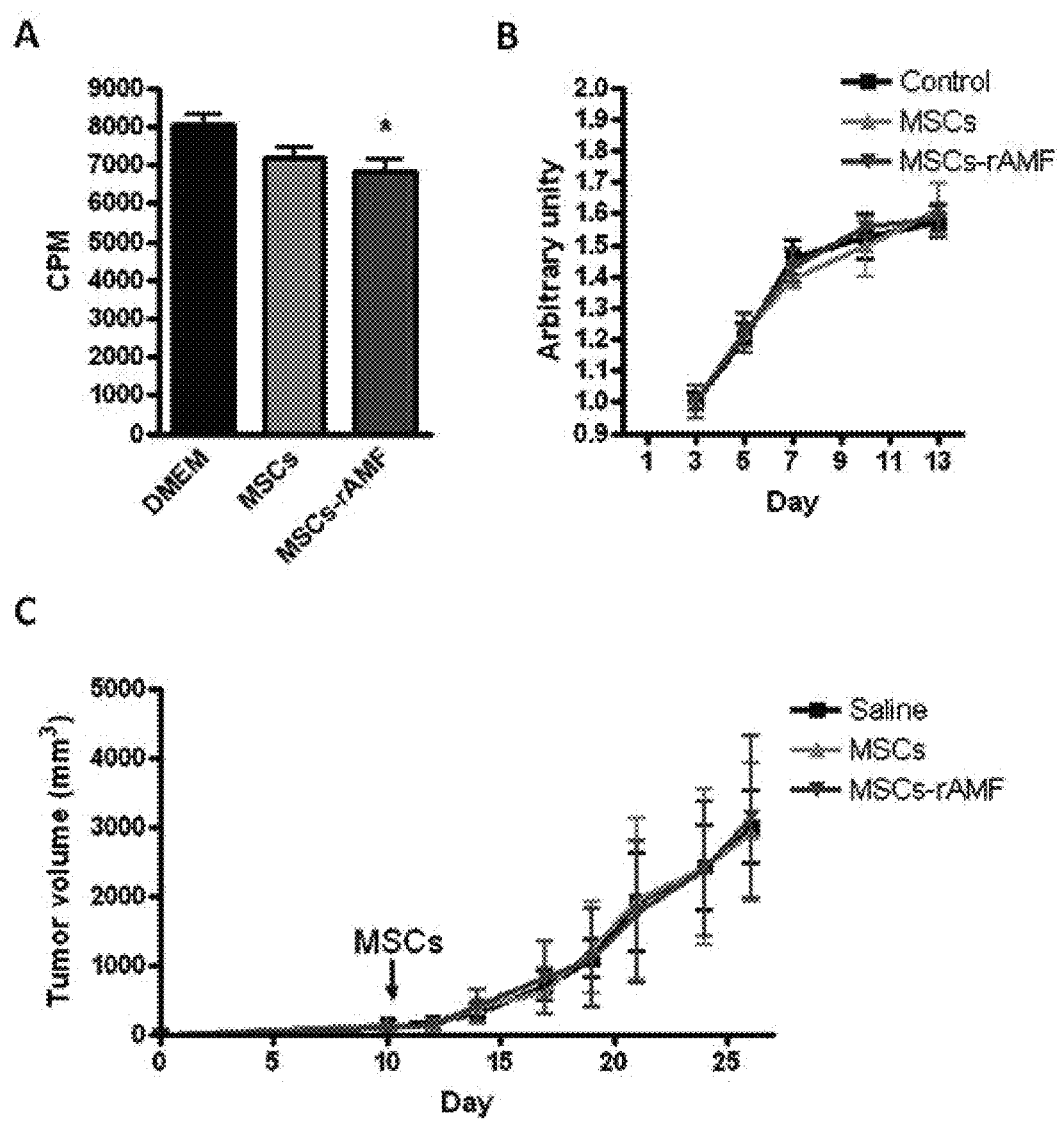
FIG. 6A-C

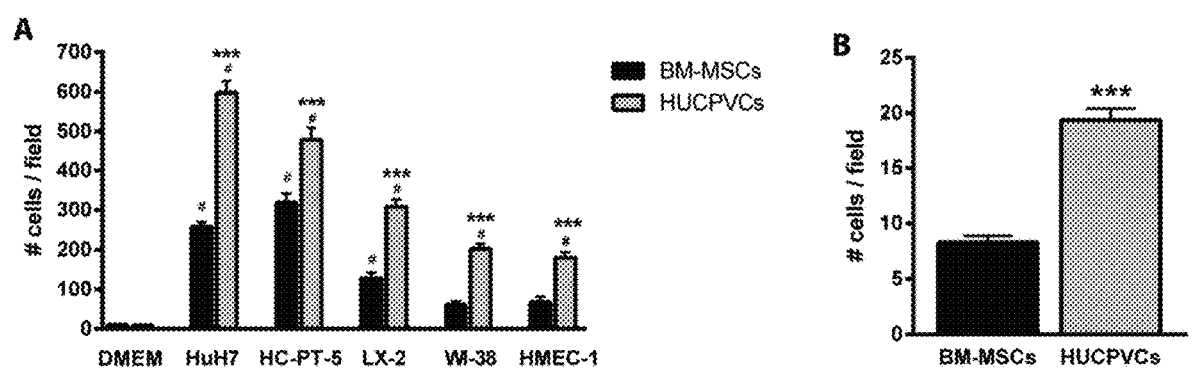
FIG. 7A-B

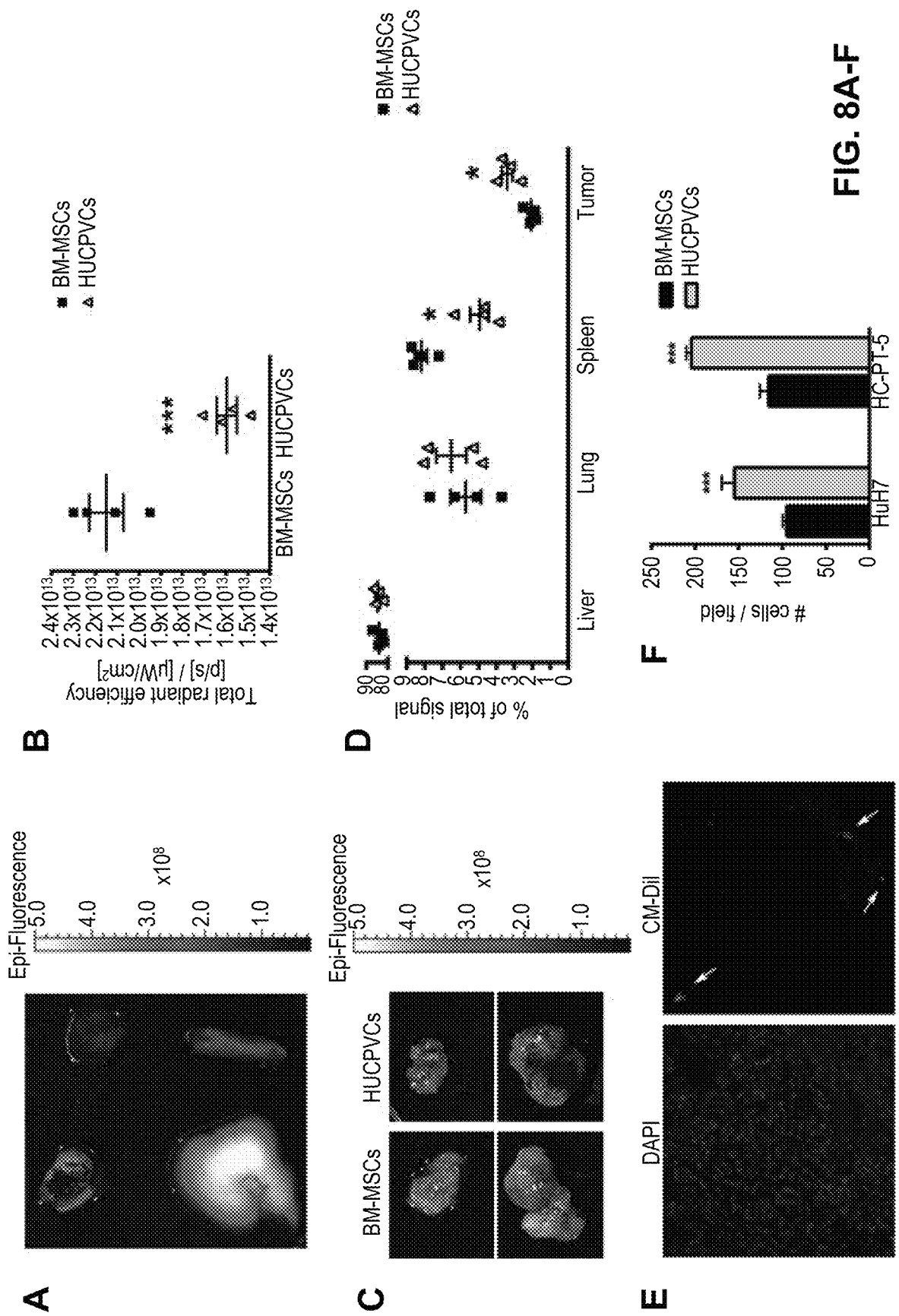
FIG. 8A-F

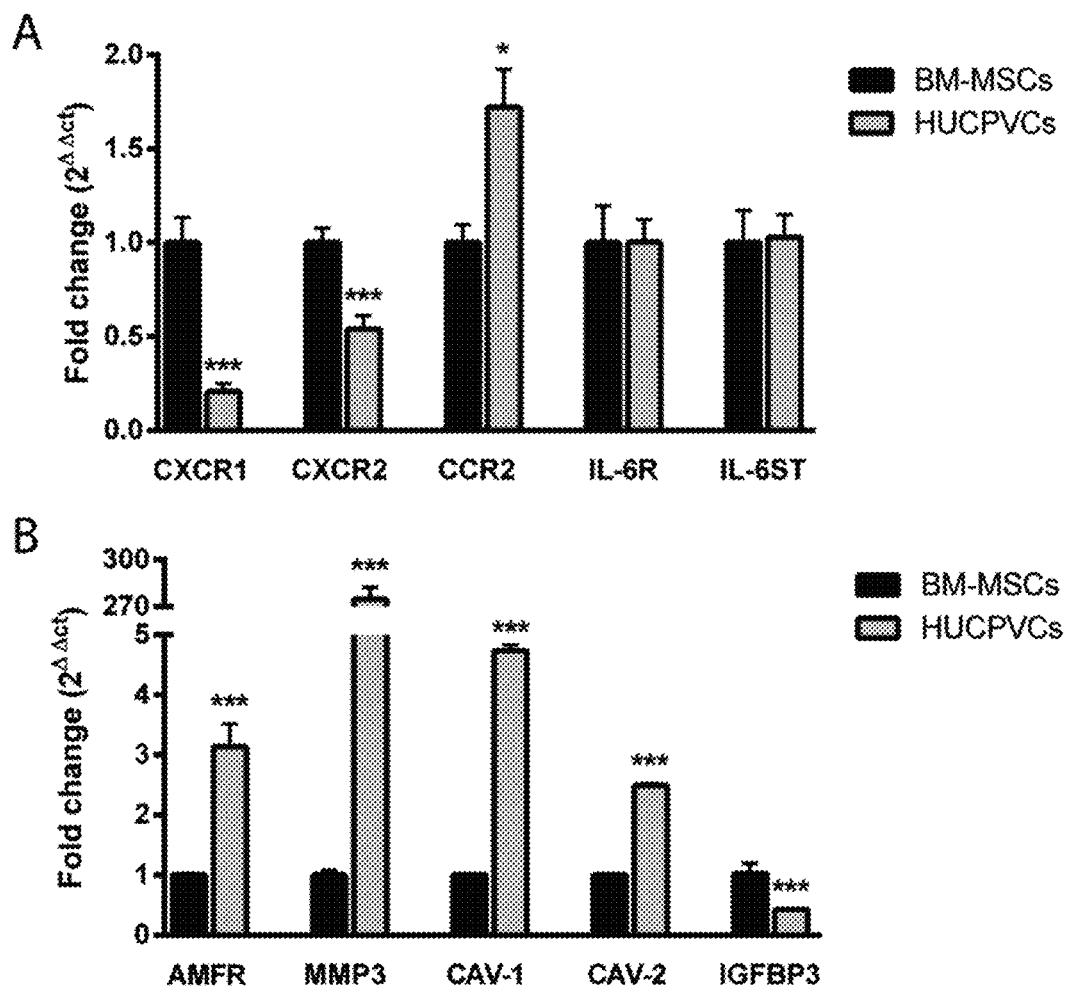
FIG. 9A-B

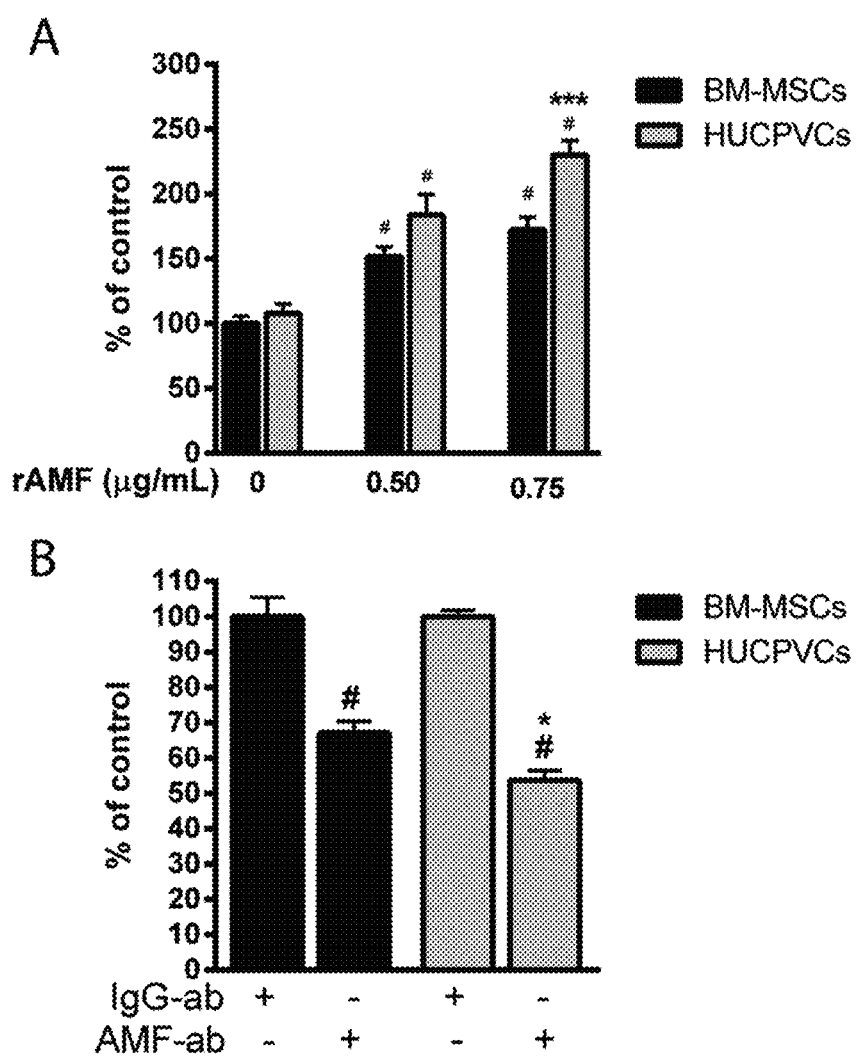
FIG. 10A-B

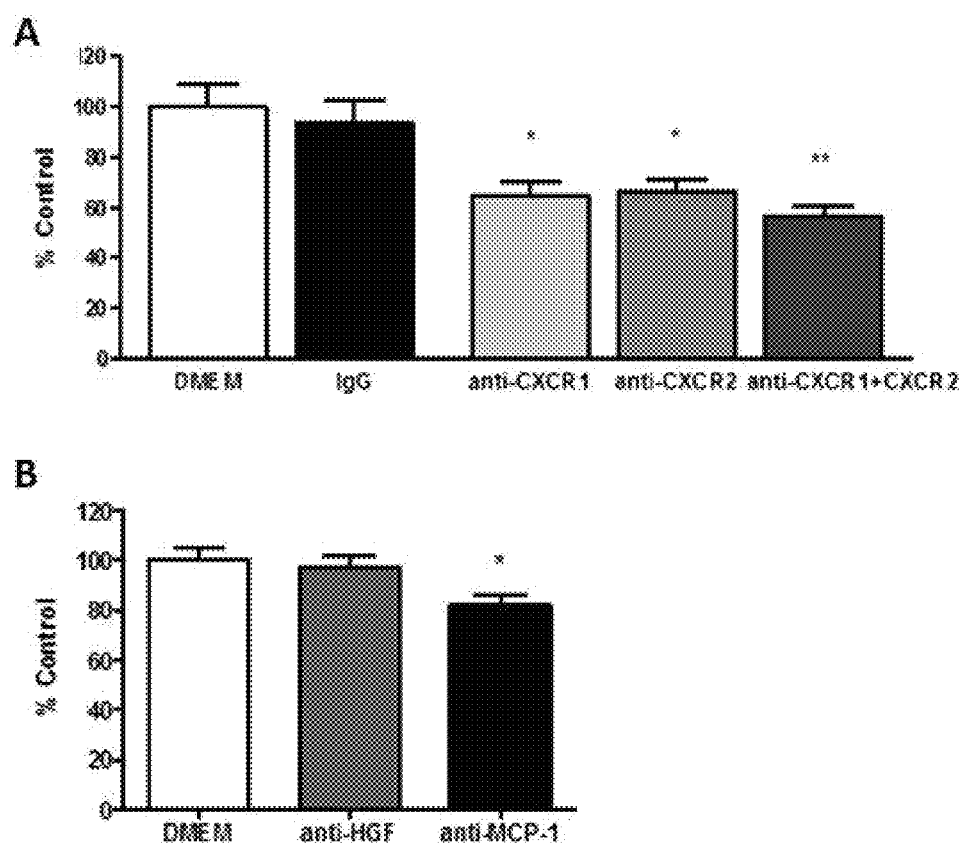
FIG. 11A-B

SEQUENCE LISTING

```
<160> NUMBER OF SEQ ID NOS: 25

<210> SEQ ID NO 1
<211> LENGTH: 558
<212> TYPE: PRT
<213> ORGANISM: Homo sapiens

<400> SEQUENCE: 1

Met Ala Ala Leu Thr Arg Asp Pro Gln Phe Gln Lys Leu Gln Gln Trp
1               5                   10                  15

Tyr Arg Glu His Arg Ser Glu Leu Asn Leu Arg Arg Leu Phe Asp Ala
                20                  25                  30

Asn Lys Asp Arg Phe Asn His Phe Ser Leu Thr Leu Asn Thr Asn His
            35                  40                  45

Gly His Ile Leu Val Asp Tyr Ser Lys Asn Leu Val Thr Glu Asp Val
        50                  55                  60

Met Arg Met Leu Val Asp Leu Ala Lys Ser Arg Gly Val Glu Ala Ala
65                  70                  75                  80

Arg Glu Arg Met Phe Asn Gly Glu Lys Ile Asn Tyr Thr Glu Gly Arg
                85                  90                  95

Ala Val Leu His Val Ala Leu Arg Asn Arg Ser Asn Thr Pro Ile Leu
            100                 105                 110

Val Asp Gly Lys Asp Val Met Pro Glu Val Asn Lys Val Leu Asp Lys
        115                 120                 125

Met Lys Ser Phe Cys Gln Arg Val Arg Ser Gly Asp Trp Lys Gly Tyr
    130                 135                 140

Thr Gly Lys Thr Ile Thr Asp Val Ile Asn Ile Gly Ile Gly Ser
145                 150                 155                 160

Asp Leu Gly Pro Leu Met Val Thr Glu Ala Leu Lys Pro Tyr Ser Ser
                165                 170                 175

Gly Gly Pro Arg Val Trp Tyr Val Ser Asn Ile Asp Gly Thr His Ile
            180                 185                 190

Ala Lys Thr Leu Ala Gln Leu Asn Pro Glu Ser Ser Leu Phe Ile Ile
        195                 200                 205

Ala Ser Lys Thr Phe Thr Thr Gln Glu Thr Ile Thr Asn Ala Glu Thr
    210                 215                 220

Ala Lys Glu Trp Phe Leu Gln Ala Ala Lys Asp Pro Ser Ala Val Ala
225                 230                 235                 240

Lys His Phe Val Ala Leu Ser Thr Asn Thr Thr Lys Val Lys Glu Phe
                245                 250                 255
```

-continued

Gly Ile Asp Pro Gln Asn Met Phe Glu Phe Trp Asp Val Gly
                260                 265                 270

Arg Tyr Ser Leu Trp Ser Ala Ile Gly Leu Ser Ile Ala Leu His Val
            275                 280                 285

Gly Phe Asp Asn Phe Glu Gln Leu Leu Ser Gly Ala His Trp Met Asp
        290                 295                 300

Gln His Phe Arg Thr Thr Pro Leu Glu Lys Asn Ala Pro Val Leu Leu
305                 310                 315                 320

Ala Leu Leu Gly Ile Trp Tyr Ile Asn Cys Phe Gly Cys Glu Thr His
                325                 330                 335

Ala Met Leu Pro Tyr Asp Gln Tyr Leu His Arg Phe Ala Ala Tyr Phe
            340                 345                 350

Gln Gln Gly Asp Met Glu Ser Asn Gly Lys Tyr Ile Thr Lys Ser Gly
        355                 360                 365

Thr Arg Val Asp His Gln Thr Gly Pro Ile Val Trp Gly Glu Pro Gly
370                 375                 380

Thr Asn Gly Gln His Ala Phe Tyr Gln Leu Ile His Gln Gly Thr Lys
385                 390                 395                 400

Met Ile Pro Cys Asp Phe Leu Ile Pro Val Gln Thr Gln His Pro Ile
                405                 410                 415

Arg Lys Gly Leu His His Lys Ile Leu Leu Ala Asn Phe Leu Ala Gln
            420                 425                 430

Thr Glu Ala Leu Met Arg Gly Lys Ser Thr Glu Glu Ala Arg Lys Glu
        435                 440                 445

Leu Gln Ala Ala Gly Lys Ser Pro Glu Asp Leu Glu Arg Leu Leu Pro
450                 455                 460

His Lys Val Phe Glu Gly Asn Arg Pro Thr Asn Ser Ile Val Phe Thr
465                 470                 475                 480

Lys Leu Thr Pro Phe Met Leu Gly Ala Leu Val Ala Met Tyr Glu His
                485                 490                 495

Lys Ile Phe Val Gln Gly Ile Ile Trp Asp Ile Asn Ser Phe Asp Gln
            500                 505                 510

Trp Gly Val Glu Leu Gly Lys Gln Leu Ala Lys Lys Ile Glu Pro Glu
        515                 520                 525

Leu Asp Gly Ser Ala Gln Val Thr Ser His Asp Ala Ser Thr Asn Gly
530                 535                 540

Leu Ile Asn Phe Ile Lys Gln Gln Arg Glu Ala Arg Val Gln
545                 550                 555

<210> SEQ ID NO 2
<211> LENGTH: 21
<212> TYPE: DNA
<213> ORGANISM: Artificial Sequence
<220> FEATURE:
<223> OTHER INFORMATION: MMP-3
<220> FEATURE:
<221> NAME/KEY: misc_feature
<222> LOCATION: (1)..(21)
<223> OTHER INFORMATION: MMP-3 forward primer

<400> SEQUENCE: 2
acgccagcca actgtgatcc t                                              21

<210> SEQ ID NO 3
<211> LENGTH: 22
<212> TYPE: DNA
<213> ORGANISM: Artificial Sequence

```
<220> FEATURE:
<223> OTHER INFORMATION: MMP-3
<220> FEATURE:
<221> NAME/KEY: misc_feature
<222> LOCATION: (1)..(22)
<223> OTHER INFORMATION: MMP-3 reverse primer

<400> SEQUENCE: 3
atatgcggca tccacgcctg aa                                              22

<210> SEQ ID NO 4
<211> LENGTH: 22
<212> TYPE: DNA
<213> ORGANISM: Artificial Sequence
<220> FEATURE:
<223> OTHER INFORMATION: AMFR
<220> FEATURE:
<221> NAME/KEY: misc_feature
<222> LOCATION: (1)..(22)
<223> OTHER INFORMATION: AMFR forward primer

<400> SEQUENCE: 4
acaagatgtg ggccttgcaa ga                                              22

<210> SEQ ID NO 5
<211> LENGTH: 22
<212> TYPE: DNA
<213> ORGANISM: Artificial Sequence
<220> FEATURE:
<223> OTHER INFORMATION: AMFR
<220> FEATURE:
<221> NAME/KEY: misc_feature
<222> LOCATION: (1)..(22)
<223> OTHER INFORMATION: AMFR reverse primer

<400> SEQUENCE: 5
aaaacgcagt gctcccagga ta                                              22

<210> SEQ ID NO 6
<211> LENGTH: 20
<212> TYPE: DNA
<213> ORGANISM: Artificial Sequence
<220> FEATURE:
<223> OTHER INFORMATION: GDI-2
<220> FEATURE:
<221> NAME/KEY: misc_feature
<222> LOCATION: (1)..(20)
<223> OTHER INFORMATION: GDI-2 forward primer

<400> SEQUENCE: 6
gaccagcttt ggagctcttg                                                 20

<210> SEQ ID NO 7
<211> LENGTH: 20
<212> TYPE: DNA
<213> ORGANISM: Artificial Sequence
<220> FEATURE:
<223> OTHER INFORMATION: GDI-2
<220> FEATURE:
<221> NAME/KEY: misc_feature
<222> LOCATION: (1)..(20)
<223> OTHER INFORMATION: GDI-2 reverse primer

<400> SEQUENCE: 7
tgcgggaaat aaagatctgg                                                 20

<210> SEQ ID NO 8
<211> LENGTH: 22
<212> TYPE: DNA
```

```
<213> ORGANISM: Artificial Sequence
<220> FEATURE:
<223> OTHER INFORMATION: CAV-1
<220> FEATURE:
<221> NAME/KEY: misc_feature
<222> LOCATION: (1)..(22)
<223> OTHER INFORMATION: CAV-1 forward primer

<400> SEQUENCE: 8
aatccaagca tccctttgcc ca                                              22

<210> SEQ ID NO 9
<211> LENGTH: 21
<212> TYPE: DNA
<213> ORGANISM: Artificial Sequence
<220> FEATURE:
<223> OTHER INFORMATION: CAV-1
<220> FEATURE:
<221> NAME/KEY: misc_feature
<222> LOCATION: (1)..(21)
<223> OTHER INFORMATION: CAV-1 reverse primer

<400> SEQUENCE: 9
accaggcagc tttctgtacg a                                               21

<210> SEQ ID NO 10
<211> LENGTH: 24
<212> TYPE: DNA
<213> ORGANISM: Artificial Sequence
<220> FEATURE:
<223> OTHER INFORMATION: CAV-2
<220> FEATURE:
<221> NAME/KEY: misc_feature
<222> LOCATION: (1)..(24)
<223> OTHER INFORMATION: CAV-2  forward primer

<400> SEQUENCE: 10
gagagacagg ggagttgtca actt                                            24

<210> SEQ ID NO 11
<211> LENGTH: 23
<212> TYPE: DNA
<213> ORGANISM: Artificial Sequence
<220> FEATURE:
<223> OTHER INFORMATION: CAV-2
<220> FEATURE:
<221> NAME/KEY: misc_feature
<222> LOCATION: (1)..(23)
<223> OTHER INFORMATION: CAV-2  reverse primer

<400> SEQUENCE: 11
gcccggccca gaaataatga gat                                             23

<210> SEQ ID NO 12
<211> LENGTH: 20
<212> TYPE: DNA
<213> ORGANISM: Artificial Sequence
<220> FEATURE:
<223> OTHER INFORMATION: GAPDH
<220> FEATURE:
<221> NAME/KEY: misc_feature
<222> LOCATION: (1)..(20)
<223> OTHER INFORMATION: GAPDH forward primer

<400> SEQUENCE: 12
catctctgcc ccctctgctg                                                 20

<210> SEQ ID NO 13
<211> LENGTH: 21
```

```
<212> TYPE: DNA
<213> ORGANISM: Artificial Sequence
<220> FEATURE:
<223> OTHER INFORMATION: GAPDH
<220> FEATURE:
<221> NAME/KEY: misc_feature
<222> LOCATION: (1)..(21)
<223> OTHER INFORMATION: GAPDH reverse primer

<400> SEQUENCE: 13
gcctgcttca ccaccttctt g                                              21

<210> SEQ ID NO 14
<211> LENGTH: 20
<212> TYPE: DNA
<213> ORGANISM: Artificial Sequence
<220> FEATURE:
<223> OTHER INFORMATION: CXCR1 forward primer

<400> SEQUENCE: 14
ttttccgcca ggcttaccat                                                20

<210> SEQ ID NO 15
<211> LENGTH: 20
<212> TYPE: DNA
<213> ORGANISM: Artificial Sequence
<220> FEATURE:
<223> OTHER INFORMATION: CXCR1 reverse primer

<400> SEQUENCE: 15
aacaccatcc gccattttgc                                                20

<210> SEQ ID NO 16
<211> LENGTH: 19
<212> TYPE: DNA
<213> ORGANISM: Artificial Sequence
<220> FEATURE:
<223> OTHER INFORMATION: CXCR2 Forward Primer

<400> SEQUENCE: 16
taagtggagc cccgtgggg                                                 19

<210> SEQ ID NO 17
<211> LENGTH: 19
<212> TYPE: DNA
<213> ORGANISM: Artificial Sequence
<220> FEATURE:
<223> OTHER INFORMATION: CXCR reverse primer

<400> SEQUENCE: 17
tgggctcagg ggcaggatg                                                 19

<210> SEQ ID NO 18
<211> LENGTH: 20
<212> TYPE: DNA
<213> ORGANISM: Artificial Sequence
<220> FEATURE:
<223> OTHER INFORMATION: CCR2 forward primer

<400> SEQUENCE: 18
cgagagcggt gaagaagtca                                                20

<210> SEQ ID NO 19
<211> LENGTH: 20
<212> TYPE: DNA
<213> ORGANISM: Artificial Sequence
<220> FEATURE:
```

-continued

```
<223> OTHER INFORMATION: CCR2 reverse primer

<400> SEQUENCE: 19
agcatgttgc ccacaaaacc                                           20

<210> SEQ ID NO 20
<211> LENGTH: 20
<212> TYPE: DNA
<213> ORGANISM: Artificial Sequence
<220> FEATURE:
<223> OTHER INFORMATION: IL-6R forward primer

<400> SEQUENCE: 20
gcacttgctg gtggatgttc                                           20

<210> SEQ ID NO 21
<211> LENGTH: 20
<212> TYPE: DNA
<213> ORGANISM: Artificial Sequence
<220> FEATURE:
<223> OTHER INFORMATION: IL-6R reverse primer

<400> SEQUENCE: 21
agcctttgtc gtcagggatg                                           20

<210> SEQ ID NO 22
<211> LENGTH: 20
<212> TYPE: DNA
<213> ORGANISM: Artificial Sequence
<220> FEATURE:
<223> OTHER INFORMATION: IL-6ST forward primer

<400> SEQUENCE: 22
cccacctcat gcactgttga                                           20

<210> SEQ ID NO 23
<211> LENGTH: 20
<212> TYPE: DNA
<213> ORGANISM: Artificial Sequence
<220> FEATURE:
<223> OTHER INFORMATION: IL-6T reverse primer

<400> SEQUENCE: 23
ttatgtggcg gattcggctt                                           20

<210> SEQ ID NO 24
<211> LENGTH: 18
<212> TYPE: DNA
<213> ORGANISM: Artificial Sequence
<220> FEATURE:
<223> OTHER INFORMATION: IGFBP3 forward primer

<400> SEQUENCE: 24
actgtggcca tgactgag                                             18

<210> SEQ ID NO 25
<211> LENGTH: 19
<212> TYPE: DNA
<213> ORGANISM: Artificial Sequence
<220> FEATURE:
<223> OTHER INFORMATION: IGFBP3 reverse primer

<400> SEQUENCE: 25
agagtctccc tgagcctga                                            19
```

COMPOSITIONS AND METHODS FOR INCREASING MESENCHYMAL STROMAL CELL MIGRATION TO TUMORS

REFERENCE TO SEQUENCE LISTING SUBMITTED ELECTRONICALLY

The content of the electronically submitted sequence listing in ASCII text file (Name: "3181_0060002_Sequence_Listing_ST25.txt"; Size: 10,719; and Date of Creation: Feb. 7, 2018) filed with the application is incorporated herein by reference in its entirety.

BACKGROUND

Mesenchymal stromal cells (MSCs) (also referred to as fibroblastic colony forming units or mesenchymal stem cells) constitute a heterogeneous cell population, characterized by their adherence to plastic, fibroblast-like morphology, expression of specific markers (e.g., CD105+, CD90+, CD73+), lack of hematopoietic markers (e.g., CD45, CD34, CD14 or CD11b, CD79a or CD19) and HLA class II and capability to differentiate in vitro into osteoblasts, adipocytes and chondroblasts (Dominici, M., K. Le Blanc, et al. (2006) Cytotherapy 8(4): 315-317). MSCs are most often derived from bone marrow (BM), but can also be isolated from adipose tissue (AT) or from umbilical cord; from the latter case, MSC are isolated from the Wharton's jelly (WJ-MSCs), perivascular areas (mesenchymal cells harvested from umbilical cord perivascular tissue) or umbilical cord blood (CB-MSCs) (Bernardo, M. E., F. Locatelli, et al. (2009) Ann N Y Acad Sci 1176: 101-117). MSCs show tropism for inflamed, injured or tumorigenic sites and their ability to be cultured and expanded in vitro, their self-renewal properties and low immunogenicity make these cells useful for cell therapy (Prockop, D. J. and J. Y. Oh (2012) J Cell Biochem 113(5): 1460-1469). However, the mechanisms involved in MSCs recruitment to tumors in general, and to specific tumors, e.g., hepatocellular carcinoma (HCC), are not fully understood.

Autocrine motility factor (AMF) is a 55-kDa cytokine (SEQ ID NO:1) secreted by tumors that regulates cell motility (Liotta, L. A., R. Mandler, et al. (1986) Proc Natl Acad Sci USA 83(10): 3302-3306). AMF was isolated, purified, and partially characterized from the serum-free conditioned medium of human A2058 melanoma cells (Liotta, L. A., R. Mandler, et al. (1986)). AMF exhibits sequence identity with glucose-6-phosphate isomerase (GPI) (alternatively known as phosphoglucose isomerase or phosphohexose isomerase (PHI)), a glycolytic enzyme involved in carbohydrate metabolism (Watanabe, H., K. Takehana, et al. (1996) Cancer Res 56(13): 2960-2963). The stimulation of cell motility is induced by the binding to the autocrine motility factor receptor (AMFR), a 78-kDa seven transmembrane glycoprotein with leucine zipper and RING-H2 motifs (Shimizu, K., M. Tani, et al. (1999) FEBS Lett 456(2): 295-300). AMFR is stably localized in caveolae, and caveolin-1 (Cav-1) has the ability to regulate the endocytic pathway through the stabilization of caveolae expression (Le, P. U., G. Guay, et al. (2002) J Biol Chem 277(5): 3371-3379).

AMF is secreted by different tumors such as lung (Dobashi, Y., H. Watanabe, et al. (2006) J Pathol 210(4): 431-440), gastrointestinal, kidney and mammary (Baumann, M., A. Kappl, et al. (1990) Cancer Invest 8(3-4): 351-356) as well as by hepatocellular carcinomas (Torimura, T., T. Ueno, et al. (2001) Hepatology 34(1): 62-71). Migration of hepatocellular carcinoma cells upon AMF stimulation has been associated to upregulation of metalloproteinase 3 (MMP3) (Yu, F. L., M. H. Liao, et al. (2004) Biochem Biophys Res Commun 314(1): 76-82) and activation of the small G-protein RhoC (Yanagawa, T., H. Watanabe, et al. (2004) Lab Invest 84(4): 513-522).

Hepatocellular carcinoma (HCC) is the sixth most common cancer worldwide and the third cause of cancer-related death (Ferenci, P., M. Fried, et al. (2010) J Gastrointestin Liver Dis 19(3): 311-317). Most cases of HCC are secondary to either a viral hepatitis infection (hepatitis B or C) or cirrhosis. Curative therapies such as resection or liver transplantation have been demonstrated to improve patient survival (de Lope, C. R., S. Tremosini, et al. (2012) J Hepatol 56 Suppl 1: S75-87); however, these strategies can only be applied to a minority of patients. Therefore, there is an urgent therapeutic need for patients with HCC.

BRIEF SUMMARY

The present application relates to the combined use of cellular and gene therapy to deliver therapeutic genes, e.g., an anti-tumor agent, into tumoral or peritumoral tissues. In some embodiments, the application relates to compositions and methods for treating a subject with cancer and/or increasing migration of a mesenchymal stromal cells (MSCs) to a tumor or a tumor cell, e.g. hepatocellular carcinoma (HCC), wherein the MSC comprises a therapeutic agent, e.g., an anti-tumor agent, and is stimulated with a recombinant autocrine motility factor (rAMF). In addition, methods for increasing adhesion of MSCs to endothelial cells with rAMF are disclosed.

BRIEF DESCRIPTION OF THE DRAWINGS/FIGURES

FIG. 1A-B. Shows real-time PCR (RT-PCR) relative expression of (A) up-regulated and (B) down-regulated genes in MSCs exposed to tumor conditioned media (TCM).

FIG. 2A-G. Shows (A) detection of AMF (55 kDa) by Western blot in CCM derived from HCC cells and TCM from ex vivo HCC s.c. tumors (upper panel). Colloidal Coomassie staining was performed as loading control (lower panel). MSCs migration was analyzed using Boyden chamber assays with rAMF as chemoattractant for (B) BM-MSCs, (C) Mesenchymal cells harvested from umbilical cord perivascular tissue or (D) AT-MSCs. Results are expressed as percentage of control (DMEM) SEM. *p<0.05 and **p<0.01 vs DMEM (ANOVA and Dunnett's test). Cell migration of (E) BM-MSCs, (F) Mesenchymal cells harvested from umbilical cord perivascular tissue or (G) AT-MSCs towards TCM derived from HuH7 (gray bars) or HC-PT-5 (black bars) pretreated with anti-AMF-Ab (AMF-ab) or control isotype IgG (IgG-ab) is shown. Results are expressed as percentage of control (isotype control) SEM. *p<0.05 and **p<0.01 vs isotype control (ANOVA and Dunnett's comparison test). Results are representative of 3 independent experiments.

FIG. 3A-D. Shows (A) MMP3 expression determined by qRT-PCR in BM-MSCs (black bars), Mesenchymal cells harvested from umbilical cord perivascular tissue (white bars) or AT-MSCs (gray bars) stimulated with 1 μg/ml of rAMF. ** p<0.01 vs unstimulated cells (DMEM, unpaired Student's t test). (B) MMP2 activity evaluated by zymography in supernatants of BM-MSCs (black bars), Mesenchymal cells harvested from umbilical cord perivascular tissue (white bars) or AT-MSCs (gray bars) pre-stimulated with 1 μg/mL of rAMF. Band intensity of 3 independent experiments was detected by densitometric evaluation and plotted as MMP2 relative activity. One representative image of the zymography is shown. * p<0.05,  p<0.01 and * p<0.001 vs untreated cells (DMEM, ANOVA and Tukey's comparison test). (C) MMP2 activity was evaluated by zymography in MSCs (BM-MSCs, black bars; Mesenchymal cells harvested from umbilical cord perivascular tissue, white bars; and AT-MSCs, gray bars) culture supernatant stimulated with TCM from HuH7 cells. TCM from HuH7 cells was blocked with anti-AMF (AMF-ab) or isotype control (IgG-ab). Band intensity of 3 independent experiments was detected by densitometric evaluation and plotted as MMP2 relative activity. One representative image of the zymography is shown. * p<0.05 and  p<0.01 vs DMEM (ANOVA); # p<0.05, ## p<0.01 and ### p<0.001 vs AMF-blocked TCM from HuH7 (HuH7 TCM+/AMF-ab+, ANOVA and Tukey's comparison test). (D) Invasion capacity of untreated BM-MSCs (white bars) or BM-MSCs stimulated with rAMF (black bars) to type IV collagen using TCM from HuH7 or HC-PT-5 preincubated with different doses of the MMP inhibitor 1,10 phenantroline (Phe). * p<0.001 vs without stimulation with rAMF and aaa p<0.001 vs without preincubation with Phe (ANOVA). Results are representative of 3 independent experiments.

FIG. 4A-E. Shows (A) pretreatment of BM-MSCs with 1 μg/mL rAMF (black bars) increases chemotaxis towards TCM derived from HuH7 or HC-PT-5 cells compared to untreated cells (white bars). (B) Shows a wound-healing assay of MSCs after pretreatment with rAMF or control (DMEM). Representative images were taken 24 hours after scratching. (C) Adhesion to HMEC-1 endothelial cells was increased in BM-MSCs exposed to rAMF. (D) Shows expression of AMF receptor (AMFR), GDP dissociation inhibitor 2 (GDI-1), caveolin-1 (CAV-1) and caveolin-2 (CAV-2) by qRT-PCR. * p<0.05,  p<0.01 and * p<0.001 vs untreated cells (DMEM, white bars, unpaired Student's t-test. (E) Shows increased expression of AMFR, JNK, p-JNK, c-Fos, p-c-Fos and p-CREB in AMF-treated MSCs evaluated by western blot.

FIG. 5A-G. BM-MSCs pre-stimulated with Ig/ml of rAMF were labeled with DiR and CMDiI cell trackers and i.v. injected in s.c. HuH7 tumor-bearing mice. After 3 days, tumors were removed and fluorescence imaging (FI) was performed. (A) Shows total fluorescent intensity as calculated by measuring the region of interest (ROI) for all the tissues isolated and the results were expressed as total radiant efficiency. ns, non significant. (B) Shows representative tumors images of mice inoculated with rAMF-pre-stimulated BM-MSCs (MSC-rAMF) or unstimulated cells (MSCs). Images represent the average radiant efficiency. Region of interest (ROI) was calculated for the isolated (C) tumor, (D) liver, (E) lung and (F) spleen and the results were expressed as the average radiant efficiency. **p<0.01 vs unstimulated BM-MSCs (unpaired Student's t-test). (G) Shows microscopic analysis of transplanted CM-DiI-labeled MSCs (red signal indicated by arrows) and DAPI staining in frozen sections of tumors. Magnification ×200.

FIG. 6A-C. (A) Shows in vitro proliferation of HuH7 cells exposed to MSCs, AMF-pretreated MSCs (MSC-rAMF) or unexposed cells (DMEM). *p<0.05 vs DMEM (ANOVA and Tukey's comparison test). (B) Multicellular spheroid growth composed by HCC tumor cells, hepatic stellate cells and endothelial cells (control) or also by MSCs or MSCs prestimulated with rAMF (ANOVA and Tukey's comparison test). (C) In vivo tumor growth of s.c. HuH7 (saline) and also i.v. injected with MSCs or AMF-pretreated MSCs (ANOVA and Tukey's comparison test).

FIG. 7A-B. (A) Shows in vitro migration of BM-MSCs (black bars) or HUCPVCs (grey bars) towards CCM from HCC (HuH7 and HC-PT-5), hepatic stellate cells (LX-2), fibroblasts (WI-38) or endothelial cells (HMEC-1). Bars represent the average of MSCs/field (10×) SEM from three representative visual fields. Results are representative of 3 independent experiments. # p<0.001 vs DMEM; * p<0.001 vs BM-MSCs. (B) Adhesion towards endothelial cells of BM-MSCs (black bars) or HUCPVCs (grey bars) was measured. Results are representative of 3 independent experiments. * p<0.001 vs BM-MSCs.

FIG. 8A-F. CM-DiI and DiR pre-labeled MSCs were i.v. injected in s.c. HuH7 bearing mice. At day 3, mice were sacrificed and organs were removed: (A) lungs, livers, spleen and (C) tumors were exposed to obtain fluorescent images. Images represent the average radiant efficiency. Representative images are shown. (B) Total fluorescent intensity for injected BM-MSCs or HUCPVCs was calculated by measuring the region of interest (ROI) for all the tissues isolated and results were expressed as total radiant efficiency $[p/s]/[\mu W/cm^2]$. *** p<0.001. (D) Signal present in the isolated liver, spleen, lungs and tumors was represented as percentage of total signal for BM-MSCs or HUCPVCs injected mice. * p<0.05 vs BM-MSCs. (E) Microscopic analysis of transplanted CM-DiI-labeled MSCs (red signal indicated by arrows) and DAPI staining in frozen sections of tumors. 200× magnification. (F) In vitro migration of MSCs to TCM derived from HuH7 or HC-PT-5 s.c. tumors. Bars represent the average of MSCs/field (10×) SEM from three representative visual fields. Results are representative of 3 independent experiments. * p<0.001vs BM-MSCs FIG. 9A-B. Expression of (A) cytokines and chemokines receptors and (B) AMF/AMFR axis proteins was evaluated in BM-MSCs (black bars) or HUCPVCs (grey bars) by qPCR. * p<0.001 vs BM-MSCs.

FIG. 10A-B. (A) In vitro migration of BM-MSCs (black bars) or HUCPVCs (grey bars) towards rAMF was measured. # p<0.05 vs DMEM (0 μg/ml rAMF); * p<0.05 vs BM-MSCs. (B) In vitro migration of BM-MSCs (black bars) or HUCPVCs (grey bars) towards HC-PT-5 TCM preincubated with anti-AMF antibody (AMF-ab) or control isotype (IgG-ab) was evaluated. # p<0.05 vs IgG-ab; * p<0.05 vs BM-MSCs. Bars represent the average of MSCs/field (10×) SEM from three representative visual fields. Results are representative of 3 independent experiments.

FIG. 11A-B. Shows (A) Migration (% of control) towards CM-HuH7of MSCs pre-incubated with anti-CXCR1, anti-CXCR2 or both (anti-CXCR1+ anti-CXCR2) or isotype control (IgG) for 1 h. *p<0.05 and **p<0.01 vs IgG isotype control. (B) Migration (% of control) of MSCs towards CM-HuH7 pre-incubated with anti-HGF or anti-MCP-1 for 1 h. *p<0.05 vs DMEM. Results were expressed as percentage of control (DMEM).

DETAILED DESCRIPTION

Definitions

To facilitate an understanding of the present invention, a number of terms and phrases are defined below:

"Isolated" in regard to cells, refers to a cell that is removed from its natural environment (such as in a solid tumor) and that is isolated or separated, and is at least about 30% free, about 50% free, about 75% free, about 90% free, about 95% free, or 100% free, from other cells with which it is naturally present, but which lack the marker based on which the cells were isolated.

As used herein, the term "heterologous" refers to, e.g., a gene, polypeptide or cell that is not in its natural environment; thus, it is non-naturally-occurring. For example, a heterologous gene or polypeptide includes a gene or polypeptide from one species introduced into another species. A heterologous gene or polypeptide also includes a gene or polypeptide native to an organism that has been altered in some way (e.g., mutated, added in multiple copies, linked to non-native regulatory sequences, etc.). In another example, a heterologous cell includes a cell native to an organism that has been altered in some way (e.g., genetically modified to include a recombinant gene, protein, or virus).

"Tumor" and "neoplasm" as used herein refer to any mass of tissue that results from excessive cell growth or proliferation, either benign (noncancerous) or malignant (cancerous) including pre-cancerous lesions.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include liver cancer (e.g., hepatocellular carcinoma (HCC)), colon cancer, colorectal cancer (e.g., colorectal carcinoma), gastrointestinal cancer, pancreatic cancer, lung cancer, breast cancer, and kidney cancer.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer cell", "tumor cell" and grammatical equivalents refer to the total population of cells derived from a tumor or a pre-cancerous lesion including both non-tumorigenic cells, which comprise the bulk of the tumor cell population, and tumorigenic cells (e.g., cancer stem cells).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer can also have one or more risk factors. A subject suspected of having cancer has generally not been tested for cancer. However, a "subject suspected of having cancer" encompasses an individual who has received an initial diagnosis but for whom the stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, gender, age, genetic predisposition, environmental exposure, previous incidents of cancer, pre-existing non-cancer diseases, and lifestyle.

As used herein, the term "subject diagnosed with a cancer" refers to a subject who has been tested and found to have cancerous cells. The cancer can be diagnosed using any suitable method, including but not limited to, biopsy, x-ray, blood test, and the diagnostic methods of the present invention.

As used herein, the terms "biopsy tissue", "patient sample", "tumor sample", and "cancer sample" refer to a sample of cells, tissue or fluid that is removed from a subject for the purpose of determining if the sample contains cancerous tissue, including cancer stem cells or for determining gene expression profile of that cancerous tissue. In some embodiments, biopsy tissue or fluid is obtained because a subject is suspected of having cancer. The biopsy tissue or fluid is then examined for the presence or absence of cancer, cancer stem cells, and/or cancer stem cell gene signature expression.

As used herein, the term "characterizing cancer in a subject" refers to the identification of one or more properties of a cancer sample in a subject, including but not limited to, the presence of benign, pre-cancerous or cancerous tissue, the stage of the cancer, and the subject's prognosis. Cancers can be characterized by the identification of the expression of one or more cancer marker genes, including but not limited to, any cancer markers disclosed herein.

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

The terms "high levels", "increased levels", "high expression", "increased expression", "elevated levels" or "up-regulated expression" in regard to gene expression are used herein interchangeably to refer to expression of a gene in a cell or population of cells at levels higher than the expression of that gene in a second cell or population of cells. In certain embodiments, "high levels", "increased levels", "high expression", "increased expression", "elevated levels" or "up-regulated expression" can be determined by detecting the amount of a polynucleotide (mRNA, cDNA, etc.) in tumor cells, for example, by quantitative RT-PCR or microarray analysis; or by detecting the amount of a protein in tumor cells, for example, by ELISA, Western blot, quantitative immunofluorescence.

As used herein, the terms "low levels", "decreased levels", "low expression", "reduced expression" or "decreased expression" in regards to gene expression are used herein interchangeably to refer to expression of a gene in a cell or population of cells, at levels less than the expression of that gene in a second cell or population of cells. "Low levels" of gene expression can be determined by detecting decreased to nearly undetectable amounts of a polynucleotide (mRNA, cDNA, etc.) in tumor cells, for example, by quantitative RT-PCR or microarray analysis. Alternatively "low levels" of gene expression can be determined by detecting decreased to nearly undetectable amounts of a protein in tumor cells, for example, ELISA, Western blot, or quantitative immunofluorescence.

The term "undetectable levels" or "loss of expression" in regards to gene expression as used herein refers to expression of a gene in a cell or population of cells, at levels that cannot be distinguished from background using conventional techniques such that no expression is identified. "Undetectable levels" of gene expression can be determined by the inability to detect levels of a polynucleotide (mRNA, cDNA, etc.) in tumor cells above background by, for example, quantitative RT-PCR or microarray analysis. Alternatively "undetectable levels" of gene expression can be determined by the inability to detect levels of a protein in tumor cells above background by, for example, ELISA, Western blot, or immunofluorescence.

As used herein, if the expression is "below the level of detection" for a given assay, the expression may still be detectable by another assay.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full-length coding sequence or by any portion of the coding sequence so long as the desired activities or functional properties (e.g., enzymatic activity, ligand binding, signal transduction, immunogenicity, etc.) of the full-length polypeptide or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns can contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. A cDNA form of a gene is "intron-free" and non-naturally-occurring.

As used herein, the term "heterologous gene" refers to a gene that is not in its natural environment; thus, it is non-naturally-occurring. For example, a heterologous gene includes a gene from one species introduced into another species. A heterologous gene also includes a gene native to an organism that has been altered in some way (e.g., mutated, added in multiple copies, linked to non-native regulatory sequences, etc.). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene can also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region can contain regulatory sequences such as promoters and enhancers that control or influence the transcription of the gene. The 3' flanking region can contain sequences that direct the termination of transcription, post-transcriptional cleavage and polyadenylation.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

"Polypeptide," "peptide" and "protein" are used interchangeably and refer to a polymeric compound comprised of covalently linked amino acid residues.

An "isolated polypeptide," "isolated peptide" or "isolated protein" refer to a polypeptide or protein that is substantially free of those compounds that are normally associated therewith in its natural state (e.g., other proteins or polypeptides, nucleic acids, carbohydrates, lipids). "Isolated" is not meant to exclude artificial or synthetic mixtures with other compounds, or the presence of impurities which do not interfere with biological activity, and which can be present, for example, due to incomplete purification, addition of stabilizers, or compounding into a pharmaceutically acceptable preparation.

As used herein, the term "heterologous polypeptide" refers to a polypeptide that is not in its natural environment; thus, it is non-naturally-occurring. For example, a heterologous polypeptide includes a polypeptide from one species introduced into another species. A heterologous polypeptide also includes a polypeptide native to an organism that has been altered in some way (e.g., mutated, added in multiple copies, linked to non-polypeptide, etc.). Heterologous polypeptide are distinguished from endogenous polypeptide in that the heterologous polypeptide sequences are typically encoded by cDNA sequences that are not found naturally associated with the gene sequences in the chromosome or are associated with portions of the chromosome not found in nature (e.g., genes expressed in loci where the gene is not normally expressed).

A mutation can be made by any technique for mutagenesis known in the art, including but not limited to, in vitro site-directed mutagenesis (Hutchinson et al. *J. Biol. Chem.* 253:6551 (1978); Zoller et al. *DNA* 3:479 (1984); Oliphant et al. *Gene* 44:177 (1986); Hutchinson et al. *Proc. Natl. Acad. Sci. USA* 83:710 (1986)), use of TAB@linkers (Pharmacia), restriction endonuclease digestion/fragment deletion and substitution, PCR-mediated/oligonucleotide-directed mutagenesis, and the like. PCR-based techniques are preferred for site-directed mutagenesis (see Higuchi, 1989, "Using PCR to Engineer DNA", in PCR Technology: Principles and Applications for DNA Amplification, H. Erlich, ed., Stockton Press, Chapter 6, pp. 61-70).

A "variant" of a polypeptide or protein refers to any analogue, fragment, derivative, or mutant which is derived from a polypeptide or protein and which retains at least one biological property of the polypeptide or protein. Different variants of the polypeptide or protein can exist in nature. These variants can be allelic variations characterized by differences in the nucleotide sequences of the structural gene coding for the protein, or can involve differential splicing or post-translational modification. The skilled artisan can produce non-naturally-occurring variants having single or multiple amino acid substitutions, deletions, additions, or replacements. These variants can include, inter alia: (a) variants in which one or more amino acid residues are substituted with conservative or non-conservative amino acids, (b) variants in which one or more amino acids are added to the polypeptide or protein, (c) variants in which one or more of the amino acids includes a substituent group, and (d) variants in which the polypeptide or protein is fused with another polypeptide such as serum albumin. The techniques for obtaining non-naturally-occurring variants, including genetic (suppressions, deletions, mutations, etc.), chemical, and enzymatic techniques, are known to persons having ordinary skill in the art.

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: Computational Molecular Biology (Lesk, A. M., ed.) Oxford University Press, New York (1988); Biocomputing: Informatics and Genome Projects (Smith, D. W., ed.) Academic Press, New York (1993); Computer Analysis of Sequence Data, Part I (Griffin, A. M., and Griffin, H. G., eds.) Humana Press, New Jersey (1994); Sequence Analysis in Molecular Biology (von Heinje, G., ed.) Academic Press (1987); and Sequence Analysis Primer (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations can be performed using sequence analysis software such as the Megalign program of the LASERGENE bioinformatics computing suite (DNASTAR Inc., Madison, Wis.). Multiple alignment of the sequences can be performed using the Clustal method of alignment (Higgins et al., CABIOS. 5:151 (1989)) with the default parameters (GAP PENALTY=10, GAP LENGTH PENALTY=10). Default parameters for pairwise alignments using the Clustal method can be selected: KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" can be commercially available or independently developed. Typical sequence analysis software includes, but is not limited to, the GCG suite of programs (Wisconsin Package Version 9.0, Genetics Computer Group (GCG), Madison, Wis.), BLASTP, BLASTN, BLASTX (Altschul et al., J. Mol. Biol. 215:403 (1990)), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) that can be, but are not limited to, processes or reaction that occur within a natural environment.

As used herein, the term "ex vivo" refers to "outside" the body. The terms "ex vivo" and "in vitro" can be used interchangeably herein.

As used herein, the term "sample" is used in its broadest sense. In one sense, it is meant to include a specimen or culture obtained from any source, as well as biological and environmental samples. Biological samples can be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

In certain embodiments, terms such as "treating" or "treatment" or "to treat" refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus, those in need of treatment include those already with the disorder; those prone to have the disorder; those who may have had the disorder and in whom the disorder may recur; and, those in whom the disorder is to be prevented. In certain embodiments, a subject is successfully "treated" if the patient shows one or more of the following: a reduction in the number of or complete absence of cancer cells; a reduction in the tumor size; inhibition of or an absence of cancer cell infiltration into peripheral organs including the spread of cancer into soft tissue and bone; inhibition of or an absence of tumor metastasis; inhibition or an absence of tumor growth; relief of one or more symptoms associate with the specific cancer; reduced morbidity and/or mortality; improvement in quality of life; a reduction in the number of or complete absence of cancer stem cells; a decrease in the proportion of cancer stem cells in a solid tumor (relative to cells in the tumor that are not cancer stem cells); inhibit the proliferation of cancer stem cells; and a delay in or an absence of relapse.

In certain embodiments, the term "therapeutically effective amount" refers to an amount of a therapeutic agent, e.g., an antibody, polypeptide, polynucleotide, small organic molecule, or other drug effective to "treat" a disease or disorder in a subject. In the case of cancer, the therapeutically effective amount of the therapeutic agent can, in certain embodiments, reduce the number of cancer cells; reduce the proportion of cancer cells in a solid tumor; reduce the tumor size; inhibit or stop cancer cell infiltration into peripheral organs; inhibit and/or stop tumor metastasis; inhibit and stop tumor growth; relieve to some extent one or more of the symptoms associated with the cancer; inhibit the proliferation of cancer cells; or result in a combination of such effects on cancer cells.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells presented herein, its use in therapeutic compositions is contemplated. Supplementary active ingredients also can be incorporated into the compositions.

Mesenchymal Stromal Cell (MSC)

Mesenchymal stromal cells (MSCs) (also referred to as fibroblastic colony forming units or mesenchymal stem cells) constitute a heterogeneous cell population, characterized by their adherence to plastic, fibroblast-like morphology, expression of specific markers (CD105+, CD90+, CD73+), lack of hematopoietic markers (CD45, CD34, CD14 or CD11b, CD79α or CD19) and HLA class II and capability to differentiate in vitro into osteoblasts, adipocytes and chondroblasts (Dominici, M., K. Le Blanc, et al. (2006) Cytotherapy 8(4): 315-317). MSCs are most often derived from bone marrow (BM), but can also be isolated from adipose tissue (AT) or from umbilical cord (youngest, most primitive MSCs); from the latter case, MSCs are isolated from the Wharton's jelly (WJ-MSCs), perivascular areas (Mesenchymal cells harvested from umbilical cord perivascular tissue) or umbilical cord blood (CB-MSCs) (Bernardo, M. E., F. Locatelli, et al. (2009) Ann N Y Acad Sci 1176: 101-117). Other rich sources for MSCs are the developing tooth bud of the mandibular third molar and amniotic fluid. It has also been reported that MSCs can be successfully isolated from human peripheral blood (Chong P P et al. (2012) J Orthop Res. 30(4):634-42). The MSCs can be isolated from the whole umbilical cord and in this case can be referred to as "mesenchymal cells derived from umbilical cord." It is noted that as the umbilical cord has different structures, and the isolation of MSCs can also be made or harvested from only a "region" or "structure" such as the perivascular tissue, the Wharton's jelly, or the umbilical cord blood.

MSCs have a great capacity for self-renewal while maintaining their multipotency. A standard test to confirm multipotency is differentiation of the cells into osteoblasts, adipocytes, and chondrocytes as well as myocytes and neurons. Other attractive features of MSCs include that they are readily isolated from bone marrow by their adherence to tissue culture surfaces, they rapidly expanded in culture, they are highly clonogenic in that they efficiently generated single-cell derived colonies, and they are readily seen to differentiate in culture or in vivo into several cellular phenotypes such as osteoblasts, adipocytes, and chondrocytes. These properties are retained as the cells are expanded through 20 or so population doublings, particularly if the cells were plated at low density and passed before they reach confluency (Gregory C A, et al. (2005) Sci STKE 294:pe37). The plasticity of MSCs was also illustrated by experiments in which MSCs were cultured without fetal calf serum (Pochampally et al. (2004) Blood 103:1647-1652) or, even more dramatically, when the MSCs were subjected to environmental stress in culture to generate multi-lineage-differentiating stress-enduring MSCs or Muse cells (Wakao et al. (2011) Proc Nal Acad Sci USA 108:9875-9880). Under such circumstances, the MSCs reverted to a more primitive phenotype and expressed genes characteristic of embryonic genes.

MCSs have been observed to have anti-inflammatory effects. The disease models in which MSCs have produced beneficial effects include diabetes, stroke, spinal cord injury, Parkinsonism, Alzheimer's disease, liver disease, kidney disease, and some cancers. See Prockop, D. J. and J. Y. Oh (2012) J Cell Biochem 113(5): 1460-1469. MSCs have also been shown to contribute to cancer progression, e.g., hematological malignancies (Torsvik A. and Bjerkvig R. (2013) Cancer Treat Rev. 39(2)180-8).

MSCs have the ability to migrate and engraft tumors and it is thought that factors produced by tumor cells and their microenvironments are responsible. MSC motility in vitro has been induced after stimulation with different cytokines (Ries, Egea et al. (2007). Blood 109(9): 4055-4063), growth factors (Ponte, Marais et al. (2007) Stem Cells 25(7): 1737-1745), or chemokines such as CXCL7 (Kalwitz, Endres et al. (2009) Int J Biochem Cell Biol 41(3): 649-658) or SDF-1 (Gao, Priebe et al. (2009) Stem Cells 27(4): 857-865). However, this application is the first report demonstrating the increased MSCs in vivo migration towards HCC with a simple treatment with rAMF. Reports have demonstrated MSC migration towards a number of tumor-released factors (e.g., VEGF, PDGF, TGF-O, MCP-1, IL-8, TNF-α, IL-10, IL-6, SDF-1, and HGF). However, there is a lack of robust data confirming the role of any specific factors in the recruitment of MSCs towards tumors such as HCC.

MSCs show tropism for inflamed, injured or tumorigenic sites and their ability to be cultured and expanded in vitro, their self-renewal properties and low immunogenicity make these cells useful for cell therapy (Prockop, D. J. and J. Y. Oh (2012) J Cell Biochem 113(5): 1460-1469). Although there are some promising results with MSCs genetically modified as a therapeutic option for HCC (Gao, Yao et al. (2010) Oncogene 29(19): 2784-2794; Niess, Bao et al. (2011) Ann Surg 254(5): 767-774; discussion 774-765), these reports left a need to enhance the efficacy of MSCs migration towards tumor (e.g., HCC) microenvironment. The current application includes certain embodiments where MSCs, e.g., MSCs genetically modified to express an anti-tumor gene, are pretreated with rAMF to increase migration toward a tumor microenvironment.

In some embodiments a method for the genetic modification of MSCs is by chemical (e.g. Lipofectamine) or physical (e.g. electroporation) transfection or viral vectors. Afterwards stably transfected cells can be selected, where the transgene cassette has integrated by chance into the MSC genome. In another embodiment, the genetic modification of MSCs is by using non-viral vector systems derived from transposons. After flanking of an expression cassette with terminal inverted repeats, a construct can be transferred into MSC via transfection. If a transposase is expressed in trans during the transfection, the expression cassette will be stably integrated into the genome of the MSC.

A genetically modified MSC according to some embodiments of the invention can be prepared by transduction of native MSCs with pseudotyped virions, expressing foreign glycoproteins on their surface, which alter the tropism and often the titer of the virion.

A genetically modified MSC according to some embodiments can be engineered to express an oncolytic virus expressing anti-tumor genes.

Autocrine Motility Factor (AMF)

Autocrine motility factor (AMF) is a 55-kDa cytokine secreted by tumors that regulates cell motility (Liotta, L. A., R. Mandler, et al. (1986) Proc Natl Acad Sci USA 83(10): 3302-3306). AMF exhibits sequence identity with glucose-6-phosphate isomerase (GPI), a glycolytic enzyme involved in carbohydrate metabolism (Watanabe, H., K. Takehana, et al. (1996) Cancer Res 56(13): 2960-2963). The stimulation of cell motility is induced by the binding to the autocrine motility factor receptor (AMFR), a 78-kDa seven transmembrane glycoprotein with leucine zipper and RING-H2 motifs (Shimizu, K., M. Tani, et al. (1999) FEBS Lett 456(2): 295-300). AMFR is stably localized in caveolae, and caveolin-1 (Cav-1) has the ability to regulate the endocytic pathway through the stabilization of caveolae expression (Le, P. U., G. Guay, et al. (2002) J Biol Chem 277(5): 3371-3379).

One of the key steps in the transmigration process across the basement membrane is dependent on the proteolytic activity of metalloproteinases. In tumor cells, AMF-induced motility is mediated by upregulation of MMP2 and MMP3 (Torimura, Ueno et al. (2001) Hepatology 34(1): 62-71; Yu, Liao et al. (2004) Biochem Biophys Res Commun 314(1): 76-82). As disclosed herein, AMF was shown to increase the expression of mRNA MMP3 in MSCs. It was previously reported that MSCs exposed to CM derived from HCC cell lines increased their MMP2 activity (Garcia, Bayo et al. (2011) Mol Pharm 8(5): 1538-1548). As disclosed herein, AMF present in the CM is, at least in part, responsible for the increased MMP2 activity since blockage of AMF decreased MMP2 activity. In addition, stimulation with rAMF increased the invasion capacity of MSCs across collagen and the MMPs inhibitor significantly decreased the invasion capacity of MSCs.

AMF is produced by several tumors, such as lung (Dobashi, Watanabe et al. (2006) J Pathol 210(4):431-440), gastrointestinal, kidney and breast (Baumann, Kappl et al. (1990) Cancer Invest 8(3-4):351-356 as well as hepatocellular carcinomas (HCC) (Ogata, Torimura et al. (1999) Hum Pathol 30(4): 443-450). It is also reported herein that AMF is secreted in the CM from HCC s.c tumors.

AMF is not considered a typical chemotactic factor such as VEGF, PDGF, TGF-β, MCP-1, IL-8, TNF-α, IL-10, IL-6, SDF-1, and HGF. Instead, intracellular AMF has been shown to be involved in glucose metabolism in all types of cells and some reports have described the extracellular form of AMF as inducing tumor migration and endothelial cell migration related to angiogenesis.

AMF-induced migration has been described in tumor cells and its role in metastasis. In vitro studies have demonstrated that exogenous AMF stimulated migration of human cancer melanoma, fibrosarcoma and HCC cells as well as human umbilical vein endothelial cells (HUVECs) (Liotta, Mandler et al. (1986) Proc Natl Acad Sci USA 83(10): 3302-3306; Silletti, Watanabe et al. (1991) Cancer Res 51(13): 3507-3511; Watanabe, Carmi et al. (1991) J Biol Chem 266(20): 13442-13448; Torimura, Ueno et al. (2001) Hepatology 34(1): 62-71). Overexpression of AMF in NIH-3T3 fibroblasts was reported to induce malignant transformation (Tsutsumi, Hogan et al. (2003) Cancer Res 63(1): 242-249). In embodiments of the current application, rAMF treatment does not induce malignant transformation in MSCs or promote increased tumor development or metastasis.

In cancer cells, it has been observed that AMF-induced migration is mediated by its interaction with AMF receptor (AMFR) on cell surface (Silletti, Watanabe et al. (1991) Cancer Res 51(13): 3507-3511). AMFR has been found stably localized to caveolae at the plasma membrane caveolin-1, a caveolar coat protein that has been described as a negative regulator of caveolae-mediated endocytosis of AMFR to the endoplasmic reticulum (Le, Guay et al. (2002) J Biol Chem 277(5): 3371-3379). It is disclosed herein that rAMF treatment of MSCs induced AMFR and caveolin-1 and -2 expressions, supporting their role in the maintenance of the receptor on the cell surface. Moreover, in cancer cells AMF enhances integrin 01 activity leading to activation of mitogen activated protein kinase (MAPK) and Rho pathways (Torimura, Ueno et al. (2001) Hepatology 34(1): 62-71). Small GTPase is largely involved in motility and cell adhesion due to its role in cytoskeleton organization. GTPase activity is regulated by GTPase-activating proteins (GAPs) and GDP dissociation inhibitors (GDIs). In bladder cancer, Rho GDP dissociation inhibitor (GDI) 0 (GDI2) is diminished in cells with higher motility indicating its role as suppressor of migration. However other reports indicated that GDI2 is upregulated in tumors with a more aggressive phenotype (Tapper, Kettunen et al. (2001) Cancer Genet Cytogenet 128(1): 1-6; Yanagawa, Watanabe et al. (2004) Lab Invest 84(4): 513-522). As disclosed herein, rAMF treatment decreased mRNA of GDI-2, supporting its role as inhibitor of migration. In certain embodiments, rAMF is a chemoattractant factor for MSCs, e.g., MSCs comprising a therapeutic agent.

The AMF can be naturally produced or recombinant. In certain embodiments, the AMF is human AMF. In some embodiments, the AMF comprises the polypeptide sequence of SEQ ID NO:1 or a functional fragment thereof. In some embodiments, the AMF comprises a polypeptide having an amino acid sequence that is at least 80%, at least 85%, at least 90%, at least 95%, at least 99%, or 100% identical to an AMF amino acid sequence that is naturally produced in an animal (e.g., SEQ ID NO:1). In some embodiments, the AMF comprises or consists of a sequence having at least 80%, at least 85%, at least 90%, at least 95%, at least 99%, or 100% sequence identity to SEQ ID NO:1 or a functional fragment thereof.

Compositions

Certain embodiments are directed to a composition comprising a mesenchymal stromal cell (MSC) stimulated with a recombinant autocrine motility factor (rAMF), wherein the MSC comprises a therapeutic agent and wherein the MSC of the composition has (1) increased migration to a tumor or a tumor cell after rAMF stimulation and/or (2) increased adhesion to an endothelial cell, e.g., a vascular endothelial cell, after rAMF stimulation.

Certain embodiments are directed to a composition comprising a mesenchymal stromal cell (MSC) stimulated with a recombinant autocrine motility factor (rAMF), wherein the MSC comprises a therapeutic agent and wherein the MSC of the composition has increased migration to a tumor or a tumor-derived cell. In some embodiments, the increased migration is relative to or compared to MSC without rAMF stimulation.

Certain embodiments are directed to a composition comprising a mesenchymal stromal cell (MSC) stimulated with a recombinant autocrine motility factor (AMF), wherein the MSC comprises a therapeutic agent and wherein the MSC of the composition has increased adhesion to an endothelial cell, e.g., a vascular endothelial cell. In some embodiments, the increased adhesion is relative to or compared to MSC without rAMF stimulation.

In some embodiments, the increased migration and/or adhesion is about 1.5-fold, about 2-fold, about 2.5-fold, or about 3-fold greater than migration and/or adhesion of the MSC without rAMF stimulation. In some embodiments, the increase in migration and/or adhesion is at least about 20-60%, 30-60%, 40-60%, 30-50%, or 20-40% greater than migration and/or adhesion of the MSC without rAMF stimulation.

In some embodiments, the MSC of the composition is selected from the group consisting of bone marrow MSC, adipose tissue MSC, umbilical cord MSC, and any combination thereof.

In some embodiments, the tumor is a solid tumor or cancer. In some embodiments, the tumor is a liver cancer, a colon cancer, a pancreatic cancer, a lung cancer, a gastrointestinal cancer, a kidney cancer, a breast cancer, or a combination thereof. In some embodiments, the tumor is a carcinoma, e.g., hepatocellular carcinoma (HCC) or colorectal carcinoma. In some embodiments, the tumor or the tumor cell expresses endogenous AMF.

In some embodiments, the therapeutic agent is a recombinant anti-tumor gene (e.g., an interferon (e.g., interferon α, interferon β), an interleukin (interleukin 1, interleukin 12), a chemokine (e.g., CX3CL1), a suicide gene (e.g., thymidine kinase, IL-12, IFN-gamma, TNF-alpha), or any combination thereof), a cytotoxic drug, an antibody, or an oncolytic virus.

In some embodiments, the therapeutic agent is an oncolytic virus (OV), i.e., a virus that preferentially infects and kills cancer cells (e.g., adenovirus (e.g., H101), Reovirus, measles, herpes simplex (e.g., HSV1716), Newcastle disease virus and vaccinia). See, e.g., Nakashima et al. (2010) Cytokine Growth Factor Rev. 21(2-3):119-26. In some embodiments, the oncolytic virus is engineered to expresses a recombinant anti-tumor gene. In one embodiment, the recombinant oncolytic virus is an oncolytic adenovirus. In some embodiments, the therapeutic agent is an oncolytic virus (see, e.g., Dwyer R M et al. (2010) Stem Cell Res Ther. 1(3):25), e.g., onyx-015 (see, e.g., Khuri F R et al. (2000) Nat Med. 6(8):879-85); Ad-F512(H-N)5/3 (see, e.g., Viale D. L., et al. (2013) J Invest Dermatol doi: 10.1038/jid.2013.191 (e-publication ahead of print)). In some embodiments, the oncolytic virus can be used as a vector for delivery of anti-tumor genes, e.g., an interferon (e.g., interferon α, interferon β), an interleukin (e.g., interleukin 1, interleukin 12), a chemokine (e.g., CX3CL1), or a suicide gene (e.g., encoding enzymes that can metabolize a separately administered non-toxic pro-drug into a potent cytotoxin, which can diffuse to and kill neighboring cells). In some embodiments, the MSC comprises a recombinant AMF receptor, CXCR1, CXCR2, or MCP-1.

Methods of Increasing Migration or Anchorage

Certain embodiments are directed to a method for increasing migration or anchorage of a mesenchymal stromal cell (MSC) to a tumor comprising (a) stimulating the MSC with a recombinant autocrine motility factor (rAMF), and (b) administering the stimulated MSC of (a) to the tumor, wherein the MSC comprises a therapeutic agent.

In some embodiments, the methods of the application include increasing migration or anchorage of MSCs to a tumor, e.g., a solid tumor or cancer. In some embodiments, the tumor is selected from the group consisting of a liver cancer, a colon cancer, a pancreatic cancer, a lung cancer, a gastrointestinal cancer, a kidney cancer, a breast cancer, and any combination thereof. In some embodiments, the tumor is a carcinoma, e.g., hepatocellular carcinoma (HCC) or colorectal carcinoma. In some embodiments, the tumor or the tumor cell expresses endogenous AMF.

In some embodiments, the methods of the application include increasing migration or anchorage of MSCs to a tumor wherein the MSCs comprise a therapeutic agent, e.g., a recombinant anti-tumor gene (e.g., an interferon (e.g., interferon α, interferon β), an interleukin (interleukin 1, interleukin 12), a chemokine (e.g., CX3CL1), a suicide gene (e.g., thymidine kinase, IL-12, IFN-gamma, TNF-alpha), or any combination thereof), a cytotoxic drug, an antibody, or an oncolytic virus.

In some embodiments, the methods of the application include increasing migration or anchorage of MSCs to a tumor wherein the MSCs comprise a therapeutic agent, e.g., an oncolytic virus (OV), i.e., a virus that preferentially infects and kills cancer cells (e.g., adenovirus (e.g., H101), Reovirus, measles, herpes simplex (e.g., HSV1716), Newcastle disease virus and vaccinia). See, e.g., Nakashima et al. (2010) Cytokine Growth Factor Rev. 21(2-3):119-26. In some embodiments, the oncolytic virus is engineered to expresses a recombinant anti-tumor gene. In one embodiment, the recombinant oncolytic virus is an oncolytic adenovirus, e.g., Ad-F512(H-N)5/3 (see, e.g., Lopez, et al. (2012) Mol Ther. 20(12):2222-33). In some embodiments, the oncolytic virus can be used as a vector for delivery of anti-tumor genes, e.g., an interferon (e.g., interferon α, interferon β), an interleukin (e.g., interleukin 1, interleukin 12), a chemokine (e.g., CX3CL1), or a suicide gene (e.g., encoding enzymes that can metabolize a separately administered non-toxic pro-drug into a potent cytotoxin, which can diffuse to and kill neighboring cells). In some embodiments, the MSC comprises a recombinant AMF receptor, CXCR1, CXCR2, or MCP-1.

Methods of Treatment

Certain aspects of the application are related to cell therapies using cells genetically engineered to express a heterologous gene, e.g., an anti-cancer gene. Some embodiments are directed to a method for treating a subject with a tumor comprising administering to the subject a composition of the application.

Some embodiments are directed to a method for treating a subject with a tumor comprising (a) stimulating a mesenchymal stromal cell (MSC) comprising a therapeutic agent with a recombinant autocrine motility factor (rAMF), and (b) administering the stimulated MSC of (a) to the subject.

In some embodiments, stimulating a MSC with a recombinant protein of the application, e.g., rAMF, is accomplished by pretreatment of the MSC prior to administration to a subject. Methods for pretreating the MSC include, e.g., culturing MSCs with the recombinant protein, e.g., rAMF, for about 1-48 hours, about 6-48 hours, about 6-36 hours, about 6-24 hours, about 12-24 hours, about 12-36 hours, about 12-48 hours, about 18-48 hours, about 18-36 hours, or about 18-24 hours prior to administration of the stimulated MSC.

In some embodiments, the subject's tumor is a solid tumor or cancer. In some embodiments, the tumor is selected from the group consisting of a liver cancer, a colon cancer, a pancreatic cancer, a lung cancer, a gastrointestinal cancer, a kidney cancer, a breast cancer, and any combination thereof. In some embodiments, the tumor is a carcinoma, e.g., hepatocellular carcinoma (HCC) or colorectal carcinoma. In some embodiments, the tumor expresses endogenous AMF. In some embodiments, the tumor is metastatic and/or vascularized.

In some embodiments, the methods of the application treating a tumor wherein the MSCs comprise a therapeutic agent, e.g., a recombinant anti-tumor gene (e.g., an interferon (e.g., interferon α, interferon β), an interleukin (interleukin 1, interleukin 12), a chemokine (e.g., CX3CL1), a suicide gene (e.g., thymidine kinase, IL-12, IFN-gamma, TNF-alpha), or any combination thereof), a cytotoxic drug, an antibody, or an oncolytic virus.

In some embodiments, the therapeutic agent is an oncolytic virus, i.e., a virus that preferentially infects and kills cancer cells (e.g., adenovirus (e.g., H101), Reovirus, measles, herpes simplex (e.g., HSV1716), Newcastle disease virus and vaccinia). See, e.g., Nakashima et al. (2010) Cytokine Growth Factor Rev. 21(2-3):119-26. In some embodiments, the oncolytic virus is engineered to expresses a recombinant anti-tumor gene. In one embodiment, the recombinant oncolytic virus is an oncolytic adenovirus, e.g., Ad-F512(H-N)5/3 (see, e.g., Lopez, et al. (2012) Mol Ther. 20(12):2222-33). In some embodiments, the oncolytic virus can be used as a vector for delivery of anti-tumor genes, e.g., an interferon (e.g., interferon α, interferon β), an interleukin (e.g., interleukin 1, interleukin 12), a chemokine (e.g., CX3CL1), or a suicide gene (e.g., encoding enzymes that can metabolize a separately administered non-toxic pro-drug into a potent cytotoxin, which can diffuse to and kill neighboring cells). In one embodiment, the suicide gene encodes Herpes simplex viral thymidine kinase, and the subject ideally is treated with ganciclovir in a manner permitting the Herpes simplex viral thymidine kinase to render the ganciclovir cytotoxic. Another possibility is the use of cytosine deaminase as a cytotoxic protein, which converts 5-fluorocytosine to the toxic compound 5-fluorouracil.

In some embodiments, the method for treating a subject with a tumor comprises introducing into the subject's bloodstream a therapeutically effective amount of a rAMF stimulated MSC or composition of the application. In some embodiments, the administration to the subject is systemic (e.g., parenteral) or local, e.g., to an intra-hepatic artery.

In some embodiments, the therapeutically effective number of MSCs includes, without limitation, the following amounts and ranges of amounts: (i) from about $1\times10^5$ to about $1\times10^9$ cells/kg body weight; (ii) from about $1\times10^6$ to about $1\times10^8$ cells/kg body weight; (iii) from about $5\times10^6$ to about $2\times10^7$ cells/kg body weight; (iv) from about $5\times10^6$ to about $1\times10^7$ cells/kg body weight; (v) from about $1\times10^7$ to about $2\times10^7$ cells/kg body weight; (vi) from about $7\times10^6$ to about $9\times10$ cells/kg body weight; (vii) about $1\times10$ cells/kg body weight; (viii) about $1\times10^6$ cells/kg body weight; (ix) about $5\times10^6$ cells/kg body weight; (x) about $1\times10^7$ cells/kg body weight; (xi) about $6\times10^6$ cells/kg body weight; (xii) about $7\times10^6$ cells/kg body weight; (xiii) about $8\times10$ cells/kg body weight; and (ix) about $9\times10^6$ cells/kg body weight. Human body weights envisioned include, without limitation, about 50 kg, about 60 kg; about 70 kg; about 80 kg, about 90 kg; and about 100 kg. Therapeutically effective amounts can be based on pre-clinical animal experiments and standard protocols from the transplantation of MSCs.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

The following examples are offered by way of illustration and not by way of limitation.

EXAMPLES

Example 1

Materials and Methods

Cell Lines

Human HCC cell line HuH7 were kindly provided by Prof. Jesus Prieto (CIMA, University of Navarra, Pamplona, Spain). LX-2 cell line (human HSCs generated by spontaneous immortalization in low serum conditions) was kindly provided by Dr. Scott Friedman (Division of Liver Diseases, Mount Sinai School of Medicine, New York, N.Y., USA). Human microvascular endothelial cells (HMEC-1) were provided by CDC (Centers for Disease Control, Atlanta, Ga., USA). Cell lines were cultured in complete DMEM (2 μmol/L glutamine, 100 U/mL penicillin, 100 mg/mL streptomycin and 10% heat-inactivated fetal bovine serum (FBS)). Primary culture of HCC cells (HC-PT-5) was previously generated in our laboratory and cultured the eight passage in 70% DMEM/30% F12 (Invitrogen/Life Technologies) culture medium supplemented with 2 μmol/L glutamine, 100 units/mL penicillin, 100 mg/mL streptomycin and 10% FBS.

Isolation of MSCs, AT-MSCs and Mesenchymal Cells Harvested from Umbilical Cord Perivascular Tissue Cells were obtained from allogeneic bone marrow transplantation of healthy donors after informed consent (Hospital Naval Pedro Mallo, Buenos Aires, Argentina). Mononuclear cells were plated in complete DMEM low glucose/20% FBS (Internegocios S.A., Argentina). After 2 h incubation, non-adherent cells were removed and adherent hMSCs were cultured and used for different experiments between passages 4 to 6. For AT-MSCs generation, cells were isolated from discarded fat from esthetical liposuctions after informed consent as described previously Zuk et al. (Zuk, Zhu et al. (2001). Tissue Eng 7(2):211-228). Briefly, discarded lipoaspirates were washed extensively with sterile phosphate-buffered saline. Washed aspirates were treated with 0.075% type collagenase (Sigma-Aldrich) in PBS for 30 min at 37° C. with agitation. The cells were centrifugated and cellular pellet was plated in complete DMEM low glucose/20% FBS (Intemegocios S.A., Argentina) and used for different experiments between passages 4 to 6.

Mesenchymal cells harvested from umbilical cord perivascular tissue were isolated from discarded umbilical cord obtained from healthy donors from the Service of Gynaecology and Obstetrics after informed consent in our institution adapted from the protocol previously described in Sarugaser, Lickorish et al. (2005). Stem Cells 23(2):220-229). Umbilical cords were dissected and vessels with its surrounding Warthon's Jelly were pulled out. Then the perivascular Wharton's Jelly were removed from the vessels and mechanically disrupted. Minced fragments were plated in complete DMEM low glucose/20% FBS (Intemegocios S.A., Argentina). After 7 days incubation, non-adherent cells and minced fragments were removed and adherents Mesenchymal cells harvested from umbilical cord perivascular tissue were cultured and used for different experiments between passages 4 to 6.

MSCs were characterized according to the guidelines from International society for cellular therapy (ISCT).

Conditioned Medium

To obtain tumor conditioned medium (TCM), HuH7 or HC-PT-5 subcutaneous tumors (s.c.) were dissected and minced into pieces smaller than 1 mm$^3$ and transferred into a 24 wells tissue culture plate (6 fragments/well) with 500 µl of DMEM supplemented with 2 µmol/l glutamine, 100 units/ml penicillin, and 100 mg/ml streptomycin. Cell conditioned medium (CCM) was obtained from HCC cell lines cultured as described above to 90% confluence and then were washed with PBS and cultured with DMEM without FBS. In both cases, 18 hours later conditioned medium was harvested and stored at −80° C. until use.

Western Blot

BM-MSCs or AMF stimulated BM-MSC were lysed with 150 mmol/L NaCl, 20 mmol/L Tris-HCl, pH 7.4, 0.1% SDS, 1.0% Nonidet P-40, 0.5% Na-deoxycholate, 0.2 mmol/L phenylmethylsulfonyl fluoride, and protease inhibitor cocktail. Lysates were centrifuged at 12,000 g for 20 min and the supernatants were used as total cell lysates. CCM and TCM were concentrated 100-fold using Vivaspin 6 centrifugal concentrator (Sartorius-Stedim Biotech). The protein concentration was determined by Bradford protein assay (Bio-Rad). Protein was separated by SDS-PAGE and transferred onto nitrocellulose membrane (Hybond-ECL, Amersham Biosciences). Blots were blocked and incubated with anti-AMF (1:700) polyclonal antibody (sc-33777, Santa Cruz Biotechnology), anti-AMFR (1:1000) polyclonal antibody (AP2162a, ABGENT), anti-JNK (1:1000) polyclonal antibody (9252, Cell Signaling), anti-phospho-JNK (1:1000) polyclonal antibody (9251, Cell Signaling), anti-c-Fos (1:1000) monoclonal antibody (2250, Cell Signaling), anti-phospho-c-Fos (1:1000) monoclonal antibody (5348, Cell Signaling), anti-phospho-CREB (1:1000) monoclonal antibody (9198, Cell Signaling) or anti-Actin (1:700) polyclonal antibody (sc-1615, Santa Cruz Biotechnology) at 4° C. overnight. Finally, blots were then incubated with the corresponding HRP-conjugated IgG at room temperature for 1 hour. The reactions were visualized using the enhanced chemiluminescence (ECL) reagent (Sigma). Staining with colloidal Coomassie was performed as loading control for conditioned medium as was reported previously (Welinder, Ekblad. (2011) J Proteome Res 10(3):1416-1419). Density of each band was quantified with Scion Image software (Scion Corporation, Frederick, Md.).

In Vitro Migration, Invasion, and Wound-Healing Assays

In vitro migration was performed using a 48-Transwell microchemotaxis Boyden Chamber unit (Neuroprobe, Inc.). In brief, MSCs ($1.2 \times 10^3$ cells/well) were placed in the upper chamber and DMEM, TCM or recombinant human AMF (rAMF) where placed in the lower chamber of the Transwell unit. Both chambers were separated by 8 µm pore polycarbonate filters (Nucleopore membrane, Neuroprobe). For blocking experiments, TCM were pre-incubated for 60 min with anti-AMF polyclonal antibody (sc-33777, Santa Cruz Biotechnology) or isotype control IgG. For AMF pre-treatment BM-MSCs were incubated overnight (O.N.) with 1 µg/ml of rAMF in DMEM without FBS or DMEM without FBS as control.

For the invasion assay the polycarbonate filters were previously incubated with 10 mg/ml type IV collagen (Sigma-Aldrich) for 18 h at 4° C.; for MMP inhibition, BM-MSCs were preincubated with 1,10 phenantroline (0.5 or 1 mM) (Sigma-Aldrich). MSCs viability was not affected by 1,10 phenantroline (not shown). All the systems were incubated for 4 h at 37° C. in a 5% $CO_2$ humidified atmosphere. After that, the membrane was carefully removed and cells on the upper side of the membrane were scraped off with a blade. Cells attached to the lower side of the membrane were fixed in 2% formaldehyde, and stained with 40,6-diamidino-2-phenylindole dihydrochloride (DAPI, Sigma-Aldrich). Cells were counted using fluorescent-field microscopy and a 10× objective lens: the images captured in three representative visual fields were analyzed using CellProfiler world wide web A software (world wide web.cellprofile.com), and the mean number of cells/field+ SEM was calculated.

For the wound-healing assay, Fast-DiO-stained MSCs were seeded at $2.5 \times 104$ cell/cm$^2$ in DMEM with 10% FBS for 24 hours. Then, cells were preincubated overnight with 1 µg/ml rAMF or DMEM without FBS. The monolayers were then scratched by a 200 ml-tip, washed with PBS and incubated for 24 hours more in DMEM without FBS. Cells within the scratched area were counted under a fluorescent-field microscope at 40× and the number of cells/field were determined. Additionally, adherent cells were counted at the end of the experiment confirming the same number of cells in all the conditions.

Gelatin Zymography Assay

To evaluate whether AMF induced gelatinolytic activity in MSCs, $5 \times 10^4$ cells were seeded in 24-well plates for 18 h. Cells were treated with 1 µg/ml of rAMF, TCM or serum-free DMEM as untreated control for 2 h; then, MSCs were washed with PBS and cultured in DMEM for 6 h before supernatants were collected. For blocking experiments, TCM were pre-incubated for 60 min with anti-AMF polyclonal antibody (sc-33777, Santa Cruz Biotechnology) or isotype control IgG. MMP2 activity was determined by zymography. Briefly, 20 µL of MSC supernatant was run on a 10% SDS-PAGE containing 0.1% gelatin (Sigma-Aldrich). The gel was stained with Coomassie Brilliant Blue R-250 for 30 min at room temperature. Gelatinase activity was visualized by negative staining; el images were obtained with a digital camera (Canon EOS 5D), and were subjected to densitometry analysis using Scion Image software (Scion Corporation, Frederick, Md.). Relative MMP2 activity was obtained by normalizing values to untreated samples (DMEM).

Cell Adhesion Assays

For analyses of MSC adhesion to endothelial cells, $2\times10^5$ HMEC-1 were seeded in 96-well microplates and cultured for 1 day prior the assay. Coated wells were incubated for 5 minutes with 0.1 ml of $5\times10^4$ cells/ml of Fast-DiO labeled MSCs O.N. pretreated or not with 1 µg/ml rAMF. The cell suspension was discarded and the cells were fixed with 2% paraformaldehyde. Cells were counted using fluorescent-field microscopy and a 20× objective lens: the images captured in ten representative visual fields were analyzed using CellProfiler software (cellprofiler.com) and normalizing to untreated control.

Reverse Transcription-Polymerase Chain Reaction (RT-PCR)

Total mRNA of BM-MSCs O.N. pretreated or not with 1 µg/ml rAMF was extracted using Trizol Reagent (Sigma-Aldrich Co., St. Louis, Mo.). For quantification of MMP3 mRNA level, MSCs were 24 h starved before rAMF pre-treatment. Total mRNA (4 µg) was reverse transcribed with 200 U of SuperScript II Reverse Transcriptase (Invitrogen, Carlsbad, Calif.) using 500 ng of Oligo (dT) primers. cDNAs were subjected to real-time polymerase chain reaction (qPCR) (Stratagene Mx3005p, Stratagene, La Jolla, Calif., USA). For qRT-PCR, the mRNA levels of metalloproteinase 3 MMP3, AMF receptor (AMFR), GDP dissociation inhibitor 2 (GDI-2), caveolin-1 (CAV-1) and caveolin-2 (CAV-2) were quantified by SYBR® Green (Invitrogen), using the following primer pairs:

```
                                           (SEQ ID NO: 2)
MMP3 5'-ACGCCAGCCAACTGTGATCCT-3' (forward), (SEQ ID NO: 3)
5'-ATATGCGGCATCCACGCCTGAA-3' (reverse);

(SEQ ID NO: 4)
AMFR 5'-ACAAGATGTGGGCCTTGCAAGA -3 (forward), (SEQ ID NO: 5)
5'-AAAACGCAGTGCTCCCAGGATA-3' (reverse);

(SEQ ID NO: 6)
GDI-2 5'-GACCAGCTTTGGAGCTCTTG-3' (forward), (SEQ ID NO: 7)
5'-TGCGGGAAATAAAGATCTGG-3' (reverse);

(SEQ ID NO: 8)
CAV-1 5'-AATCCAAGCATCCCTTTGCCCA-3' (forward), (SEQ ID NO: 9)
5'-ACCAGGCAGCTTTCTGTACGA-3' (reverse);

(SEQ ID NO: 10)
CAV-2 5'-GAGAGACAGGGGAGTTGTCAACTT-3' (forward), (SEQ ID NO: 11)
5'-GCCCGGCCCAGAAATAATGAGAT-3' (reverse);

(SEQ ID NO: 14)
CXCR1 5'-TTTTCCGCCAGGCTTACCAT-3' (forward),
and (SEQ ID NO: 15)
5'-AACACCATCCGCCATTTTGC-3' (reverse);

(SEQ ID NO: 16)
CXCR2 5'-TAAGTGGAGCCCCGTGGGG-3' (forward),
and (SEQ ID NO: 17)
5'-TGGGCTCAGGGGCAGGATG-3' (reverse);

(SEQ ID NO: 18)
CCR2 5'-CGAGAGCGGTGAAGAAGTCA-3' (forward),
and (SEQ ID NO: 19)
5'-AGCATGTTGCCCACAAAACC-3' (reverse);

(SEQ ID NO: 20)
IL-6R 5'-GCACTTGCTGGTGGATGTTC-3 (forward),
and (SEQ ID NO: 21)
5'-AGCCTTTGTCGTCAGGGATG-3' (reverse);

(SEQ ID NO: 22)
IL-65T 5'-CCCACCTCATGCACTGTTGA-3' (forward),
and (SEQ ID NO: 23)
5'-TTATGTGGCGGATTCGGCTT-3' (reverse);
and (SEQ ID NO: 24)
IGFBP3 5'-ACTGTGGCCATGACTGAG-3' (forward),
and (SEQ ID NO: 25)
5'-AGAGTCTCCCTGAGCCTGA-3' (reverse).
```

All PCR amplifications were carried out using a cycle of 95° C. for 10 min and 45 cycles under the following parameters: 95° C. for 30 sec, 58° C. for 30 sec, 72° C. for 1 min. At the end of the PCR reaction, the temperature was increased from 60° C. to 95° C. at a rate of 2° C./min, and the fluorescence was measured every 15 sec to construct the melting curve. Values were normalized to levels of glyceraldehyde-3-phosphate dehydrogenase (GAPDH; used as housekeeping) transcript (forward 5'-CATCTCTGCCCCCTCTGCTG-3' (SEQ ID NO: 12); reverse 5'-GCCTGCTTCACCACCTTCTTG-3' (SEQ ID NO: 13)). Data were processed by the ΔΔCt method (Livak K J, Schmittgen T D. (2001) Methods 25(4):402-408).

The relative amount of the PCR product amplified from untreated cells was set as 1. A non-template control (NTC) was run in every assay, and all determinations were performed in triplicate in three separated experiments.

Proliferation Assays

HCC cells were seeded in 96-well culture tissue plates at $3\times10^4$ cells/cm$^2$ density for 1 day prior to the assay. Then cells were cultured with CM of BM-MSCs pre-treated with 1 µg/ml of rAMF for 48 h. DMEM and CM of untreated BM-MSCs were used as control. Cell proliferation was evaluated by [3H]-thymidine incorporation assay. Each sample was assayed in sextuplicate and normalized to DMEM control.

Three-Dimensional Spheroids

Ninety-six-well tissue culture plates were coated with 2% agarose in PBS. A total of $3\times10^3$ HuH7 cells, $1\times10^3$ LX-2, $1\times10^3$ HMEC-1 with or without $1\times10^3$ BM-MSC per spheroid were mixed in complete DMEM to obtain a single multicellular spheroid per well. Seventy-five microliters of supernatant was carefully removed from each well every 2 days and replaced with fresh medium or CM from BM-MSC. Viability above 75% was confirmed by Trypan blue exclusion test in all experiments. Spheroid size was evaluated using inverted microscopy and a 4× objective lens: the images were captured and diameters determined using ImageJ software (National Institute of Health, NIH), finally spheroid volume was determined was calculated by the formula π/6×larger diameter×(smaller diameter)$^2$ and expressed as arbitrary unity.

Mice and In Vivo Experiments

Six- to eight-week-old male nude BALB/c mice were purchased from CNEA (Comisión Nacional de Energia Atómica, Ezeiza, Buenos Aires, Argentina). The animals were maintained at our Animal Resources Facilities (School of Biomedical Sciences, Austral University) in accordance with the experimental ethical committee and the NIH guidelines on the ethical use of animals. Subcutaneous model: HuH7 cells ($2\times10^6$) or HC-PT-5 cells ($5\times10^6$) were inoculated subcutaneously (s.c.) into the right flank of nude mice. To evaluate the effect of BM-MSCs pre-treated with recombinant human AMF (rAMF) on tumor development, s.c. HuH7 tumors were established and after 10 days BM-MSCs or BM-MSCs pre-treated with rAMF were intravenously (i.v.) injected. Tumor growth was assessed by calliper measurement, and tumor volume (mm$^3$) was calculated by the formula $\pi/6\times$ larger diameter$\times$(smaller diameter)$^2$. For in vivo migration studies, BM-MSCs or BM-MSCs pre-treated with rAMF were prestained with CMDiI for histological analysis and DiR (Molecular Probes, Invitrogen) for fluorescence imaging (FI) and were i.v. injected ($5\times10$ cells/mice) 10 days after tumor inoculation. FI was performed using the Xenogen In Vivo Imaging System (IVIS; Caliper Life Sciences, Hopkinton, Mass., USA). Mice injected with CMDiI-DiR-labeled MSCs were analyzed 1 h after MSC injection and every day until the experimental end point. Images represent the radiant efficiency and were analyzed with IVIS Living Image (Caliper Life Sciences) software. Regions of interest (ROI) were automatically drawn around the isolated organs to assess the fluorescence signal emitted. Results were expressed as average radiant efficiency in units of photons/second within the region of interest [p/s/cm$^2$/sr]/[$\mu$W/cm$^2$] or as total radiant efficiency in units of photons/second within the region of interest [p/s]/$\mu$W/cm$^2$.

Detection of BM-MSC by Fluorescence

To detect CMDiI+ cells within tumors, frozen sections were mounted in mounting media with DAPI (Vector Laboratories, Inc.) and observed under a fluorescence microscope using a 20× objective lens.

Statistical Analyses

Unpaired Student's t test, one-way analysis of variance following by post tests or Kruskal-Wallis and Dunn's post-tests (GraphPad Prism Software) were used for statistical analyses. Differences with p values lower than 0.05 were considered as statistically significant.

Example 2

Identification of Secreted Factors from HCC Microenvironment

Factors secreted from hepatocellular carcinoma (HCC) microenvironment were identified. Tumor conditioned media (TCM) were obtained from fresh HCC samples or tumors generated from primary cultured human HCC cells (HC-PT-5) or the HuH7 cell line in BALB/c nude mice.

In vitro migratory capacity of MSCs to different TCM samples was analyzed using a 48-Transwell microchemotaxis Boyden Chamber unit (Neuroprobe, Inc.).

Factors present in the different TCM were identified using two Human Cytokine and Chemokine Antibody Arrays (RayBiotech). The factors identified are shown in Tables 1 and 2.

Changes in the gene expression patterns in MSCs exposed to TCM derived from HCC samples were also analyzed. MSCs were exposed overnight to TCM or DMEM (as control) and studied using a microarray gene expression analysis with the aim to identify genes that were differentially expressed in MSCs exposed or not to TCM. Table 3 shows 445 genes differentially expressed in MSC exposed to TCM from sample 1 in comparison with non-exposed cells. Table 4 shows 511 genes differentially expressed in MSC exposed to TCM from sample 2 in comparison with non-exposed cells. Table 5 shows 521 genes differentially expressed in MSC exposed to TCM from sample 4 in comparison with non-exposed cells. Table 6 shows 511 genes differentially expressed in MSC exposed to TCM from sample 5 in comparison with non-exposed cells.

Expression of receptors recognized by soluble factors were analyzed. Receptors with positive signal in at least two of the three replicates of microarray are listed in Table 7.

Real-time PCR (qRT-PCR) was used to analyze the expression of selected genes related to migration in MSCs exposed to TCM. FIG. 1A shows the relative mRNA expression of up-regulated genes CTGF, CYR61, GJA1, SPARC, and AMFR. Autocrine Motility Factor Receptor (AMFR) was up-regulated in MSCs exposed to all CM derived from HCC samples. FIG. 1 shows relative mRNA expression of down-regulated genes HSPA1A, HSP1B, and IGFBP3.

Example 3

Recombinant AMF Exerts a Specific Chemoatractant Activity on MSCs from Different Sources The tumor conditioned media (TCM) from ex vivo subcutaneous (s.c.) tumors derived from HuH7 cell line or HC-PT-5 HCC primary culture and conditioned media from cell culture monolayers (CCM) were subjected to western blot analysis according to the method described in Example 1. A 55 kDa soluble AMF was detected in CCM and TCM (FIG. 2A).

The ability of recombinant human AMF (rAMF) to induce MSCs chemotaxis in vitro was analyzed. MSCs from different sources were evaluated by in vitro migration assay with modified Boyden chambers as described in Example 1. Human MSCs derived from bone marrow (BM-MSCs), perivascular umbilical cord region (Mesenchymal cells harvested from umbilical cord perivascular tissue), or adipose tissue (AT-MSCs) were used in a modified Boyden chamber assay.

The MSCs from the different sources migrated in a dose-dependent manner towards recombinant AMF (FIG. 2B-D). The most significant migration degree was shown in the dose ranging between 0.5 μg/mL and 1 μg/mL (p<0.01) of rAMF for both BM-MSC and Mesenchymal cells harvested from umbilical cord perivascular tissue (FIG. 2B-C), while AT-MSCs migrated better at 0.75 μg/mL of rAMF (FIG. 2D). Interestingly, higher rAMF concentration (5 μg/mL or 10 μg/mL) were not capable of inducing migration neither in BM-MSCs nor in Mesenchymal cells harvested from umbilical cord perivascular tissue and AT-MSCs.

Next, TCM were pretreated with polyclonal antibody against AMF (anti-AMF) to examine whether HCC tumor-secreted AMF was involved in MSC migration as described in the methods of Example 1. As shown in FIG. 2E-G, antibody blocking of AMF present in the TCM from either HuH7 or HC-PT-5 reduced their capability to induce MSC migration in a dose dependent manner. At 1 μg/mL of anti-AMF, BM-MSCs showed a 40% reduction of migration in response to TCM derived from both HCC tumors. A similar effect was observed in Mesenchymal cells harvested from umbilical cord perivascular tissue with a reduction of 30% and 40% in the response to TCM from HuH7 and HC-PT-5, respectively. Finally, the reduction in AT-MSC migration potential was 30% and 20% towards TCM from HuH7 and HC-PT-5, respectively. These results show that AMF exerted a potent chemotactic role in HCC tumor cells.

These results show that AMF was secreted in the culture monolayers from HCC s.c tumors. Moreover, the results show for the first time that AMF produced by HCC is a chemoattractant factor for MSCs and induces migration of MSCs. The migration was shown using MSCs from different sources (i.e., bone marrow (BM), perivascular cells from umbilical cord (Mesenchymal cells harvested from umbilical cord perivascular tissue) and adipose tissue (AT-MSCs)) and the MSCs from all of he tested sources exhibited migration towards AMF in a dose-dependent manner. 1 µg/ml of AMF was sufficient to induce MSCs migration.

Example 4

AMF Stimulates Matrix Metalloproteinase (MMPs) Activity on MSCs

One of the key steps in the transmigration process across the basement membrane is dependent on the proteolytic activity of metalloproteinases. The effect of rAMF on the MSC metalloproteinase activity needed for cell migration was characterized.

MMP3 mRNA level in MSCs was evaluated by qRT-PCR as described in Example 1. MMP3 transcripts showed a 2.4-fold increase in BM-MSCs and Mesenchymal cells harvested from umbilical cord perivascular tissue, and 1.4-fold in AT-MSCs exposed to rAMF compared to unexposed cells (FIG. 3A).

BM-MSCs stimulated with HCC CCM had increased MMP2 activity. As previously reported (Garcia, Bayo et al. (2011). Mol Pharm 8(5):1538-1548), gelatinolytic activity corresponding to MMP2 was detected in supernatants from BM-MSCs and also from Mesenchymal cells harvested from umbilical cord perivascular tissue and AT-MSCs. In the present example, MMP2 activity was measured by zymography (as described in Example 1) in MSCs culture supernatant pre-stimulated with 1 µg/mL of rAMF or from un-stimulated cells as control to determine whether the induction of MMP2 was dependent on the presence of AMF in the TCM. MMP2 activity was significantly enhanced when different sources MSCs were stimulated with rAMF (FIG. 3B).

MMP2 activity was also measured in MSC culture supernatant stimulated with TCM derived from HuH7 previously blocked with polyclonal Ab anti-AMF. As a result, the increased MMP2 activity previously observed was completely abolished when MSCs were treated with AMF blocked-TCM showing a similar level of MMP2 activity than untreated cells (FIG. 3C).

Stimulation with rAMF increased the invasion capacity of MSCs across collagen and the MMPs inhibitor significantly decreased the invasion capacity of MSCs. (FIG. 3D).

These results show that MMP3 expression and MMP2 activity was induced in MSCs by rAMF. In particular, rAMF increased the expression of mRNA MMP3 in MSCs. The results also show that AMF present in the TCM was, at least in part, responsible for the increased in MMP2 activity, which supports a critical role for AMF in MSC migration and invasion since blockage of AMF decreased MMP2 activity and inhibition of MMP2 decreased invasion in vitro.

Example 5

AMF Enhances BM-MSCs Migration Towards HCC by Stimulating Endothelial Cell Adhesion and Modulating Critical Related Genes Specific MSC migration to HCC is critical for their use as cell carriers of therapeutic genes. MSCs were pretreated with rAMF to determine the effect of MSC migration towards the HCC TCMs. In vitro migration assay was used to measure migration of MSCs as described in Example 1.

As shown in FIG. 4A, rAMF pretreatment induced a 40% increase in BM-MSCs migration to conditioned medium from ex vivo s.c. tumors (TCM) derived from HuH7 or HC-PT-5 cell lines. These results show that rAMF pretreatment influenced migration of MSCs towards TCM.

By wound-healing assay, it was observed that overnight rAMF pretreatment did not modify MSC general motility (FIG. 4B) indicating that rAMF pretreatment increases specific chemotaxis towards HCC.

Adhesion to endothelial cells is considered a crucial event for the efficient arrest of MSCs within tumor vasculature for subsequent transmigration. The effect of rAMF on cell adhesion was tested by pretreating MSCs with rAMF and measuring cell adhesion as described in Example 1. Pretreatment with rAMF resulted in a 2-fold enhancement in BM-MSCs adhesion to human endothelial cells HMEC-1 (FIG. 4C).

Genes related to the AMF-AMFR pathway were also studied. As shown in FIG. 4D, a 1.8-fold induction of AMF receptor mRNA was observed when BM-MSCs were stimulated with rAMF. Additionally, mRNA levels of caveolin-1 (CAV-1) and caveolin-2 (CAV-2) were increased in 2.4-fold and 2.3-fold respectively, while Rho GDP dissociation inhibitor (GDI) 0 (GDI-2) expression was reduced 10% after rAMF treatment in BM-MSCs. Moreover, rAMF treatment induced the expression of AMFR, and the proteins involved in AMF-AMFR signaling pathways such as JNK, p-JNK, c-Fos, p-c-Fos and p-CREB (FIG. 4E).

These results demonstrated that pretreatment with rAMF significantly increased MSC migration towards HCC in vitro and increased MSC adhesion to endothelial cells. Furthermore, these results show that rAMF treatment induced AMFR and caveolin-1 and -2 (genes having a possible role in maintenance of the receptor on the cell surface) expression and decreased GDI-2 (a gene having a possible role as inhibitor of migration) mRNA expression. AMFR and activation of mitogen activated protein kinase (MAPK) pathway was observed after rAMF treatment.

Example 6

Recombinant AMF Increases the In Vivo Homing of MSCs into HCC

Enhancement of MSC migration towards HCC by rAMF stimulation was studied in vivo. Noninvasive fluorescence imaging (FI) was used to measure migration of MSCs as described in Example 1. Human MSCs derived from bone marrow (BM-MSCs) pre-stimulated with rAMF (1pg/mL) or control BM-MSCs (no stimulation) were stained with cell trackers DiR and CM-DiI prior to intravenous injection in mice carrying s.c. HuH7 tumor nodules as described in Example 1. Three days later, mice were sacrificed and the fluorescence signal in the isolated tumors was analyzed. The total fluorescent intensity in both groups of animals were similar, indicating no differences in the quantity of injected BM-MSCs (FIG. 5A). Tumors from animals injected with rAMF-pretreated BM-MSCs showed a stronger DiR signal in comparison with control mice (FIG. 5B-C). Mice that received BM-MSC pretreated with rAMF did not show increased signal in liver, lung or spleen (FIG. 5D-F), indicating a specific increased recruitment of BM-MSCs in tumor microenvironment. The presence of BM-MSCs in the isolated tumors was confirmed by cell visualization under fluorescence microscopy (FIG. 5G). rAMF increased in vivo migration to HCC tumors. These results show that stimulation of MSCs with rAMF increased in vivo migration of MSCs towards experimental HCC tumors in comparison with non-stimulated MSCs.

In vitro studies indicated that HuH7 HCC cells exposed to CCM from MSC pre-treated with rAMF did not enhance cell proliferation compared to unexposed cells or to HuH7 cells exposed to CCM from untreated MSCs (FIG. 6A). Moreover, pretreatment of MSCs with AMF did not affect the in vitro growth of multicellular spheroids composed of HuH7 HCC cells, hepatic stellate cells LX-2 and HMEC-1 endothelial cells (FIG. 6B). Finally, AMF-prestimulated MSCs did not enhance tumor growth compared to control tumor-bearing mice (saline) or to the group of mice administered with unstimulated MSCs (FIG. 6C). These studies indicated, as a whole, that AMF promoted MSC homing to the HCC niche without affecting tumor growth.

Pretreatment with rAMF was shown to significantly increase (by 30%, p0,01) MSCs migration towards HCC in vivo. This is the first report demonstrating the increased in vivo migration of MSCs towards HCC with pretreatment of MSCs with rAMF.

Example 7

HUCPVCs Presented Higher Migration and Adhesion than BM-MSCs

In vitro migration assays were performed as described in Example 1. Specifically, in vitro migration of bone marrow-derived mesenchymal stem cells (BM-MSCs) (black bars) or human umbilical cord perivascular cells (HUCPVCs) (grey bars) towards CCM from HCC (HuH7 and HC-PT-5), hepatic stellate cells (LX-2), fibroblasts (WI-38) or endothelial cells (HMEC-1) was measured (FIG. 7A). In each case, a higher migratory capacity towards all the CCM was found for HUCPVCs when compared to BM-MSCs. Moreover, in contrast to BM-MCSs, HUCPVCs showed capability to migrate to CCM derived from nontumoral components (fibroblast and endothelial cells).

Besides their capacity to migrate toward factors secreted by HCC, the arrest of MSCs within the microvasculature is considered a critical step for an efficient homing and anchorage to tumors. Therefore, cell adhesion assays were also performed as described in Example 1 to evaluate adhesion ability of MSCs. In that assay, HUCPVCs showed an increased in vitro adhesion to HMEC-1 endothelial cells in comparison with BM-MSCs (FIG. 7B).

Example 8

HUCPVCs Presented In Vivo Migration Towards HCC Tumors

To further characterize MSC behavior in vivo, noninvasive migration assays were performed as described in Example 1. CM-DiI and DiR prelabelled BM-MSCs or HUCPVCs were i.v. injected in HCC tumor-bearing mice in order to evaluate MSC recruitment. Similar to our previous observation with BM-MSCs (FIG. 5), at 3 days after cell transplantation a positive signal corresponding to HUCPVCs was found in liver, lungs, spleen, and s.c. tumors (FIG. 8A). Despite the fact that total signal was lower in mice injected with HUCPVCs compared to those injected with BM-MSCs (FIG. 8B), the percentage of total signal corresponding to s.c. tumor locations was increased in mice administered with HUCPVCs in comparison with animals that received BM-MSCs (FIGS. 8C and 8D), indicating an enhanced engrafiment of HUCPVCs into HCC tumors. In the other evaluated tissues, signal intensity was similar for BM-MSC or HUCPVCs in lung and liver and it was comparatively reduced in the spleen of HUCPVCs-injected mice (FIG. 8D). Presence of MSCs in the s.c. tumors was also confirmed by fluorescence microscopy (Figure E). Finally, MSCs were evaluated for whether they might present differential migratory capacity towards CM obtained from s.c. tumors (TCM). A greater in vitro migratory capacity towards TCM from HCC was observed for HUCPVCs when compared to BM-MSCs (FIG. 8F).

Example 9

Differential Expression of Cytokines/Chemokines Receptors and AMF/AAMFR Pathway in MSCs In order to evaluate mechanisms partially explaining the differential migratory capacity of HUCPVCs compared to BM-MSCs towards tumor released factors, the expression of some chemokine receptors likely involved in MSC recruitment towards HCC was analyzed. Because interleukin- (IL-) 8, GRO, chemokine (C—C motif) ligand (CCL)-2, and IL-6 are among the most relevant factors in HCC (Bayo et al., Liver International 34(3):330-334 (2014)), qPCR (as described in Example 1) was used to evaluate the expression of CXCR1, CXCR2, CCR2, IL-6R, and IL-6ST. Constitutive CXCR1 and CXCR2 mRNA expression was found to be lower and CCR2 slightly higher in HUCPVCs when compared to BM-MSCs, while IL-6R and IL-6ST expression was similar in both MSCs sources (FIG. 9A). Next, the axis of the autocrine motility factor (AMF) was evaluated. By qPCR, a significantly higher expression of the AMF receptor (AMFR) was found in HUCPVCs when compared to BM-MSCs. Similarly, genes known to be related to the availability of the receptor in the cell surface such as caveolin-1 (CAV-1) and caveolin-2 (CAV-2) were also highly expressed in HUCPVCs as well as the metalloproteinase 3 (MMP3), necessary to the transmigration process. In contrast, expression levels of insulin-like growth factor-binding protein 3 (IGFBP3), a protein that negatively regulates AMF/AMFR pathway, were found to be reduced in HUCPVCs when compared to BM-MSCs (FIG. 9B).

Example 10

HUCPVCs Showed Enhanced Migration Towards AMF

The in vitro migration response to the recombinant AMF (rAMF) of both BM-MSCs (black bars) or HUCPVCs (grey bars) was tested using a chemotaxis assay (FIG. 10A). A significantly higher migration to different doses of rAMF (0.5 and 0.75 μg/mL) was observed for HUCPVCs when compared to BM-MSCs. In spite of different types of MSCs showing similar reduction in migration levels (50% of control) towards HuH7 TCM after the blockage with anti- AMF antibody (data not shown), preincubation of HC-PT-5 TCM with anti-AMF antibody (AMF-ab) resulted in a further reduction in HUCPVCs migration capacity (54% of control) when compared to BM-MSCs (67% of control) (FIG. 10B).

Example 11

Anti-CXCR1, Anti-CXCR2, and Anti-MCP-1 Antibodies Inhibit MSC Migration

Blocking experiments were performed by preincubating TCM-HuH7 or TCM-HC-PT-5 with anti-HGF (10 µg/ml), anti-MCP-1 (10 µg/ml) or isotype control IgG for 1 hour. Similarly, anti-CXCR1 (10 µg/ml), anti-CXCR2 (10 µg/ml), both anti-CXCR1/anti-CXCR2, or isotype control IgG were pre-incubated with MSC for 1 hour. In vitro migration of MSCs towards TCM-HuH7 or TCM-HC-PT-5 were evaluated using the methods described in Example 1.

Antibody inhibition of CXCR1 or CXCR2 decreased MSC migration around 30% and incubation with both anti-CXCR1 and anti-CXCR2 antibodies inhibited migration around 40% (FIG. 11A). Moreover, anti-MCP-1 inhibited MSC migration around 20%, but anti-HGF had no effect on MSC migration towards CM-HuH7 (FIG. 11B).

Example 12

Migration of MSCs Engineered to Express Oncolytic Viruses Expressing Anti-Tumor Genes MSCs will be engineered to express oncolytic virus expressing or not anti-tumor genes (including e.g., an interferon (e.g., interferon α, interferon β), an interleukin (e.g., interleukin 1, interleukin 12), a chemokine (e.g., CX3CL1), or a suicide gene (e.g., thymidine kinase, IL-12, IFN-gamma, TNF-alpha). First, MSCs will be infected in vitro at different MOIs (multiplicity of infection) ranging from 10 to 1000 in complete DMEM without SFB during 2 hours. Then, infected MSCs will be stimulated in culture with rAMF for about 18 h and systemically injected ($5 \times 10^5$) in HCC, colorectal cancer, and/or breast cancer tumor-bearing mice. Tumor growth will be assessed by calliper and tumor volume (mm$^3$) will be calculated using the formula π/6× larger diameter×(smaller diameter)$^2$.

TABLE 1

Factors identified with the RayBio Human Cytokine Antibody Array 5 (Cat# AAH-CYT-5) in the TCM from samples 1 to 4, and their relative levels to positive control. Data are grouped according to the lane presented in the membrane.

| | | RayBio Human Cytokine Antibody Array 5 | | | |
|---|---|---|---|---|---|
| Line | | TCM sample 1 | TCM sample 2 | TCM sample 3 | TCM sample 4 |
| 1 | Pos | 130.3 | 103.7 | 101.9 | 102.7 |
| | Pos | 122.2 | 103.5 | 94.0 | 95.9 |
| | Pos | 124.8 | 96.4 | 91.0 | 102.3 |
| | Pos | 105.0 | 96.4 | 91.1 | 99.1 |
| | Neg | 0.0 | 0.0 | 0.0 | 0.0 |
| | Neg | 0.0 | 0.0 | 0.0 | 0.0 |
| | ENA-78 | 0.3 | 4.2 | 0.6 | 0.0 |
| | GCSF | 0.1 | 0.0 | 0.0 | 0.0 |
| | GM-CSF | 0.0 | 0.0 | 0.0 | 0.0 |
| | Gro | 16.1 | 4.2 | 11.1 | 51.0 |
| | Gro-alpha | 0.0 | 0.0 | 0.0 | 0.0 |
| 2 | I-309 | 0.9 | 13.7 | 3.0 | 0.0 |
| | IL-1alpha | 2.4 | 3.1 | 3.4 | 0.0 |
| | IL-1beta | 4.3 | 3.4 | 5.7 | 0.0 |
| | IL-2 | 3.2 | 5.9 | 3.6 | 2.7 |
| | IL-3 | 12.5 | 4.6 | 17.0 | 5.6 |
| | IL-4 | 0.0 | 11.5 | 0.6 | 0.0 |
| | IL-5 | 0.0 | 1.5 | 0.0 | 0.0 |
| | IL-6 | 17.3 | 66.9 | 74.4 | 0.0 |
| | IL-7 | 0.0 | 0.0 | 0.0 | 0.0 |
| | IL-8 | 261.2 | 129.0 | 117.6 | 83.3 |
| | IL-10 | 0.0 | 0.0 | 0.0 | 0.0 |
| 3 | IL-12 p40p70 | 7.5 | 7.3 | 7.8 | 4.1 |
| | IL-13 | 0.1 | 1.0 | 1.0 | 0.0 |
| | IL-15 | 6.0 | 5.9 | 5.2 | 1.2 |
| | IFN-GAMMA | 12.6 | 7.6 | 7.6 | 4.7 |
| | MCP-1 | 124.2 | 66.0 | 41.0 | 84.2 |
| | MCP-2 | 1.2 | 2.8 | 4.3 | 0.0 |
| | MCP-3 | 0.0 | 1.7 | 0.7 | 0.0 |
| | MCSF | 0.5 | 1.0 | 1.8 | 1.7 |
| | MDC | 0.4 | 0.0 | 0.2 | 0.0 |
| | MIG | 1.5 | 0.0 | 0.1 | 0.0 |
| | MIP-1-beta | 7.8 | 0.0 | 0.1 | 0.0 |
| 4 | MIP-1-delta | 1.6 | 7.0 | 5.4 | 0.0 |
| | RANTES | 9.6 | 11.4 | 8.5 | 3.2 |
| | SCF | 6.3 | 9.2 | 4.3 | 1.4 |
| | SDF-1 | 3.8 | 4.5 | 2.5 | 1.5 |
| | TARC | 17.3 | 16.1 | 10.7 | 3.6 |
| | TGF-beta1 | 5.5 | 6.1 | 4.2 | 2.0 |
| | TNF-alpha | 7.2 | 5.9 | 3.7 | 2.6 |
| | TNF-beta | 4.2 | 2.6 | 2.7 | 2.1 |
| | EGF | 0.9 | 0.5 | 2.4 | 1.5 |
| | IGF-1 | 0.0 | 0.0 | 0.0 | 0.0 |
| | Angiogenin | 22.9 | 28.9 | 42.8 | 0.9 |
| 5 | Oncostatin M | 16.4 | 16.3 | 16.0 | 5.2 |
| | Thrombopoietin | 2.0 | 2.3 | 1.0 | 3.8 |
| | VEGF | 12.1 | 8.0 | 7.2 | 4.6 |
| | PDGF-BB | 13.3 | 8.6 | 6.4 | 2.8 |
| | Leptin | 12.2 | 6.8 | 5.5 | 2.4 |
| | BDFN | 25.0 | 11.9 | 16.1 | 8.0 |
| | BLC | 3.2 | 3.2 | 2.6 | 2.2 |
| | Ck beta 8-1 | 4.3 | 2.7 | 1.6 | 1.7 |
| | Eotaxin | 1.9 | 1.5 | 2.3 | 2.4 |
| | Eotaxin-2 | 0.3 | 0.0 | 0.0 | 0.0 |
| | Eotaxin-3 | 0.0 | 0.0 | 0.0 | 1.1 |
| 6 | FGF-4 | 6.6 | 5.1 | 7.6 | 2.4 |
| | FGF-6 | 10.2 | 7.7 | 5.0 | 1.5 |
| | FGF-7 | 4.4 | 2.6 | 2.7 | 0.8 |
| | FGF-9 | 16.9 | 9.2 | 7.4 | 5.0 |
| | Flt-3 Ligand | 4.2 | 2.2 | 1.3 | 1.5 |
| | Fractalkine | 4.3 | 2.4 | 1.4 | 2.1 |
| | GCP-2 | 2.6 | 2.3 | 0.8 | 1.9 |
| | GDNF | 7.0 | 3.4 | 2.9 | 5.5 |
| | HGF | 0.1 | 0.0 | 74.2 | 0.0 |
| | IGFBP-1 | 6.9 | 0.0 | 71.6 | 0.0 |
| | IGFBP-2 | 5.4 | 0.0 | 25.7 | 10.0 |
| 7 | IGFBP-3 | 7.5 | 7.4 | 9.1 | 2.8 |
| | IGFBP-4 | 3.0 | 1.3 | 1.6 | 0.6 |
| | IL-16 | 11.7 | 12.7 | 9.4 | 1.0 |
| | IP-10 | 27.3 | 11.3 | 1.8 | 5.3 |
| | LIF | 32.4 | 10.6 | 52.6 | 6.8 |
| | LIGHT | 5.0 | 1.3 | 12.6 | 1.5 |
| | MCP-4 | 0.8 | 13.0 | 13.0 | 0.0 |
| | MIF | 45.4 | 0.3 | 0.9 | 29.4 |
| | MIP-3 alpha | 0.0 | 0.0 | 21.0 | 8.6 |
| | NAP-2 | 7.7 | 0.0 | 75.1 | 2.3 |
| | NT-3 | 5.6 | 0.0 | 28.2 | 5.6 |
| 8 | NT-4 | 1.1 | 1.6 | 2.3 | 0.0 |
| | Osteopontin | 12.4 | 11.9 | 41.8 | 3.0 |
| | osteoprotegerin | 8.0 | 3.8 | 9.7 | 0.0 |
| | PARC | 4.3 | 1.2 | 0.5 | 0.0 |
| | PIGF | 0.2 | 0.0 | 0.0 | 0.0 |
| | TGF-beta 2 | 27.2 | 7.7 | 12.7 | 11.2 |

TABLE 1-continued

Factors identified with the RayBio Human Cytokine Antibody Array 5 (Cat# AAH-CYT-5) in the TCM from samples 1 to 4, and their relative levels to positive control. Data are grouped according to the lane presented in the membrane.

RayBio Human Cytokine Antibody Array 5

| Line | TCM sample 1 | TCM sample 2 | TCM sample 3 | TCM sample 4 |
|---|---|---|---|---|
| TGF-beta 3 | 1.6 | 0.0 | 0.3 | 1.8 |
| TIMP-1 | 31.4 | 9.4 | 21.7 | 36.5 |
| TIMP-2 | 0.0 | 0.0 | 8.1 | 16.1 |
| POS | 69.6 | 0.0 | 112.8 | 72.8 |
| POS | 48.3 | 0.0 | 109.3 | 66.3 |

TABLE 2

Factors identified with the RayBio Human Chemokine Antibody array 1 (Cat# AAH-CHE-1) in the TCM from samples 3 and 4, and their relative levels to positive control. Data are presented as the average of the dot and grouped according to the lane presented in the membrane.

RayBio Human Chemokine antibody array 1

| Line | | TCM sample 3 | TCM sample 4 |
|---|---|---|---|
| 1 and 2 Average | POS | 100.01 | 102.48 |
| | POS | 95.86 | 110.67 |
| | NEG | 0.00 | 0.00 |
| | NEG | 0.00 | 0.00 |
| | BCL | 0.00 | 0.00 |
| | CCL28 | 0.00 | 0.00 |
| | Ck beta 8-1 | 0.00 | 0.00 |
| | CTACK | 0.00 | 0.00 |
| | CXCL16 | 0.00 | 0.00 |
| | ENA78 | 0.00 | 0.00 |
| | Eotaxin | 0.00 | 0.00 |
| | Eotaxin-2 | 0.00 | 0.00 |
| 3 and 4 Average | Eotaxin-3 | 3.81 | 0.00 |
| | Fractalkine | 2.65 | 0.00 |
| | GCP-2 | 1.58 | 0.00 |
| | GRO | 139.84 | 107.13 |
| | GRO-alpha | 5.58 | 9.76 |
| | HCC-4 | 0.00 | 0.00 |
| | I-309 | 0.00 | 0.00 |
| | I-TAC | 0.00 | 0.00 |
| | IL-8 | 157.61 | 72.43 |
| | Ip-10 | 5.38 | 3.92 |
| | Lymphotactin | 0.00 | 0.00 |
| | MCP-1 | 6.54 | 30.94 |
| 5 and 6 Average | MCP-2 | 1.04 | 0.00 |
| | MCP-3 | 0.59 | 0.00 |
| | MCP-4 | 0.43 | 0.00 |
| | MDC | 2.13 | 0.00 |
| | MIG | 6.81 | 0.00 |
| | MIP-1alpha | 1.47 | 0.00 |
| | MIP-1beta | 5.16 | 2.41 |
| | MIP-1delta | 2.03 | 0.00 |
| | MIP-3alpha | 2.40 | 8.38 |
| | MIP-3beta | 0.00 | 0.00 |
| | MPIF-1 | 0.00 | 0.00 |
| | NAP-2 | 57.44 | 0.00 |
| 7 and 8 Average | PARC | 0.68 | 0.00 |
| | RANTES | 3.16 | 0.00 |
| | SDF-1 alpha | 1.01 | 0.00 |
| | SDF-1 beta | 0.68 | 0.00 |
| | TARC | 0.00 | 0.00 |
| | TECK | 0.00 | 0.00 |
| | BLANK | 0.00 | 0.00 |
| | BLANK | 0.00 | 0.00 |
| | BLANK | 0.00 | 0.00 |
| | BLANK | 0.00 | 0.00 |
| | POS | 0.00 | 0.00 |
| | POS | 108.86 | 77.72 |

TABLE 3

445 genes differentially expressed in MSC non-exposed in comparison with cells exposed to TCM from sample 1 in comparison with non-exposed cells. The magnitude of the expression change is represented as the logarithm of the fold change.

| | GeneID | Name | Description | PValue | Log2FC |
|---|---|---|---|---|---|
| 1 | 11137 | PWP1 | PWP1 homolog (S. cerevisiae) | 0.004 | −0.409 |
| 2 | 100133941 | CD24 | CD24 molecule | 0.005 | 0.448 |
| 3 | 1968 | EIF2S3 | eukaryotic translation initiation factor 2, subunit 3 gamma, 52 kDa | 0.047 | −0.368 |
| 4 | 386679 | KRTAP10-2 | keratin associated protein 10-2 | 0.016 | −0.519 |
| 5 | 6782 | HSPA13 | heat shock protein 70 kDa family, member 13 | 0.018 | −0.52 |
| 6 | 817 | CAMK2D | calcium/calmodulin-dependent protein kinase II delta | 0.039 | −0.379 |
| 7 | 81626 | SHCBP1L | SHC SH2-domain binding protein 1-like | 0.016 | 0.375 |
| 8 | 51278 | IER5 | immediate early response 5 | <0.001 | 0.873 |
| 9 | 54541 | DDIT4 | DNA-damage-inducible transcript 4 | 0.007 | 0.349 |
| 10 | 2199 | FBLN2 | fibulin 2 | 0.001 | 0.491 |
| 11 | 3488 | IGFBP5 | insulin-like growth factor binding protein 5 | 0.023 | 0.306 |
| 12 | 57104 | PNPLA2 | patatin-like phospholipase domain containing 2 | 0.033 | 0.957 |
| 13 | 10659 | CELF2 | CUG8P, Elav-like family member 2 | 0.004 | 0.538 |
| 14 | 50613 | UBQLN3 | ubiquilin 3 | 0.034 | 0.335 |
| 15 | 6396 | SEC13 | SEC13 homolog (S. cerevisiae) | 0.047 | −0.32 |
| 16 | 8624 | PSMG1 | proteasome (prosome, macropain) assembly chaperone 1 | 0.008 | 0.481 |
| 17 | 51310 | SLC22A17 | solute carrier family 22, member 17 | 0.048 | 0.232 |
| 18 | 5066 | PAM | peptidylglycine alpha-amidating monooxygenase | 0.027 | −0.427 |
| 19 | 10938 | EHD1 | EH-domain containing 1 | 0.021 | 0.427 |
| 20 | 10777 | ARPP21 | cAMP-regulated phosphoprotein, 21 kDa | 0.025 | −0.331 |
| 21 | 51727 | CMPK1 | cytidine monophosphate (UMP-CMP) kinase 1, cytosolic | 0.046 | −0.294 |
| 22 | 56951 | C5orf15 | chromosome 5 open reading frame 15 | 0.026 | 0.305 |
| 23 | 3954 | LETM1 | leucine zipper-EF-hand containing transmembrane protein 1 | 0.007 | −0.363 |
| 24 | 7278 | TUBA3C | tubulin, alpha 3c | 0.007 | 0.323 |

TABLE 3-continued 445 genes differentially expressed in MSC non-exposed in comparison with cells exposed to TCM from sample 1 in comparison with non-exposed cells. The magnitude of the expression change is represented as the logarithm of the fold change.

|    | GeneID | Name | Description | PValue | Log2FC |
|---|---|---|---|---|---|
| 25 | 2574 | GAGE2C | G antigen 2C | 0.001 | 0.546 |
| 26 | 10476 | ATP5H | ATP synthase, H+ transporting, mitochondrial Fo complex, subunit d | 0.025 | −0.361 |
| 27 | 7323 | U8E2D3 | ubiquitin-conjugating enzyme E2D 3 (U8C4/5 homolog, yeast) | 0.037 | 0.289 |
| 28 | 29893 | PSMC3IP | PSMC3 interacting protein | 0.034 | 0.281 |
| 29 | 8404 | SPARCL1 | SPARC-like 1 (hevin) | 0.025 | 0.472 |
| 30 | 55062 | WIPI1 | WD repeat domain, phosphoinositide interacting 1 | 0.03 | −0.391 |
| 31 | 55907 | CMAS | cytidine monophosphate N-acetylneuraminic acid synthetase | 0.048 | 0.317 |
| 32 | 84661 | DPY30 | dpy-30 homolog (C. elegans) | 0.05 | 0.368 |
| 33 | 55000 | TUG1 | taurine unregulated 1 (non-protein coding) | 0.014 | 0.48 |
| 34 | 4809 | NHP2L1 | NHP2 non-histone chromosome protein 2-like 1 (S. cerevisiae) | 0.042 | 0.313 |
| 35 | 1672 | DEFB1 | defensin, beta 1 | 0.004 | 0.53 |
| 36 | 10769 | PLK2 | polo-like kinase 2 | 0.033 | 0.348 |
| 37 | 2191 | FAP | fibroblast activation protein, alpha | 0.009 | −0.403 |
| 38 | 1634 | DCN | decorin | 0.015 | −0.248 |
| 39 | 4779 | NFE2L1 | nuclear factor (erythroid-derived 2)-like 1 | 0.013 | 0.281 |
| 40 | 386677 | KRTAP10-1 | keratin associated protein 10-1 | 0.039 | −0.271 |
| 41 | 1912 | PHC2 | polyhomeotic homolog 2 (Drosophila) | 0.033 | −0.502 |
| 42 | 100271071 | RPS17P10 | ribosomal protein S17 pseudogene 10 | 0.025 | −0.514 |
| 43 | 7184 | HSP90B1 | heat shock protein 90 kDa beta (Grp94), member 1 | 0.039 | 0.348 |
| 44 | 10961 | ERP29 | endoplasmic reticulum protein 29 | 0.022 | 0.365 |
| 45 | 7117 | TMSL3 | thymosin-like 3 | 0.04 | −0.285 |
| 46 | 283131 | NEAT1 | nuclear paraspeckle assembly transcript 1 (non-protein coding) | 0.013 | −0.584 |
| 47 | 467 | ATF3 | activating transcription factor 3 | <0.001 | 1.057 |
| 48 | 51322 | WAC | WW domain containing adaptor with coiled-coil | 0.006 | 0.504 |
| 49 | 54600 | UGT1A9 | UDP glucuronosyltransferase 1 family, polypeptide A9 | 0.042 | 0.313 |
| 50 | 8653 | DDX3Y | DEAD (Asp-Glu-Ala-Asp) box polypeptide 3, Y-linked | 0.015 | −0.589 |
| 51 | 89941 | RHOT2 | ras homolog gene family, member T2 | 0.024 | −0.315 |
| 52 | 64855 | FAM1298 | family with sequence similarity 129, member B | 0.043 | −0.278 |
| 53 | 10135 | NAMPT | nicotinamide phosphoribosyltransferase | 0.029 | −0.493 |
| 54 | 51460 | SFMBT1 | Scm-like with four mbt domains 1 | 0.044 | 0.366 |
| 55 | 8778 | SIGLEC5 | sialic acid binding Ig-like lectin 5 | 0.043 | −0.345 |
| 56 | 200185 | KRTCAP2 | keratinocyte associated protein 2 | 0.017 | −0.294 |
| 57 | 3295 | HSD17B4 | hydroxysteroid (17-beta) dehydrogenase 4 | 0.026 | −0.432 |
| 58 | 58515 | SELK | selenoprotein K | 0.009 | 0.302 |
| 59 | 4097 | MAFG | v-maf musculoaponeurotic fibrosarcoma oncogene homolog G (avian) | 0.022 | 0.281 |
| 60 | 51071 | DERA | deoxyribose- phosphate aldolase (putative) | 0.023 | 0.275 |
| 61 | 11149 | BVES | blood vessel epicardial substance | 0.027 | 0.281 |
| 62 | 10808 | HSPH1 | heat shock 105 kDa/110 kDa protein 1 | <0.001 | 1.029 |
| 63 | 56110 | PCDHGA5 | protocadherin gamma subfamily A, 5 | 0.045 | −0.278 |
| 64 | 4758 | NEU1 | sialidase 1 (lysosomal sialidase) | 0.003 | 0.439 |
| 65 | 4627 | MYH9 | myosin, heavy chain 9, non-muscle | 0.048 | −0.243 |
| 66 | 2323 | FLT3LG | fms-related tyrosine kinase 3 ligand | 0.026 | −0.363 |
| 67 | 23218 | NBEAL2 | neurobeachin-like 2 | 0.007 | −0.276 |
| 68 | 1003 | CDH5 | cadherin 5, type 2 (vascular endothelium) | 0.04 | 0.486 |
| 69 | 9531 | BAG3 | BCL2-associated athanogene 3 | <0.001 | 0.69 |
| 70 | 51726 | DNAJB11 | DnaJ (Hsp40) homolog, subfamily B, member 11 | <0.001 | 0.514 |
| 71 | 8878 | SQSTM1 | sequestosome 1 | 0.047 | 0.241 |
| 72 | 10963 | STIP1 | stress-induced-phosphoprotein 1 | 0.044 | 0.352 |
| 73 | 478 | ATP1A3 | ATPase, Na+/K+ transporting, alpha 3 polypeptide | 0.013 | 0.545 |
| 74 | 338799 | LOC338799 | hypothetical LOC338799 | 0.043 | −0.307 |
| 75 | 5476 | CTSA | cathepsin A | 0.033 | −0.261 |
| 76 | 158056 | MAMDC4 | MAM domain containing 4 | 0.008 | −0.474 |
| 77 | 533 | ATP6V0B | ATPase, H+ transporting, lysosomal 21 kDa, V0 subunit b | 0.05 | 0.31 |
| 78 | 3313 | HSPA9 | heat shock 70 kDa protein 9 (mortalin) | 0.034 | 0.308 |
| 79 | 2578 | GAGE6 | G antigen 6 | 0.038 | 0.389 |
| 80 | 6125 | RPL5 | ribosomal protein L5 | 0.01 | −0.392 |
| 81 | 3336 | HSPE1 | heat shock 10 kDa protein 1 (chaperonin 10) | 0.003 | 0.526 |
| 82 | 80279 | CDKSRAP3 | CDK5 regulatory subunit associated protein 3 | 0.004 | 0.418 |
| 83 | 5707 | PSMD1 | proteasome (prosome, macropain) 26S subunit, non-ATPase, 1 | 0.044 | 0.3 |
| 84 | 57222 | ERGIC1 | endoplasmic reticulum-goigi intermediate compartment (ERGIC) 1 | 0.036 | −0.321 |
| 85 | 8566 | PDXK | pyridoxal (pyridoxine, vitamin B6) kinase | 0.003 | 0.441 |
| 86 | 3703 | STT3A | STT3, subunit of the oligosaccharyltransferase complex, homolog A (S. cerevisiae) | 0.037 | −0.283 |
| 87 | 4884 | NPTX1 | neuronal pentraxin I | 0.041 | 0.393 |
| 88 | 5573 | PRKAR1A | protein kinase, cAMP-dependent, regulatory, type I, alpha (tissue specific extinguisher 1) | 0.009 | −0.612 |
| 89 | 3397 | ID1 | Inhibitor of DNA binding 1, dominant negative helix-loop-helix protein | 0.032 | 0.236 |
| 90 | 57677 | ZFP14 | zinc finger protein 14 homolog (mouse) | 0.047 | 0.334 |
| 91 | 53826 | FXYD6 | FXYD domain containing ion transport regulator 6 | 0.035 | 0.282 |
| 92 | 1164 | CKS2 | CDC28 protein kinase regulatory subunit 2 | <0.001 | 0.454 |
| 93 | 7120 | TMSL6 | thymosin-like 6 (pseudogene) | 0.034 | −0.312 |
| 94 | 4673 | NAP1L1 | nucleosome assembly protein 1-like 1 | 0.01 | 0.342 |

TABLE 3-continued 445 genes differentially expressed in MSC non-exposed in comparison with
cells exposed to TCM from sample 1 in comparison with non-exposed cells. The
magnitude of the expression change is represented as the logarithm of the fold change.

|     | GeneID | Name | Description | PValue | Log2FC |
|-----|--------|------|-------------|--------|--------|
| 95  | 23621  | BACE1 | beta-site APP-cleaving enzyme 1 | 0.005 | −0.416 |
| 96  | 8424   | BBOX1 | butyrobetaine (gamma), 2-oxoglutarate dioxygenase (gamma-butyrobetaine hydroxylase) 1 | 0.04 | 0.365 |
| 97  | 56944  | OLFML3 | olfactomedin-like 3 | 0.003 | −0.338 |
| 98  | 51081  | MRPS7 | mitochondrial ribosomal protein S7 | 0.007 | 0.304 |
| 99  | 665    | BNIP3L | BCL2/adenovirus E1B 19 kDa interacting protein 3-like | 0.025 | −0.295 |
| 100 | 3032   | HADHB | hydroxyacyl-CoA dehydrogenase/3-ketoacyl-CoA thiolase/enoyl-CoA hydratase (trifunctional protein), beta subunit | 0.012 | −0.313 |
| 101 | 3301   | DNAJA1 | DnaJ (Hsp40) homolog, subfamily A, member 1 | <0.001 | 0.624 |
| 102 | 9315   | C5orf13 | chromosome 5 open reading frame 13 | 0.013 | −0.266 |
| 103 | 468    | ATF4 | activating transcription factor 4 (tax-responsive enhancer element B67) | 0.009 | 0.29 |
| 104 | 91624  | NEXN | nexilin (F actin binding protein) | 0.048 | 0.243 |
| 105 | 5358   | PLS3 | plastin 3 | 0.015 | −0.448 |
| 106 | 23603  | CORO1C | coronin, actin binding protein, 1C | 0.03 | −0.306 |
| 107 | 813    | CALU | calumenin | 0.017 | −0.457 |
| 108 | 6046   | BRD2 | bromodomain containing 2 | 0.022 | 0.336 |
| 109 | 25879  | DCAF13 | DDB1 and CUL4 associated factor 13 | 0.05 | 0.394 |
| 110 | 6390   | SDHB | succinate dehydrogenase complex, subunit B, iron sulfur (Ip) | 0.001 | 0.414 |
| 111 | 26528  | DAZAP1 | DAZ associated protein 1 | 0.032 | 0.376 |
| 112 | 54504  | CPVL | carboxypeptidase, vitellogenic-like | 0.016 | 0.344 |
| 113 | 7058   | THBS2 | thrombospondin 2 | 0.026 | −0.325 |
| 114 | 2131   | EXT1 | exostosin 1 | 0.007 | −0.444 |
| 115 | 65055  | REEP1 | receptor accessory protein 1 | 0.012 | 0.371 |
| 116 | 90701  | SEC11C | SEC11 homolog C (*S. cerevisiae*) | 0.018 | 0.407 |
| 117 | 71     | ACTG1 | actin, gamma 1 | 0.022 | −0.296 |
| 118 | 84681  | HINT2 | histidine triad nucleotide binding protein 2 | 0.013 | 0.382 |
| 119 | 79048  | SECISBP2 | SECIS binding protein 2 | 0.017 | −0.332 |
| 120 | 231    | AKR1B1 | aldo-keto reductase family 1, member B1 (aldose reductase) | 0.027 | −0.268 |
| 121 | 501    | ALDH7A1 | aldehyde dehydrogenase 7 family, member A1 | 0.007 | −0.424 |
| 122 | 84545  | MRPL43 | mitochondrial ribosomal protein L43 | 0.007 | −0.509 |
| 123 | 4358   | MPV17 | MpV17 mitochondrial inner membrane protein | 0.015 | −0.355 |
| 124 | 103    | ADAR | adenosine deaminase, RNA-specific | 0.035 | 0.344 |
| 125 | 961    | CD47 | CD47 molecule | 0.024 | −0.518 |
| 126 | 54881  | TEX10 | testis expressed 10 | 0.023 | −0.339 |
| 127 | 7072   | TIA1 | TIA1 cytotoxic granule-associated RNA binding protein | 0.025 | −0.482 |
| 128 | 11217  | AKAP2 | A kinase (PRKA) anchor protein 2 | 0.041 | −0.275 |
| 129 | 5431   | POLR2B | polymerase (RNA) II (DNA directed) polypeptide B, 140 kDa | 0.038 | −0.26 |
| 130 | 84817  | TXNDC17 | thioredoxin domain containing 17 | 0.012 | 0.396 |
| 131 | 8829   | NRP1 | neuropilin 1 | 0.015 | −0.389 |
| 132 | 79096  | C11orf49 | chromosome 11 open reading frame 49 | 0.046 | −0.331 |
| 133 | 1164   | CKS2 | CDC28 protein kinase regulatory subunit 2 | <0.001 | 0.363 |
| 134 | 10146  | G3BP1 | GTPase activating protein (SH3 domain) binding protein 1 | 0.033 | 0.315 |
| 135 | 5690   | PSMB2 | proteasome (prosome, macropain) subunit, beta type, 2 | 0.047 | −0.233 |
| 136 | 81688  | C6orf62 | chromosome 6 open reading frame 62 | 0.001 | 0.359 |
| 137 | 54658  | UGT1A1 | UDP glucuronosyltransferase 1 family, polypeptide A1 | 0.049 | 0.257 |
| 138 | 65009  | NDRG4 | NDRG family member 4 | 0.043 | 0.241 |
| 139 | 387707 | CC2D2B | coiled-coil and C2 domain containing 2B | 0.037 | 0.287 |
| 140 | 54840  | APTX | aprataxin | 0.025 | 0.339 |
| 141 | 29995  | LMCD1 | LIM and cysteine-rich domains 1 | 0.049 | −0.406 |
| 142 | 9354   | UBE4A | ubiquitination factor E4A (UFD2 homolog, yeast) | 0.036 | −0.379 |
| 143 | 1435   | CSF1 | colony stimulating factor 1 (macrophage) | 0.011 | −0.445 |
| 144 | 390714 | LOC390714 | similar to Ig heavy chain V-III region VH26 precursor | 0.02 | −0.272 |
| 145 | 3337   | DNAJB1 | DnaJ (Hsp40) homolog, subfamily B, member 1 | <0.001 | 0.442 |
| 146 | 51023  | MRPS18C | mitochondrial ribosomal protein S18C | 0.03 | 0.3 |
| 147 | 2171   | FABP5 | fatty acid binding protein 5 (psoriasis-associated) | 0.006 | 0.369 |
| 148 | 653450 | FAM21D | family with sequence similarity 21, member D | 0.044 | 0.261 |
| 149 | 4054   | LTBP3 | latent transforming growth factor beta binding protein 3 | 0.017 | −0.863 |
| 150 | 2619   | GAS1 | growth arrest-specific 1 | <0.001 | −0.547 |
| 151 | 25     | ABL1 | c-abl oncogene 1, non-receptor tyrosine kinase | 0.023 | −0.261 |
| 152 | 51655  | RASD1 | RAS, dexamethasone-induced 1 | 0.027 | −0.319 |
| 153 | 83955  | NACAP1 | nascent-polypeptide-associated complex alpha polypeptide pseudogene 1 | 0.034 | −0.35 |
| 154 | 9689   | BZW1 | basic leucine zipper and W2 domains 1 | 0.017 | −0.277 |
| 155 | 900    | CCNG1 | cyclin G1 | 0.012 | −0.317 |
| 156 | 387763 | C11orf96 | chromosome 11 open reading frame 96 | <0.001 | 0.589 |
| 157 | 7955   | STL | six-twelve leukemia | 0.031 | 0.629 |
| 158 | 7873   | MANF | mesencephalic astrocyte-derived neurotrophic factor | 0.004 | 0.417 |
| 159 | 51714  | SELT | selenoprotein T | 0.027 | 0.25 |
| 160 | 3476   | IGBP1 | immunoglobulin (CD79A) binding protein 1 | 0.005 | −0.397 |
| 161 | 10370  | CITED2 | Cbp/p300-interacting transactivator, with Glu/Asp-rich carboxy-terminal domain, 2 | 0.048 | −0.328 |
| 162 | 84886  | C1orf198 | chromosome 1 open reading frame 198 | 0.003 | −0.395 |
| 163 | 1490   | CTGF | connective tissue growth factor | 0.01 | −0.395 |

TABLE 3-continued 445 genes differentially expressed in MSC non-exposed in comparison with cells exposed to TCM from sample 1 in comparison with non-exposed cells. The magnitude of the expression change is represented as the logarithm of the fold change.

| | GeneID | Name | Description | PValue | Log2FC |
|---|---|---|---|---|---|
| 164 | 6734 | SRPR | signal recognition particle receptor (docking protein) | 0.035 | −0.238 |
| 165 | 79594 | MUL1 | mitochondral E3 ubiquitin protein ligase 1 | 0.022 | 0.434 |
| 166 | 9181 | ARHGEF2 | Rho/Rac guanine nucleotide exchange factor (GEF) 2 | 0.018 | 0.27 |
| 167 | 55695 | NSUN5 | NOP2/Sun domain family, member 5 | 0.023 | 0.268 |
| 168 | 5937 | RBMS1 | RNA binding motif, single stranded interacting protein 1 | 0.001 | −0.447 |
| 169 | 3312 | HSPA8 | heat shock 70 kDa protein 8 | 0.007 | 0.316 |
| 170 | 127933 | UHMK1 | U2AF homology motif (UHM) kinase 1 | 0.037 | −0.251 |
| 171 | 25978 | CHMP2B | chromatin modifying protein 2B | 0.035 | −0.356 |
| 172 | 8553 | BHLHE40 | basic helix-loop-helix family, member e40 | <0.001 | 0.629 |
| 173 | 79770 | TXNDC15 | thioredoxin domain containing 15 | 0.048 | −0.302 |
| 174 | 10079 | ATP9A | ATPase, class II, type 9A | 0.039 | −0.277 |
| 175 | 5045 | FURIN | furin (paired basic amino acid cleaving enzyme) | 0.019 | −0.398 |
| 176 | 267 | AMFR | autocrine motility factor receptor | 0.024 | −0.316 |
| 177 | 3827 | KNG1 | kininogen 1 | 0.016 | −0.464 |
| 178 | 5682 | PSMA1 | proteasome (prosome, macropain) subunit, alpha type, 1 | 0.047 | −0.213 |
| 179 | 57449 | PLEKHG5 | pleckstrin homology domain containing, family G (with RhoGef domain) member 5 | 0.025 | −0.255 |
| 180 | 441204 | LOC441204 | hypothetical locus LOC441204 | 0.024 | −0.464 |
| 181 | 23654 | PLXNB2 | plexin B2 | 0.022 | −0.289 |
| 182 | 2745 | GLRX | glutaredoxin (thioltransferase) | 0.009 | 0.352 |
| 183 | 2939 | GSTA2 | glutathione S-transferase alpha 2 | 0.006 | 0.493 |
| 184 | 29968 | PSAT1 | phosphoserine aminotransferase 1 | 0.014 | 0.42 |
| 185 | 151579 | BZW1P2 | basic leucine zipper and W2 domains 1 pseudogene 2 | <0.001 | −0.517 |
| 186 | 11079 | RER1 | RER1 retention in endoplasmic reticulum 1 homolog (S. cerevisiae) | 0.044 | −0.247 |
| 187 | 115207 | KCTD12 | potassium channel tetramerisation domain containing 12 | <0.001 | −0.632 |
| 188 | 283711 | LOC283711 | ubiquitin-conjugating enzyme E2C pseudogene | 0.041 | 0.323 |
| 189 | 3225 | HOXC9 | homeobox C9 | 0.05 | 0.333 |
| 190 | 1348 | COX7A2P2 | cytochrome c oxidase subunit VIIa polypeptide 2 (liver) pseudogene 2 | 0.044 | 0.277 |
| 191 | 442454 | LOC442454 | ubiquinol-cytochrome c reductase binding protein pseudogene | 0.028 | −0.389 |
| 192 | 4553 | TRNA | tRNA | <0.001 | 0.882 |
| 193 | 55002 | TMCO3 | transmembrane and coiled-coil domains 3 | 0.005 | −0.34 |
| 194 | 4853 | NOTCH2 | notch 2 | 0.031 | −0.294 |
| 195 | 10133 | OPTN | optineurin | 0.028 | 0.224 |
| 196 | 51533 | PHF7 | PHD finger protein 7 | 0.024 | 0.263 |
| 197 | 3322 | HSP90AA3P | heat shock protein 90 kDa alpha (cytosolic), class A member 3 (pseudogene) | 0.002 | 0.481 |
| 198 | 345645 | LOC345645 | proteasome (prosome, macropain) 26S subunit, ATPase, 1 pseudogene | 0.034 | 0.319 |
| 199 | 5934 | RBL2 | retinoblastoma-like 2 (p130) | 0.025 | −0.372 |
| 200 | 29080 | CCDC59 | coiled-coil domain containing 59 | 0.011 | 0.464 |
| 201 | 3032 | HADHB | hydroxyacyl-CoA dehydrogenase/3-ketoacyl-CoA thiolase/enoyl-CoA hydratase (trifunctional protein), beta subunit | 0.038 | −0.211 |
| 202 | 51339 | DACT1 | dapper, antagonist of beta-catenin, homolog 1 (Xenopus laevis) | 0.011 | −0.4 |
| 203 | 5550 | PREP | prolyl endopeptidase | <0.001 | −0.499 |
| 204 | 2581 | GALC | galactosylceramidase | 0.02 | −0.59 |
| 205 | 4311 | MME | membrane metallo-endopeptidase | 0.009 | −0.337 |
| 206 | 28970 | C11orf54 | chromosome 11 open reading frame 54 | 0.012 | 0.398 |
| 207 | 196500 | C12orf53 | chromosome 12 open reading frame 53 | 0.024 | −0.482 |
| 208 | 51191 | HERC5 | hect domain and RLD 5 | 0.004 | 0.472 |
| 209 | 84270 | C9orf89 | chromosome 9 open reading frame 39 | 0.018 | −0.268 |
| 210 | 9672 | SDC3 | syndecan 3 | 0.023 | 0.239 |
| 211 | 84445 | LZTS2 | leucine zipper, putative tumor suppressor 2 | 0.031 | 0.256 |
| 212 | 1528 | CYB5A | cytochrome b5 type A (microsomal) | 0.011 | 0.443 |
| 213 | 7316 | UBC | ubiquitin C | <0.001 | 0.512 |
| 214 | 10576 | CCT2 | chaperonin containing TCP1, subunit 2 (beta) | 0.037 | 0.397 |
| 215 | 401967 | N8PF17P | neuroblastoma breakpoint family, member 17 (pseudogene) | 0.034 | 0.347 |
| 216 | 441198 | LOC441198 | similar to Heat shock cognate 71 kDa protein | 0.031 | 0.284 |
| 217 | 29982 | NRBF2 | nuclear receptor binding factor 2 | 0.003 | 0.317 |
| 218 | 9082 | XKRY | XK, Kell blood group complex subunit-related, Y-linked | 0.038 | 0.276 |
| 219 | 3856 | KRT8 | keratin 8 | 0.033 | 0.28 |
| 220 | 349114 | NCRNA00265 | non-protein coding RNA 265 | 0.031 | 0.331 |
| 221 | 10961 | ERP29 | endoplasmic reticulum protein 29 | 0.019 | 0.334 |
| 222 | 1305 | COL13A1 | collagen, type XIII, alpha 1 | 0.007 | 0.365 |
| 223 | 3304 | HSPA1B | heat shock 70 kDa protein 1B | <0.001 | 0.816 |
| 224 | 80255 | SLC35F5 | solute carrier family 35 member F5 | 0.039 | −0.307 |
| 225 | 84791 | C1orf97 | chromosome 1 open reading frame 97 | 0.013 | 0.345 |
| 226 | 91012 | LASS5 | LAG1 homolog, ceramide synthase 5 | 0.034 | −0.327 |
| 227 | 124446 | TMEM219 | transmembrane protein 219 | 0.027 | 0.27 |
| 228 | 63908 | NAPB | N-ethylmaleimide-sensitive factor attachment protein, beta | 0.013 | 0.328 |
| 229 | 6590 | SLPI | secretory leukocyte peptidase inhibitor | 0.026 | 0.261 |
| 230 | 144110 | TMEM86A | transmembrane protein 86A | 0.018 | 0.375 |
| 231 | 9326 | ZNHIT3 | zinc finger, HIT-type containing 3 | 0.046 | −0.276 |
| 232 | 9719 | ADAMTSL2 | ADAMTS-like 2 | 0.039 | 0.306 |

TABLE 3-continued 445 genes differentially expressed in MSC non-exposed in comparison with cells exposed to TCM from sample 1 in comparison with non-exposed cells. The magnitude of the expression change is represented as the logarithm of the fold change.

| | GeneID | Name | Description | PValue | Log2FC |
|---|---|---|---|---|---|
| 233 | 84866 | TMEM25 | transmembrane protein 25 | <0.001 | −0.5 |
| 234 | 340198 | IFITM4P | interferon induced transmembrane protein 4 pseudogene | 0.043 | 0.351 |
| 235 | 253832 | ZDHHC20 | zinc finger, DHHC-type containing 20 | 0.038 | −0.328 |
| 236 | 284672 | LOC284672 | prostaglandin E synthase 3 (cytosolic) pseudogene | 0.009 | 0.303 |
| 237 | 376497 | SLC27A1 | solute carrier family 27 (fatty acid transporter), member 1 | 0.002 | −0.5 |
| 238 | 51510 | CHMP5 | chromatin modifying protein 5 | 0.004 | 0.335 |
| 239 | 4282 | MIF | macrophage migration inhibitory factor (glycosylation-inhibiting factor) | 0.035 | −0.203 |
| 240 | 65110 | UPF3A | UPF3 regulator of nonsense transcripts homolog A (yeast) | 0.031 | 0.381 |
| 241 | 83999 | KREMEN1 | kringle containing transmembrane protein 1 | 0.049 | 0.263 |
| 242 | 5412 | UBL3 | ubiquitin-like 3 | 0.038 | −0.323 |
| 243 | 391356 | C2orf79 | chromosome 2 open reading frame 79 | 0.049 | 0.229 |
| 244 | 6890 | TAP1 | transporter 1, ATP-binding cassette, sub-family B (MDR/TAP) | 0.005 | 0.318 |
| 245 | 388581 | FAM132A | family with sequence similarity 132, member A | 0.009 | 0.364 |
| 246 | 22936 | ELL2 | elongation factor, RNA polymerase II, 2 | 0.002 | −0.411 |
| 247 | 55138 | FAM90A1 | family with sequence similarity 90, member A1 | 0.03 | 0.313 |
| 248 | 10252 | SPRY1 | sprouty homolog 1, antagonist of FGF signaling (Drosophila) | 0.007 | −0.439 |
| 249 | 1827 | RCAN1 | regulator of calcineurin 1 | <0.001 | −0.69 |
| 250 | 345757 | FAM174A | family with sequence similarity 174, member A | 0.026 | −0.257 |
| 251 | 3434 | IFIT1 | interferon-induced protein with tetratricopeptide repeats 1 | <0.001 | 0.471 |
| 252 | 26160 | IFT172 | intraflagellar transport 172 homolog (Chlamydomonas) | 0.018 | 0.299 |
| 253 | 51019 | CCDC53 | coiled-coil domain containing 53 | 0.032 | 0.314 |
| 254 | 1845 | DUSP3 | dual specificity phosphatase 3 | 0.015 | 0.375 |
| 255 | 51569 | UFM1 | ubiquitin-fold modifier 1 | 0.034 | 0.478 |
| 256 | 400 | ARL1 | ADP-ribosylation factor-like 1 | 0.032 | −0.499 |
| 257 | 7177 | TPSAB1 | tryptase alpha/beta 1 | 0.042 | 0.244 |
| 258 | 1213 | CLTC | clathrin, heavy chain (Hc) | 0.034 | 0.291 |
| 259 | 283070 | LOC283070 | hypothetical LOC283070 | 0.032 | 0.339 |
| 260 | 5217 | PFN2 | profilin 2 | 0.016 | −0.266 |
| 261 | 55818 | KDM3A | lysine (K)-specific demethylase 3A | 0.003 | 0.44 |
| 262 | 51652 | VPS24 | vacuolar protein sorting 24 homolog (S. cerevisiae) | 0.007 | 0.347 |
| 263 | 994 | CDC25B | cell division cycle 25 homolog B (S. pombe) | 0.006 | 0.456 |
| 264 | 4170 | MCL1 | myeloid cell leukemia sequence 1 (BCL2-related) | 0.001 | 0.417 |
| 265 | 1593 | CYP27A1 | cytochrome P450, family 27, subfamily A, polypeptide 1 | 0.042 | −0.312 |
| 266 | 10123 | ARL4C | ADP-ribosylation factor-like 4C | 0.003 | 0.437 |
| 267 | 83658 | DYNLRB1 | dynein, light chain, roadblock-type 1 | 0.035 | −0.318 |
| 268 | 516 | ATP5G1 | ATP synthase, H+ transporting, mitochondrial Fo complex, subunit C1 (subunit 9) | 0.012 | −0.396 |
| 269 | 3324 | HSP90AA2 | heat shock protein 90 kDa alpha (cytosolic), class A member 2 | <0.001 | 0.608 |
| 270 | 57092 | PCNP | PEST proteolytic signal containing nuclear protein | 0.006 | −0.394 |
| 271 | 4499 | MT1M | metallothionein 1M | 0.013 | 0.349 |
| 272 | 2745 | GLRX | glutaredoxin (thioltransferase) | <0.001 | 0.783 |
| 273 | 23559 | WBP1 | WW domain binding protein 1 | 0.032 | −0.261 |
| 274 | 4048 | LTA4H | leukotriene A4 hydrolase | 0.046 | −0.344 |
| 275 | 23210 | JMJD6 | jumonji domain containing 6 | 0.017 | −0.272 |
| 276 | 5578 | PRKCA | protein kinase C, alpha | 0.032 | −0.384 |
| 277 | 54538 | ROBO4 | roundabout homolog 4, magic roundabout (Drosophila) | 0.035 | 0.371 |
| 278 | 260436 | C4orf7 | chromosome 4 open reading frame 7 | 0.01 | 0.437 |
| 279 | 7280 | TUBB2A | tubulin, beta 2A | 0.018 | 0.313 |
| 280 | 286157 | PCBP2P2 | poly(rC) binding protein 2 pseudogene 2 | 0.023 | −0.224 |
| 281 | 4499 | MT1M | metallothionein 1M | <0.001 | 0.415 |
| 282 | 284861 | LOC284861 | hypothetical LOC284861 | 0.044 | 0.439 |
| 283 | 10159 | ATP6AP2 | ATPase, H+ transporting, lysosomail accessory protein 2 | 0.032 | −0.376 |
| 284 | 8522 | GAS7 | growth arrest-specific 7 | 0.026 | −0.272 |
| 285 | 3930 | LBR | lamin B receptor | 0.034 | 0.388 |
| 286 | 51645 | PPIL1 | peptidylprolyl isomerase (cyclophilin)-like 1 | 0.04 | 0.309 |
| 287 | 23174 | ZCCHC14 | zinc finger, CCHC domain containing 14 | 0.006 | 0.396 |
| 288 | 23451 | SF3B1 | splicing factor 3b, subunit 1, 155 kDa | 0.029 | −0.245 |
| 289 | 604 | BCL6 | B-cell CLL/lymphoma 6 | 0.023 | −0.452 |
| 290 | 8537 | BCAS1 | breast carcinoma amplified sequence 1 | 0.015 | 0.337 |
| 291 | 5522 | PPP2R2C | protein phosphatase 2, regulatory subunit B, gamma | 0.01 | 0.306 |
| 292 | 4567 | TRNL1 | tRNA | 0.014 | 0.375 |
| 293 | 1073 | CFL2 | cofilin 2 (muscle) | 0.015 | −0.357 |
| 294 | 30001 | ERO1L | ERO1-like (S. cerevisiae) | 0.021 | 0.459 |
| 295 | 115207 | KCTD12 | potassium channel tetramerisation domain containing 12 | 0.01 | −0.527 |
| 296 | 201595 | STT3B | STT3, subunit of the oligosaccharyltransferase complex, homolog B (S. cerevisiae) | 0.04 | 0.325 |
| 297 | 3303 | HSPA1A | heat shock 70 kDa protein 1A | <0.001 | 1.471 |
| 298 | 4314 | MMP3 | matrix metallopeptidase 3 (stromelysin 1, progelatinase) | 0.013 | 0.48 |
| 299 | 10628 | TXNIP | thioredoxin interacting protein | <0.001 | −0.817 |
| 300 | 2137 | EXTL3 | exostoses (multiple)-like 3 | 0.028 | 0.335 |
| 301 | 9636 | ISG15 | ISG15 ubiquitin-like modifier | 0.001 | 1.023 |
| 302 | 7207 | TRNAL1 | transfer RNA leucine 1 (anticodon AAG) | 0.005 | 0.371 |
| 303 | 2876 | GPX1 | glutathione peroxidase 1 | 0.029 | −0.232 |

TABLE 3-continued 445 genes differentially expressed in MSC non-exposed in comparison with
cells exposed to TCM from sample 1 in comparison with non-exposed cells. The
magnitude of the expression change is represented as the logarithm of the fold change.

| | GeneID | Name | Description | PValue | Log2FC |
|---|---|---|---|---|---|
| 304 | 9709 | HERPUD1 | homocysteine-inducible, endoplasmic reticulum stress-inducible, ubiquitin-like domain member 1 | <0.001 | 0.58 |
| 305 | 56034 | PDGFC | platelet derived growth factor C | 0.049 | −0.241 |
| 306 | 123811 | FOPNL | FGFR1OP N-terminal like | 0.022 | −0.291 |
| 307 | 55827 | DCAF6 | DDB1 and CUL4 associated factor 6 | 0.021 | 0.301 |
| 308 | 81894 | SLC25A28 | solute carrier family 25, member 28 | 0.002 | 0.336 |
| 309 | 5654 | HTRA1 | HtrA serine peptidase 1 | 0.028 | −0.478 |
| 310 | 6652 | SORD | sorbitol dehydrogenase | 0.047 | 0.321 |
| 311 | 402562 | HNRNPA1P8 | heterogeneous nuclear ribonucleoprotein A1 pseudogene 8 | 0.017 | −0.324 |
| 312 | 6428 | SRSF3 | serine/arginine-rich splicing factor 3 | <0.001 | 0.468 |
| 313 | 55920 | RCC2 | regulator of chromosome condensation 2 | 0.01 | 0.322 |
| 314 | 79600 | TCTN1 | tectonic family member 1 | 0.026 | 0.306 |
| 315 | 433 | ASGR2 | asialoglycoprotein receptor 2 | 0.015 | 0.306 |
| 316 | 9510 | ADAMTS1 | ADAM metallopeptidase with thrombospondin type 1 motif, 1 | 0.002 | −0.542 |
| 317 | 7754 | ANF204P | zinc finger protein 204, pseudogene | 0.02 | 0.314 |
| 318 | 11098 | PRSS23 | protease, serine, 23 | 0.019 | 0.333 |
| 319 | 79174 | CRELD2 | cysteine-rich with EGF-like domains 2 | 0.004 | 0.496 |
| 320 | 7453 | WARS | tryptophanyl-tRNA synthetase | 0.024 | 0.396 |
| 321 | 51660 | BRP44L | brain protein 44-like | 0.014 | 0.393 |
| 322 | 7307 | U2AF1 | U2 small nuclear RNA auxiliary factor 1 | 0.038 | 0.245 |
| 323 | 7358 | UGDH | UDP-glucose 6-dehydrogenase | 0.02 | 0.373 |
| 324 | 2743 | GLRB | glycine receptor, beta | 0.03 | 0.272 |
| 325 | 7180 | CRISP2 | cysteine-rich secretory protein 2 | 0.009 | 0.445 |
| 326 | 9728 | SECISBP2L | SECIS binding protein 2-like | 0.047 | −0.284 |
| 327 | 9467 | SH3BP5 | SH3-domain binding protein 5 (BTK-associated) | 0.006 | 0.394 |
| 328 | 9246 | UBE2L6 | ubiquitin-conjugating enzyme E2L 6 | <0.001 | 0.561 |
| 329 | 6236 | RRAD | Ras-related associated with diabetes | <0.001 | 0.756 |
| 330 | 114822 | RHPN1 | rhophilin, Rho GTPase binding protein 1 | 0.01 | −0.268 |
| 331 | 55752 | sep-11 | septin 11 | 0.028 | 0.419 |
| 332 | 91614 | DEPDC7 | DEP domain containing 7 | 0.041 | −0.251 |
| 333 | 3207 | HOXA11 | homeobox A11 | 0.009 | 0.66 |
| 334 | 116254 | C6orf72 | chromosome 6 open reading frame 72 | 0.006 | −0.306 |
| 335 | 51187 | RSL24D1 | ribosomal L24 domain containing 1 | 0.042 | −0.253 |
| 336 | 10728 | PTGES3 | prostaglandin E synthase 3 (cytosolic) | 0.012 | 0.279 |
| 337 | 284361 | C19orf63 | chromosome 19 open reading frame 63 | 0.043 | 0.271 |
| 338 | 143689 | PIWIL4 | piwi-like 4 (*Drosophila*) | 0.001 | 0.525 |
| 339 | 85363 | TRIM5 | tripartite motif containing 5 | 0.005 | 0.373 |
| 340 | 9520 | NPEPPS | aminopeptidase puromycin sensitive | 0.005 | −0.352 |
| 341 | 29880 | ALG5 | asparagine linked glycosylation 5, dolichyl-phosphate beta-glucosyltransferase homolog (*S. cerevisiae*) | 0.033 | 0.235 |
| 342 | 55937 | APOM | apolipoprotein M | 0.022 | 0.321 |
| 343 | 54206 | ERRFI1 | ERB8 receptor feedback inhibitor 1 | 0.016 | −1.044 |
| 344 | 283131 | NEAT1 | nuclear paraspeckle assembly transcript 1 (non-protein coding) | <0.001 | −0.528 |
| 345 | 5202 | PFDN2 | prefoldin subunit 2 | 0.04 | −0.285 |
| 346 | 123 | PLIN2 | perilipin 2 | 0.016 | 0.43 |
| 347 | 81689 | ISCA1 | iron-sulfur cluster assembly 1 homolog (*S. cerevisiae*) | 0.034 | 0.305 |
| 348 | 6129 | RPL7 | ribosomal protein L7 | 0.047 | −0.2 |
| 349 | 79370 | BCL2L14 | BCL2-like 14 (apoptosis facilitator) | 0.042 | 0.25 |
| 350 | 7052 | TGM2 | transglutaminase 2 (C polypeptide, protein-glutamine-gamma-glutamyltransferase) | 0.038 | −0.264 |
| 351 | 2332 | FMR1 | fragile X mental retardation 1 | 0.002 | 0.518 |
| 352 | 23066 | CAND2 | cullin-associated and neddylation-dissociated 2 (putative) | 0.031 | −0.404 |
| 353 | 4085 | MAD2L1 | MAD2 mitotic arrest deficient-like 1 (yeast) | 0.009 | −0.348 |
| 354 | 161 | AP2A2 | adaptor-related protein complex 2, alpha 2 subunit | 0.032 | 0.374 |
| 355 | 5265 | SERPINA1 | serpin peptidase inhibitor, clade A (alpha-1 antiproteinase, antitrypsin), member 1 | 0.041 | −0.219 |
| 356 | 388401 | RPL7P48 | ribosomal protein L7 pseudogene 48 | 0.016 | −0.513 |
| 357 | 51764 | GNG13 | guanine nucleotide binding protein (G protein), gamma 13 | 0.047 | 0.451 |
| 358 | 6720 | SREBF1 | sterol regulatory element binding transcription factor 1 | 0.015 | 0.424 |
| 359 | 610 | HCN2 | hyperpolarization activated cyclic nucleotide-gated potassium channel 2 | 0.017 | 0.262 |
| 360 | 5721 | PSME2 | proteasome (prosome, macropain) activator subunit 2 (PA28 beta) | 0.005 | 0.774 |
| 361 | 55140 | ELP3 | elongation protein 3 homolog (*S. cerevisiae*) | 0.002 | 0.596 |
| 362 | 55754 | TMEM30A | transmembrane protein 30A | 0.023 | −0.304 |
| 363 | 1938 | EEF2 | eukaryotic translation elongation factor 2 | 0.045 | −0.253 |
| 364 | 3843 | IPO5 | importin 5 | 0.023 | −0.315 |
| 365 | 55967 | NDUFA12 | NADH dehydrogenase (ubiquinone) 1 alpha subcomplex, 12 | 0.039 | −0.409 |
| 366 | 51136 | RNFT1 | ring finger protein, transmembrane 1 | 0.018 | 0.351 |
| 367 | 95 | ACY1 | aminoacylase 1 | 0.032 | 0.223 |
| 368 | 3312 | HSPA8 | heat shock 70 kDa protein 8 | 0.007 | 0.277 |
| 369 | 768211 | RELL1 | RELT-like 1 | 0.025 | −0.304 |
| 370 | 492 | ATP2B3 | ATPase, Ca++ transporting, plasma membrane 3 | 0.042 | 0.251 |
| 371 | 5507 | PPP1R3C | protein phosphatase 1, regulatory (inhibitor) subunit 3C | 0.022 | 0.445 |
| 372 | 11189 | CELF3 | CUGBP, Elav-like family member 3 | 0.007 | 0.42 |

TABLE 3-continued 445 genes differentially expressed in MSC non-exposed in comparison with cells exposed to TCM from sample 1 in comparison with non-exposed cells. The magnitude of the expression change is represented as the logarithm of the fold change.

| | GeneID | Name | Description | PValue | Log2FC |
|---|---|---|---|---|---|
| 373 | 55177 | FAM82A2 | family with sequence similarity 82, member 62 | 0.028 | 0.382 |
| 374 | 64773 | EAM113A | family with sequence similarity 113, member A | 0.046 | −0.234 |
| 375 | 23612 | PHLDA3 | pleckstrin homology-like domain, family A, member 3 | 0.032 | 0.292 |
| 376 | 9704 | DHX34 | DEAH (Asp-Glu-Ala-His) box polypeptide 34 | 0.018 | 0.26 |
| 377 | 10189 | THOC4 | THO complex 4 | 0.005 | 0.74 |
| 378 | 80196 | RNF34 | ring finger protein 34 | 0.029 | 0.302 |
| 379 | 1303 | COL12A1 | collagen, type XII, alpha 1 | 0.013 | −0.605 |
| 380 | 26872 | STEAP1 | six transmembrane epithelial antigen of the prostate 1 | 0.01 | −0.821 |
| 381 | 23645 | PPP1R15A | protein phosphatase 1, regulatory (inhibitor) subunit 15A | 0.003 | 0.778 |
| 382 | 3320 | HSP90AA1 | heat shock protein 90 kDa alpha (cytosolic), class A member 1 | 0.019 | 0.418 |
| 383 | 23543 | RBFOX2 | RNA binding protein, fox-1 homolog (C. elegans) 2 | 0.026 | −0.234 |
| 384 | 4540 | ND5 | NADH dehydrogenase, subunit 5 (complex I) | 0.025 | −0.228 |
| 385 | 3329 | HSPD1 | heat shock 60 kDa protein 1 (chaperonin) | 0.003 | 0.472 |
| 386 | 3336 | HSPE1 | heat shock 30 kDa protein 1 (chaperonin 10) | 0.002 | 0.419 |
| 387 | 2192 | FBLN1 | fibulin 1 | 0.009 | −0.301 |
| 388 | 55450 | CAMK2N1 | calcium/calmodulin-dependent protein kinase II inhibitor 1 | 0.019 | 0.274 |
| 389 | 80036 | TRPM3 | transient receptor potential cation channel, subfamily M, member 3 | 0.012 | 0.35 |
| 390 | 6330 | SCN4B | sodium channel, voltage-gated, type IV, beta | 0.045 | 0.379 |
| 391 | 151300 | LOC151300 | hypothetical LOC151300 | 0.028 | 0.32 |
| 392 | 81614 | NIPA2 | non imprinted in Prader-Willi/Angelman syndrome 2 | 0.043 | −0.242 |
| 393 | 63910 | SLC17A9 | solute carrier family 17, member 9 | 0.015 | 0.376 |
| 394 | 51386 | EIF3L | eukaryotic translation initiation factor 3, subunit L | 0.025 | −0.252 |
| 395 | 2346 | FOLH1 | folate hydrolase (prostate-specific membrane antigen) 1 | 0.013 | −0.338 |
| 396 | 3491 | CYR61 | cysteine-rich, angiogenic inducer, 61 | <0.001 | −0.829 |
| 397 | 2730 | GCLM | glutamate-cysteine ligase, modifier subunit | <0.001 | 0.508 |
| 398 | 10957 | PNRC1 | proline-rich nuclear receptor coactivator 1 | 0.041 | 0.215 |
| 399 | 25805 | BAMBI | BMP and activin membrane-bound inhibitor homolog (Xenopus laevis) | 0.034 | 0.315 |
| 400 | 1831 | TSC22D3 | TSC22 domain family, member 3 | 0.019 | 0.349 |
| 401 | 3161 | HMMR | hyaluronan-mediated motility receptor (RHAMM) | 0.041 | 0.27 |
| 402 | 81567 | TXNDC5 | thioredoxin domain containing 5 (endoplasmic reticulum) | 0.026 | −0.324 |
| 403 | 5955 | RCN2 | reticulocalbin 2, EF-hand calcium binding domain | 0.001 | −0.414 |
| 404 | 3920 | LAMP2 | lysosomal-associated membrane protein 2 | 0.017 | −0.223 |
| 405 | 254128 | LOC254128 | hypothetical LOC254128 | 0.019 | 0.284 |
| 406 | 51734 | SEPX1 | selenoprotein X, 1 | 0.027 | 0.241 |
| 407 | 10105 | PPIF | peptidylprolyl isomerase F | 0.003 | 0.455 |
| 408 | 284630 | LOC284630 | hypothetical protein LOC284630 | 0.038 | −0.355 |
| 409 | 51187 | RSL24D1 | ribosomal L24 domain containing 1 | 0.026 | −0.439 |
| 410 | 8227 | AKAP17A | A kinase (PRKA) anchor protein 17A | 0.018 | 0.376 |
| 411 | 29081 | METTL5 | methyltransferase like 5 | 0.009 | −0.516 |
| 412 | 10379 | IRF9 | interferon regulatory factor 9 | <0.001 | 0.427 |
| 413 | 4071 | TMSF1 | transmembrane 4 L six family member 1 | 0.01 | −0.337 |
| 414 | 83667 | SESN2 | sestrin 2 | 0.003 | 0.491 |
| 415 | 1649 | DDIT3 | DNA-damage-inducible transcript 3 | <0.001 | 1.17 |
| 416 | 5708 | PSMD2 | proteasome (prosome, macropain) 26S subunit, non-ATPase, 2 | 0.015 | −0.289 |
| 417 | 223082 | ZNRF2 | zinc and ring finger 2 | 0.018 | 0.389 |
| 418 | 64778 | FNDC3B | fibronectin type III domain containing 38 | 0.028 | −0.339 |
| 419 | 388533 | KRTDAP | keratinocyte differentiation-associated protein | 0.027 | −0.258 |
| 420 | 3646 | EIF3E | eukaryotic translation initiation factor 3, subunit E | 0.036 | −0.277 |
| 421 | 56917 | MEIS3 | Meis homeobox 3 | 0.033 | 0.274 |
| 422 | 10410 | IFITM3 | interferon induced transmembrane protein 3 (1-8U) | 0.017 | 0.243 |
| 423 | 55970 | GNG12 | guanine nucleotide binding protein (G protein), gamma 12 | 0.04 | −0.31 |
| 424 | 7474 | WNT5A | wingless-type MMTV integration site family, member 5A | 0.04 | −0.489 |
| 425 | 84231 | TRAF2 | TNF receptor-associated factor 7 | 0.039 | −0.429 |
| 426 | 329 | BIRC2 | baculoviral IAP repeat containing 2 | 0.043 | −0.352 |
| 427 | 9518 | GDF15 | growth differentiation factor 15 | <0.001 | 0.604 |
| 428 | 83606 | C22orf13 | chromosome 22 open reading frame 13 | 0.049 | −0.411 |
| 429 | 3337 | DNAJB1 | DnaJ (Hsp40) homolog, subfamily B, member 1 | <0.001 | 0.945 |
| 430 | 389223 | EEF1A1P35 | eukaryotic translation elongation factor 1 alpha 1 pseudogene 35 | 0.027 | −0.218 |
| 431 | 26118 | WSB1 | WD repeat and SOCS box containing 1 | <0.001 | −0.583 |
| 432 | 79368 | FCRL2 | Fc receptor-like 2 | 0.01 | −0.388 |
| 433 | 1809 | DPYSL3 | dihydropyrimidinase-like 3 | 0.043 | −0.235 |
| 434 | 2744 | GLS | glutaminase | 0.016 | −0.348 |
| 435 | 4735 | SEPT2 | septin 2 | 0.022 | −0.38 |
| 436 | 79670 | ZCCHC6 | zinc finger, CCHC domain containing 6 | 0.044 | 0.222 |
| 437 | 29115 | SAP30BP | SAP30 binding protein | 0.011 | 0.259 |
| 438 | 5252 | PHF1 | PHD finger protein 1 | 0.042 | 0.275 |
| 439 | 3312 | HSPA8 | heat shock 70 kDa protein 8 | 0.004 | 0.369 |
| 440 | 3725 | JUN | jun proto-oncogene | 0.014 | 0.36 |
| 441 | 3638 | INSIG1 | insulin induced gene 1 | 0.02 | 0.333 |
| 442 | 146225 | CMTM2 | CKLF-like MARVEL transmembrane domain containing 2 | 0.049 | 0.289 |
| 443 | 5440 | POLR2K | polymerase (RNA) II (DNA directed) polypeptide K, 7.0 kDa | 0.03 | −0.288 |

TABLE 3-continued 445 genes differentially expressed in MSC non-exposed in comparison with cells exposed to TCM from sample 1 in comparison with non-exposed cells. The magnitude of the expression change is represented as the logarithm of the fold change.

|  | GeneID | Name | Description | PValue | Log2FC |
|---|---|---|---|---|---|
| 444 | 157317 | CYCSP55 | cytochrome c, somatic pseudogene 5S | 0.01 | 0.35 |
| 445 | 6520 | SLC3A2 | solute carrier family 3 (activators of dibasic and neutral amino acid transport), member 2 | 0.005 | 0.468 |

TABLE 4

511 genes differentially expressed in MSC non-exposed in comparison with cells exposed to TCM from sample 2 in comparison with non-exposed cells. The magnitude of the expression change is represented as the logarithm of the fold change.

|  | GeneID | Name | Description | PValue | Log2FC |
|---|---|---|---|---|---|
| 1 | 54769 | DIRAS2 | DIRAS family, GTP-binding RAS-like 2 | 0.024 | 0.445 |
| 2 | 1958 | EGR1 | early growth response 1 | 0.002 | −0.727 |
| 3 | 56109 | PCDHGA6 | protocadherin gamma subfamily A, 6 | 0.041 | −0.303 |
| 4 | 11137 | PWP1 | PWP1 homolog (S. cerevisiae) | 0.01 | −0.356 |
| 5 | 92609 | TIMM50 | translocase of inner mitochondrial membrane 50 homolog (S. cerevisiae) | 0.045 | 0.341 |
| 6 | 1968 | EIF2S3 | eukaryotic translation initiation factor 2, subunit 3 gamma, 52 kDa | 0.02 | −0.443 |
| 7 | 1719 | DHFR | dihydrofolate reductase | 0.03 | 0.325 |
| 8 | 1728 | NQO1 | NAD(P)H dehydrogenase, quinone 1 | 0.03 | −0.639 |
| 9 | 85445 | CNTNAP4 | contactin associated protein-like 4 | 0.006 | 0.445 |
| 10 | 6782 | HSPA13 | heat shock protein 70 kDa family, member 13 | 0.011 | −0.57 |
| 11 | 81626 | SHC8P1L | SHC SH2 domain binding protein 1-like | <0.001 | 0.751 |
| 12 | 2959 | GTF2B | general transcription factor IIB | 0.041 | 0.462 |
| 13 | 51278 | IER5 | immediate early response 5 | <0.001 | 0.774 |
| 14 | 8028 | MLLT10 | myeloid/lymphoid or mixed-lineage leukemia (trithorax homolog, Drosophila) translocated to, 10 | 0.039 | 0.516 |
| 15 | 1282 | COL4A1 | collagen, type IV, alpha 1 | 0.019 | −0.377 |
| 16 | 2199 | FBLN2 | fibulin 2 | <0.001 | 0.676 |
| 17 | 3438 | IGF8P5 | insulin-like growth factor binding proten 5 | <0.001 | 0.602 |
| 18 | 57104 | PNPLA2 | patatin-like phospholipase domain containing 2 | 0.033 | 0.956 |
| 19 | 10659 | CELF2 | CUGBP, Elav-like family member 2 | <0.001 | 1.078 |
| 20 | 635 | BHMT | betaine-homocysteine S-methyltransferase | 0.042 | 0.414 |
| 21 | 50613 | UBQLN3 | ubiquilin 3 | 0.011 | 0.417 |
| 22 | 56950 | SMYD2 | SET and MYND domain containing 2 | 0.009 | 0.835 |
| 23 | 56097 | PCDHGC5 | protocadherin gamma subfamily C, 5 | 0.042 | −0.408 |
| 24 | 6396 | SEC13 | SEC13 homolog (S. cerevisiae) | 0.048 | −0.318 |
| 25 | 51310 | SLC22A17 | solute carrier family 22, member 17 | 0.004 | 0.362 |
| 26 | 10945 | KDELR1 | KDEL (Lys-Asp-Glu-Leu) endoplasmic reticulum protein retention receptor 1 | 0.033 | −0.342 |
| 27 | 10938 | EHD1 | EH-domain containing 1 | 0.002 | 0.61 |
| 28 | 79370 | BCL2L14 | BCL2-like 14 (apoptosis facilitator) | 0.027 | 0.387 |
| 29 | 2657 | GDF1 | growth differentiation factor 1 | 0.014 | 0.407 |
| 30 | 3954 | LETM1 | leucine zipper-EF-hand containng transmembrane protein 1 | 0.003 | −0.407 |
| 31 | 7278 | TUBA3C | tubulin, alpha 3c | <0.001 | 0.507 |
| 32 | 2574 | GAGE2C | G antigen 2C | 0.002 | 0.522 |
| 33 | 10476 | ATP5H | ATP synthase, H+ transporting, mitochondrial Fo complex, subunit d | 0.029 | −0.352 |
| 34 | 7323 | UBE2D3 | ubiquitin-conjugating enzyme E2D 3 (UBC4/5 homolog, yeast) | 0.014 | 0.35 |
| 35 | 8404 | SPARCL1 | SPARC-like 1 (hevin) | 0.007 | 0.592 |
| 36 | 55062 | WIPI1 | WD repeat domain, phosphoinositide interacting 1 | <0.001 | −0.696 |
| 37 | 29116 | MYLIP | myosin regulatory light chain interacting protein | <0.001 | 0.871 |
| 38 | 55907 | CMAS | cytidine monophosphate N-acetyineuraminic acid synthetase | 0.033 | 0.346 |
| 39 | 55000 | TUG1 | taurine upregulated 1 (non-protein coding) | 0.004 | 0.59 |
| 40 | 1672 | DEFB1 | defensin, beta 1 | <0.001 | 0.721 |
| 41 | 11145 | PLA2G16 | phospholipase A2, group XVI | 0.005 | 0.402 |
| 42 | 10814 | CPLX2 | complexin 2 | 0.004 | 0.458 |
| 43 | 2191 | FAP | fibroblast activation protein, alpha | <0.001 | −0.59 |
| 44 | 1634 | DCN | decorin | 0.004 | −0.311 |
| 45 | 114804 | RNF157 | ring finger protein 157 | 0.031 | 0.385 |
| 46 | 972 | CD74 | CD74 molecule, major histocompatibility complex, class II invariant chain | 0.042 | 0.344 |
| 47 | 26137 | 2BTB20 | zinc finger and BTB domain containing 20 | 0.003 | 0.536 |
| 48 | 10524 | KATS | K(lysine) acetyltransferase S | 0.043 | −0.329 |
| 49 | 266655 | NCRNA00094 | non-protein coding RNA 94 | 0.043 | −0.307 |
| 50 | 100271071 | RPS17P10 | ribosomal protein S17 pseudogene 10 | 0.025 | −0.513 |
| 51 | 56970 | ATXN7L3 | ataxin 7-like 3 | 0.013 | −0.418 |
| 52 | 7117 | TMSL3 | thymosin-like 3 | 0.022 | −0.322 |
| 53 | 9789 | SPCS2 | signal peptidase complex subunit 2 homolog (S. cerevisiae) | 0.038 | 0.334 |
| 54 | 2969 | GTF2I | general transcription factor III | 0.02 | 0.37 |

TABLE 4-continued 511 genes differentially expressed in MSC non-exposed in comparison with cells exposed to TCM from sample 2 in comparison with non-exposed cells. The magnitude of the expression change is represented as the logarithm of the fold change.

|  | GeneID | Name | Description | PValue | Log2FC |
|---|---|---|---|---|---|
| 55 | 6129 | RPL7 | ribosomal protein L7 | 0.02 | −0.304 |
| 56 | 388692 | LOC388692 | hypothetical LOC388692 | 0.019 | 0.404 |
| 57 | 9524 | TECR | trans-2,3-enoyl-CoA reductase | 0.038 | 0.42 |
| 58 | 79630 | C1orf54 | chromosome 1 open reading frame 54 | 0.032 | −0.481 |
| 59 | 5138 | PDE2A | phosphodiesterase 2A cGMP-stimulated | 0.022 | 0.61 |
| 60 | 283131 | NEAT1 | nuclear paraspeckle assembly transcript 1 (non-protein coding) | 0.038 | −0.471 |
| 61 | 8943 | AP3D1 | adaptor-related protein complex 3, delta 1 subunit | 0.007 | 0.309 |
| 62 | 467 | ATF3 | activating transcription factor 3 | <0.001 | 1.187 |
| 63 | 54996 | MOSC2 | MOCO sulphurase C-terminal domain containing 2 | 0.004 | 0.736 |
| 64 | 54600 | UGT1A9 | UDP glucuronosyltransferase 1 family, polypeptide A9 | <0.001 | 0.686 |
| 65 | 23450 | SF3B3 | splicing factor 3b, subunit 3, 130 kDa | 0.044 | 0.503 |
| 66 | 221035 | REEP3 | receptor accessory protein 3 | 0.04 | 0.336 |
| 67 | 22907 | DHX30 | DEAH (Asp-Glu-Ala-His) box polypeptide 30 | 0.005 | −0.339 |
| 68 | 1345 | COX6C | cytochrome c oxidase subunit VIc | 0.002 | 0.375 |
| 69 | 219402 | MTIF3 | mitochondrial translational initiation factor 3 | 0.013 | 0.315 |
| 70 | 200185 | KRTCAP2 | keratinocyte associated protein 2 | <0.001 | −0.617 |
| 71 | 118945 | CTSL1P1 | cathepsin L1 pseudogene 1 | 0.019 | −0.467 |
| 72 | 58515 | SELK | selenoprotein K | 0.006 | 0.324 |
| 73 | 23095 | KIF18 | kinesin family member 1B | 0.004 | 0.474 |
| 74 | 9861 | PSMD6 | proteasome (prosome, macropain) 26S subunit, non-ATPase, 6 | 0.012 | 0.366 |
| 75 | 10808 | HSPH1 | heat shock 105 kDa/110 kDa protein 1 | <0.001 | 0.761 |
| 76 | 9988 | DMTF1 | cyclin D binding myb-like transcription factor 1 | 0.015 | 0.389 |
| 77 | 56110 | PCDHGA5 | protocadherin gamma subfamily A, 5 | 0.011 | −0.368 |
| 78 | 1387 | CREBBP | CREB binding protein | 0.033 | 0.406 |
| 79 | 25907 | TMEM158 | transmembrane protein 158 (gene/pseudogene) | 0.026 | −0.494 |
| 80 | 1003 | CDH5 | cadherin 5, type 2 (vascular endothelium) | 0.03 | 0.518 |
| 81 | 9531 | BAG3 | BCL2-associated athanogene 3 | <0.001 | 0.78 |
| 82 | 79696 | FAM164C | family with sequence similarity 164, member C | 0.017 | 0.465 |
| 83 | 23761 | PISD | phosphatidylserine decarboxylase | 0.006 | 0.388 |
| 84 | 2824 | GPM6B | glycoprotein M68 | 0.004 | 0.429 |
| 85 | 51726 | DNAJB11 | DnaJ (Hsp40) homolog, subfamily B, member 11 | <0.001 | 0.495 |
| 86 | 478 | ATP1A3 | ATPase, Na+/K+ transporting, alpha 3 polypeptide | 0.003 | 0.692 |
| 87 | 338799 | LOC338799 | hypothetical LOC338799 | 0.016 | −0.375 |
| 88 | 9261 | MAPKAPK2 | mitogen-activaied protein kinase-activated protein kinase 2 | 0.019 | 0.408 |
| 89 | 5476 | CTSA | cathepsin A | 0.004 | −0.381 |
| 90 | 533 | ATP6V08 | ATPase, H+ transporting, lysosomal 21 kDa, V0 subunit b | 0.009 | 0.438 |
| 91 | 6125 | RPL5 | ribosomal protein E5 | 0.001 | −0.527 |
| 92 | 3336 | HSPE1 | heat shock 10 kDa protein 1 (chaperonin 10) | 0.004 | 0.509 |
| 93 | 80279 | CDK5RAP3 | CDK5 regulatory subunit associated protein 3 | 0.002 | 0.474 |
| 94 | 441533 | RPL26P37 | ribosomal protein 126 pseudogene 37 | 0.003 | −0.442 |
| 95 | 6141 | RPL18 | ribosomal protein L18 | 0.044 | −0.305 |
| 96 | 55964 | sep-03 | septin 3 | 0.003 | 0.54 |
| 97 | 5707 | PSMD1 | proteasome (prosome, macropain) 26S subunit, non-ATPase, 1 | 0.036 | 0.314 |
| 98 | 2353 | FOS | FBJ murine osteosarcoma viral oncogene homolog | 0.003 | 0.482 |
| 99 | 55228 | PNMAL1 | PNMA-like 1 | 0.011 | 0.569 |
| 100 | 11215 | AKAP11 | A kinase (PRKA) anchor protein 11 | 1.017 | 0.443 |
| 101 | 57222 | ERGIC1 | endoplasmic reticulum-golgi intermediate compartment (ERGIC) 1 | 0.04 | −0.314 |
| 102 | 8566 | PDXK | pyridoxal (pyridoxine, vitamin B6) kinase | 0.002 | 0.486 |
| 103 | 3703 | STT3A | STT3, subunit of the oligosaccharyltransferase complex homolog A (*S. cerevisiae*) | 0.004 | −0.415 |
| 104 | 4884 | NPTX1 | neuronal pentraxin I | <0.001 | 0.762 |
| 105 | 7485 | WRB | tryotophan rich basic protein | 0.016 | 0.403 |
| 106 | 11179 | ZNF277 | zinc finger protein 277 | 0.004 | −0.744 |
| 107 | 3397 | ID1 | inhibitor of DNA binding 1, dominant negative helix-loop-helix protein | 0.001 | 0.402 |
| 108 | 1611 | DAP | death-associated protein | 0.042 | −0.445 |
| 109 | 53826 | FXYD6 | FXYD domain containing ion transport regulator 6 | <0.001 | 0.546 |
| 110 | 11170 | FAM107A | family with sequence similarity 107, member A | <0.001 | 0.405 |
| 111 | 66501 | SOLH | small optic lobes homolog (*Drosophila*) | 0.046 | −0.381 |
| 112 | 8985 | PLOD3 | procollagen-lysine, 2-oxoglutarate 5-dioxygenase 3 | 0.007 | −0.555 |
| 113 | 2496 | FTH1P1 | ferritin, heavy polypeptide 1 pseudogene | 0.006 | −0.353 |
| 114 | 3972 | LHB | luteinizing hormone beta polypeptide | 0.025 | −0.31 |
| 115 | 1164 | CKS2 | CDC28 protein kinase regulatory subunit 2 | <0.001 | 0.712 |
| 116 | 6152 | RPL24 | ribosomal protein L24 | 0.006 | −0.31 |
| 117 | 145767 | RPS3AP6 | ribosomal protein S3A pseudogene 6 | 0.004 | −0.361 |
| 118 | 150221 | RIMBP3C | RIMS binding protein 3C | 0.003 | 0.388 |
| 119 | 6733 | SRPK2 | SRSF protein kinase 2 | 0.008 | −0.362 |
| 120 | 23621 | BACE1 | beta-site APP-cleaving enzyme 1 | 0.028 | −0.307 |
| 121 | 1964 | EIF1AX | eukaryotic translation initiation factor 1A, X-linked | 0.012 | −0.488 |
| 122 | 2983 | GUCY1B3 | guanylate cyclase 1, soluble, beta 3 | <0.001 | 0.663 |
| 123 | 7546 | ZIC2 | Zic family member 2 (odd-paired homolog, *Drosophila*) | 0.002 | 0.75 |
| 124 | 51617 | HMP19 | HMP19 protein | 0.003 | 0.517 |
| 125 | 54476 | RNF216 | ring finger protein 216 | 0.004 | 0.434 |
| 126 | 54657 | UGT1A4 | UDP glucuronosyltransferase 1 family, polypeptide A4 | 0.003 | 0.508 |

TABLE 4-continued 511 genes differentially expressed in MSC non-exposed in comparison with
cells exposed to TCM from sample 2 in comparison with non-exposed cells. The
magnitude of the expression change is represented as the logarithm of the fold change.

| | GeneID | Name | Description | PValue | Log2FC |
|---|---|---|---|---|---|
| 127 | 23786 | BCL2L13 | BCL2-like 13 (apoptosis facilitator) | <0.001 | 0.926 |
| 128 | 387103 | CENPW | centromere protein W | 0.018 | 0.544 |
| 129 | 5420 | PODXL | podocalyxin-like | 0.003 | 0.574 |
| 130 | 23209 | MLC1 | megalencephalic leukoencephalopathy with subcortical cysts 1 | 0.005 | 0.582 |
| 131 | 84303 | CHCHD6 | coiled-coil-helix-coiled-coil-helix domain containing 6 | 0.037 | 0.395 |
| 132 | 392358 | RPS6P13 | ribosomal protein S6 pseudogene 13 | 0.006 | −0.319 |
| 133 | 3032 | HADHB | hydroxyacyl-CoA dehydrogenase/3-ketoacyl-CoA thiolase/enoyl-CoA hydratase (trifunctional protein), beta subunit | 0.005 | −0.355 |
| 134 | 3301 | DNAJA1 | DnaJ (Hsp40) homolog, subfamily A, member 1 | 0.002 | 0.441 |
| 135 | 3047 | HBG1 | hemoglobin, gamma A | 0.023 | 0.306 |
| 136 | 112714 | TUBA3E | tubulin, alpha 3e | 0.011 | 0.301 |
| 137 | 283971 | CLEC18C | C-type lectin domain family 18, member C | <0.001 | 0.588 |
| 138 | 4783 | NFIL3 | nuclear factor, interleukin 3 regulated | 0.013 | −0.408 |
| 139 | 6678 | SPARC | secreted protein, acidic, cysteine-rich (osteonectin) | 0.008 | −0.416 |
| 140 | 813 | CALU | calumenin | 0.042 | −0.377 |
| 141 | 116151 | C20orf108 | chromosome 20 open reading frame 108 | 0.013 | −0.641 |
| 142 | 57730 | ANKRD36B | ankyrin repeat domain 368 | 0.018 | 0.336 |
| 143 | 6154 | RPL26 | ribosomal protein L26 | 0.031 | −0.307 |
| 144 | 51386 | EIF3L | eukaryotic translation initiation factor 3, subunit L | 0.034 | −0.32 |
| 145 | 7175 | TPR | translocated promoter region (to activated MET oncogene) | 0.009 | 0.489 |
| 146 | 54504 | CPVL | carboxypeptidase, vitellogenic-like | 0.003 | 0.442 |
| 147 | 7058 | THBS2 | thrombosporidin 2 | 0.025 | −0.328 |
| 148 | 9452 | ITM2A | integral membrane protein 2A | 0.009 | 0.621 |
| 149 | 2131 | EXT1 | exostosin 1 | 0.009 | −0.426 |
| 150 | 65055 | REEP1 | receptor accessory protein 1 | 0.033 | 0.308 |
| 151 | 79791 | FBXO31 | F-box protein 31 | 0.005 | 0.42 |
| 152 | 3936 | LCP1 | lymphocyte cytosolic protein 1 (L-plastin) | 0.029 | 0.528 |
| 153 | 90701 | SEC11C | SEC11 homolog C (S. cerevisiae) | 0.002 | 0.569 |
| 154 | 84681 | HINT2 | histidine triad nucleotide binding protein 2 | 0.02 | 0.354 |
| 155 | 26749 | GAGE2E | G antigen 2E | 0.039 | 0.312 |
| 156 | 7644 | ZNF91 | zinc finger protein 91 | 0.034 | 0.335 |
| 157 | 231 | AKR1B1 | aldo-keto reductase family 1, member B1 (aldose reductase) | <0.001 | −0.543 |
| 158 | 91942 | NDUFAF2 | NADH dehydrogenase (ubiquinone) 1 alpha subcomplex, assembly factor 2 | 0.032 | 0.419 |
| 159 | 501 | ALDH7A1 | aldehyde dehydrogenase 7 family, member A1 | 0.008 | −0.422 |
| 160 | 26099 | C1orf144 | chromosome 1 open reading frame 144 | 0.036 | 0.333 |
| 161 | 4131 | MAP1B | microtubule-associated protein 1B | <0.001 | 0.724 |
| 162 | 84545 | MRPL43 | mitochondrial ribosomal protein L43 | 0.007 | −0.515 |
| 163 | 4358 | MPV17 | MpV17 mitochondrial inner membrane protein | 0.017 | −0.345 |
| 164 | 51031 | GLOD4 | glyoxalase domain containing 4 | 0.029 | 0.407 |
| 165 | 22928 | SEPH52 | selenophosphate synthetase 2 | 0.003 | 0.413 |
| 166 | 60312 | AFAP1 | actin filament associated protein 1 | <0.001 | −0.632 |
| 167 | 291 | SLC25A4 | solute carrier family 25 (mitochondrial carrier adenine nucleotide translocator), member 4 | 0.019 | 0.313 |
| 168 | 26608 | TBL2 | transducin (beta)-like 2 | 0.02 | 0.391 |
| 169 | 55753 | OGDHL | oxoglutarate dehydrogenase-like | 0.01 | 0.37 |
| 170 | 8468 | FK8P6 | FK506 binding protein 6, 36 kDa | 0.002 | 0.418 |
| 171 | 10472 | ZNF238 | zinc finger protein 238 | 0.034 | 0.384 |
| 172 | 1164 | CKS2 | CDC28 protein kinase regulatory subunit 2 | <0.001 | 0.345 |
| 173 | 132864 | CPEB2 | cytoplasmic polyadenylation element binding protein | <0.001 | 0.475 |
| 174 | 55731 | C17orf63 | chromosome 17 open reading frame 63 | 0.016 | 0.341 |
| 175 | 54752 | FNDC8 | fibronectin type III domain containing 8 | 0.011 | −0.373 |
| 176 | 89958 | C9orf140 | chromosome 9 open reading frame 140 | 0.041 | −0.328 |
| 177 | 220594 | LOC220594 | ubiquitin specific peptidase 6 (Tre-2 oncogene) pseudogene | 0.044 | 0.32 |
| 178 | 51616 | TAF9B | TAF9B RNA polymerase II, TATA box binding protein (TBP)-associated factor, 31 kDa | 0.049 | 0.325 |
| 179 | 5297 | PI4KA | phosphatidylinositol 4-kinase, catalytic, alpha | 0.017 | 0.332 |
| 180 | 8802 | SUCLG1 | succinate-CoA ligase, alpha subunit | <0.001 | 0.594 |
| 181 | 6601 | SMARCC2 | SWI/SNF related, matrix associated, actin dependent regulator of chromatin subfamily c, member 2 | 0.033 | −0.854 |
| 182 | 81688 | C6orf62 | chromosome 6 open reading framed | <0.001 | 0.413 |
| 183 | 54658 | UGT1A1 | UDP glucuronosyltransferase 1 family, polypeptide A1 | 0.013 | 0.336 |
| 184 | 79753 | SNIP1 | Smad nuclear interacting protein 1 | <0.001 | 0.364 |
| 185 | 65009 | NDRG4 | NDRG family member 4 | <0.00 | 0.452 |
| 186 | 51596 | CUTA | cutA divalent cation tolerance homolog (E. coli) | 0.005 | −0.363 |
| 187 | 2938 | GSTA1 | glutathione S-transferase alpha 1 | 0.025 | 0.367 |
| 188 | 3337 | DNAJB1 | DnaJ (Hsp40) homolog, subfamily B, member 1 | <0.001 | 0.581 |
| 189 | 6189 | RPS3A | ribosomal protein S3A | 0.024 | −0.313 |
| 190 | 113457 | TUBA3D | tubulin, alpha 3d | 0.028 | 0.673 |
| 191 | 2171 | FABP5 | fatty acid binding protein 5 (psoriasis-associated) | 0.006 | 0.374 |
| 192 | 2619 | GAS1 | growth arrest-specific 1 | 0.001 | −0.481 |
| 193 | 7980 | TFPI2 | tissue factor pathway inhibitor 2 | 0.001 | −0.97 |
| 194 | 51655 | RASD1 | RAS, dexamethasone-induced 1 | <0.001 | −0.827 |
| 195 | 1293 | COL6A3 | collagen, type VI, alpha 3 | 0.032 | −0.342 |

TABLE 4-continued 511 genes differentially expressed in MSC non-exposed in comparison with cells exposed to TCM from sample 2 in comparison with non-exposed cells. The magnitude of the expression change is represented as the logarithm of the fold change.

| | GeneID | Name | Description | PValue | Log2FC |
|---|---|---|---|---|---|
| 196 | 83955 | NACAP1 | nascent-polypeptide-associated complex alpha polypeptide pseudogene 1 | 0.009 | −0.447 |
| 197 | 9444 | QKI | quaking homolog, KH domain RNA binding (mouse) | 0.01 | 0.553 |
| 198 | 387763 | C11orf96 | chromosome 11 open reading frame 96 | 0.001 | 0.447 |
| 199 | 128218 | TMEM125 | transmembrane protein 125 | 0.03 | 0.419 |
| 200 | 7873 | MANF | mesencephalic astrocyte-derived neurotrophic factor | 0.003 | 0.44 |
| 201 | 64750 | SMURF2 | SMAD specific E3 ubiquitin protein ligase 2 | <0.001 | −0.495 |
| 202 | 3476 | IGBP1 | immunoglobulin (CD79A) binding protein 1 | <0.001 | −0.551 |
| 203 | 400963 | RPS2P17 | ribosomal protein S2 pseudogene 17 | 0.008 | −0.346 |
| 204 | 79925 | SPEF2 | sperm flagellar 2 | 0.014 | 0.38 |
| 205 | 9736 | KIAA0S86 | KIAA0S86 | 0.031 | 0.349 |
| 206 | 25874 | BRP44 | brain protein 44 | 0.018 | 0.722 |
| 207 | 55964 | sep-03 | septin 3 | 0.019 | 0.579 |
| 208 | 84935 | C13orf33 | chromosome 13 open reading frame 33 | 0.011 | −0.35 |
| 209 | 10370 | CITED2 | Cbp/p300-interacting transactivator, with Glu/Asp-rich carboxy-terminal domain, 2 | 0.013 | −0.429 |
| 210 | 55693 | KDM4D | lysine (K)-specific demethylase 4D | 0.046 | 0.483 |
| 211 | 1490 | CTGF | connective tissue growth factor | 0.004 | −0.456 |
| 212 | 89781 | HPS4 | Hermansky-Pudlak syndrome 4 | 0.004 | 0.6 |
| 213 | 9547 | CXCL14 | chemokine (C-X-C motif) ligand 14 | <0.001 | 0.831 |
| 214 | 121549 | ASCL4 | achaete-scute complex homolog 4 (Drosophila) | 0.028 | 0.324 |
| 215 | 7415 | VCP | valosin containing protein | 0.007 | 0.368 |
| 216 | 29118 | DDX25 | DEAD (Asp-Glu-Ala-Asp) box polypeptide 25 | 0.009 | 0.645 |
| 217 | 100271475 | RPL31P51 | ribosomal protein L31 pseudogene 51 | 0.035 | −0.31 |
| 218 | 55695 | NSUNU | NOP2/Sun domain family, member 5 | 0.01 | 0.315 |
| 219 | 5937 | RBMS1 | RNA binding motif, single stranded interacting protein 1 | <0.001 | −0.521 |
| 220 | 127933 | UHMK1 | U2AF homology motif (UHM) kinase 1 | 0.015 | −0.301 |
| 221 | 8553 | 8HLHE40 | basic helix-loop-helix family, member e40 | <0.001 | 0.905 |
| 222 | 54659 | UGT1A3 | UDP glucuronosyltransferase 1 family, polypeptide A3 | 0.026 | 0.704 |
| 223 | 83639 | TEX101 | testis expressed 101 | 0.035 | 0.378 |
| 224 | 8742 | TNFSF12 | tumor necrosis factor (ligand) superfamily, member 12 | 0.01 | −0.548 |
| 225 | 5045 | FURIN | furin (paired basic amino acid cleaving enzyme) | 0.005 | 0.502 |
| 226 | 267 | AMFR | autocrine motility factor receptor | 0.022 | −0.324 |
| 227 | 390158 | RPLSP29 | ribosomal protein LS pseudogene 29 | 0.002 | −0.477 |
| 228 | 2939 | GSTA2 | glutathione S-transferase alpha 2 | 0.007 | 0.474 |
| 229 | 29968 | PSAT1 | phosphoserine aminotransferase 1 | 0.007 | 0.476 |
| 230 | 151579 | BZW1P2 | basic leucine zipper and W2 domains 1 pseudogene 2 | 0.004 | −0.344 |
| 231 | 115207 | KCTD12 | potassium channel tetramerisation domain containing 12 | <0.001 | −0.807 |
| 232 | 26353 | HSP88 | heat shock 22 kDa protein 8 | 0.038 | 0.461 |
| 233 | 283711 | LOC283711 | ubiquitin-conjugating enzyme E2C pseudogene | 0.017 | 0.388 |
| 234 | 3225 | HOXC9 | homeobox C9 | 0.031 | 0.371 |
| 235 | 4553 | TRNA | tRNA | <0.001 | 1.002 |
| 236 | 255313 | CT47A11 | cancer/testis antigen family 47, member A11 | 0.014 | 0.368 |
| 237 | 55002 | TMCO3 | transmembrane and coiled-coil domains 3 | 0.003 | −0.366 |
| 238 | 79143 | MBOAT7 | membrane bound O-acyltransferase domain containing 7 | 0.019 | −0.321 |
| 239 | 9547 | CXCL14 | chemokine (C-X-C motif) ligand 14 | 0.025 | 0.392 |
| 240 | 130827 | TMEM182 | transmembrane protein 182 | 0.011 | 0.434 |
| 241 | 3322 | HSP90AA3P | heat shock protein 90 kDa alpha (cytosolic), class A member 3 (pseudogene) | <0.001 | 0.764 |
| 242 | 345645 | LOC345645 | proteasome (prosome, macropain) 26S subunit, ATPase, 1 pseudogene | 0.023 | 0.346 |
| 243 | 5539 | PPY | pancreatic polypeptide | 0.008 | 1.063 |
| 244 | 5934 | RBL2 | retinoblastoma-like 2 (p130) | 0.02 | −0.388 |
| 245 | 1743 | DLST | dihydrolipoamide S-succinyltransferase (E2 component of oxo-glutarate complex) | 0.006 | 0.37 |
| 246 | 10054 | UBA2 | ubiquitin-like modifier activating enzyme 2 | 0.013 | 0.407 |
| 247 | 7196 | TRNAG2 | transfer RNA glycine 2 (anticodon GCC) | 0.013 | 0.693 |
| 248 | 114569 | MAL2 | mal, T-cell differentiation protein 2 (gene/pseudogene) | 0.049 | 0.342 |
| 249 | 8491 | MAP4K3 | mitogen-activated protein kinase kinase kinase kinase 3 | 0.025 | 0.32 |
| 250 | 4609 | MYC | v-myc myelocytomatosis viral oncogene homolog (avian) | 0.029 | 0.369 |
| 251 | 28970 | C11orf54 | chromosome 11 open reading frame 54 | 0.035 | 0.321 |
| 252 | 1462 | VCAN | versican | 0.013 | 0.419 |
| 253 | 51191 | HERC5 | hect domain and RLD 5 | 0.006 | 0.44 |
| 254 | 92591 | ASB16 | ankyrin repeat and SOCS box containing 16 | 0.007 | 0.407 |
| 255 | 341032 | C11orf53 | chromosome 11 open reading frame 53 | 0.046 | −0.405 |
| 256 | 6446 | SGK1 | serum/glucocorticoid regulated kinase 1 | 0.04 | 0.36 |
| 257 | 9082 | XKRY | XK, Kell blood group complex subunit-related, Y-linked | 0.003 | 0.433 |
| 258 | 349114 | NCRNA00265 | non-protein coding RNA 265 | 0.002 | 0.512 |
| 259 | 3304 | HSPA1B | heat shock 70 kDa protein 1B | <0.001 | 0.919 |
| 260 | 122953 | JDP2 | Jun dimerization protein 2 | 0.007 | 0.447 |
| 261 | 84791 | C1orf97 | chromosome 1 open reading frame 97 | 0.001 | 0.478 |
| 262 | 4649 | MYO9A | myosin IXA | 0.008 | 0.351 |
| 263 | 91012 | LASS5 | LAG1 homolog, ceramide synthase 5 | 0.009 | −0.42 |
| 264 | 4070 | TACSTD2 | tumor-associated calcium signal transducer 2 | 0.04 | 0.319 |

TABLE 4-continued 511 genes differentially expressed in MSC non-exposed in comparison with
cells exposed to TCM from sample 2 in comparison with non-exposed cells. The
magnitude of the expression change is represented as the logarithm of the fold change.

| | GeneID | Name | Description | PValue | Log2FC |
|---|---|---|---|---|---|
| 265 | 63908 | NAPB | N-ethylmaleimide-sensitive factor attachment protein, beta | 0.013 | 0.328 |
| 266 | 144110 | TMEM86A | transmembrane protein 86A | 0.027 | 0.348 |
| 267 | 51659 | GINS2 | GINS complex subunit 2 (Psf2 homolog) | 0.018 | 0.321 |
| 268 | 51009 | DERL2 | Derl-like domain family, member 2 | 0.003 | 0.334 |
| 269 | 5936 | RBM4 | RNA binding motif protein 4 | 0.031 | 0.336 |
| 270 | 4353 | MPO | myeloperoxidase | 0.048 | 0.327 |
| 271 | 23014 | FBXO21 | F-box protein 21 | 0.018 | −0.359 |
| 272 | 283711 | LOC283711 | ubiquitin-conjugating enzyme E2C pseudogene | 0.035 | 0.35 |
| 273 | 376497 | SLC27A1 | solute carrier family 27 (fatty acid transporter), member 1 | 0.012 | −0.372 |
| 274 | 7381 | UQCRB | ubiquinol-cytochrome c reductase binding protein | 0.038 | 0.346 |
| 275 | 6888 | TALDO1 | transaldolase 1 | 0.008 | −0.436 |
| 276 | 9052 | GPRC5A | G protein-coupled receptor, family C, group 5, member A | 0.008 | 0.313 |
| 277 | 23394 | ADNP | activity-dependent neuroprotector homeobox | 0.01 | 0.419 |
| 278 | 6303 | SAT1 | spermidine/spermine N1-acetyltransferase 1 | 0.001 | −0.444 |
| 279 | 390638 | LOC390638 | Golgin subfamily A member 2-like | 0.041 | −0.356 |
| 280 | 339799 | EIF3FP3 | eukaryotic translation initiation factor 3, subunit F pseudogene 3 | 0.008 | −0.357 |
| 281 | 55138 | FAM90A1 | family with sequence similarity 90, member A1 | 0.023 | 0.33 |
| 282 | 5721 | PSME2 | proteasome (prosome, macropain) activator subunit 2 (PA28 beta) | 0.007 | 0.328 |
| 283 | 26262 | TSPAN17 | tetraspanin 17 | 0.012 | −0.411 |
| 284 | 1827 | RCAN1 | regulator of calcineurin 1 | <0.001 | −0.991 |
| 285 | 8660 | IRS2 | insulin receptor substrate 2 | 0.018 | 0.339 |
| 286 | 8490 | RGS5 | regulator of G-protein signaling 5 | 0.044 | 0.393 |
| 287 | 3043 | HBB | hemoglobin, beta | 0.009 | 0.519 |
| 288 | 9099 | USP2 | ubiquitin specific peptidase 2 | 0.029 | 0.373 |
| 289 | 388815 | C21orf34 | chromosome 21 open reading frame 34 | 0.035 | 0.308 |
| 290 | 3434 | IFIT1 | interferon-induced protein with tetratricopeptide repeats 1 | <0.001 | 0.426 |
| 291 | 51019 | CCDC53 | coiled-coil domain containing 53 | 0.014 | 0.37 |
| 292 | 116832 | RPL39L | riposomal protein L39-like | 0.042 | 0.368 |
| 293 | 389180 | S-HT3C2 | S-HT3c2 serotonin receptor-like protein pseudogene | 0.013 | 0.341 |
| 294 | 55319 | C4orf43 | chromosome 4 open reading frame 43 | 0.014 | 0.316 |
| 295 | 150160 | CCT8L2 | chaperonin containing TCP1 subunit 8 (theta)-like 2 | 0.019 | 0.335 |
| 296 | 3398 | ID2 | inhibitor of DNA binding 2, dominant negative helix-loop-helix protein | <0.001 | −0.452 |
| 297 | 6166 | RPL36AL | ribosomal protein L36a-like | 0.008 | −0.327 |
| 298 | 284996 | RNF149 | ring finger protein 149 | 0.005 | 0.408 |
| 299 | 283070 | LOC283070 | hypothetical LOC283070 | 0.016 | 0.386 |
| 300 | 7447 | VSNL1 | visinin-like 1 | 0.047 | 0.306 |
| 301 | 151636 | DTX3L | deltex 3-like (*Drosophila*) | 0.049 | 0.638 |
| 302 | 1612 | DAPK1 | death-associated protein kinase 1 | 0.02 | 0.493 |
| 303 | 55818 | KDM3A | lysine (K)-specific demethylase 3A | 0.002 | 0.451 |
| 304 | 83447 | SLC25A31 | solute carrier family 25 (mitochondrial carrier, adenine nucleotide translocator), member 31 | 0.033 | 0.447 |
| 305 | 9555 | H2AFY | H2A histone family member 7 | 0.031 | −0.613 |
| 306 | 10523 | CHERP | calcium homeostasis endoplasmic reticulum protein | 0.008 | 0.423 |
| 307 | 51652 | VPS24 | vacuolar protein sorting 24 homolog (*S. cerevisiae*) | 0.011 | 0.322 |
| 308 | 64215 | DNAJC1 | DnaJ (Hsp40) homolog, subfamily C, member 1 | 0.007 | −0.457 |
| 309 | 4170 | MCL1 | myeloid cell leukemia sequence 1 (BCL2-related) | <0.001 | 0.484 |
| 310 | 3324 | HSP90AA2 | heat shock protein 90 kDa alpha (cytosolic), class A member 2 | <0.001 | 0.624 |
| 311 | 57092 | PCNP | PEST proteolytic signal containing nuclear protein | 0.012 | −0.355 |
| 312 | 2697 | GJA1 | gap junction protein, alpha 1, 43 kDa | 0.029 | −0.335 |
| 313 | 2745 | GLRX | glutaredoxin (thioltransferase) | 0.013 | 0.468 |
| 314 | 4048 | LTA4H | leukotriene A4 hydrolase | 0.026 | −0.39 |
| 315 | 6899 | TBX1 | T-box 1 | 0.019 | −0.359 |
| 316 | 10241 | CALCOCO2 | calcium binding and coiled-coil domain 2 | 0.007 | 0.322 |
| 317 | 260436 | C4orf7 | chromosome 4 open reading frame 7 | 0.004 | 0.504 |
| 318 | 7280 | TUBB2A | tubulin, beta 2A | 0.001 | 0.474 |
| 319 | 3930 | L8R | lamin 8 receptor | 0.042 | 0.372 |
| 320 | 5638 | PRRG1 | proline rich Gla (G-carboxyglutamic acid) 1 | 0.016 | −0.389 |
| 321 | 23174 | ZCCHC14 | zinc finger, CCHC domain containing 14 | 0.007 | 0.392 |
| 322 | 399665 | FAM102A | family with sequence similarity 102, member A | 0.013 | 0.314 |
| 323 | 10450 | PPIE | peptidylprolyl isomerase E (cyclophilin E) | 0.005 | −0.384 |
| 324 | 26232 | FBXO2 | F-box protein 2 | 0.009 | −0.378 |
| 325 | 4567 | TRNL1 | tRNA | 0.001 | 0.527 |
| 326 | 83880 | EIF3FP2 | eukaryotic translation initiation factor 3, subunit F pseudogene 2 | 0.024 | −0.389 |
| 327 | 51074 | APIP | APAF1 interacting protein | 0.035 | 0.383 |
| 328 | 30001 | ERO1L | ERO1-like (*S. cerevisiae*) | 0.033 | 0.418 |
| 329 | 115207 | KCTD12 | potassium channel tetramerisation domain containing 12 | 0.03 | −0.431 |
| 330 | 5159 | PDGFRB | platelet-derived growth factor receptor, beta polypeptide | 0.029 | −0.419 |
| 331 | 23201 | FAM168A | family with sequence similarity 168, member A | 0.016 | 0.311 |
| 332 | 339229 | C17orf90 | chromosome 17 open reading frame 90 | 0.022 | 0.336 |
| 333 | 3303 | HSPA1A | heat shock 70 kDa protein 1A | <0.001 | 1.468 |
| 334 | 23024 | PDZRN3 | PDZ domain containing ring finger 3 | 0.039 | −0.403 |
| 335 | 10628 | TXNIP | thioredoxin interacting protein | <0.001 | −0.764 |
| 336 | 84272 | YIPF4 | Yip1 domain family, member 4 | 0.022 | −0.373 |

TABLE 4-continued 511 genes differentially expressed in MSC non-exposed in comparison with cells exposed to TCM from sample 2 in comparison with non-exposed cells. The magnitude of the expression change is represented as the logarithm of the fold change.

| | GeneID | Name | Description | PValue | Log2FC |
|---|---|---|---|---|---|
| 337 | 9636 | ISG15 | ISG15 ubiquitin-like modifier | 0.003 | 0.937 |
| 338 | 391656 | RPS1SAPI7 | ribosomal protein S1Sa pseudogene 17 | 0.046 | −0.302 |
| 339 | 7207 | TRNAL1 | transfer RNA leucine 1 (anticodon AAG) | 0.003 | 0.407 |
| 340 | 51454 | GULP1 | GULP, engulfment adaptor PT8 domain containing 1 | 0.001 | −0.685 |
| 341 | 9709 | HERPUD1 | homocysteine-inducible, endoplasmic reticulum stress-inducible, ubiquitin-like domain member 1 | <0.001 | 0.719 |
| 342 | 55032 | SLC35A5 | solute carrier family 35, member A5 | 0.021 | 0.503 |
| 343 | 885 | CCK | cholecystokinin | 0.009 | 0.569 |
| 344 | 1728 | NQO1 | NAD(P)H dehydrogenase, quinone 1 | 0.003 | −0.757 |
| 345 | 9445 | ITM2B | integral membrane protein 2B | 0.021 | 0.424 |
| 346 | 2 | A2M | alpha-2-macroglobulin | 0.047 | 0.571 |
| 347 | 3766 | RA811A | RA811A, member RAS oncogene family | 0.017 | −0.31 |
| 348 | 55251 | PCMTD2 | protein-L-isoaspartate (D-aspartate) O-methyltransferase domain containing 2 | 0.011 | −0.485 |
| 349 | 6428 | SRSF3 | serine/arginine- rich splicing factor 3 | <0.001 | 0.575 |
| 350 | 10922 | FASTK | Fas-activated serine/threonine kinase | 0.021 | −0.409 |
| 351 | 433 | ASGR2 | asialoglycoprotein receptor 2 | 0.012 | 0.318 |
| 352 | 9510 | ADAMTS1 | ADAM metallopeptidase with thrombospondin type 1 motif, 1 | 0.002 | −0.556 |
| 353 | 7754 | ZNF204P | zinc finger protein 204, pseudogene | 0.014 | 0.335 |
| 354 | 440275 | EIF2AK4 | eukaryotic translation initiation factor alpha kinase 4 | 0.025 | −0.796 |
| 355 | 11098 | PRSS23 | protease, serine, 23 | 0.027 | 0.311 |
| 356 | 79174 | CRELD2 | cysteine-rich with EGF-like domains 2 | 0.008 | 0.458 |
| 357 | 25946 | ZNF385A | zinc finger protein 385A | 0.003 | −0.458 |
| 358 | 26053 | AUTS2 | autism susceptibility candidate 2 | 0.032 | 0.46 |
| 359 | 2743 | GLRB | glycine receptor, beta | 0.013 | 0.322 |
| 360 | 440073 | IQSEC3 | IQ motif and Sec7 domain 3 | 0.008 | 0.464 |
| 361 | 7180 | CRISP2 | cysteine-rich secretory protein 2 | 0.007 | 0.459 |
| 362 | 2297 | FOXD1 | forkhead box D1 | 0.04 | 0.311 |
| 363 | 9246 | UBE2L6 | ubiquitin-conjugating enzyme E2L6 | 0.005 | 0.391 |
| 364 | 6236 | RRAD | Ras-related associated with diabetes | <0.001 | 0.841 |
| 365 | 7291 | TWIST1 | twist homolog 1 (Drosophila) | 0.041 | −0.488 |
| 366 | 4982 | TNFRSF11B | tumor necrosis factor receptor superfamily, member 11b | 0.006 | −0.567 |
| 367 | 57212 | KIAA0495 | KIAA0495 | 0.038 | 0.351 |
| 368 | 28999 | KLF15 | Kruppel-like factor 15 | <0.001 | 0.852 |
| 369 | 3207 | HOXA11 | homeobox A11 | 0.02 | 0.576 |
| 370 | 6938 | TCF12 | transcription factor 12 | 0.026 | 0.422 |
| 371 | 116254 | C6orf72 | chromosome 6 open reading frame 72 | 0.003 | −0.346 |
| 372 | 51187 | RSL24D1 | ribosomal L24 domain containing 1 | 0.012 | −0.327 |
| 373 | 7804151 | SNORD3A | small nucleolar RNA, C/D box 3A | 0.043 | 0.576 |
| 374 | 731275 | LOC731275 | hypothetical LOC731275 | 0.032 | −0.339 |
| 375 | 143689 | PIWIL4 | piwi-like 4 (Drosophila) | <0.001 | 0.592 |
| 376 | 85363 | TRIM5 | tripartite motif containing 5 | 0.006 | 0.366 |
| 377 | 9520 | NPEPPS | aminopeptidase puromycin sensitive | 0.002 | −0.387 |
| 378 | 290 | ANPEP | alanyl (membrane) aminopeptidase | 0.01 | −0.314 |
| 379 | 1317 | SLC31A1 | solute carrier family 31 (copper transporters), member 1 | 0.002 | 0.461 |
| 380 | 55197 | RPRD1A | regulation of nuclear pre-mRNA domain containing 1A | 0.049 | −0.322 |
| 381 | 9670 | IPO13 | importin 13 | 0.033 | −0.408 |
| 382 | 90850 | ZNF598 | zinc finger protein 598 | 0.046 | −0.34 |
| 383 | 92258 | CCDC645 | coiled-coil domain containing 64 | 0.014 | −0.474 |
| 384 | 165215 | FAM171B | family with sequence similarity 171, member B | 0.038 | 0.353 |
| 385 | 283131 | NEAT1 | nuclear paraspeckle assembly transcript 1 (non-protein coding) | 0.002 | −0.396 |
| 386 | 5202 | PFDN2 | prefoldin subunit 2 | 0.005 | −0.417 |
| 387 | 57106 | NAT14 | N-acetyltransferase 14 (GCN5-related, putative) | 0.037 | −0.399 |
| 388 | 255512 | LOC255512 | hypothetical LOC255512 | 0.039 | 0.442 |
| 389 | 123 | PLIN2 | perilipin 2 | 0.018 | 0.423 |
| 390 | 6389 | SDHA | succinate dehydrogenase complex, subunit A, flavoprotein (Fp) | 0.037 | −0.317 |
| 391 | 2577 | GAGE5 | G antigen 5 | 0.037 | 0.31 |
| 392 | 10487 | CAP1 | CAP, adenylate cyclase-associated protein 1 (yeast) | 0.033 | −0.369 |
| 393 | 79370 | BCL2L14 | BCL2-like 14 (apoptosis facilitator) | 0.012 | 0.32 |
| 394 | 2332 | FMR1 | fragile X mental retardation 1 | 0.006 | 0.436 |
| 395 | 56105 | PCDHGA11 | protocadherin gamma subfamily A, 11 | 0.014 | −0.316 |
| 396 | 3976 | LIF | leukemia inhibitory factor (cholinergic differentiation factor) | 0.01 | −0.469 |
| 397 | 8701 | DNAH11 | dynein, axonernal, heavy chain 11 | 0.012 | 0.363 |
| 398 | 58512 | DLGAP3 | discs, large (Drosophila) homolog-associated protein 3 | 0.025 | 0.361 |
| 399 | 51764 | GNG13 | guanine nucleotide binding protein (G protein), gamma 13 | 0.043 | 0.462 |
| 400 | 9043 | SPAG9 | sperm associated antigen 9 | 0.032 | −0.38 |
| 401 | 8754 | ADAM9 | ADAM metallopeptidase domain 9 | 0.037 | −0.399 |
| 402 | 57466 | SCAF4 | SR-related CTD-associated factor 4 | 0.018 | 0.32 |
| 403 | 51495 | PTPLAD1 | protein tyrosine phosohatase-like A domain containing 1 | 0.011 | −0.359 |
| 404 | 8495 | PPFIBP2 | PTPRF interacting protein, binding protein 2 (liprin beta 2) | 0.042 | −0.381 |
| 405 | 10777 | ARPP21 | cAMP-regulated phosphoprotein, 21 kDa | 0.01 | 0.324 |
| 406 | 1938 | EEF2 | eukaryotic translation elongation factor 2 | 0.019 | −0.305 |
| 407 | 6007 | RHD | Rh blood group, D antigen | 0.003 | 0.644 |
| 408 | 4363 | ABCC1 | ATP-binding cassette, sub-family C (CFTR/MRP), member 1 | 0.015 | −0.441 |

TABLE 4-continued 511 genes differentially expressed in MSC non-exposed in comparison with
cells exposed to TCM from sample 2 in comparison with non-exposed cells. The
magnitude of the expression change is represented as the logarithm of the fold change.

| | GeneID | Name | Description | PValue | Log2FC |
|---|---|---|---|---|---|
| 409 | 26585 | GREM1 | gremlin 1 | 0.02 | −0.568 |
| 410 | 492 | ATP2B3 | ATPase, Ca++ transporting, plasma membrane 3 | 0.006 | 0.358 |
| 411 | 5507 | PPP1R3C | protein phosphatase 1, regulatory (inhibitor) subunit 3C | 0.002 | 0.644 |
| 412 | 51635 | DHRS7 | dehydrogenase/reductase (SDR family) member 7 | 0.006 | −0.362 |
| 413 | 26025 | PCDHGA12 | protocadherin gamma subfamily A, 12 | 0.005 | −0.513 |
| 414 | 1808 | DPYSL2 | dihydropyrimidinase-like 2 | 0.037 | 0.355 |
| 415 | 9704 | DHX34 | DEAH (Asp-Glu-Ala-His) box polyoeptide 34 | 0.008 | 0.301 |
| 416 | 80196 | RNF34 | ring finger protein 34 | 0.016 | 0.34 |
| 417 | 26872 | STEAP1 | six transmembrane epithelial antigen of the prostate 1 | 0.015 | −0.768 |
| 418 | 23645 | PPP1R15A | protein phosphatase 1, regulatory (inhibitor) subunit 15A | <0.001 | 0.923 |
| 419 | 729171 | ANKRD20A8P | ankyrin repeat domain 20 family, member A8, pseudogene | 0.023 | 0.351 |
| 420 | 3320 | HSP90AA1 | heat shock protein 90 kDa alpha (cytosolic), class A member 1 | 0.006 | 0.505 |
| 421 | 10539 | GLRX3 | glutaredoxin 3 | 0.014 | 0.388 |
| 422 | 2585 | GALK2 | galactokinase 2 | 0.037 | −0.31 |
| 423 | 5707 | PSMD1 | proteasome (prosome, macropain) 26S subunit, non-ATPase, 1 | 0.043 | −0.756 |
| 424 | 2791 | GNG11 | guanine nucleotide binding protein (G protein), gamma 11 | 0.005 | −0.511 |
| 425 | 3371 | TNC | tenascin C | 0.015 | −0.327 |
| 426 | 5036 | PA2G4 | proliferation-associated 2G4, 38 kDa | 0.005 | 0.4 |
| 427 | 3329 | HSPD1 | heat shock 60 kDa protein 1 (chaperonin) | 0.009 | 0.398 |
| 428 | 3336 | HSPE1 | heat shock 10 kDa protein 1 (chaperonin 10) | 0.012 | −0.331 |
| 429 | 80036 | TRPM3 | transient receptor potential cation channel, subfamily M, member 3 | 0.009 | 0.368 |
| 430 | 158293 | FAM120AOS | family with sequence similarity 120A opposite strand | 0.006 | 0.376 |
| 431 | 6330 | SON4B | sodium channel, voltage-gated, type IV, beta | 0.028 | 0.421 |
| 432 | 151300 | LOC151300 | hypothetical LOC151300 | 0.018 | 0.35 |
| 433 | 63910 | SLC17A9 | solute carrier family 17, member 9 | 0.007 | 0.429 |
| 434 | 51386 | EIF3L | eukaryotic translation initiation factor 3, subunit L | <0.001 | −0.417 |
| 435 | 4728 | NDUFS8 | NADH dehydrogenase (ubiquinone) Fe-S protein 8, 23 kDa (NADH-coenzyme Q reductase) | 0.045 | 0.307 |
| 436 | 6899 | TBX1 | T-box 1 | 0.018 | −0.357 |
| 437 | 3491 | CYR61 | cysteine-rich, angiogenic inducer, 61 | <0.001 | −0.767 |
| 438 | 2730 | GCLM | glutamate-cysteine ligase, modifier subunit | 0.002 | 0.445 |
| 439 | 8438 | RAD54L | RAD54-like (S. cerevisiae) | 0.003 | 0.398 |
| 440 | 1831 | TSC22D3 | TSC22 domain family, member 3 | 0.016 | 0.359 |
| 441 | 81567 | TXNDCS | thioredoxin domain containing S (endoplasmic reticulum) | 0.016 | −0.357 |
| 442 | 5955 | RCN2 | reticulocalbin 2, EF-hand calcium binding domain | 0.013 | −0.302 |
| 443 | 523 | ATP6V1A | ATPase, H+ transporting, lysosomal 70 kDa, V1 subunit A | 0.028 | −0.319 |
| 444 | 254128 | LOC254128 | hypothetical LOC254128 | <0.001 | 0.442 |
| 445 | 9184 | BUB3 | budding uninhibited by benzimidazoles 3 homolog (yeast) | 0.032 | −0.336 |
| 446 | 9045 | RPL14 | ribosomal protein L14 | 0.049 | −0.369 |
| 447 | 402207 | LOC402207 | putative TAF11-like protein ENSP00000332601-like | 0.025 | 0.64 |
| 448 | 27245 | AHDC1 | AT hook, DNA binding motif, containing 1 | 0.029 | 0.378 |
| 449 | 10105 | PPIF | peptidylprolyl isomerase F | 0.02 | 0.338 |
| 450 | 4616 | GADD45B | growth arrest and DNA-damage-inducible, beta | 0.002 | 0.513 |
| 451 | 29081 | METTL5 | methyltransferase like 5 | 0.005 | −0.565 |
| 452 | 4071 | TM4SF1 | transmembrane 4 L six family member 1 | 0.001 | −0.46 |
| 453 | 23339 | VPS39 | vacuolar protein sorting 39 homolog (S. cerevisiae) | 0.031 | −0.36 |
| 454 | 1649 | DDIT3 | DNA-damage-inducible transcript 3 | <0.001 | 1.049 |
| 455 | 55704 | ARHGEF40 | Rho guanine nucleotide exchange factor (GEF) 40 | 0.015 | −0.355 |
| 456 | 10159 | ATP6AP2 | ATPase, H+ transporting, lysosomal accessory protein 2 | 0.024 | −0.305 |
| 457 | 5708 | PSMD2 | proteasome (prosome, macropain) 26S subunit, non-ATPase, 2 | 0.008 | −0.319 |
| 458 | 223082 | ZNRF2 | zinc and ring finger 2 | 0.03 | 0.351 |
| 459 | 64778 | FNDC38 | fibronectin type II domain containing 3B | 0.04 | −0.314 |
| 460 | 4430 | MYO1B | myosin IB | 0.032 | −0.442 |
| 461 | 11098 | PRSS23 | protease, serine, 23 | 0.019 | 0.302 |
| 462 | 2066 | ER884 | v-erb-a erythroblastic leukemia viral oncogene homolog 4 (avian) | 0.007 | 0.333 |
| 463 | 9092 | SART1 | squamous cell carcinoma antigen recognized by T cells | 0.019 | 0.374 |
| 464 | 2339 | FNTA | farnesyltransferase, CAAX box, alpha | 0.027 | −0.301 |
| 465 | 23433 | RHOQ | ras homolog gene family, member Q | 0.01 | 0.384 |
| 466 | 5230 | PGK1 | phosphoglycerate kinase 1 | 0.04 | 0.345 |
| 467 | 84231 | TRAF7 | TNF receptor-associated factor 7 | 0.026 | −0.468 |
| 468 | 9518 | GDF15 | growth differentiation factor 15 | <0.001 | 0.601 |
| 469 | 23265 | EXOC7 | exocyst complex component 7 | 0.03 | −0.305 |
| 470 | 4017 | LOXL2 | lysyl oxidase-like 2 | 0.034 | −0.407 |
| 471 | 7374 | UNG | uracil-DNA glycosylase | 0.047 | −0.313 |
| 472 | 3337 | DNAJB1 | DnaJ (Hsp40) homolog, subfamily B, member 1 | <0.001 | 0.977 |
| 473 | 729992 | ST13P1 | suppression of tumorigenicity 13 (colon carcinoma) (Hsp70 interacting protein) pseudogene 1 | 0.014 | −0.345 |
| 474 | 10777 | ARPP21 | cAMP-regulated phosphoprotein, 21 kDa | 0.006 | 0.353 |
| 475 | 1809 | DPYSL3 | dihydropyrimidinase-like 3 | 0.007 | −0.33 |
| 476 | 3480 | IGF1R | insulin-like growth factor 1 receptor | 0.002 | −0.893 |
| 477 | 51471 | NAT8B | N-acetyltransferase 8B (GCNS-related, putative, gene/pseudogene) | 0.04 | 0.395 |
| 478 | 10550 | ARL6IP5 | ADP-ribosylation-like factor 6 interacting protein 5 | 0.023 | −0.389 |
| 479 | 57092 | PCNP | PEST proteolytic signal containing nuclear protein | 0.006 | −0.338 |
| 480 | 9276 | COPB2 | coatomer protein complex, subunit beta 2 (beta prime) | 0.01 | −0.464 |

TABLE 4-continued 511 genes differentially expressed in MSC non-exposed in comparison with cells exposed to TCM from sample 2 in comparison with non-exposed cells. The magnitude of the expression change is represented as the logarithm of the fold change.

| | GeneID | Name | Description | PValue | Log2FC |
|---|---|---|---|---|---|
| 481 | 388394 | RPRML | reprimo-like | 0.008 | −0.447 |
| 482 | 51124 | IER3IP1 | immediate early response 3 interacting protein 1 | 0.003 | −0.648 |
| 483 | 7763 | ZFAND5 | zinc finger, AN1-type domain 5 | 0.019 | −0.345 |
| 484 | 11171 | STRAP | serine/threonine kinase receptor associated protein | 0.01 | −0.441 |
| 485 | 2203 | FBP1 | fructose-1,6-bisphosphatase 1 | 0.044 | −0.474 |
| 486 | 125 | ADH1B | alcohol dehydrogenase 1B (class I), beta polypeptide | 0.036 | −0.68 |
| 487 | 10494 | STK75 | serine/threonine kinase 25 | 0.008 | −0.367 |
| 488 | 285902 | LOC285902 | hypothetical LOC285902 | 0.026 | 0.454 |
| 489 | 51255 | RNF181 | ring finger protein 181 | 0.045 | −0.349 |
| 490 | 2787 | GNG5 | guanine nuceotide binding protein (6 protein), gamma 5 | 0.031 | −0.554 |
| 491 | 6319 | SCD | stearoyl-CoA desaturase (delta-9-desaturase) | 0.045 | 0.362 |
| 492 | 442582 | STAG3L2 | stromal antigen 3-like 2 | 0.046 | −0.361 |
| 493 | 9085 | CDY1 | chromodomain protein, Y-linked, 1 | 0.014 | 0.39 |
| 494 | 6443 | SGCB | sarcoglycan, beta (43 kDa dystrophin-associated glycoprotein) | 0.028 | −0.712 |
| 495 | 6347 | CCL2 | chemokine (C-C motif) ligand 2 | 0.02 | 0.465 |
| 496 | 10289 | EIF1B | eukaryotic translation initiation factor 1B | 0.023 | −0.378 |
| 497 | 51699 | VPS29 | vacuolar protein sorting 29 homolog (*S. cerevisiae*) | 0.001 | −0.546 |
| 498 | 3725 | JUN | jun proto-oncogene | 0.027 | 0.317 |
| 499 | 3476 | IG8P1 | immunoglobulin (CD79A) binding protein 1 | 0.023 | −0.363 |
| 500 | 2794 | GNL1 | guanine nucleotide binding protein-like 1 | 0.006 | −0.353 |
| 501 | 9689 | BZW1 | basic leucine zipper and W2 domains 1 | 0.047 | −0.312 |
| 502 | 5791 | PTPRE | protein tyrosine phosphatase, receptor type, E | 0.002 | −0.388 |
| 503 | 150962 | PUS10 | pseudouridylate synthase 10 | 0.007 | 0.332 |
| 504 | 409 | ARRB2 | arrestin, beta 2 | 0.046 | −0.388 |
| 505 | 5440 | POLR2K | polymerase (RNA) II (DNA directed) polypeptide K, 7.0 kDa | 0.005 | −0.396 |
| 506 | 9159 | PCSK7 | proprotein convertase subtilisin/kexin type 7 | 0.048 | −0.401 |
| 507 | 53340 | SPA17 | sperm autoantigenic protein 17 | 0.045 | −0.328 |
| 508 | 10776 | ARPP19 | cAMP-regulated phosphoprotein, 19 kDa | 0.017 | 0.474 |
| 509 | 440595 | EEF1A1P11 | eukaryotic translation elongation factor 1 alpha 1 pseudogene 11 | 0.002 | −0.402 |
| 510 | 157317 | CYCSP55 | cytochrome c, somatic pseudogene 55 | 0.023 | 0.3 |
| 511 | 6520 | SLC3A2 | solute carrier family 3 (activators of dibasic and neutral amino acid transport), member 2 | 0.002 | 0.553 |

TABLE 5

521 genes differentially expressed in MSC non-exposed in comparison with cells exposed to TCM from sample 4 in comparison with non-exposed cells. The magnitude of the expression change is represented as the logarithm of the fold change.

| | GeneID | Name | Description | PValue | Log2FC |
|---|---|---|---|---|---|
| 1 | 54769 | DIRAS2 | DIRAS family, GTP-binding RAS-like 2 | 0.016 | 0.483 |
| 2 | 1314 | COPA | coatomer protein complex, subunit alpha | 0.001 | −0.507 |
| 3 | 25912 | C1orf43 | chromosome 1 open reading frame 43 | <0.001 | −0.567 |
| 4 | 10625 | IVNS1ABP | influenza virus NS1A binding protein | 0.036 | −0.403 |
| 5 | 23516 | SLC39A14 | solute carrier family 39 (zinc transporter), member 14 | 0.001 | −0.527 |
| 6 | 11137 | PWP1 | PWP1 homolog (*S. cerevisiae*) | 0.011 | −0.35 |
| 7 | 100133941 | CD24 | CD24 molecule | <0.001 | 0.757 |
| 8 | 51375 | SNX7 | sorting nexin 7 | 0.007 | 0.748 |
| 9 | 378 | ARF4 | ADP-ribosylation factor 4 | 0.006 | −0.34 |
| 10 | 302 | ANAX2 | annexin A2 | 0.008 | 0.388 |
| 11 | 85445 | CNTNAP4 | contactin associated protein-like 4 | 0.006 | 0.445 |
| 12 | 5214 | PFKP | phosphofructokinase, platelet | 0.018 | 0.372 |
| 13 | 6782 | HSPA13 | heat shock protein 70 kDa family, member 13 | <0.001 | −1.416 |
| 14 | 817 | CAMK2D | calcium/calmodulin-dependent protein kinase II delta | 0.043 | −0.369 |
| 15 | 81626 | SHCBP1L | SHC SH2-domain binding protein 1-like | <0.001 | 0.905 |
| 16 | 2959 | GTF2B | general transcription factor IIB | 0.033 | 0.487 |
| 17 | 51278 | IER5 | immediate early response 5 | 0.008 | 0.516 |
| 18 | 54541 | DDIT4 | DNA-damage-inducible transcript 4 | <0.001 | −0.472 |
| 19 | 2199 | FBLN2 | fibulin 2 | 0.015 | 0.338 |
| 20 | 3488 | IGFBP5 | insulin-like growth factor binding protein 5 | <0.001 | 0.63 |
| 21 | 57104 | PNPLA2 | patatin-like phospholipase domain containing 2 | 0.046 | 0.887 |
| 22 | 10659 | CELF2 | CUGBP, Elav-like family member 2 | <0.001 | 0.903 |
| 23 | 635 | BHMT | betaine--homocysteine S-methyltransferase | 0.004 | 0.635 |
| 24 | 50613 | UBQLN3 | ubiquilin 3 | 0.001 | 0.57 |
| 25 | 3569 | IL6 | interleukin 6 (interferon, beta 2) | 0.024 | −0.515 |
| 26 | 1123 | CHN1 | chimerin (chimaerin) 1 | 0.046 | 0.33 |
| 27 | 6396 | SEC13 | SEC13 homolog (*S. cerevisiae*) | 0.002 | −0.557 |
| 28 | 51310 | SLC22A17 | solute carrier family 22, member 17 | 0.002 | 0.396 |
| 29 | 10938 | EHD1 | EH-domain containing 1 | 0.01 | 0.49 |
| 30 | 2657 | GDF1 | growth differentiation factor 1 | 0.026 | 0.362 |

TABLE 5-continued 521 genes differentially expressed in MSC non-exposed in comparison with cells exposed to TCM from sample 4 in comparison with non-exposed cells. The magnitude of the expression change is represented as the logarithm of the fold change.

| | GeneID | Name | Description | PValue | Log2FC |
|---|---|---|---|---|---|
| 31 | 51727 | CMPK1 | cytidine monophosphate (UMP-CMP) kinase 1, cytosolic | 0.034 | −0.317 |
| 32 | 56951 | C5orf15 | chromosome 5 open reading frame 15 | 0.003 | 0.429 |
| 33 | 3954 | LETM1 | leucine zipper-EF-hand containing transmembrane protein 1 | 0.015 | −0.323 |
| 34 | 7278 | TUBA3C | tubulin, alpha 3c | 0.004 | 0.354 |
| 35 | 2574 | GAGE2C | G antigen 2C | <0.001 | 0.722 |
| 36 | 10476 | ATP5H | ATP synthase, H+ transporting, mitochondrial Fo complex, subunit d | 0.047 | −0.315 |
| 37 | 9588 | PRDX6 | peroxiredoxin 6 | 0.049 | 0.339 |
| 38 | 5756 | TWF1 | twinfilin, actin-binding protein, homolog 1 (Drosophila) | 0.041 | −0.729 |
| 39 | 3091 | HIF1A | hypoxia inducible factor 1, alpha subunit (basic helix-loop-helix transcription factor) | <0.001 | −0.808 |
| 40 | 8404 | SPARCL1 | SPARC-like 1 (hevin) | <0.001 | 0.82 |
| 41 | 55062 | WIPI1 | WD repeat domain, phosphoinositide interacting 1 | <0.001 | −0.729 |
| 42 | 55273 | TMEM100 | transmembrane protein 100 | 0.029 | 0.523 |
| 43 | 29116 | MYLIP | myosin regulatory light chain interacting protein | 0.003 | 0.53 |
| 44 | 55907 | CMAS | cytidine monophosphate N-acetylneuraminic acid synthetase | 0.027 | 0.36 |
| 45 | 4809 | NHP2L1 | NHP2 non-histone chromosome protein 2-like 1 (S. cerevisiae) | 0.017 | 0.38 |
| 46 | 1672 | DEFB1 | defensin, beta 1 | <0.001 | 0.679 |
| 47 | 11145 | PLA2G16 | phospholipase A2, group XVI | 0.003 | 0.436 |
| 48 | 10769 | PLK2 | polo-like kinase 2 | <0.001 | 0.684 |
| 49 | 10618 | TGOLN2 | trans-golgi network protein 2 | 0.03 | 0.427 |
| 50 | 10814 | CPLX2 | complexin 2 | 0.013 | 0.379 |
| 51 | 2191 | FAP | fibroblast activation protein, alpha | 0.007 | −0.424 |
| 52 | 90507 | SCRN2 | secernin 2 | 0.043 | 0.37 |
| 53 | 386677 | KRTAP10-1 | keratin associated protein 10-1 | 0.008 | −0.367 |
| 54 | 1912 | PHC2 | polyhomeotic homolog 2 (Drosophila) | 0.046 | −0.466 |
| 55 | 2969 | GTF2I | general transcription factor III | 0.041 | 0.318 |
| 56 | 8894 | EIF2S2 | eukaryotic translation initiation factor, subunit 2 beta, 38 kDa | 0.012 | −0.668 |
| 57 | 79630 | C1orf54 | chromosome 1 open reading frame 54 | 0.044 | −0.448 |
| 58 | 10099 | TSPAN3 | tetraspanin 3 | 0.025 | 0.339 |
| 59 | 3486 | IGF8P3 | insulin-like growth factor binding protein 3 | 0.004 | 0.453 |
| 60 | 8943 | AP3D1 | adaptor-related protein complex 3, delta 1 subunit | 0.006 | −0.319 |
| 61 | 467 | ATF3 | activating transcription factor 3 | <0.001 | 0.801 |
| 62 | 54704 | PDP1 | pyruvate dehydrogenase phosphatase catalytic subunit 1 | 0.03 | 0.384 |
| 63 | 90411 | MCFD2 | multiple coagulation factor deficiency 2 | 0.013 | −0.414 |
| 64 | 4141 | MARS | methionyl-tRNA synthetase | 0.004 | −0.446 |
| 65 | 54996 | MOSC2 | MOCO sulphurase C-terminal domain containing 2 | 0.018 | 0.583 |
| 66 | 7127 | TNFAIP2 | tumor necrosis factor, alpha-induced protein | <0.001 | 1.116 |
| 67 | 54600 | UGT1A9 | UDP glucuronosyltransferase 1 family, polypeptide A9 | 0.002 | 0.523 |
| 68 | 23471 | TRAM1 | translocation associated membrane protein 1 | 0.005 | −0.513 |
| 69 | 64065 | PERP | PERP, TP53 apoptosis effector | 0.014 | 0.413 |
| 70 | 10135 | NAMPT | nicotinamide phosphoribosyltransferase | <0.001 | −1.102 |
| 71 | 4637 | MYL6 | myosin, light chain 6, alkali, smooth muscle and non-muscle | 0.002 | 0.338 |
| 72 | 389493 | LOC389493 | hypothetical protein LOC389493 | 0.035 | 0.576 |
| 73 | 3295 | HSD17B4 | hydroxysteroid (17-beta) dehydrogenase 4 | <0.001 | −0.726 |
| 74 | 112936 | VPS268 | vacuolar protein sorting 26 homolog B (S. pombe) | 0.019 | 0.527 |
| 75 | 58515 | SELK | selenoprotein K | <0.001 | −0.514 |
| 76 | 4739 | NEDD9 | neural precursor cell expressed, developmentally down-regulated 9 | 0.012 | 0.495 |
| 77 | 10808 | HSPH1 | heat shock 105 kDa/110 kDa protein 1 | 0.011 | 0.359 |
| 78 | 60685 | ZFAND3 | zinc finger, AN1-type domain 3 | 0.005 | −0.413 |
| 79 | 64208 | POPDC3 | popeye domain containing 3 | 0.044 | −0.41 |
| 80 | 3399 | ID3 | inhibitor of DNA binding 3, dominant negative helix-loop-helix protein | <0.001 | 0.659 |
| 81 | 8092 | ALX1 | ALX homeobox 1 | 0.043 | −0.449 |
| 82 | 8480 | RAE1 | RAE1 RNA export 1 homolog (S. pombe) | 0.005 | 0.488 |
| 83 | 813 | CALU | calumenin | 0.023 | −0.407 |
| 84 | 4190 | MDH1 | malate dehydrogenase 1, NAD (soluble) | 0.021 | 0.308 |
| 85 | 23562 | CLDN14 | claudin 14 | 0.006 | −0.575 |
| 86 | 7184 | HSP90B1 | heat shock protein 90 kDa beta (Grp94), member 1 | <0.001 | −0.603 |
| 87 | 6418 | SET | SET nuclear oncogene | 0.045 | 0.316 |
| 88 | 3376 | IARS | isoleucyl-tRNA synthetase | <0.001 | −0.663 |
| 89 | 92140 | MTDH | metadherin | 0.002 | −0.496 |
| 90 | 8321 | F2D1 | frizzled homolog 1 (Drosophila) | 0.006 | 0.582 |
| 91 | 5270 | SERPINE2 | serpin peptidase inhibitor, clade E (nexin, plasminogen activator inhibitor type 1), member 2 | 0.008 | −0.373 |
| 92 | 55829 | SELS | selenoprotein S | <0.001 | −0.604 |
| 93 | 25907 | TMEM158 | transmembrane protein 158 (gene/pseudogene) | 0.004 | −0.673 |
| 94 | 1003 | CDH5 | cadherin 5, type 2 (vascular endothelium) | <0.001 | 0.969 |
| 95 | 9919 | SEC16A | SEC16 homolog A (S. cerevisiae) | 0.017 | −0.325 |
| 96 | 9531 | BAG3 | BCL2-associated athanogene 3 | 0.021 | 0.349 |
| 97 | 79696 | FAM164C | family with sequence similarity 164, member C | 0.032 | 0.413 |
| 98 | 2824 | GPM6B | glycoprotein M6B | <0.001 | 0.643 |
| 99 | 478 | ATP1A3 | ATPase, Na+/K+ transporting, alpha 3 polypeptide | 0.034 | 0.454 |
| 100 | 338799 | LOC338799 | hypothetical LOC338799 | 0.025 | −0.347 |
| 101 | 9261 | MAPKAPK2 | mitogen-activated protein kinase-activated protein kinase 2 | 0.031 | 0.369 |
| 102 | 158056 | MAMDC4 | MAM domain containing 4 | 0.034 | −0.366 |

TABLE 5-continued 521 genes differentially expressed in MSC non-exposed in comparison with cells exposed to TCM from sample 4 in comparison with non-exposed cells. The magnitude of the expression change is represented as the logarithm of the fold change.

| | GeneID | Name | Description | PValue | Log2FC |
|---|---|---|---|---|---|
| 103 | 5908 | RAP1B | RAP1B, member of RAS oncogene family | 0.014 | −0.315 |
| 104 | 3313 | HSPA9 | heat shock 70 kDa protein 9 (mortalin) | <0.001 | −0.595 |
| 105 | 2578 | GAGE6 | G antigen 6 | 0.03 | 0.411 |
| 106 | 3336 | HSPE1 | heat shock 10 kDa protein 1 (chaperosin 10) | 0.004 | 0.516 |
| 107 | 441533 | RPL26P37 | ribosomal protein L26 pseudogene 37 | 0.022 | −0.312 |
| 108 | 10987 | COPS5 | COP constitutive photomorphogenic homolog subunit 5 (Arabidopsis) | 0.041 | 0.337 |
| 109 | 23648 | SSBP3 | single stranded DNA binding protein 3 | 0.038 | −0.308 |
| 110 | 55964 | SEPT3 | septin 3 | 0.008 | 0.475 |
| 111 | 2353 | FOS | FBJ murine osteosarcoma viral oncogene homolog | 0.004 | 0.464 |
| 112 | 55228 | PNMAL1 | PNMA-like 1 | 0.001 | 0.764 |
| 113 | 3306 | HSPA2 | heat shock 70 kDa protein 2 | 0.007 | 0.49 |
| 114 | 57222 | ERGIC1 | endoplasmic reticulum-golgi intermediate compartment (ERGIC) 1 | 0.033 | −0.328 |
| 115 | 51727 | CMPK1 | cytidine monophosphate (UMP-CMP) kinase 1, cytosolic | 0.035 | −0.383 |
| 116 | 8566 | PDXK | pyridoxal (pyridoxine, vitamin B6) kinase | 0.007 | 0.397 |
| 117 | 3703 | STT3A | STT3, subunit of the oligosaccharyltransferase complex, homolog A (S. cerevisiae) | <0.001 | −0.54 |
| 118 | 55182 | RNF220 | ring finger protein 220 | 0.047 | 0.465 |
| 119 | 4884 | NPTX1 | neuronal pentraxin I | 0.001 | 0.697 |
| 120 | 7485 | WRB | tryptophan rich basic protein | 0.021 | 0.38 |
| 121 | 3397 | ID1 | inhibitor of DNA binding 1, dominant negative helix-loop-helix protein | 0.006 | 0.317 |
| 122 | 1611 | DAP | death-associated protein | 0.046 | −0.436 |
| 123 | 391165 | RPS26P17 | ribosomal protein S26 pseudogene 17 | 0.02 | 0.351 |
| 124 | 79039 | DDX54 | DEAD (Asp-Glu-Ala-Asp) box polypepticle 54 | 0.018 | −0.316 |
| 125 | 8985 | PLOD3 | procollagen-lysine, 2-oxoglutarate 5-dioxygenase 3 | 0.028 | −0.432 |
| 126 | 28964 | GIT1 | G protein-coupled receptor kinase interacting ArfGAP 1 | <0.001 | −0.516 |
| 127 | 2496 | FTH1P1 | ferritin, heavy polypeptide 1 pseudogene | 0.01 | −0.326 |
| 128 | 1164 | CKS2 | CDC28 protein kinase regulatory subunit | <0.001 | 0.638 |
| 129 | 8662 | EIF3B | eukaryotic translation initiation factor 3, subunit B | 0.014 | −0.378 |
| 130 | 51014 | TMED7 | transmembrane emp24 protein transport domain containing 7 | 0.013 | −0.374 |
| 131 | 1513 | CTSK | cathepsin K | 0.013 | 0.387 |
| 132 | 7546 | ZIC2 | Zic family member (odd-paired homolog, Drosophila) | 0.044 | 0.433 |
| 133 | 1266 | CNN3 | calponin 3, acidic | <0.001 | 0.432 |
| 134 | 81552 | VOPP1 | vesicular, overexpressed in cancer, prosurvival protein 1 | 0.033 | 0.314 |
| 135 | 23209 | MLC1 | megalencephalic leukoencephalopathy with subcortical cysts 1 | 0.019 | 0.465 |
| 136 | 6472 | SHMT2 | serine hydroxymethyltransferase 2 (mitochondrial) | 0.017 | −0.46 |
| 137 | 51081 | MRPS7 | mitochondrial ribosomal protein S7 | 0.002 | 0.36 |
| 138 | 665 | BNIP3L | BCL2/adenovirus E1B 19 kDa interacting protein 3-like | 0.004 | −0.398 |
| 139 | 3032 | HADHB | hydroxyacyl-CoA dehydrogenase/3-ketoacyl-CoA thialase/enoyl-CoA hydratase (trifunctional protein), beta subunit | 0.003 | −0.38 |
| 140 | 4493 | MT1E | metallothionein 1E | 0.049 | −0.322 |
| 141 | 3301 | DNAJA1 | DnaJ (Hsp40) homolog, subfamily A, member 1 | <0.001 | 0.654 |
| 142 | 9315 | C5orf13 | chromosome 5 open reading frame 13 | <0.001 | 0.51 |
| 143 | 7102 | TSPAN7 | tetraspanin 7 | 0.034 | 0.411 |
| 144 | 4783 | NFIL3 | nuclear factor, interleukin 3 regulated | 0.03 | −0.348 |
| 145 | 81669 | CCNL2 | cyclin L2 | 0.005 | −0.361 |
| 146 | 81892 | C14orf156 | chromosome 14 open reading frame 156 | 0.006 | −0.354 |
| 147 | 813 | CALU | calumenin | 0.001 | −0.656 |
| 148 | 23352 | UBR4 | ubiquitin protein ligase E3 component n-recognin 4 | 0.002 | −0.44 |
| 149 | 113246 | C12orf57 | chromosome 12 open reading frame 57 | 0.04 | −0.313 |
| 150 | 2697 | GJA1 | gap junction protein, alpha 1, 43 kDa | 0.023 | −0.469 |
| 151 | 10439 | OLFM1 | olfactomedin 1 | 0.027 | 0.39 |
| 152 | 83692 | CD99L2 | CD99 molecule 0.008 | 0.323 | |
| 153 | 7175 | TPR | translocated promoter region (to activated MET oncogene) | 0.008 | 0.495 |
| 154 | 25840 | METTL7A | methyltransferase like 7A | 0.036 | 0.413 |
| 155 | 26528 | DAZAP1 | DAZ associated protein 1 | 0.02 | 0.413 |
| 156 | 10484 | SEC23A | Sec23 homolog A (S. cerevisiae) | 0.045 | −0.312 |
| 157 | 7058 | THBS2 | thrombospondin 2 | 0.008 | −0.399 |
| 158 | 9452 | ITM2A | integral membrane protein 2A | 0.002 | 0.769 |
| 159 | 65055 | REEP1 | receptor accessory protein 1 | <0.001 | 0.604 |
| 160 | 9581 | PREPL | prolyl endopeptidase-like | 0.028 | 0.711 |
| 161 | 79791 | FBXO31 | F-box protein 31 | 0.013 | 0.367 |
| 162 | 3936 | LCP1 | lymphocyte cytosolic protein 1 (L- lastin) | <0.001 | 0.89 |
| 163 | 9536 | PTGES | prostaglandin E synthase | 0.012 | −0.623 |
| 164 | 83657 | DYNLRB2 | dynein, light chain, roadblock-type 2 | 0.02 | 0.357 |
| 165 | 6892 | TAPBP | TAP binding protein (tapasin) | 0.005 | 0.379 |
| 166 | 10797 | MTFHD2 | methylenetetrahydrofolate dehydrogenase (NADP+ dependent) 2, methenyltetrahydrofolate cyclohydrolase | 0.004 | −0.401 |
| 167 | 26749 | GAGE2E | G antigen 2E | 0.016 | 0.373 |
| 168 | 231 | AKR1B1 | aldo-keto reductase family 1, member B1 (aldose reductase) | <0.001 | −0.473 |
| 169 | 6175 | RPLP0 | ribosomal protein, large, P0 | 0.003 | −0.319 |
| 170 | 501 | ALDH7A1 | aldehyde dehydrogenase 7 family, member A1 | 0.028 | −0.335 |
| 171 | 4358 | MPV17 | MpV17 mitochondrial inner membrane protein | 0.02 | −0.336 |
| 172 | 54881 | TEX10 | testis expressed 10 | 0.011 | −0.39 |
| 173 | 60312 | AFAP1 | actin filament associated protein 1 | 0.023 | −0.381 |

TABLE 5-continued 521 genes differentially expressed in MSC non-exposed in comparison with cells exposed to TCM from sample 4 in comparison with non-exposed cells. The magnitude of the expression change is represented as the logarithm of the fold change.

|     | GeneID | Name | Description | PValue | Log2FC |
| --- | --- | --- | --- | --- | --- |
| 174 | 291 | SLC25A4 | solute carrier family 25 (mitochondrial carrier adenine nucleotide translocator), member 4 | 0.012 | 0.339 |
| 175 | 10472 | ZNF238 | zinc finger protein 238 | 0.049 | 0.353 |
| 176 | 1164 | CKS2 | CDC28 protein kinase regulatory subunit 2 | <0.001 | 0.394 |
| 177 | 4710 | NDUF134 | NADH dehydrogenase (ubiquinone) 1 beta subcomplex, 4 15 kDa | 0.018 | −0.363 |
| 178 | 653639 | LYPLA2P1 | lysophospholipase II pseuclogene 1 | 0.033 | −0.376 |
| 179 | 51616 | TAF9B | TAF9B RNA polymerase II, TATA box binding protein (TBP)-associated factor, 31 kDa | 0.026 | 0.374 |
| 180 | 55829 | SELS | selenoprotein S | 0.004 | −0.394 |
| 181 | 8802 | SUCLG1 | succinate-CoA ligase, alpha subunit | 0.017 | 0.365 |
| 182 | 196 | AHR | aryl hydrocarbon receptor | 0.042 | −0.367 |
| 183 | 11100 | HNRNPLU1 | heterogeneous nuclear ribonucleoprotein U-like 1 | 0.006 | −0.33 |
| 184 | 7184 | HSP90B1 | heat shock protein 90 kDa beta (Grp94), member 1 | 0.009 | −0.321 |
| 185 | 51693 | TRAPPC2L | trafficking protein particle complex 2-like | 0.008 | −0.467 |
| 186 | 7930 | TFPI2 | tissue factor pathway inhibitor 2 | <0.001 | −1.357 |
| 187 | 25 | ABL1 | c-abi oncogene 1, non receptor tyrosine kinase | 0.004 | −0.351 |
| 188 | 51655 | RASD1 | RAS, dexamethasone-induced 1 | 0.001 | −0.513 |
| 189 | 821 | CANX | calnexin | <0.001 | −0.664 |
| 190 | 27288 | RBMXL2 | RNA binding motif protein, X-linked-like 2 | 0.03 | 0.424 |
| 191 | 83955 | NACAP1 | nascent-polypeptide-associated complex alpha polypeptide pseudogene 1 | 0.01 | −0.445 |
| 192 | 9689 | BZW1 | basic leucine zipper and W2 domains 1 | <0.001 | −0.587 |
| 193 | 6387 | CXCL12 | chemokine (C-X-C motif) ligand 12 | 0.008 | 0.399 |
| 194 | 11031 | RAB31 | RAB31, member RAS oncogene family | 0.046 | −0.331 |
| 195 | 7873 | MANF | mesencephalic astrocyte-derived neurotrophic factor | <0.001 | −0.658 |
| 196 | 3476 | IGBP1 | immunoglobulin (CD79A) binding protein 1 | 0.005 | −0.395 |
| 197 | 5791 | PTPRE | protein tyrosine phosphatase, receptor type, E | 0.001 | −0.458 |
| 198 | 9690 | U8E3C | ubiquitin protein ligase E3C | 0.002 | −0.512 |
| 199 | 84935 | C13orf33 | chromosome 13 open reading frame 33 | 0.008 | −0.367 |
| 200 | 6734 | SRPR | signal recognition particle receptor (docking protein) | <0.001 | −0.534 |
| 201 | 445 | ASS1 | argininosuccinate synthase 1 | 0.028 | −0.402 |
| 202 | 3312 | HSPA8 | heat shock 70 kDa protein 8 | 0.001 | 0.394 |
| 203 | 8553 | BHLHE40 | basic helix-icop-helix family, member e40 | 0.003 | 0.404 |
| 204 | 79770 | TXNDC15 | thioredoxin domain containing 15 | 0.018 | −0.373 |
| 205 | 84525 | HOPX | HOP homeobox | 0.015 | 0.505 |
| 206 | 10079 | ATP9A | ATPase, class II, type 9A | 0.015 | −0.337 |
| 207 | 267 | AMFR | autocrine motility factor receptor | <0.001 | −0.543 |
| 208 | 694 | BTG1 | B-cell translocation gene 1, anti-proliferative | 0.004 | −0.329 |
| 209 | 6281 | S100A10 | S100 calcium binding protein A10 | 0.005 | 0.357 |
| 210 | 2939 | GSTA2 | glutathione S-transferase alpha 2 | 0.01 | 0.452 |
| 211 | 151579 | BZW1P2 | basic leucine zipper and W2 domains 1 pseudogene 2 | <0.001 | −0.59 |
| 212 | 51669 | TMEM66 | transmembrane protein 66 | <0.001 | −0.42 |
| 213 | 56113 | PCDHGA2 | protocadherin gamma subfamily A, 2 | 0.048 | −0.305 |
| 214 | 150372 | NFAM1 | NFAT activating protein with ITAM motif 1 | 0.011 | −0.302 |
| 215 | 442454 | LOC442454 | ubiqunol-cytochrome c reductase binding protein pseudogene | 0.047 | −0.346 |
| 216 | 8894 | EIF2S2 | eukaryotic translation initiation factor , subunit 2 beta. 38 kDa | <0.001 | −0.447 |
| 217 | 4553 | TRNA | tRNA | 0.005 | 0.499 |
| 218 | 283820 | NOMO2 | NODAL modulator 2 | 0.003 | −0.323 |
| 219 | 858 | CAV2 | caveolin 2 | 0.001 | 0.493 |
| 220 | 55002 | TMCO3 | transmembrane and coiled-coil domains 3 | <0.001 | −0.459 |
| 221 | 4179 | CD46 | CD46 molecule, complement regulatory protein | 0.007 | −0.421 |
| 222 | 29015 | SLC43A3 | solute carrier family 43 member 3 | 0.014 | −0.442 |
| 223 | 2058 | EPRS | glutamyl-prolyl-tRNA synthetase | 0.006 | −0.485 |
| 224 | 10237 | SLC35B1 | solute carrier family 35, member B1 | 0.004 | −0.468 |
| 225 | 10113 | PREB | prolactin regulatory element binding | <0.001 | −0.521 |
| 226 | 58986 | TMEM8A | transmembrane protein 8A | 0.03 | −0.43 |
| 227 | 10730 | YME1L1 | YME1-like 1 (*S. cerevisiae*) | 0.01 | −0.451 |
| 228 | 27044 | SND1 | staphylococcal nuclease and tudor domain containing 1 | 0.009 | −0.476 |
| 229 | 83548 | COG3 | component of oligomeric golgi complex 3 | 0.023 | −0.387 |
| 230 | 5539 | PPY | pancreatic polypeptide | 0.043 | 0.766 |
| 231 | 1979 | EIF4EBP2 | eukaryotic translation initiation factor 4E binding protein 2 | 0.046 | 0.367 |
| 232 | 7196 | TRNAG2 | transfer RNA glycine 2 (anticodon GCC | 0.021 | −0.638 |
| 233 | 23384 | SPECC1L | sperm antigen with calponin homology and coiled-coil domains 1-like | 0.025 | −0.364 |
| 234 | 2581 | GALC | galactosylceramidase | 0.029 | −0.548 |
| 235 | 4311 | MME | membrane metailo-endopeptidase | 0.006 | −0.358 |
| 236 | 857 | CAV1 | caveolin 1, caveolae protein, 22 kDa | 0.001 | 0.394 |
| 237 | 84961 | FBXL20 | F-box and leucine-rich repeat protein 20 | 0.009 | −0.492 |
| 238 | 10130 | PDIA6 | protein disulfide isomerase family A, member 6 | <0.001 | −0.533 |
| 239 | 1462 | VCAN | versican | 0.028 | 0.364 |
| 240 | 2926 | GRSF1 | G-rich RNA sequence binding factor 1 | 0.002 | −0.383 |
| 241 | 84270 | C9orf89 | chromosome 9 open reading frame 89 | <0.001 | −0.493 |
| 242 | 341032 | C11orf53 | chromosome 11 open reading frame 53 | 0.033 | −0.436 |
| 243 | 4191 | MDH2 | malate dehydrogenase 2, NAD (mitochondrial) | 0.004 | −0.308 |
| 244 | 7979 | SHFM1 | split hand/foot malformation (ectrodactyly) type 1 | 0.03 | 0.37 |
| 245 | 51458 | RHCG | Rh family, C glycoprotein | 0.012 | 0.369 |

TABLE 5-continued 521 genes differentially expressed in MSC non-exposed in comparison with cells exposed to TCM from sample 4 in comparison with non-exposed cells. The magnitude of the expression change is represented as the logarithm of the fold change.

| | GeneID | Name | Description | PValue | Log2FC |
|---|---|---|---|---|---|
| 246 | 441198 | LOC441198 | similar to Heat shock cogntate 71 kDa protein | 0.01 | 0.351 |
| 247 | 29982 | NRBF2 | nuclear receptor binding factor | 0.001 | −0.361 |
| 248 | 23546 | SYNGR4 | synaptogyrin 4 | 0.028 | 0.352 |
| 249 | 3304 | HSPA1B | heat shock 70 kDa protein B | 0.001 | 0.505 |
| 250 | 57580 | PREX1 | phosphatidylinositol-3,4,5-trisphosphate-dependent Rac exchange factor 1 | 0.022 | −0.401 |
| 251 | 56005 | C19orf10 | chromosome 19 open reading frame 10 | 0.006 | −0.356 |
| 252 | 9326 | ZNHIT3 | zinc finger, HIT-type containing 3 | 0.03 | −0.304 |
| 253 | 65980 | BRD9 | bromodomain containing 9 | 0.002 | −0.51 |
| 254 | 58515 | SELK | selenoprotein K | <0.001 | −0.785 |
| 255 | 84866 | TMEM25 | transmembrane protein 25 | 0.005 | −0.386 |
| 256 | 51009 | DERL2 | Der-like domain family, member 2 | <0.001 | −0.603 |
| 257 | 5886 | RAD23A | RAD23 homolog A (S. cerevisiae) | 0.038 | −0.332 |
| 258 | 304 | ANXA2P2 | annexin A2 pseudogene 2 | 0.023 | 0.313 |
| 259 | 253832 | ZDHHC20 | zinc finger, DHHC-type containing 20 | 0.003 | −0.511 |
| 260 | 376267 | RAB15 | RAB15, member RAS onocogene family | 0.02 | −0.425 |
| 261 | 79139 | DERL1 | Der1-like domain family, member 1 | 0.004 | −0.534 |
| 262 | 376497 | SLC27A1 | solute carrier family 27 (fatty acid transporter), member 1 | 0.019 | −0.343 |
| 263 | 58472 | SQRDL | sulfide quinone reductase-like (yeast) | 0.028 | −0.376 |
| 264 | 9810 | RNF40 | ring finger protein 40 | 0.044 | −0.3 |
| 265 | 10959 | TMED2 | transmembrane emp24 domain trafficking protein 2 | 0.002 | −0.434 |
| 266 | 200316 | APOBEC3F | apolipoprotein B mRNA editing enzyme, catalytic poiypeptide-like 3F | 0.046 | −0.36 |
| 267 | 1645 | AKR1C1 | aldo-keto reductase family 1, member C1 (dihydrodiol dehydrogenase 1; 20-alpha (3-alpha)-hydroxysteroid dehydrogenase) | 0.006 | −0.579 |
| 268 | 10383 | TUBB2C | tubulin beta 2C | <0.001 | 0.421 |
| 269 | S1030 | FAM1881 | family with sequence similarity 18, member 81 | <0.003 | −0.56 |
| 270 | 29781 | NCAPH2 | non-SMC condensin II complex, subunit H2 | 0.012 | −0.511 |
| 271 | 1153 | CIRBP | cold inducible RNA binding protein | 0.02 | −0.306 |
| 272 | 6303 | SAT1 | spermidine/spermine N1-acetyltransferase 1 | <0.001 | −0.615 |
| 273 | 10620 | ARID3B | AT rich interactive domain 3B (BRIGHT-like) | 0.025 | −1.399 |
| 274 | 22936 | ELL2 | elongation factor, RNA polymerase II, 2 | 0.003 | −0.372 |
| 275 | 26262 | TSPAN17 | tetraspanin 17 | 0.032 | −0.34 |
| 276 | 149428 | BNIPL | BCL2/adenovirus E1B 19kD interacting protein like | 0.027 | 0.33 |
| 277 | 5111 | PCNA | proliferating cell nuclear antigen | 0.028 | 0.43 |
| 278 | 1827 | RCAN1 | regulator of calcineurin 1 | <0.001 | −0.555 |
| 279 | 92140 | MTDH | metadherin | 0.005 | −0.412 |
| 280 | 56674 | TMEM9B | TMEM9 domain family, member 8 | 0.034 | 0.325 |
| 281 | 5916 | RARG | retinoic acid receptor, gamma | 0.046 | −0.425 |
| 282 | 51569 | UFM1 | ubiquitin-fold modifier 1 | 0.002 | −0.763 |
| 283 | 400 | ARL1 | ADP-ribosylation factor-like 1 | 0.032 | −0.5 |
| 284 | 10952 | SEC61B | Sec61 beta subunit | 0.002 | −0.416 |
| 285 | 729148 | NUS1P1 | nuclear undecaprenyl pyrophosphate synthase 1 homolog (S. cerevisiae) pseudogene 1 | 0.011 | −0.451 |
| 286 | 9315 | C5orf13 | chromosome 5 open reading frame 13 | 0.002 | 0.388 |
| 287 | 130535 | KCTD18 | potassium channel tetramerisation domain containing 18 | 0.039 | −0.354 |
| 288 | 5611 | DNAJC3 | DnaJ (Hsp40) homolog, subfamily C, member 3 | <0.001 | −1.192 |
| 289 | 54808 | DYM | dymeclin | 0.003 | −0.34 |
| 290 | 51652 | VPS24 | vacuolar protein sorting 24 homolog (S. cerevisiae) | 0.007 | 0.345 |
| 291 | 9527 | GOSR1 | golgi SNAP receptor complex member 1 | 0.013 | −0.45 |
| 292 | 64215 | DNAJC1 | DnaJ (Hsp40) homolog, subfamily C, member 1 | <0.001 | −0.626 |
| 293 | 4170 | MCL1 | myeloid cell leukemia sequence 1 (BCL2-related) | <0.001 | 0.46 |
| 294 | 29927 | SEC61A1 | Sec61 alpha 1 subunit (S. cerevisiae) | <0.001 | −0.686 |
| 295 | 10123 | ARL4C | ADP-ribosylation factor-like 4C | 0.004 | 0.417 |
| 296 | 516 | ATP5G1 | ATP synthase, H+ transporting, mitochondrial Fo complex, subunit C1 (subunit 9) | 0.009 | −0.414 |
| 297 | 337973 | KRTAP19-6 | keratin associated protein 19-6 | 0.039 | −0.304 |
| 298 | 3324 | HSP90AA2 | heat shock proten 90 kDa alpha (cytosolic), class A member | 0.001 | 0.432 |
| 299 | 57092 | PCNP | PEST proteolytic signal containing nuciear protein | 0.019 | −0.329 |
| 300 | 339122 | RAB43 | RAB43, member RAS oncogene family | 0.003 | −0.623 |
| 301 | 54538 | ROBO4 | roundabout homolog 4, magic roundabout (Drosophila) | 0.028 | 0.388 |
| 302 | 7280 | TUBB2A | tubulin, beta 2A | <0.001 | 0.566 |
| 303 | 5168 | ENPP2 | ectonucleotide pyrophosphatase/phosphodiesterase 2 | 0.006 | 0.409 |
| 304 | 1116 | CHI3L3 | chitinase 3-like1 (cartliage glycoprotein-39) | 0.015 | −0.315 |
| 305 | 4256 | MGP | matrix Gla protein | 0.021 | 0.325 |
| 306 | 81621 | KAZALD1 | Kazal-type serine peptidase inhibitor domain 1 | 0.035 | −0.388 |
| 307 | 3930 | LBR | lamin B receptor | 0.026 | 0.414 |
| 308 | 5638 | PRRG1 | proline rich Gla (G-carboxyglutamic acid) 1 | <0.001 | −0.638 |
| 309 | 27309 | ZNF330 | zinc finger protein 330 | 0.044 | 0.488 |
| 310 | 23451 | SF3B1 | splicing factor 3b, subunit 1, 155 kDa | 0.006 | −0.32 |
| 311 | 5684 | PSMA3 | proteasome (prosome, macropain) subunit, alpha type, 3 | 0.003 | −0.337 |
| 312 | 8537 | BCAS1 | breast carcinoma amplified sequence 1 | 0.017 | 0.329 |
| 313 | 133619 | PRRC1 | proline-rich coiled-coil 1 | 0.05 | −0.306 |
| 314 | 57570 | TRMT5 | TRM5 tRNA methyltransferase 5 homolog (S. cerevisiae) | 0.003 | 0.357 |
| 315 | 1073 | CFL2 | cofilin 2 (muscle) | 0.019 | −0.344 |

TABLE 5-continued 521 genes differentially expressed in MSC non-exposed in comparison with cells exposed to TCM from sample 4 in comparison with non-exposed cells. The magnitude of the expression change is represented as the logarithm of the fold change.

| | GeneID | Name | Description | PValue | Log2FC |
|---|---|---|---|---|---|
| 316 | 115207 | KCTD12 | potassium channel tetramerisation domain containing 12 | 0.048 | 0.389 |
| 317 | 8577 | TMEFF1 | transmembrane protein with EGF-like and two follistatin-like domains 1 | 0.019 | −0.395 |
| 318 | 57798 | GATAD1 | GATA zinc finger domain containing 1 | 0.023 | −0.304 |
| 319 | 201595 | STT3B | STT3, subunit of the oligosaccharyltransferase complex, homolog B (*S. cerevisiae*) | 0.022 | −0.367 |
| 320 | 3303 | HSPA1A | heat shock 70 kDa protein 1A | 0.002 | 0.652 |
| 321 | 27332 | ZNF638 | zinc finger protein 638 | 0.045 | −0.392 |
| 322 | 4314 | MMP3 | matrix metallopeptidase 3 (stromelysin 1, progelatinase) | 0.035 | −0.398 |
| 323 | 84272 | YIPF4 | Yip1 domain family, member 4 | 0.001 | −0.583 |
| 324 | 65108 | MARCKSL1 | MARCKS-like 1 | 0.01 | 0.346 |
| 325 | 284257 | BOD1P | biorientation of chromosomes in cell division 1 pseudogene | 0.027 | 0.37 |
| 326 | 51454 | GULP1 | GULP, engulfment adaptor PTB domain containing 1 | 0.002 | −0.647 |
| 327 | 949 | SCARB1 | scavenger receptor class B, member 1 | 0.004 | −0.361 |
| 328 | 9709 | HERPUD1 | homocystaine-inducible, endoplasmic reticulum stress-inducible, ubiquitin-like domain member 1 | <0.001 | −0.48 |
| 329 | 2195 | FAT1 | FAT tumor suppressor homolog 1 (*Drosophila*) | 0.011 | 0.423 |
| 330 | 135138 | PACRG | PARK2 co-regulated | 0.045 | 0.412 |
| 331 | 10980 | COPS6 | COP9 constitutive photomorphogenic homolog subunit 6 (*Arabidopsis*) | 0.043 | −0.343 |
| 332 | 81502 | HM13 | histocompatibility (minor) 13 | <0.001 | −0.383 |
| 333 | 85302 | FBF1 | Fas (TNFRSF6) binding factor 1 | 0.011 | 0.31 |
| 334 | 55329 | SELS | selenoprotein S | 0.01 | −0.456 |
| 335 | 55154 | MSTO1 | misato homolog 1 (*Drosophila*) | 0.01 | −0.387 |
| 336 | 29058 | C20orf30 | chromosome 20 open reading frame 30 | 0.007 | −0.357 |
| 337 | 6428 | SRSF3 | serine/arginine-rich splicing factor 3 | 0.001 | 0.397 |
| 338 | 55920 | RCC2 | regulator of chromosome condensation 2 | 0.011 | 0.318 |
| 339 | 92086 | GGTLC1 | gamma-glutamyltransferase light chain 1 | 0.008 | −0.338 |
| 340 | 3295 | HSD17B4 | hydroxysteroid (17-beta) dehydrogenase 4 | 0.004 | −0.635 |
| 341 | 23296 | SCFD1 | sec1 family domain containing 1 | 0.008 | −0.392 |
| 342 | 5479 | PPIB | peptidylprolyl isomerase B (cyclophilin 8) | <0.001 | −0.61 |
| 343 | 79174 | CRELD2 | cysteine-rich with EGF-like domains 2 | <0.001 | −0.928 |
| 344 | 124685 | LOC124685 | hCG1644301 | 0.026 | 0.322 |
| 345 | S1043 | ZBTB7B | zinc finger and BTB domain containing 7B | 0.02 | −0.311 |
| 346 | 2576 | GAGE4 | G antigen 4 | 0.012 | 0.419 |
| 347 | 6917 | TCEA1 | transcription elongation factor A (SII), 1 | 0.016 | −0.52 |
| 348 | 202459 | OSTCL | oligosaccharyltransferase complex subunit-like | 0.035 | −0.449 |
| 349 | 51075 | TMX2 | thioredoxin- related transmembrane protein 2 | 0.008 | −0.452 |
| 350 | 3685 | ITGAV | integrin, alpha V (vitronectin receptor, alpha polypeptide, antigen CD51) | 0.022 | −0.411 |
| 351 | 7358 | UGDH | UDP-glucose 6-dehydrogenase | 0.037 | −0.327 |
| 352 | 7180 | CRISP2 | cysteine-rich secretory protein 2 | 0.004 | 0.502 |
| 353 | 372 | ARCN1 | archain 1 | <0.001 | −0.45 |
| 354 | 283902 | HTA | hypothetical LOC283902 | <0.001 | −0.633 |
| 355 | 2035 | EPB41 | erythrocyte membrane protein band 4.1 (elliptocytosis 1, RH-linked) | 0.026 | −0.324 |
| 356 | 9246 | UBE2L6 | ubiquitin-conjugating enzyme E2L 6 | 0.003 | 0.424 |
| 357 | 6236 | RRAD | Ras-related associated with diabetes | <0.003. | 0.625 |
| 358 | 6876 | TAGLN | transgelin | 0.015 | 0.482 |
| 359 | 84522 | JAGN1 | jagunal homolog 1 (*Drosophila*) | 0.012 | −0.36 |
| 360 | 2938 | GSTA1 | glutathione S-transferase alpha 1 | 0.001 | 0.413 |
| 361 | 92305 | TMEM129 | transmembrane protein 129 | 0.017 | −0.369 |
| 362 | 2475 | MTOR | mechanistic target of rapamycin (serine/threonine kinase) | 0.011 | −0.352 |
| 363 | 57110 | HRASLS | HRAS-like suppressor | 0.013 | 0.4 |
| 364 | 2802 | GOLGA3 | golgin A3 | 0.028 | −0.339 |
| 365 | 6711 | SPTBN1 | spectrin, beta, non-erythrocytic 1 | 0.034 | 0.393 |
| 366 | 51187 | RSL24D1 | ribosomal L24 domain containing 1 | <0.001 | −0.501 |
| 367 | 10952 | SEC61B | Sec61 beta subunit | 0.009 | −0.348 |
| 368 | 10730 | YME1L1 | YME1-like 1 (*S. cerevisiae*) | 0.011 | −0.352 |
| 369 | 3459 | IFNGR1 | interferon gamma receptor 1 | 0.005 | −0.421 |
| 370 | 9520 | NPEPPS | aminopeptidase puromycin sensitive | 0.012 | −0.302 |
| 371 | 290 | ANPEP | alanyl (membrane) aminopeptidase | 0.005 | −0.348 |
| 372 | 246243 | RNASEH1 | ribonuclease H1 | 0.004 | −0.355 |
| 373 | 2919 | CXCL1 | chemokine (C-X-C motif) ligand 1 (melanoma growth stimulating activity, alpha) | 0.019 | 0.516 |
| 374 | 29880 | ALG5 | asparagine-linked glycosylation 5, dolichyl-phosphate beta-glucosyltransferase homolog (*S. cerevisiae*) | 0.006 | −0.315 |
| 375 | 5935 | RBM3 | RNA binding motif (RNP1, RRM) protein 3 | 0.005 | 0.354 |
| 376 | 55197 | RPRD1A | regulation of nuclear pre-mRNA domain containing 1A | 0.001 | −0.587 |
| 377 | 11260 | XPOT | exportin, tRNA (nuclear export receptor for tRNAs) | 0.01 | −0.454 |
| 378 | 27244 | SESN1 | sestrin 1 | 0.001 | 0.443 |
| 379 | 6382 | SDC1 | syndecan 1 | 0.025 | 0.301 |
| 380 | 283131 | NEAT1 | nuclear paraspeckle assembly transcript 1 (non-protein coding) | <0.001 | −0.607 |
| 381 | 5202 | PFDN2 | prefoldin subunit 2 | 0.001 | −0.505 |
| 382 | 4490 | MT18 | metallothionein 18 | 0.011 | −0.47 |
| 383 | 1363 | CPE | carboxypeptidase E | 0.012 | 0.36 |
| 384 | 2498 | FTH1P3 | ferritin, heavy polypeptide 1 pseudogene 3 | 0.012 | −0.361 |
| 385 | 123 | PLIN2 | perillipin 2 | 0.003 | −0.563 |

TABLE 5-continued 521 genes differentially expressed in MSC non-exposed in comparison with cells exposed to TCM from sample 4 in comparison with non-exposed cells. The magnitude of the expression change is represented as the logarithm of the fold change.

| | GeneID | Name | Description | PValue | Log2FC |
|---|---|---|---|---|---|
| 386 | 100287551 | LOC100287551 | heat shock 70 kDa protein 8 pseudogene | 0.009 | 0.316 |
| 387 | 2577 | GAGE5 | G antigen 5 | 0.003 | 0.473 |
| 388 | 2919 | CXCL1 | chemokine (C-X-C, motif) ligand 1 (melanoma growth stimulating activity, alpha) | 0.006 | −0.981 |
| 389 | 6767 | ST13 | suppression of tumorigenicity 13 (colon carcinoma) (Hsp70 interacting protein) | 0.031 | −0.356 |
| 390 | 6372 | CXCL6 | chemokine (C-X-C motif) ligand 6 (granulocyte chemotactic protein 2) | 0.044 | −0.434 |
| 391 | 56311 | ANKRD7 | ankyrin repeat domain 7 | 0.049 | 0.344 |
| 392 | 57561 | ARRDC3 | arrestin domain containing 3 | 0.025 | 0.425 |
| 393 | 2332 | FMR1 | fragile X mental retardation 1 | 0.018 | 0.362 |
| 394 | 7298 | TYMS | thymidyiate synthetase | 0.003 | 0.388 |
| 395 | 9792 | SERTAD2 | SERTA domain containing 2 | 0.045 | −0.363 |
| 396 | 5376 | PMP22 | peripheral myelin protein 22 | 0.003 | 0.432 |
| 397 | 5232 | PGK2 | phosphoglycerate kinase 2 | 0.015 | 0.498 |
| 398 | 5477 | SIAH1 | seven in absentia homolog 1 (*Drosophila*) | 0.046 | −0.318 |
| 399 | 8870 | IER3 | immediate early response 3 | 0.033 | −0.307 |
| 400 | 3976 | LIF | leukemia inhibitory factor (cholinergic differentiation factor) | <0.001 | −0.681 |
| 401 | 5631 | PRPS1 | phosphoribosyl pyrophosphate synthetase 1 | 0.029 | 0.445 |
| 402 | 51663 | ZFR | zinc finger RNA binding protein | 0.003 | −0.417 |
| 403 | 11260 | XPOT | exportin, tRNA (nuclear export receptor for tRNAs) | 0.037 | −0.436 |
| 404 | 147166 | TRIM16L | tripartite motif containing 16-like | 0.048 | −0.311 |
| 405 | 55140 | ELP3 | elongation protein 3 homolog (*S. cerevisiae*) | 0.001 | 0.627 |
| 406 | 6387 | CXCL12 | chemokine (C-X-C motif) ligand 12 | 0.003 | 0.478 |
| 407 | 57216 | VANGL2 | vang-like 2 (van gogh, *Drosophila*) | 0.049 | −0.39 |
| 408 | 8864 | PER2 | period homolog 2 (*Drosophila*) | 0.046 | −0.389 |
| 409 | 54963 | UCKL1 | uridine-cytidine kinase 1-like 1 | 0.033 | −0.361 |
| 410 | 9695 | EDEM1 | ER degradation enhancer, mannosidase alpha -like 1 | <0.001 | −0.67 |
| 411 | 1807 | DPYS | dihydropyrimidinase | 0.019 | 0.314 |
| 412 | 3988 | LIPA | lipase A, lysosomal acid, cholesterol esterase | 0.02 | 0.347 |
| 413 | 3843 | IPO5 | importin 5 | <0.001 | −0.801 |
| 414 | 10440 | TIMM17A | translocase of inner mitochondrial membrane 17 homolog A (yeast) | <0.001 | −0.633 |
| 415 | 2923 | PDIA3 | protein disulfide isomerase family A, member 3 | 0.008 | −0.405 |
| 416 | 768211 | RELL1 | RELT-like 1 | 0.006 | −0.387 |
| 417 | 6432 | SRSF7 | serine/arginine-rich splicing factor | 0.001 | 0.562 |
| 418 | 55323 | LARP6 | La ribonucleoprotein domain family, member 6 | <0.001 | −0.545 |
| 419 | 51635 | DHRS7 | dehydrogenase/reductase (SDR family) member 7 | 0.014 | −0.318 |
| 420 | 23187 | PHLDB1 | pleckstrin homology-like domain, family B, member 1 | 0.016 | 0.479 |
| 421 | 221458 | KIF6 | kinesin family member 6 | 0.045 | 0.328 |
| 422 | 337967 | KRTAP6-2 | keratin associated protein 6-2 | 0.019 | 0.404 |
| 423 | 665 | BNIP3L | BCL2/adenovirus EIB 19 kDa interacting protein 3-like | 0.002 | −0.464 |
| 424 | 400322 | HERC2P2 | hect domain and RLD 2 pseudogene 2 | 0.024 | −0.353 |
| 425 | 8528 | DDO | D-aspartate oxidase | 0.049 | 0.323 |
| 426 | 26872 | STEAP1 | six transmembrane epithelial antigen of the prostate 1 | 0.024 | −0.703 |
| 427 | 83853 | ROPN1L | rhophilin associated tail protein 1-like | <0.001 | 0.692 |
| 428 | 51022 | GLRX2 | glutaredoxin 2 | 0.005 | −0.452 |
| 429 | 2273 | FHL1 | four and a half LIM domains 1 | 0.004 | 0.379 |
| 430 | 729495 | FAM108A5P | (putative abhydrolase domain-containing protein FAM108A5 | 0.004 | 0.355 |
| 431 | 57149 | LYRM1 | LYR motif containing 1 | 0.04 | 0.365 |
| 432 | 2585 | GALK2 | galactokinase 2 | 0.031 | −0.322 |
| 433 | 2791 | GNG11 | guanine nucleotide binding protein (G protein), gamma 11 | <0.001 | −0.75 |
| 434 | 134492 | NUDCD2 | NudC domain containing 2 | 0.022 | −0.452 |
| 435 | 23576 | DDAH1 | dimethylarginine dimethylaminohydrolase 1 | 0.003 | 0.413 |
| 436 | 29970 | SCHIP1 | schwannomin interacting protein 1 | 0.003 | 0.445 |
| 437 | 387758 | FIBIN | fin bud initiation factor homolog (zebrafish) | 0.034 | −0.515 |
| 438 | 5156 | PDGFRA | platelet-derived growth factor receptor, alpha polypeptide | 0.036 | −0.443 |
| 439 | 6746 | SSR2 | signal sequence receptor, beta (translocon -associated protein beta) | 0.002 | −0.339 |
| 440 | 908 | CCT6A | chaperonin containing TCP1, subunit 6A (zeta 1) | 0.004 | −0.401 |
| 441 | 80204 | FBXO11 | F-box protein 11 | 0.001 | −0.52 |
| 442 | 25805 | BAMBI | BMP and activin membrane-bound inhibitor homolog (*Xenopus laevis*) | 0.012 | 0.387 |
| 443 | 124512 | METTL23 | methyltransferase like 23 | 0.015 | −0.362 |
| 444 | 1831 | TSC22D3 | TSC22 domain family, member 3 | 0.016 | 0.362 |
| 445 | 54529 | ASNSD1 | asparagine synthetase domain containing 1 | 0.02 | −0.408 |
| 446 | 6786 | STIM1 | stromal interaction molecule 1 | 0.022 | −0.312 |
| 447 | 60673 | C12orf44 | chromosome 12 open reading frame 44 | 0.002 | −0.401 |
| 448 | 170261 | ZCCHC12 | zinc finger, CCHC domain containing 12 | 0.002 | 0.633 |
| 449 | 84076 | TKTL2 | transketalase-like 2 | 0.014 | 0.569 |
| 450 | 10186 | LHFP | lipoma HMGIC fusion partner | 0.001 | 0.476 |
| 451 | 4702 | NDUFA8 | NADH dehydrogenase (ubiquinone) 1 alpha subcomplex, 8, 19 kDa | 0.042 | 0.301 |
| 452 | 1267 | CNP | 2',3'-cyclic nucleotide 3' phosphodiesterase | 0.011 | 0.423 |
| 453 | 5535 | PPP3R2 | protein phosphatase 3, regulatory subunit B, beta | 0.003 | 0.853 |
| 454 | 10105 | PPIF | peptidylprolyl isomerase F | 0.013 | 0.369 |
| 455 | 29993 | PACSIN1 | protein kinase C and casein kinase substrate in neurons 1 | 0.015 | 0.435 |
| 456 | 4616 | GADD45B | growth arrest and DNA-damage-inducible, beta | <0.001 | 0.588 |
| 457 | 7364 | UGT2B7 | UDP glucuronosyltransferase 2 family, polypeptide B7 | 0.05 | 0.377 |

TABLE 5-continued 521 genes differentially expressed in MSC non-exposed in comparison with cells exposed to TCM from sample 4 in comparison with non-exposed cells. The magnitude of the expression change is represented as the logarithm of the fold change.

| | GeneID | Name | Description | PValue | Log2FC |
|---|---|---|---|---|---|
| 458 | 51187 | RSL24D1 | ribosomal L24 domain containing 1 | 0.044 | −0.391 |
| 459 | 26748 | GAGE12I | G antigen 12I | 0.004 | 0.484 |
| 460 | 55872 | PBK | PDZ binding kinase | <0.001 | 0.68 |
| 461 | 11332 | ACOT7 | acyl-CoA thioesterase 7 | 0.002 | 0.543 |
| 462 | 229 | ALDOB | aldolase B, fructose-bisphosphate | 0.005 | 0.413 |
| 463 | 10960 | LMAN2 | lectin, mannose-binding 2 | 0.005 | −0.319 |
| 464 | 1316 | KLF6 | Kruppel-like factor 6 | <0.001 | 0.605 |
| 465 | 9915 | ARNT2 | aryl-hydrocarbon receptor nuclear translocator 2 | 0.002 | 0.732 |
| 466 | 1075 | CTSC | cathepsin C | 0.02 | 0.423 |
| 467 | 1649 | DDIT3 | DNA-damage-inducible transcript 3 | <0.001 | −0.567 |
| 468 | 254778 | C8orf46 | chromosome 8 open reading frame 46 | 0.008 | 0.481 |
| 469 | 146849 | CCDC42 | coiled-coil domain containing 42 | 0.01 | 0.39 |
| 470 | 84951 | TNS4 | tensin 4 | 0.012 | −0.528 |
| 471 | 223082 | | zinc and ring finger 2 | 0.01 | 0.43 |
| 472 | 64778 | FNDC3B | fibronectin type III domain containing 3B | <0.001 | −0.586 |
| 473 | 83758 | RBP5 | retinol binding protein 5, cellular | 0.05 | 0.362 |
| 474 | 4430 | MYO1B | myosin 1B | 0.021 | −0.48 |
| 475 | 11098 | PRSS23 | protease, serine, 23 | <0.001 | 1.043 |
| 476 | 8547 | FCN3 | ficolin (collagen/fibrinogen domain containing) 3 (Hakata antigen) | 0.046 | 0.327 |
| 477 | 966 | CD59 | CD59 molecule, complement regulatory protein | 0.002 | 0.415 |
| 478 | 10841 | FTCD | formiminotransferase cyclodeaminase | 0.021 | −0.41 |
| 479 | 7112 | TMPO | thymopoletin | 0.015 | −0.497 |
| 480 | 8394 | PIPSK1A | phosphatidylinositol-4-phosphate 5-kinase, type, alpha | 0.028 | −0.303 |
| 481 | 10447 | FAM3C | family with sequence similarity 3, member C | <0.001 | −0.787 |
| 482 | 7474 | WNT5A | wingless-type MMTV integration site family, member 5A | 0.042 | −0.482 |
| 483 | 3948 | LDHC | lactate dehydrogenase C | 0.016 | 0.425 |
| 484 | 3337 | DNAJB1 | DnaJ (Hsp40) homolog, subfamily B, member 1 | 0.008 | 0.452 |
| 485 | 7532 | YWHAG | tyrosine 3-monooxygenase/tryptophan 5-monooxygenase activation protein, gamma polypeptide | 0.013 | 0.328 |
| 486 | 4735 | SEPT2 | septin 2 | 0.024 | −0.374 |
| 487 | 7162 | TPBG | trophoblast glycoprotein | 0.032 | −0.507 |
| 488 | 5354 | PLP1 | proteolipid protein 1 | 0.004 | 0.504 |
| 489 | 59 | ACTA2 | actin, alpha 2, smooth muscle. aorta | 0.008 | 0.38 |
| 490 | 51471 | NAT8B | N-acetyltransferase 8B (GCNS-related, putative, gene/pseudogene) | 0.008 | 0.531 |
| 491 | 10550 | ARL6IP5 | ADP-ribosylation-like factor 6 interacting protein 5 | 0.02 | −0.401 |
| 492 | 377711 | LOC377711 | HEAT repeat-containing protein 7A-like | 0.006 | 0.497 |
| 493 | 389453 | LOC389493 | hypothetical protein LOC389493 | 0.004 | 0.416 |
| 494 | 302 | ANXA2 | annexin A2 | 0.026 | 0.326 |
| 495 | 57092 | PCNP | PEST proteolytic signal containing nuclear protein | 0.013 | −0.303 |
| 496 | 2665 | GDI2 | GDP dissociation inhibitor 2 | 0.008 | −0.349 |
| 497 | 10841 | FTCD | formiminotransferase cyclodeaminase | 0.008 | 0.39 |
| 498 | 5992 | RFX4 | regulatory factor X, 4 (influences HLA class II expression) | 0.007 | 0.534 |
| 499 | 9276 | COPB2 | coatomer protein complex, subunit beta 2 (beta prime) | 0.02 | −0.408 |
| 500 | 55352 | C17orf79 | chromosome 17 open reading frame 79 | 0.007 | 0.486 |
| 501 | 2316 | FLNA | filamin A, alpha | 0.042 | 0.314 |
| 502 | 54496 | PRMT7 | protein arginine methyltransferase 7 | 0.023 | −0.307 |
| 503 | 51255 | RNF181 | ring finger protein 181 | 0.009 | −0.476 |
| 504 | 10135 | NAMPT | nicotinamide phosphoribosyltransferase | 0.002 | −0.741 |
| 505 | 5516 | PPP2CB | protein phosphatase 2, catalytic subunit, beta isozyme | 0.042 | 0.302 |
| 506 | 6319 | SCD | stearoyl-CoA desaturase (delta-9-desaturase) | 0.013 | 0.468 |
| 507 | 202459 | OSTCL | oligosaccharyltransferase complex subunit-like | 0.002 | −0.611 |
| 508 | 5872 | RAB13 | RAB13, member RAS oncogene family | 0.02 | −0.334 |
| 509 | 1645 | AKR1C1 | aldo-keto reductase family 1, member C1 (dihydrodial dehydrogenase 1; 20-alpha (3-alpha)-hydroxysteroid dehydrogenase) | 0.001 | −0.543 |
| 510 | 3312 | HSPA8 | heat shock 70 kDa protein 8 | <0.001 | 0.443 |
| 511 | 477 | ATP1A2 | ATPase, Na+/K+ transporting, alpha 2 polypeptide | 0.009 | 0.607 |
| 512 | 1277 | COL1A1 | collagen, type 1, alpha 1 | 0.008 | 0.408 |
| 513 | 6595 | SMARCA2 | SWI/SNF related, matrix associated, actin dependent regulator of chromatin, subfamily a, member 2 | 0.037 | 0.363 |
| 514 | 9334 | B4GALT5 | UDP-GalibetaGlcNAc beta 1,4- galactosyltransferase, polypeptide 5 | <0.001 | 0.454 |
| 515 | 5743 | PTGS2 | prostaglandin-endoperoxide synthase 2 (prostaglandin G/H synthase and cyclooxygenase) | 0.005 | −0.991 |
| 516 | 3725 | JUN | jun proto-oncogene | 0.03 | 0.309 |
| 517 | 9689 | BZW1 | basic leucine zipper and W2 domains 1 | 0.003 | −0.506 |
| 518 | 8613 | PPAP2B | phosphatidic acid phosphatase type 2B | <0.001 | 0.545 |
| 519 | 54579 | UGT1A5 | UDP glucuronosyltransferase 1 family, polypeptide 45 | 0.012 | 0.39 |
| 520 | 84447 | SYVN1 | synovial apoptosis inhibitor 1, synoviolin | <0 001 | −1.573 |
| 521 | 146225 | CMTM2 | CKLF-like MARVEL transmembrane domain containing 2 | 0.032 | 0.32 |

TABLE 6

511 genes differentially expressed in MSC non-exposed in comparison with cells exposed to TCM from sample 5 in comparison with non-exposed cells. The magnitude of the expression change is represented as the logarithm of the fold change.

| | GeneID | Name | Description | PValue | Log2FC |
|---|---|---|---|---|---|
| 1 | 54769 | DIRAS2 | DIRAS family, GTP-binding RAS-like 2 | 0.002 | 0.643 |
| 2 | 9631 | NUP155 | nucleoporin 155 kDa | 0.024 | 0.337 |
| 3 | 1314 | COPA | coatomer protein complex, subunit alpha | 0.029 | −0.303 |
| 4 | 25912 | C1orf43 | chromosome 1 open reading frame 43 | 0.022 | −0.333 |
| 5 | 23516 | SLC39A14 | solute carrier family 39 (zinc vansporter), member 14 | 0.022 | −0.343 |
| 6 | 11137 | PWP1 | PWP1 homolog (S. cerevisiae) | 0.02 | −0.317 |
| 7 | 54623 | PAF1 | Paf1, RNA polymerase II associated factor, homolog (S. cerevisiae) | 0.049 | −0.451 |
| 8 | 92609 | TIMM50 | translocase of inner mitochondrial membrane 50 homolog (S. cerevisiae) | 0.008 | 0.481 |
| 9 | 100133941 | CD24 | CD24 molecule | <0.001 | 0.574 |
| 10 | 57730 | ANKRD36B | ankyrin repeat domain 36B | 0.022 | 0.43 |
| 11 | 1968 | EIF2S3 | eukaryotic translation initiation factor 2, subunit 3 gamma, 52 kDa | 0.025 | −0.422 |
| 12 | 85445 | CNTNAP4 | contactin associated protein-like 4 | 0.024 | 0.353 |
| 13 | 6782 | FISPA13 | heat shock protein 70 kDa family, member 13 | <0.001 | −1.084 |
| 14 | 81626 | SHCBP1L | SHC SH2-domain binding protein 1-like | <0.001 | 0.898 |
| 15 | 2959 | GTF2B | general transcription factor 1B | 0.004 | 0.704 |
| 16 | 51278 | IER5 | immediate early response 5 | 0.02 | 0.437 |
| 17 | 54541 | DDIT4 | DNA-damage-inducible transcript 4 | 0.001 | −0.443 |
| 18 | 2199 | FBLN2 | fibulin 2 | <0.001 | 0.632 |
| 19 | 3488 | IGFBP5 | insulin-like 2rowth factor binding protein 5 | <0.001 | 0.722 |
| 20 | 10659 | CELF2 | CUGBP, Elan-like family member 2 | <0.001 | 0.793 |
| 21 | 50613 | UBQLN3 | ublquilin 3 | 0.013 | 0.406 |
| 22 | 54629 | FAM63B | family with secluence similarity 63, member B | 0.04 | −0.426 |
| 23 | 6396 | SEC13 | SEC13 homolog (S. cerevisiae) | 0.009 | −0.439 |
| 24 | 51310 | SLC22A17 | solute carrier family 22, member 17 | 0.009 | 0.322 |
| 25 | 4357 | MPST | mercaptopyruvate sulfurtransferase | 0.044 | −1.112 |
| 26 | 10777 | ARPP21 | cAMP-regulated phosphoprotein, 21 kDa | 0.008 | −0.403 |
| 27 | 1465 | CSRP1 | cysteine and glycine-rich protein 1 | 0.007 | 0.322 |
| 28 | 391819 | KRT18P42 | keratin 18 pseudogene 42 | 0.024 | −0.513 |
| 29 | 3954 | LETM1 | leucine zipper-EF-hand containing transmembrane protein 1 | <0.001 | −0.524 |
| 30 | 7278 | TUBA3C | tubulin, alpha 3c | 0.002 | 0.381 |
| 31 | 5781 | PTPN11 | protein tyrosine phosphatase, non-receptor type 11 | 0.024 | −0.693 |
| 32 | 2574 | GAGE2C | G antigen 20 | 0.002 | 0.518 |
| 33 | 10476 | ATPSH | ATP synthase, H+ transporting, mitochondrial Fo complex, subunit d | 0.014 | −0.403 |
| 34 | 5756 | TWF1 | twinfilin, actin-binding protein, homolog 1 (Drosophila) | 0.028 | −0.796 |
| 35 | 3590 | IL11RA | interleukin 11 receptor, alpha | 0.024 | −0.371 |
| 36 | 8404 | SPARCL1 | SPARC-like 1 (hevin) | 0.007 | 0.587 |
| 37 | 55062 | WIPI1 | WD repeat domain, phosphoinositide interacting 1 | 0.009 | −0.486 |
| 38 | 29116 | MYLIP | myosin regulatory light chain interacting protein | 0.011 | 0.44 |
| 39 | 55907 | CMAS | cytidine monophosphate N-acetylneuraminic acid synthetase | 0.01 | 0.433 |
| 40 | 84661 | DPY30 | dpy-30 homolog (C. elegans) | 0.021 | 0.444 |
| 41 | 55000 | TUG1 | taurine upregulated 1 (non-protein coding) | 0.02 | 0.446 |
| 42 | 1672 | DEFB1 | defensin, beta 1 | 0.009 | 0.467 |
| 43 | 10769 | PLK2 | polo-like kinase 2 | 0.047 | 0.32 |
| 44 | 2191 | FAP | fibroblast activation protein, alpha | 0.002 | −0.504 |
| 45 | 1312 | COMT | catechol-O-methyltransferase | 0.048 | 0.305 |
| 46 | 972 | CD74 | CD74 molecule, malor histocompatibility complex, class invariant chain | 0.007 | 0.478 |
| 47 | 85414 | SLC45A3 | solute carrier family 45, member 3 | 0.013 | 0.484 |
| 48 | 5579 | PRKCB | protein kinase C, beta | 0.022 | 0.583 |
| 49 | 90507 | SCRN2 | secernin 2 | 0.05 | 0.358 |
| 50 | 386677 | KRTAP10-1 | keratin associated protein 10-1 | 0.006 | −0.387 |
| 51 | 1912 | PHC2 | polyhomeotic homolog 2 (Drosophila) | 0.001 | −0.84 |
| 52 | 100271071 | RPS17P10 | ribosomal protein S17 pseudogene 10 | 0.014 | −0.573 |
| 53 | 10961 | ERP29 | endoplasmic reticulum protein 29 | 0.024 | 0.358 |
| 54 | 80161 | ASMTL-AS1 | ASMTL antisense RNA 1 (non-protein coding) | 0.028 | −0.326 |
| 55 | 56970 | ATXN7L3 | ataxin 7-like 3 | 0.042 | −0.333 |
| 56 | 9789 | SPC52 | signal peptidase complex subunit 2 homolog (S. cerevisiae) | 0.007 | 0.455 |
| 57 | 2969 | GTF2I | general transcription factor III | 0.028 | 0.345 |
| 58 | 8894 | EIF2S2 | eukaryotic translation initiation factor 2, subunit 2 beta, 38 kDa | 0.05 | −0.5 |
| 59 | 8073 | PTP4A2 | protein tyrosine phosphatase type IVA, member 2 | 0.016 | 0.362 |
| 60 | 10099 | TSPAN3 | tetraspanin 3 | 0.013 | 0.384 |
| 61 | 9013 | TAF1C | TATA box binding protein (TBP)-associated factor, RNA polymerase I, C, 110 kDa | 0.009 | −0.387 |
| 62 | 5138 | PDE2A | phosphodiesterase 2A, cGMP-stimulated | 0.049 | 0.514 |
| 63 | 3486 | IGFBP3 | insulin-like growth factor binding protein 3 | 0.009 | 0.394 |
| 64 | 467 | ATF3 | activating transcription factor 3 | <0.001 | 0.777 |
| 65 | 23264 | ZC3H7B | zinc finger CCCH-type containing 7B | 0.034 | 0.352 |
| 66 | 51322 | WAC | WW domain containing, adaptor with coiled-coil | 0.034 | 0.37 |
| 67 | 7127 | TNFAIP2 | tumor necrosis factor, alpha-induced protein 2 | 0.022 | 0.496 |
| 68 | 54600 | UGT1A9 | UDP glucuronosyltransferase 1 family, polypeptide A9 | 0.002 | 0.51 |
| 69 | 115416 | C7orf30 | chromosome 7 open reading frame 30 | 0.035 | −0.667 |
| 70 | 64065 | PERP | PERP, TP53 apoptosis effector | 0.004 | 0.5 |
| 71 | 10135 | NAMPT | nicotinamide phosphoribosyltransferase | 0.003 | −0.724 |
| 72 | 51460 | SFMBT1 | Scm-like with four mbt domains 1 | 0.014 | 0.46 |
| 73 | 1345 | COX6C | cytochrome c oxidase subunit VIc | 0.002 | 0.381 |

TABLE 6-continued 511 genes differentially expressed in MSC non-exposed in comparison with
cells exposed to TCM from sample 5 in comparison with non-exposed cells. The
magnitude of the expression change is represented as the logarithm of the fold change.

| | GeneID | Name | Description | PValue | Log2FC |
|---|---|---|---|---|---|
| 74 | 8778 | SIGLEC5 | sialic acid binding Ig-like lectin 5 | 0.022 | −0.399 |
| 75 | 3295 | HSD1784 | hydroxysteroid (17-beta) dehydrogenase 4 | 0.013 | −0.496 |
| 76 | 112936 | VPS26B | vacuolar protein sorting 26 homolog B (*S. pombe*) | 0.034 | 0.469 |
| 77 | 284948 | SH2D6 | SH2 domain containing 6 | 0.015 | −0.446 |
| 78 | 10808 | HSPH1 | heat shock 105 kDa/110 kDa protein 1 | <0.001 | 0.619 |
| 79 | 64208 | POPDC3 | popeye domain containing 3 | 0.012 | −0.53 |
| 80 | 56110 | PCDHGA5 | protocadherin gamma subfamily A, 5 | 0.009 | −0.379 |
| 81 | 23562 | CLDN14 | claudin 14 | 0.028 | −0.433 |
| 82 | 2323 | FLT3LG | fms-related tyrosine kinase 3 ligand | 0.03 | −0.354 |
| 83 | 8321 | FZD1 | frizzled homolog 1 (*Drosophila*) | 0.007 | 0.576 |
| 84 | 5270 | SERPINE2 | serpin peptidase inhibitor, clade E (nexin, plasminogen activator inhibitor type 1), member 2 | 0.005 | −0.4 |
| 85 | 25907 | TMEM158 | transmembrane protein 158 (gene/pseudogene) | 0.01 | −0.587 |
| 86 | 1003 | CDH5 | cadherin 5, type 2 (vascular endothelium) | 0.011 | 0.629 |
| 87 | 9531 | BAG3 | BCL2-associated athanogene 3 | 0.001 | 0.537 |
| 88 | 2824 | GPM68 | glycoprotein M68 | <0.001 | 0.616 |
| 89 | 478 | ATP1A3 | ATPase, Na+/K+ transporting, alpha 3 polypeptide | 0.009 | 0.577 |
| 90 | 338799 | LOC338799 | hypothetical LOC338799 | 0.003 | −0.484 |
| 91 | 5476 | CTSA | cathepsin A | 0.016 | −0.303 |
| 92 | 79137 | FAM134A | family with sequence similarity 134, member A | 0.014 | −0.382 |
| 93 | 221143 | N6AMT2 | N-6 adenine-specific DNA methyltransferase 2 (putative) | 0.016 | −0.304 |
| 94 | 3336 | HSPE1 | heat shock 10 kDa protein 1 (chaperonin 10) | 0.002 | 0.55 |
| 95 | 80279 | CDK5RAP3 | CDK5 regulatory subunit associated protein 3 | 0.001 | 0.493 |
| 96 | 10987 | COPS5 | COP9 constitutive photomorphogenic homolog subunit 5 (*Arabidopsis*) | 0.039 | 0.34 |
| 97 | 22978 | NT5C2 | 5′-nucleotidase, cytosolic II | 0.037 | 0.35 |
| 98 | 2353 | FOS | FBJ murine osteosarcoma viral oncogene homolog | 0.001 | 0.52 |
| 99 | 55228 | PNMAL1 | PNMA-like 1 | 0.009 | 0.594 |
| 100 | 11215 | AKAP11 | A kinase (PRKA) anchor protein 11 | 0.012 | 0.477 |
| 101 | 51727 | CMPK1 | cytidine monophosphate (UMP-CMP) kinase 1, cytosolic | 0.027 | −0.405 |
| 102 | 8566 | PDXK | pyridoxal (pyridoxine, vitamin B6) kinase | 0.013 | 0.357 |
| 103 | 4884 | NPTX1 | neuronal pentraxin I | 0.003 | 0.629 |
| 104 | 7485 | WRB | tryptophan rich basic protein | 0.032 | 0.35 |
| 105 | 11179 | ZNF277 | zinc finger protein 277 | 0.024 | −0.543 |
| 106 | 55811 | ADCY10 | adenylate cyclase 10 (soluble) | 0.012 | −0.398 |
| 107 | 23070 | FTSJD2 | FtsJ methyltransferase domain containing 2 | 0.045 | 0.32 |
| 108 | 163033 | ZNF579 | zinc finger protein 579 | 0.016 | −0.339 |
| 109 | 53826 | FXYD6 | FXYD domain containing ion transport regulator 6 | 0.004 | 0.418 |
| 110 | 11170 | FAM107A | family with sequence similarity 107, member A | <0.001 | 0.402 |
| 111 | 8985 | PLOD3 | procollagen-lysine, 2-oxoglutarate 5-dioxygenase 3 | 0.02 | −0.463 |
| 112 | 1164 | CKS2 | CDC28 protein kinase regulatory subunit 2 | <0.001 | 0.694 |
| 113 | 388692 | LOC388692 | hypothetical LOC388692 | 0.006 | 0.319 |
| 114 | 8662 | EIF3B | eukaryotic translation initiation factor 3, subunit B | 0.028 | −0.329 |
| 115 | 4673 | NAP1L1 | nucleosome assembly protein 1-like 1 | 0.013 | 0.326 |
| 116 | 23621 | BACE1 | beta-site APP-cleaving enzyme 1 | 0.011 | −0.367 |
| 117 | 2983 | GUCY153 | guanylate cyclase 1, soluble, beta 3 | 0.017 | 0.309 |
| 118 | 7546 | ZIC2 | Zic family member 2 (odd-paired homolog, *Drosophila*) | 0.035 | 0.458 |
| 119 | 51617 | HMP19 | HMP19 protein | 0.01 | 0.438 |
| 120 | 54657 | UGT1A4 | UDP glucuronosyltransferase 1 family, polypeptide A4 | 0.034 | 0.329 |
| 121 | 23786 | BCL2L13 | BCL2-like 13 (apoptosis facilitator) | 0.019 | 0.469 |
| 122 | 23209 | MLC1 | megalencephalic leukoencephalopathy with subcortical cysts 1 | 0.026 | 0.44 |
| 123 | 3032 | HADHB | hydroxyacyl-CoA dehydrogenase/3-ketoacyl-CoA thiolase/enoyl-CoA hydratase (trifunctional protein), beta subunit | 0.008 | −0.332 |
| 124 | 351020 | LOC391020 | interferon induced transmembrane protein pseudogene | 0.009 | −0.318 |
| 125 | 7458 | EIF4H | eukaryotic translation initation factor 4H | 0.01 | −0.302 |
| 126 | 283971 | CLEC18C | C-type lectin domain family 18, member C | 0.022 | 0.327 |
| 127 | 7102 | TSPAN7 | tetraspanin 7 | 0.006 | 0.57 |
| 128 | 4783 | NFIL3 | nuclear factor, interleukin 3 regulated | 0.004 | −0.483 |
| 129 | 10859 | LILRB1 | leukocyte immunoglobulin-like receptor, subfamily B (with TM and ITIM domains), member 1 | 0.024 | −0.483 |
| 130 | 284257 | BOD1P | biorientation of chromosomes in cell division 1 pseudogene | 0.01 | 0.51 |
| 131 | 813 | CALU | calumenin | 0.015 | −0.469 |
| 132 | 23352 | UBR4 | ubiquitin protein ligase E3 component n-recognin 4 | 0.014 | −0.33 |
| 133 | 2697 | GJA1 | gap junction protein, alpha 1, 43 kDa | 0.038 | −0.423 |
| 134 | 6119 | RPA3 | replication protein A3, 14 kDa | 0.017 | 0.379 |
| 135 | 57730 | ANKRD36B | ankyrin repeat domain 36B | 0.011 | 0.368 |
| 136 | 112714 | TUBA3E | tubulin, alpha 3e | 0.011 | 0.418 |
| 137 | 10439 | OLFM1 | olfactomedin 1 | 0.009 | 0.48 |
| 138 | 51733 | UPB1 | ureidopropionase, beta | 0.045 | −0.323 |
| 139 | 7175 | TPR | translocated promoter region (to activated MET oncogene) | 0.022 | 0.417 |
| 140 | 25840 | METTL7A | methyltransferase like 7A | 0.017 | 0.481 |
| 141 | 26528 | DAZAP1 | DAZ associated protein 1 | 0.007 | 0.491 |
| 142 | 7058 | THBS2 | thrombospondin 2 | 0.026 | −0.325 |
| 143 | 9452 | ITM2A | integral membrane protein 2A | 0.002 | 0.748 |
| 144 | 65055 | REEP1 | receptor accessory protein 1 | 0.001 | 0.516 |

TABLE 6-continued 511 genes differentially expressed in MSC non-exposed in comparison with
cells exposed to TCM from sample 5 in comparison with non-exposed cells. The
magnitude of the expression change is represented as the logarithm of the fold change.

| | GeneID | Name | Description | PValue | Log2FC |
|---|---|---|---|---|---|
| 145 | 10531 | PITRM1 | pitrilysin metallopeptidase 1 | 0.006 | 0.334 |
| 146 | 79791 | FBXO31 | F-box protein 31 | 0.023 | 0.329 |
| 147 | 3936 | LCP1 | lymphocyte cytosolic protein 1 (L-plastin) | 0.01 | 0.646 |
| 148 | 9536 | PTGES | prostaglandin E synthase | 0.005 | −0.708 |
| 149 | 83657 | DYNLRB2 | dynein, light chain, roadblock-type 2 | 0.027 | 0.337 |
| 150 | 84681 | HINT2 | histidine triad nucleotide binding protein 2 | 0.036 | 0.314 |
| 151 | 51231 | VRK3 | vaccinia related kinase 3 | 0.025 | −0.686 |
| 152 | 26048 | ZNF500 | zinc finger protein 500 | 0.003 | −0.332 |
| 153 | 151011 | SEPT10 | septin 10 | 0.01 | −0.545 |
| 154 | 26749 | GAGE2E | G antigen 2E | 0.007 | 0.426 |
| 155 | 7644 | ZNF91 | zinc finger protein 91 | 0.04 | 0.323 |
| 156 | 231 | AKR1B1 | aldo-keto reductase family 1, member B1 (aldose reductase) | <0.001 | −0.53 |
| 157 | 501 | ALDH7A1 | aldehyde dehydrogenase 7 family, member A1 | 0.002 | −0.511 |
| 158 | 4131 | MAP1B | microtubule-associated protein 1B | 0.024 | 0.44 |
| 159 | 4358 | MPV17 | MpV17 mitochondrial inner membrane protein | 0.004 | −0.43 |
| 160 | 5913 | RAPSN | receptor-associated protein of the synapse | 0.009 | −0.378 |
| 161 | 54881 | TEX10 | testis expressed 10 | 0.003 | −0.473 |
| 162 | 8460 | TPST1 | tyrosylprotein sulfotransferase 1 | 0.005 | −0.451 |
| 163 | 60312 | AFAP1 | actin filament associated protein 1 | 0.011 | −0.436 |
| 164 | 84817 | TXNDC17 | thioredoxin domain containing 17 | 0.031 | 0.331 |
| 165 | 26608 | TBL2 | transducin (beta)-like 2 | <0.001 | 0.677 |
| 166 | 55753 | OGDHL | oxoglutarate dehydrogenase-like | 0.003 | 0.441 |
| 167 | 10472 | ZNF238 | zinc finger protein 238 | 0.011 | 0.477 |
| 168 | 1164 | CKS2 | CDC28 protein kinase regulatory subunit 2 | <0.001 | 0.513 |
| 169 | 83547 | RILP | Rab interacting lysosomal protein | 0.042 | −0.466 |
| 170 | 274 | 13161 | bridging integrator 1 | 0.042 | −0.401 |
| 171 | 89958 | C9orf140 | chromosome 9 open reading frame 140 | 0.034 | −0.341 |
| 172 | 653639 | LPLA2P1 | lysophospholipase II pseudogene 1 | 0.036 | −0.37 |
| 173 | 51616 | TAF9B | TAF9B RNA polymerase II, TATA box binding protein (TBP)-associated factor, 31 kDa | 0.029 | 0.366 |
| 174 | 1478 | CSTF2 | cleavage stimulation factor, 3'pre-RNA, subunit 2, 64 kDa | 0.048 | −0.549 |
| 175 | 22913 | RALY | RNA binding protein, autoantigenic (hnRNP-associated with lethal yellow homolog (mouse)) | 0.012 | −0.585 |
| 176 | 10808 | HSPH1 | heat shock 105 kDa/110 kDa protein 1 | 0.037 | −0.313 |
| 177 | 196 | AHR | aryl hydrocarbon receptor | <0.001 | −0.753 |
| 178 | 1429 | CRYZ | crystallin, zeta (quinone reductase) | 0.017 | 0.385 |
| 179 | 65009 | NDRG4 | NDRG family member 4 | 0.001 | 0.472 |
| 180 | 126823 | KLHDC9 | kelch domain containing 9 | 0.039 | 0.402 |
| 181 | 2938 | GSTA1 | glutathione S-transferase alpha 1 | 0.018 | 0.392 |
| 182 | 3048 | HBG2 | hemoglobin, gamma G | 0.009 | 0.375 |
| 183 | 2171 | FABP5 | fatty acid binding protein 5 (psoriasis-associated) | 0.013 | 0.328 |
| 184 | 5110 | PCMT1 | protein-L-isoaspartate (D-aspartate) O-methyltransferase | 0.005 | −0.614 |
| 185 | 3308 | HSPA4 | heat shock 70 kDa protein 4 | 0.047 | −0.439 |
| 186 | 4054 | LTBP3 | latent transforming growth factor beta binding protein 3 | 0.031 | −0.768 |
| 187 | 51693 | TRAPPC2L | trafficking protein particle complex 2-like | 0.028 | −0.372 |
| 188 | 7980 | TFPI2 | tissue factor pathway inhibitor 2 | <0.001 | −1.085 |
| 189 | 146330 | FBXL16 | F-box and leucine-rich repeat protein 16 | 0.047 | 0.524 |
| 190 | 7494 | XBP1 | X-box binding protein 1 | 0.008 | −0.306 |
| 191 | 51655 | RASD1 | RAS, dexamethasone-induced 1 | <0.001 | 0.762 |
| 192 | 9766 | KIAA0247 | KIAA0247 | 0.007 | −0.483 |
| 193 | 27288 | RBMXL2 | RNA binding motif protein, X-linked-like 2 | 0.037 | 0.405 |
| 194 | 56731 | SLC2A4RG | SLC2A4 regulator | 0.015 | −1.281 |
| 195 | 10971 | YWHAQ | tyrosine 3-monooxygenase/tryptophan 5-monooxygenase activation protein, theta polypeptide | 0.003 | 0.305 |
| 196 | 9689 | BZW1 | basic leucine zipper and W2 domains 1 | 0.004 | −0.35 |
| 197 | 9240 | PNMA1 | paraneoplastic antigen MA1 | 0.024 | 0.37 |
| 198 | 23270 | TSPYL4 | TSPY-like 4 | 0.037 | 0.305 |
| 199 | 900 | CCNG1 | cyclin G1 | 0.01 | −0.378 |
| 200 | 10542 | HBXIP | hepatitis B virus x interacting protein | 0.005 | 0.354 |
| 201 | 10147 | SUGP2 | SURP and G patch domain containing 2 | 0.035 | 0.309 |
| 202 | 128218 | TMEM125 | transmembrane protein 125 | 0.002 | 0.645 |
| 203 | 7873 | MANF | mesencephalic astrocyte-derived neurotrophic factor | <0.001 | −0.526 |
| 204 | 286204 | CRB2 | crumbs homolog 2 (Drosophila) | 0.035 | −0.305 |
| 205 | 7179 | TPTE | transmembrane phosphatase with tensin homology | 0.04 | 0.418 |
| 206 | 10523 | CHERP | calcium homeostasis endoplasmic reticulum protein | 0.017 | −0.341 |
| 207 | 64750 | SMURF2 | SMAD specific E3 ubiquitin protein ligase 2 | <0.001 | −0.42 |
| 208 | 5791 | PTPRE | protein tyrosine phosphatase, receptor type E | 0.012 | −0.333 |
| 209 | 51533 | PHF7 | PHD finger protein 7 | 0.004 | 0.444 |
| 210 | 23476 | BRD4 | bromodomain containing 4 | 0.043 | −0.319 |
| 211 | 9690 | UBE3C | ubiquitin protein ligase E3C | 0.031 | −0.375 |
| 212 | 51141 | INSIG2 | insulin induced gene | 0.004 | −0.417 |
| 213 | 84935 | C13orf33 | chromosome 13 open reading frame 33 | <0.001 | −0.71 |
| 214 | 9554 | SEC22B | SEC22 vesicle trafficking protein homolog B (S. cerevisiae) (gene/pseudogene) | 0.034 | −0.347 |

TABLE 6-continued 511 genes differentially expressed in MSC non-exposed in comparison with cells exposed to TCM from sample 5 in comparison with non-exposed cells. The magnitude of the expression change is represented as the logarithm of the fold change.

|     | GeneID | Name | Description | PValue | Log2FC |
| --- | --- | --- | --- | --- | --- |
| 215 | 114907 | FBXO32 | F-box protein 32 | 0.034 | −0.333 |
| 216 | 84532 | ACSS1 | acyl-CoA synthetase short-chain family member 1 | 0.03 | 0.356 |
| 217 | 4162 | MCAM | melanoma cell adhesion molecule | 0.017 | −0.436 |
| 218 | 5726 | PGD | phosphogluconate dehydrogenase | 0.019 | −0.378 |
| 219 | 7307 | U2AF1 | U2 small nuclear RNA auxiliary factor 1 | 0.027 | 0.312 |
| 220 | 3312 | HSPA8 | heat shock 70 kDa protein 8 | 0.004 | 0.343 |
| 221 | 8209 | C21orf33 | chromosome 21 open reading frame 33 | 0.035 | −0.36 |
| 222 | 127933 | UHMK1 | U2AF homology motif (UHM) kinase 1 | <0.001 | −0.579 |
| 223 | 55588 | MED29 | mediator complex subunit 29 | 0.023 | −0.375 |
| 224 | 84525 | HOPX | HOP homeobox | 0.024 | 0.464 |
| 225 | 4598 | MVK | mevalonate kinase | 0.038 | −0.316 |
| 226 | 8459 | TPST2 | tyrosylprotein sulfotransferase 2 | 0.003 | −0.362 |
| 227 | 10079 | ATP9A | ATPase ciass II, type 9A | 0.015 | −0.337 |
| 228 | 8742 | TNFSF12 | tumor necrosis factor (ligand) superfamily, member 12 | 0.046 | −0.405 |
| 229 | 5045 | FURIN | furin (paired basic amino acid cleaving enzyme) | 0.028 | −0.367 |
| 230 | 267 | AMFR | autocrine motility factor receptor | 0.005 | −0.418 |
| 231 | 6281 | 3100910 | S100 calcium bnding proten A10 | 0.002 | 0.425 |
| 232 | 358 | AQP1 | aquaporin 1 (Colton blood group) | 0.007 | 0.342 |
| 233 | 9070 | ASH2L | ash2 (absent, small, or homeotic)-like (Drosophila) | 0.024 | −0.507 |
| 234 | 2939 | GSTA2 | glutathione S-transferase alpha 2 | 0.003 | 0.544 |
| 235 | 29968 | PSAT1 | phosphoserine aminotransferase 1 | 0.003 | 0.524 |
| 236 | 151579 | BZW1P2 | basic leucine zipper and W2 domains 1 pseudogene 2 | 0.001 | −0.406 |
| 237 | 284942 | RPL23AP82 | ribosomal protein L23a pseudogene 82 | 0.017 | −0.444 |
| 238 | 11079 | RER1 | RER1 retention in endoplasmic reticulum 1 homolog (S. cerevisiae) | 0.004 | −0.376 |
| 239 | 9920 | KBTBD11 | kelch repeat and BTB (POZ) domain containing 11 | 0.049 | 0.327 |
| 240 | 2628 | GATM | glycine amidinotransferase (L-arginine glycine amidinotransferase) | 0.017 | 0.464 |
| 241 | 115207 | KCTD12 | potassium channel tetramerisation domain containing 12 | 0.001 | −0.575 |
| 242 | 56113 | PCDHGA2 | protocadherin gamma subfamily A, 2 | 0.026 | −0.347 |
| 243 | 84922 | FIZ1 | FLT3-interacting zinc finger 1 | 0.006 | −0.369 |
| 244 | 4833 | NME4 | non-metastatic cells 4, protein expressed in | 0.049 | −0.337 |
| 245 | 140459 | ASB6 | ankyrin repeat and SOCS box containing 6 | 0.002 | −0.528 |
| 246 | 6427 | SRSF2 | serine/arginine-rich splicing factor 2 | 0.031 | 0.312 |
| 247 | 4553 | TRNA | tRNA | <0.001 | 0.801 |
| 248 | 55002 | TMCO3 | transmembrane and coiled-coil domains 3 | 0.002 | −0.387 |
| 249 | 4853 | NOTCH2 | notch 2 | 0.008 | −0.38 |
| 250 | 29015 | SLC43A3 | solute carrier family 43, member 3 | 0.003 | −0.625 |
| 251 | 58986 | TMEM8A | transmembrane protein 89 | 0.045 | −0.393 |
| 252 | 51719 | CAB39 | calcium binding protein 39 | 0.021 | −0.318 |
| 253 | 10730 | YME1L1 | YME1-like 1(S. cerevisiae) | 0.033 | −0.36 |
| 254 | 100506243 | KRBOX1 | KRAB box domain containing 1 | 0.008 | 0.415 |
| 255 | 51533 | PHF7 | PHD finger protein 7 | 0.008 | 0.322 |
| 256 | 27044 | SND1 | staphylococcal nuclease and tudor domain containing 1 | 0.008 | −0.487 |
| 257 | 9547 | CXCL14 | chemokine (C-X-C motif) ligand 14 | 0.014 | 0.437 |
| 258 | 83548 | COG3 | component of oligomeric golgi complex 3 | 0.032 | −0.362 |
| 259 | 5164 | PDK2 | pyruvate dehydrogenase kinase isozyme 2 | 0.024 | −0.357 |
| 260 | 79140 | CCDC28B | coiled-coil domain containing 28B | 0.031 | −0.309 |
| 261 | 5539 | PPY | pancreatic polypeptide | 0.024 | 0.869 |
| 262 | 5934 | RBL2 | retinoblastoma-like 2 (p130) | 0.044 | −0.327 |
| 263 | 440533 | PSG8 | pregnancy specific beta-1-glycoprotein 8 | 0.011 | −0.376 |
| 264 | 283768 | GOLGA8G | golgin A8 family, member G | 0.002 | 0.419 |
| 265 | 7196 | TRNAG2 | transfer RNA glycine 2 (anticodon GCC) | <0.001 | −1.44 |
| 266 | 51339 | DACT1 | dapper, antagonist of beta-catenin, homolog 1 (Xenopus laevis) | 0.009 | −0.415 |
| 267 | 2581 | GALC | galactosylceramidase | 0.015 | −0.621 |
| 268 | 4311 | MME | membrane metallo-endopeptidase | 0.008 | −0.343 |
| 269 | 857 | CAV1 | caveolin 1, caveolae protein, 22 kDa | <0.001 | 0.511 |
| 270 | 84961 | FBXL20 | F-box and leucine-rich repeat protein 20 | 0.049 | −0.351 |
| 271 | 1902 | LPAR1 | lysophosphatidic acid receptor 1 | 0.024 | −0.643 |
| 272 | 9215 | LARGE | like-glycosyltransferase | 0.015 | −0.317 |
| 273 | 84270 | C9orf89 | chromosome 9 open reading frame 89 | 0.002 | −0.378 |
| 274 | 341032 | C11orf53 | chromosome 11 open reading frame 53 | 0.007 | −0.584 |
| 275 | 6494 | SIPA1 | signal-induced proliferation-associated 1 | 0.032 | −0.301 |
| 276 | 51453 | RHCG | Rh family, C glycoprotein | 0.033 | 0.301 |
| 277 | 441198 | LOC441198 | similar to Heat shock cognate 71 kDa protein | 0.023 | 0.302 |
| 278 | 349114 | NCRNA00265 | non-protein coding RNA 265 | 0.045 | 0.303 |
| 279 | 3304 | HSPA18 | heat shock 70 kDa protein 18 | 0.001 | 0.519 |
| 280 | 84791 | C1orf97 | chromosome 1 open reading frame 97 | 0.007 | 0.384 |
| 281 | 84617 | TUBB6 | tubulin, beta 6 | 0.006 | 0.313 |
| 282 | 91012 | LASS5 | LAG1 homolog, ceramide synthase 5 | 0.002 | −0.517 |
| 283 | 8766 | RAB11A | RAB11A, member RAS oncogene family | 0.007 | −0.352 |
| 284 | 4070 | TACSTD2 | tumor-associated calcium signal transducer 2 | 0.009 | 0.428 |
| 285 | 58515 | SELK | selenoprotein K | <0.001 | −0.517 |
| 286 | 54815 | GATAD2A | GATA zinc finger domain containing 2A | 0.014 | −0.341 |
| 287 | 4920 | ROR2 | receptor tyrosine kinase-like orphan receptor 2 | 0.027 | −0.312 |
| 288 | 51009 | DERL2 | Der1-like domain family member 2 | 0.004 | −0.326 |

TABLE 6-continued 511 genes differentially expressed in MSC non-exposed in comparison with
cells exposed to TCM from sample 5 in comparison with non-exposed cells. The
magnitude of the expression change is represented as the logarithm of the fold change.

| | GeneID | Name | Description | PValue | Log2FC |
|---|---|---|---|---|---|
| 289 | 335 | APOA1 | apolipoprotein A-1 | 0.043 | −0.304 |
| 290 | 340198 | IFITM4P | interferon induced transmembrane protein 4 pseudogene | 0.016 | 0.431 |
| 291 | 57214 | KIAA1199 | KIAA1199 | 0.041 | −0.602 |
| 292 | 51232 | CRIM1 | cysteine rich transmembrane BMP regulator 1 (chordin-like) | 0.046 | 0.549 |
| 293 | 124773 | C17orf64 | chromosome 17 open reading frame 64 | 0.007 | 0.398 |
| 294 | 56114 | PCDHGA1 | protocadherin gamma subfamily A, 1 | 0.012 | −0.424 |
| 295 | 112483 | SAT2 | spermidine/spermine N1-acetyltransferase family member 2 | 0.001 | −0.441 |
| 296 | 2000 | ELF4 | E74-like factor 4 (ets domain transcription factor) | 0.014 | −0.362 |
| 297 | 1645 | AKR1C1 | aldo-keto reductase family 1, member C1 (dihydrodiol dehydrogenase 1; 20-alpha (3-alpha)-hydroxysteroid dehydrogenase) | 0.003 | −0.633 |
| 298 | 10383 | TUBB2C | tubulin, beta 2C | 0.002 | 0.343 |
| 299 | 6888 | TALDO1 | transaidolase 1 | 0.035 | −0.33 |
| 300 | 5902 | RANBP1 | RAN binding protein 1 | 0.005 | −0.474 |
| 301 | 51030 | FAM18B1 | family with sequence similarity 18, member B1 | 0.016 | −0.307 |
| 302 | 7259 | TSPYL1 | TSPY-like 1 | 0.014 | 0.365 |
| 303 | 134147 | CMBL | carboxymethylenebutenolidase homolog (*Pseudomonas*) | 0.024 | 0.302 |
| 304 | 6303 | SAT1 | spermidine/spermine N1-acetyltransferase 1 | 0.011 | −0.318 |
| 305 | 83871 | RAB34 | RAB34, member RAS oncogene family | 0.003 | −0.338 |
| 306 | 6542 | SLC7A2 | solute carrier family 7 (cationic amino acid transporter, y+ system), member 2 | 0.005 | −0.304 |
| 307 | 22936 | ELL2 | elongation factor, RNA polymerase II, 2 | <0.001 | −0.709 |
| 308 | 58508 | MLL3 | myeloid/lymphoid or mixed-lineage leukemia 3 | 0.017 | −0.466 |
| 309 | 5111 | PCNA | proliferating cell nuclear antigen | 0.037 | 0.404 |
| 310 | 1827 | RCAN1 | regulator of calcineurin 1 | <0.001 | −0.676 |
| 311 | 8720 | MBTPS1 | membrane-bound transcription factor peptidase, site 1 | 0.045 | −0.329 |
| 312 | 8490 | RGS5 | regulator of G-protein signaling 5 | 0.02 | 0.465 |
| 313 | 56674 | TM EM98 | TMEM9 domain family, member 8 | 0.011 | 0.4 |
| 314 | 6713 | SQLE | squalene epoxidase | 0.009 | −0.393 |
| 315 | 3434 | IFIT1 | interferon-induced protein with tetratricopeptide repeats 1 | <0.001 | 0.422 |
| 316 | 3192 | HNRNPU | heterogeneous nuclear ribonucleoprotein U (scaffold attachment factor A) | 0.009 | 0.324 |
| 317 | 5916 | RARG | retinoic acid receptor, gamma | 0.004 | −0.65 |
| 318 | 84232 | MAF1 | MAF1 homolog (*S. cerevisiae*) | 0.022 | 0.325 |
| 319 | 729148 | NUS1P1 | nuclear undecaprenyl pyrophosphate synthase 1 homolog (*S. cerevisiae*) pseudogene 1 | 0.016 | −0.422 |
| 320 | 5611 | DNAIC3 | DnaI (Hsp40) homolog, subfamily C, member 3 | <0.001 | −0.92 |
| 321 | 151636 | DTX3L | deltex 3-like (*Drosophila*) | 0.042 | 0.664 |
| 322 | 83447 | SLC25A31 | solute carrier family 25 (mitochondrial carrier adenine nucleotide translocator), member 31 | 0.044 | 0.42 |
| 323 | 171169 | SPACA4 | sperm acrosome associated 4 | 0.038 | −0.452 |
| 324 | 51652 | VPS24 | vacuolar protein sorting 24 homolog (*S. cerevisiae*) | 0.002 | 0.419 |
| 325 | 64215 | DNAJC1 | DnaJ (Hsp40) homolog, subfamily C, member 1 | 0.004 | −0.489 |
| 326 | 63916 | ELMO2 | engulfment and cell motility 2 | 0.03 | −0.415 |
| 327 | 4170 | MCL1 | myeloid cell leukemia sequence 1 (BCL2-related) | <0.001 | 0.554 |
| 328 | 10123 | ARL4C | ADP-ribosylation factor-like 4C | 0.007 | 0.383 |
| 329 | 3324 | HSP90AA2 | heat shock protein 90 kDa alpha (cytosolic), class A member 2 | 0.002 | 0.398 |
| 330 | 10285 | SMNDC1 | survival motor neuron domain containing 1 | 0.036 | −0.761 |
| 331 | 54538 | ROBO4 | roundabout homolog 4, magic roundabout (*Drosophila*) | 0.033 | 0.375 |
| 332 | 133957 | CCDC127 | coiled-coil domain containing 127 | 0.037 | 0.327 |
| 333 | 7280 | TUBB2A | tubulin, beta 2A | <0.001 | 0.62 |
| 334 | 1116 | CHI3L1 | chitinase 3-like 1 (cartilage glycoprotein-39) | 0.008 | −0.348 |
| 335 | 4256 | MGP | matrix Gla protein | 0.003 | 0.448 |
| 336 | 4926 | NUMA1 | nuclear mitotic apparatus protein 1 | 0.038 | −0.306 |
| 337 | 3748 | KCNC3 | potassium voltage-gated channel, Shaw-related subfamily member 3 | 0.008 | −0.378 |
| 338 | 90737 | PAGE5 | P antigen family, member 5 (prostate associated) | 0.025 | 0.315 |
| 339 | 84707 | BEX2 | brain expressed X-linked 2 | 0.034 | 0.326 |
| 340 | 5901 | RAN | RAN, member RAS oncogene family | 0.001 | 0.324 |
| 341 | 56927 | GPR108 | G protein-coupled receptor 108 | 0.043 | −0.471 |
| 342 | 7832 | BTG2 | BTG family, member 2 | 0.046 | 0.316 |
| 343 | 23174 | ZCCHC14 | zinc finger, CCHC domain containing 14 | 0.017 | 0.336 |
| 344 | 60592 | SCOC | short coiled-coil protein | 0.005 | 0.413 |
| 345 | 115992 | RNF166 | ring finger protein 166 | 0.005 | −0.692 |
| 346 | 604 | BCL6 | B-cell CLL/lymphoma 6 | 0.012 | −0.512 |
| 347 | 8537 | BCA51 | breast carcinoma amplified sequence 1 | 0.016 | 0.331 |
| 348 | 432 | ASGR1 | asialoglycoprotein receptor | 0.045 | 0.386 |
| 349 | 7542 | ZFPL1 | zinc finger protein-like 1 | 0.017 | −0.514 |
| 350 | 57570 | TRMT5 | TRM5 tRNA methyltransferase 5 homolog (*S. cerevisiae*) | 0.006 | 0.324 |
| 351 | 4567 | TRNL1 | tRNA | 0.033 | 0.316 |
| 352 | 83880 | EIF3FP2 | eukaryotic translation initiation factor 3, subunit F pseudogene 2 | 0.012 | −0.44 |
| 353 | 3303 | HSPA1A | heat shock 70 kDa protein 1A | 0.002 | 0.633 |
| 354 | 63933 | CCDC90A | coiled-coil domain containing 90A | 0.035 | −0.777 |
| 355 | 81839 | VANGL1 | vang-like 1 (van gogh, *Drosophila*) | 0.045 | −0.378 |
| 356 | 220988 | HNRNPA3 | heterogeneous nuclear ribonucleoprotein A3 | <0.001 | 0.477 |
| 357 | 51454 | GULP1 | GULP engulfment adaptor PTB domain containing 1 | 0.007 | −0.535 |
| 358 | 949 | SCARB1 | scavenger receptor class B, member 1 | <0.001 | −0.582 |

TABLE 6-continued 511 genes differentially expressed in MSC non-exposed in comparison with
cells exposed to TCM from sample 5 in comparison with non-exposed cells. The
magnitude of the expression change is represented as the logarithm of the fold change.

|  | GeneID | Name | Description | PValue | Log2FC |
|---|---|---|---|---|---|
| 359 | 9709 | HERPUD1 | homocysteine-inducible endoplasmic reticulum stress-inducible, ubiquitin-like domain member 1 | 0.011 | −0.325 |
| 360 | 85021 | REPS1 | RALBP1 associated Eps domain containing 1 | 0.022 | −0.627 |
| 361 | 26273 | FBXO3 | F-box protein 3 | 0.002 | 0.34 |
| 362 | 5481 | PPID | peptidylprolyl isomerase D | 0.011 | 0.326 |
| 363 | 359948 | IRF2BP2 | interferon regulatory factor binding protein 2 | 0.014 | −0.327 |
| 364 | 1728 | NQO1 | NAD(P)H dehydrogenase, quinone 1 | 0.048 | −0.453 |
| 365 | 3119 | HLA-DQB1 | major histocornpatibility complex, class II, DQ beta | 0.003 | 0.393 |
| 366 | 2166 | FAAH | fatty acid amide hydrolase | 0.026 | 0.381 |
| 367 | 6652 | SORD | sorbitol dehydrogenase | 0.03 | 0.353 |
| 368 | 55251 | PCMTD2 | protein-L-isoaspartate (D-aspartate) O-methyltransferase domain containing 2 | 0.04 | −0.376 |
| 369 | 402562 | HNRNPA1P8 | heterogeneous nuclear ribonucleoprotein A1 pseudogene 8 | 0.013 | −0.341 |
| 370 | 6428 | SRSF3 | serine/arginine-rich splicing factor 3 | <0.001 | 0.516 |
| 371 | 55920 | RCC2 | regulator of chromosome condensation 2 | <0.001 | 0.457 |
| 372 | 10922 | FASTK | Fas-activated serine/threonine kinase | 0.008 | −0.485 |
| 373 | 3295 | HSD1784 | hydroxysteroid (17-beta) dehydrogenase 4 | 0.007 | −0.593 |
| 374 | 7453 | WARS | tryptophanyl-tRNA synthetase | 0.045 | 0.344 |
| 375 | 9823 | ARMCX2 | armadillo repeat containing, X-linked 2 | 0.012 | −0.476 |
| 376 | 51706 | CYB5R1 | cytochrome b5 reductase 1 | 0.041 | −0.46 |
| 377 | 51660 | BRP44L | brain protein 44-like | 0.049 | 0.302 |
| 378 | 51043 | ZBTB7B | zinc finger and BTB domain containing 7B | <0.001 | −0.489 |
| 379 | 6892 | TAPBP | TAP binding protein (tapasin) | <0.001 | −0.727 |
| 380 | 51075 | TMX2 | thioredoxin-related transmembrane protein 2 | 0.032 | −0.35 |
| 381 | 54617 | INO80 | INO80 homolog (S. cerevisiae) | 0.03 | −0.434 |
| 382 | 1523 | CUX1 | cut-like homeobox 1 | 0.021 | −0.413 |
| 383 | 1503 | CTPS | CTP synthase | 0.02 | −0.505 |
| 384 | 7273 | TTN | titin | 0.002 | −0.327 |
| 385 | 2036 | EPB41L1 | erythrocyte membrane protein band 4.1-like 1 | 0.043 | −0.415 |
| 386 | 8451 | CUL4A | cuilin 4A | 0.035 | −0.331 |
| 387 | 55342 | STRBP | spermatid perinuclear RNA binding protein | 0.018 | −0.427 |
| 388 | 7180 | CRISP2 | cysteine-rich secretory protein 2 | 0.005 | 0.485 |
| 389 | 283902 | HTA | hypothetical LOC283902 | 0.03 | −0.347 |
| 390 | 9246 | UBE2L6 | ubiquitin-conjugating enzyme E2L 6 | 0.003 | 0.434 |
| 391 | 6236 | RRAD | Ras-related associated with diabetes | <0.001 | 0.612 |
| 392 | 5209 | PFKF83 | 6-phosphofructo-2-kinase/fructose-2,6-biphosphatase 3 | 0.006 | 0.361 |
| 393 | 91695 | RRP78 | ribosomal RNA processing 7 homolog B (S. cerevisiae) | 0.008 | −0.333 |
| 394 | 2938 | GSTA1 | glutathione S-transferase alpha 1 | 0.006 | 0.334 |
| 395 | 3550 | IK | IK cytokine, down-regulator of HLA II | 0.012 | −0.366 |
| 396 | 3190 | HNRNPK | heterogeneous nuclear ribonucleoprotein K | 0.005 | −0.337 |
| 397 | 8277 | TKTL1 | transketolase-like 1 | 0.006 | 0.332 |
| 398 | 1982 | EIF4G2 | eukaryotic translation initiation factor 4 gamma, 2 | <0.001 | 0.436 |
| 399 | 6711 | SPTBN1 | spectrin, beta, non-erythrocytic 1 | 0.009 | 0.506 |
| 400 | 116254 | C6orf72 | chromosome 6 open reading frame 72 | <0.001 | −0.42 |
| 401 | 51187 | RSL24D1 | ribosomal L24 domain containing 1 | 0.003 | −0.406 |
| 402 | 7170 | TPM3 | tropomyosin 3 | 0.028 | −0.387 |
| 403 | 3459 | IFNGR1 | interferon gamma receptor 1 | 0.002 | −0.481 |
| 404 | 246243 | RNASEH1 | ribonuclease H1 | 0.01 | −0.302 |
| 405 | 29880 | ALG5 | asparagine-linked glycosylation 5, dolichyl-phosphate beta-glucosyltransferase homolog (S. cerevisiae) | 0.008 | −0.308 |
| 406 | 55197 | RPRD1A | regulation of nuclear pre-mRNA domain containing 1A | 0.017 | −0.405 |
| 407 | 81926 | FAM108A1 | family with sequence similarity 108, member A1 | 0.037 | 0.35 |
| 408 | 9670 | IPO13 | importin 13 | 0.033 | −0.408 |
| 409 | 92558 | CCDC64 | coiled-coil domain containing 64 | 0.019 | −0.447 |
| 410 | 5698 | 1551139 | proteasome (prosome, macropain) subunit, beta type, 9 (large multifunctional peptidase 2) | 0.003 | 0.409 |
| 411 | 283131 | NEAT1 | nuclear paraspeckle assembly transcript 1 (non-protein coding) | 0.009 | −0.309 |
| 412 | 5202 | PFDN2 | prefoldin subunit 2 | 0.004 | −0.433 |
| 413 | 43 | ACHE | acetylcholinesterase | 0.022 | −0.423 |
| 414 | 79940 | C6orf155 | chromosome 6 open reading frame 155 | 0.046 | −0.356 |
| 415 | 10330 | CNPY2 | canopy 2 homolog (zebrafish) | 0.023 | −0.348 |
| 416 | 3500 | IGHG1 | immunoglobulin heavy constant gamma 1 (G1m marker) | 0.021 | 0.53 |
| 417 | 123 | PLIN2 | perilipin 2 | 0.045 | −0.347 |
| 418 | 3184 | HNRNPD | heterogeneous nuclear ribonucleoprotein D (AU-rich element RNA binding protein 1, 37 kDa) | 0.046 | 0.383 |
| 419 | 2919 | CXCL1 | chemokine (C-X-C motif) ligand 1 (melanoma growth stimulating activity, alpha) | 0.012 | −0.886 |
| 420 | 51763 | INPP5K | inositol polyphosphate-5-phosphatase K | 0.006 | −0.313 |
| 421 | 27020 | NPTN | neuroplastin | 0.015 | 0.334 |
| 422 | 7052 | TGM2 | transglutaminase 2 (C polypeptide, protein-glutamine-gamma-glutamyltransferase) | <0.001 | −0.594 |
| 423 | 2332 | FMR1 | fragile X mental retardation 1 | 0.041 | 0.306 |
| 424 | 9792 | SERTAD2 | SERTA domain containing 2 | 0.045 | −0.363 |

TABLE 6-continued 511 genes differentially expressed in MSC non-exposed in comparison with cells exposed to TCM from sample 5 in comparison with non-exposed cells. The magnitude of the expression change is represented as the logarithm of the fold change.

| | GeneID | Name | Description | PValue | Log2FC |
|---|---|---|---|---|---|
| 425 | 10507 | SEMA4D | sema domain, immunoglobulin domain (Ig), transmembrane domain (TM) and short cytoplasmic domain, (semaphorin) 4D | 0.034 | −0.814 |
| 426 | 3976 | LIF | leukemia inhibitory factor (cholinergic differentiation factor) | 0.001 | −0.622 |
| 427 | 4085 | MAD2L1 | MAD2 mitotic arrest deficient-like 1 (yeast) | 0.002 | −0.433 |
| 428 | 84879 | MFSD2A | major facilitator superfamily domain containing 2A | 0.029 | −0.32 |
| 429 | 203068 | TUBB | tubulin, beta | 0.006 | −0.386 |
| 430 | 5721 | PSME2 | proteasome (prosome, macropain) activator subunit 2 (PA28 beta) | 0.002 | 0.874 |
| 431 | 55140 | ELP3 | elongation protein 3 homolog (*S. cerevisiae*) | 0.023 | 0.406 |
| 432 | 9043 | SPAG9 | sperm associated antigen 9 | 0.015 | −0.44 |
| 433 | 57216 | VANGL2 | vang-like 2 (van gogh, *Drosophila*) | 0.023 | −0.459 |
| 434 | 54963 | UCKL1 | uridine-cytidine kinase 1-like 1 | 0.023 | −0.39 |
| 435 | 51495 | PTPLAD1 | protein tyrosine phosphatase-like A domain containing 1 | 0.022 | −0.316 |
| 436 | 199746 | U2AF1L4 | U2 small nuclear RNA auxiliary factor 1-like 4 | 0.021 | 0.379 |
| 437 | 10555 | AGPAT2 | 1-acylglycerol-3-phosphate O-acyltransferase 2 (lysophosphatidic acid acyltransferase, beta) | 0.015 | 0.333 |
| 438 | 8650 | NUMB | numb homolog (*Drosophila*) | 0.013 | −0.374 |
| 439 | 6432 | SRSF7 | serine/arginine-rich splicing factor 7 | 0.015 | 0.388 |
| 440 | 5128 | CDK17 | cyclin-dependent kinase 17 | 0.007 | 0.514 |
| 441 | 5507 | PPP1R3C | protein phosphatase 1, regulatory (inhibitor) subunit 3C | 0.009 | 0.518 |
| 442 | 56937 | PMEPA1 | prostate transmembrane protein, androgen induced 1 | 0.017 | −0.381 |
| 443 | 11189 | CELF3 | CUGBP, Elav-like family member 3 | 0.031 | 0.324 |
| 444 | 51635 | DHRS7 | dehydrogenase/reductase (SDR family) member 7 | 0.008 | −0.352 |
| 445 | 29085 | PHPT1 | phosphohistidine phosphatase 1 | 0.031 | 0.31 |
| 446 | 64777 | RMND5B | required for meiotic nuclear division 5 homolog B (*S. cerevisiae*) | 0.039 | −0.302 |
| 447 | 284613 | CYB561D1 | cytochrome b-561 domain containing 1 | 0.024 | −0.464 |
| 448 | 665 | BNIP3L | BCL2/adenovirus E1B 19 kDa interacting protein 3-like | 0.027 | −0.309 |
| 449 | 391570 | LOC391670 | heterogeneous nuclear ribonucleoprotein A1 pseudogene | 0.042 | 0.343 |
| 450 | 51022 | GLRX2 | glutaredoxin 2 | 0.016 | −0.37 |
| 451 | 3320 | HSP90AA1 | heat shock protein 90 kDa alpha (cytosolic), class A member 1 | 0.038 | 0.363 |
| 452 | 56106 | PCDHGA10 | protocadherin gamma subfamily A, 10 | 0.019 | −0.337 |
| 453 | 56160 | NDNL2 | needin-like 2 | 0.019 | −0.327 |
| 454 | 2791 | GNG11 | guanine nucleotide binding protein (G protein), gamma 11 | 0.023 | −0.391 |
| 455 | 64834 | ELOVL1 | elongation of very long chain fatty acids (FEN1/Elo2, SUR4/Elo3, yeast)-like 1 | 0.007 | −0.55 |
| 456 | 10749 | KIF1C | kinesin family member 1C | 0.003 | 0.526 |
| 457 | 3336 | HSPE1 | heat shock 10 kDa protein 1 (chaperonin 10) | 0.003 | 0.417 |
| 458 | 84818 | IL17RC | interleukin 17 receptor C | 0.009 | −0.306 |
| 459 | 5511 | PPP1R8 | protein phosphatase 1, regulatory (inhibitor) subunit 8 | 0.032 | −0.318 |
| 460 | 134492 | NUDCD2 | NudC domain containing 2 | 0.006 | −0.557 |
| 461 | 23576 | DDAH1 | dimethylarginine dimethylaminohydrolase 1 | 0.008 | 0.359 |
| 462 | 5156 | PDGFRA | platelet-derived growth factor receptor, alpha polypeptide | 0.032 | −0.457 |
| 463 | 8831 | SYNGAP1 | synaptic Ras GTPase activating protein 1 | 0.031 | −0.324 |
| 464 | 9600 | PITPNM1 | phosphatidylinositol transfer protein membrane associated 1 | 0.007 | −0.354 |
| 465 | 1800 | DPEP1 | dipeptidase 1 (renal) | 0.002 | −0.403 |
| 466 | 79924 | ADM2 | adrenomedullin 2 | 0.031 | −0.316 |
| 467 | 2346 | FOLH1 | folate hydrolase (prostate-specific membrane antigen) 1 | 0.007 | −0.376 |
| 468 | 2787 | GNG5 | guanine nucleotide binding protein (G protein), gamma 5 | 0.025 | 0.361 |
| 469 | 23067 | SETD1B | SET domain containing 1B | <0.001 | −0.351 |
| 470 | 23042 | PDXDC1 | pyridoxal-dependent decarboxylase domain containing 1 | 0.022 | −0.302 |
| 471 | 84961 | FBXL20 | F-box and leucine-rich repeat protein 20 | 0.026 | 0.302 |
| 472 | 2992 | GYG1 | glycogenin 1 | 0.008 | 0.468 |
| 473 | 3987 | LIMS1 | LIM and senescent cell antigen-like domains 1 | 0.044 | −0.357 |
| 474 | 6426 | SRSF1 | serine/arginine-rich splicing factor 1 | 0.04 | 0.7 |
| 475 | 4616 | GADD45B | growth arrest and DNA-damage-inducible, beta | 0.005 | 0.438 |
| 476 | 27175 | TUBG2 | tubulin, gamma 2 | 0.046 | −0.377 |
| 477 | 51187 | RSL24D1 | ribosomal L24 domain containing 1 | 0.004 | −0.607 |
| 478 | 29081 | METTL5 | methyltransferase like 5 | 0.031 | −0.414 |
| 479 | 23167 | EFR3A | EFR3 homolog A (*S. cerevisiae*) | 0.045 | −0.371 |
| 480 | 4071 | TM4SF1 | transmembrane 4 L six family member 1 | 0.002 | −0.416 |
| 481 | 1316 | KLF6 | Kruppel-like factor 6 | 0.003 | 0.418 |
| 482 | 84951 | TNS4 | tensin 4 | 0.046 | −0.403 |
| 483 | 8668 | EIF3I | eukaryotic translation initiation factor 3, subunit I | 0.039 | −0.381 |
| 484 | 223082 | ZNRF2 | zinc and ring finger 2 | 0.036 | 0.336 |
| 485 | 64778 | FNDC3B | fibronectin type III domain containing 3B | 0.002 | −0.529 |
| 486 | 219654 | ZCCHC24 | zinc finger, CCHC domain containing 24 | 0.002 | −0.416 |
| 487 | 11098 | PRSS23 | protease, serine, 23 | <0.001 | 0.677 |
| 488 | 27106 | ARRDC2 | arrestin domain containing 2 | 0.009 | −0.412 |
| 489 | 8547 | FCN3 | ficolin (collagen/fibrinogen domain containing) 3 (Hakata antigen) | 0.028 | 0.365 |
| 490 | 11067 | C10orf10 | chromosome 10 open reading frame 10 | 0.042 | −0.318 |
| 491 | 7112 | TMPO | Thymopoietin | 0.048 | −0.391 |
| 492 | 84231 | TRAF7 | TNF receptor-associated factor 7 | 0.029 | −0.458 |
| 493 | 378 | ARF4 | ADP-ribosylation factor 4 | 0.015 | 0.34 |
| 494 | 3337 | DNAJB1 | DnaJ (Hsp40) homolog, subfamily B, member 1 | 0.008 | 0.449 |
| 495 | 10409 | BASP1 | brain abundant, membrane attached signal protein 1 | 0.027 | −0.314 |

TABLE 6-continued 511 genes differentially expressed in MSC non-exposed in comparison with cells exposed to TCM from sample 5 in comparison with non-exposed cells. The magnitude of the expression change is represented as the logarithm of the fold change.

| | GeneID | Name | Description | PValue | Log2FC |
|---|---|---|---|---|---|
| 496 | 8543 | LMO4 | LIM domain only 4 | 0.015 | −0.314 |
| 497 | 55352 | C17orf79 | chromosome 17 open reading frame 79 | 0.037 | 0.398 |
| 498 | 148229 | ATP883 | ATPase, aminophospholipid transporter, class I, type 8B, member 3 | 0.043 | −0.312 |
| 499 | 10135 | NAMPT | nicotinamide phosphoribosyltransferase | 0.017 | −0.536 |
| 500 | 10734 | STAG3 | stromal antigen 3 | 0.029 | 0.336 |
| 501 | 3312 | HSPA8 | heat shock 70 kDa protein 8 | <0.001 | −0.455 |
| 502 | 5743 | PTGS2 | prostaglandin-endoperoxide synthase 2 (prostaglandinG/H synthase and cyclooxygenase) | 0.026 | −0.739 |
| 503 | 3476 | IGBP1 | immunoglobulin (CD79A) binding protein 1 | 0.027 | −0.351 |
| 504 | 9689 | BZW1 | basic leucine zipper and W2 domains 1 | 0.045 | −0.315 |
| 505 | 3638 | INSIG1 | insulin induced gene 1 | <0.001 | −0.628 |
| 506 | 3340 | NDST1 | N-deacetylase/N-sulfotransferase (heparan glucosaminyl) 1 | 0.028 | 0.437 |
| 507 | 84447 | SYVN1 | synovial apoptosis inhibitor 1, synoviolin | <0.001 | −1.048 |
| 508 | 114971 | PTPMT1 | protein tyrosine phosphatase, mitochondrial 1 | 0.021 | −0.394 |
| 509 | 9415 | FADS2 | fatty acid desaturase 2 | 0.003 | −0.548 |
| 510 | 26227 | PHGDH | phosphoglycerate dehydrogenase | 0.01 | −0.367 |
| 511 | 10360 | NPM3 | nucleophosmin/nucleoplasmin 3 | 0.048 | −0.408 |

TABLE 7

Receptors expressed in control group (MSC non-exposed) and that recognize soluble factors identified in HCC samples.

| EntrezID | Name | Description |
|---|---|---|
| 1234 | CCR5 | *Homo sapiens* chemokine (C-C motif) receptor 5 (CCR5), mRNA. |
| 1236 | CCR7 | *Homo sapiens* chemokine (C-C motif) receptor 7 (CCR5), mRNA. |
| 10803 | CCR9 | *Homo sapiens* chemokine (C-C motif) receptor 9 (CCR9), transcript variant A, mRNA. |
| 960 | CD44 | *Homo sapiens* CD44 antigen (homing function and Indian blood group system) (CD44), transcript variant 1, mRNA. |
| 967 | CD63 | *Homo sapiens* CD63 antigen (melanoma 1 antigen) (CD63), mRNA. |
| 972 | CD74 | *Homo sapiens* CD74 antigen (invariant polypeptide of major histocompatibility complex, class II antigen-associated) (CD74) mRNA |
| 1524 | CX3CR1 | *Homo sapiens* chemokine (C-X3-C motif) receptor 1 (CX3CR1), mRNA. |
| 3579 | CXCR2 | *Homo sapiens* interleukin 8 receptor, beta (IL8RB), mRNA. |
| 7852 | CXCR4 | *Homo sapiens* chemokine (C-X-C motif) receptor 4 (CXCR4), transcript variant 1, mRNA. |
| 57007 | CXCR7 | *Homo sapiens* chemokine orphan receptor 1 (CMKOR1), mRNA. |
| 1956 | EGFR | *Homo sapiens* epidermal growth factor receptor (erythroblastic leukemia viral (v-erb-b) oncogene homolog, avian) (EGFR), transcript variant 1, mRNA. |
| 2022 | ENG | *Homo sapiens* endoglin (Osler-Rendu-Weber syndrome 1) (ENG), mRNA. |
| 2260 | FGFR1 | *Homo sapiens* fibroblast growth factor receptor 1 (fms-related tyrosine kinase 2, Pfeiffer syndrome) (FGFR1), transcript variant 1, mRNA. |
| 2263 | FGFR2 | *Homo sapiens* fibroblast growth factor receptor 2 (FGFR2). transcript variant 10, mRNA. |
| 2263 | FGFR2 | *Homo sapiens* fibroblast growth factor receptor 2 (FGFR2), transcript variant 2, mRNA. |
| 2261 | FGFR3 | *Homo sapiens* fibroblast growth factor receptor 3 (achondroplasia, thanatophoric dwarfism) (FGFR3), transcript variant 2, mRNA. |
| 2261 | FGFR3 | *Homo sapiens* fibroblast growth factor receptor 3 (achondroplasia, thanatophoric dwarfism) (FGFR3), transcript variant 1, mRNA. |
| 2264 | FGFR4 | *Homo sapiens* fibroblast growth factor receptor 4 (FGFR4), transcript variant 1, mRNA. |
| 2264 | FGFR4 | *Homo sapiens* fibroblast growth factor receptor 4 (FGFR4), transcript variant 2, mRNA. |
| 2321 | FLT1 | *Homo sapiens* fms-related tyrosine kinase 1 (vascular endothelial growth factor/vascular permeability factor receptor) (FLT1), mRNA. |
| 3459 | IFNGR1 | *Homo sapiens* interferon gamma receptor 1 (IFNGR1), mRNA. |
| 3480 | IGF1R | *Homo sapiens* insulin-like growth factor 1 receptor (IGF1R), mRNA. |
| 3594 | IL12RB1 | *Homo sapiens* interleukin 12 receptor, beta 1 (IL12RB1), transcript variant 1, mRNA. |
| 3601 | IL15RA | *Homo sapiens* interleukin 15 receptor, alpha (IL15RA), transcript variant 2, mRNA. |
| 3601 | IL15RA | *Homo sapiens* interleukin 15 receptor, alpha (IL15RA), transcript variant 1, mRNA. |
| 3554 | IL1R1 | *Homo sapiens* interleukin 1 receptor, type I (IL1R1), mRNA. |
| 3556 | IL1RAP | *Homo sapiens* interleukin 1 receptor accessory protein (IL1RAP), transcript variant 1, mRNA. |
| 3563 | IL3RA | *Homo sapiens* interleukin 3 receptor, alpha (low affinity) (IL3RA), mRNA. |
| 3566 | IL4R | *Homo sapiens* interleukin 4 receptor (IL4R), transcript variant. 1, mRNA. |

TABLE 7-continued

Receptors expressed in control group (MSC non-exposed) and that recognize soluble factors identified in HCC samples.

| EntrezID | Name | Description |
|---|---|---|
| 3570 | IL6R | *Homo sapiens* interleukin 6 receptor (IL6R), transcript variant 1, mRNA. |
| 3688 | ITGB1 | *Homo sapiens* integrin, beta 1 (fibronectin receptor, beta polypeptide, antigen CD29 includes MDF2, MSK32) (ITG81), transcript variant 1D, mRNA. |
| 3688 | ITGB1 | *Homo sapiens* integrin, beta 1 (fibronectin receptor, beta polypeptide, antigen CD29 includes MDF2, MSK12) (ITGB1), transcript variant 1A, mRNA. |
| 5156 | PDGFRA | *Homo sapiens* platelet-derived growth factor receptor, alpha polypeptide (PDGFRA), mRNA. |
| 5159 | PDGFRB | *Homo sapiens* platelet-derived growth factor receptor, beta polypeptide (PDGFRB), mRNA. |
| 7048 | TGFBR2 | *Homo sapiens* transforming growth factor, beta receptor II (70/80 kDa) (TGFBR2), transcript variant 2, mRNA. |

What is claimed is:

1. A method for increasing migration or anchorage of a mesenchymal stromal cell (MSC) to a tumor comprising
    (a) stimulating the MSC by in vitro pretreatment with a recombinant autocrine motility factor (rAMF) of SEQ ID NO:1, wherein the rAMF is capable of increasing migration or anchorage of a stimulated MSC, and
    (b) administering the stimulated MSC of (a) to the tumor, wherein the MSC comprises a recombinant therapeutic agent,
    wherein the vitro pretreatment comprises incubating the MSC with a medium comprising the rAMF followed by removal of the medium containing the rAMF.

2. A method for treating a subject with a tumor comprising
    (a) stimulating a mesenchymal stromal cell (MSC) comprising a recombinant therapeutic agent by in vitro pretreatment with a recombinant autocrine motility factor (rAMF) of SEQ ID NO:1, wherein the rAMF is capable of increasing migration or anchorage of a stimulated MSC, and
    (b) administering the stimulated MSC of (a) to the subject, wherein the in vitro pretreatment comprises incubating the MSC with a medium comprising the rAMF followed by removal of the medium containing the rAMF.

3. The method of claim 1, wherein the tumor is a solid tumor.

4. The method of claim 1, wherein the tumor is a cancer selected from the group consisting of a liver cancer, a colon cancer, a pancreatic cancer, a lung cancer, a gastrointestinal cancer, a kidney cancer, or a breast cancer.

5. The method of claim 1, wherein the tumor is a carcinoma.

6. The method of claim 5, wherein the carcinoma is hepatocellular carcinoma (HCC).

7. The method of claim 5, wherein the carcinoma is colorectal carcinoma.

8. The method of claim 1, wherein the tumor expresses endogenous AMF.

9. The method of claim 1, wherein the increasing migration is two-fold greater than migration of the MSC without rAMF stimulation.

10. The method of claim 1, wherein the source of the MSC is selected from the group consisting of bone marrow, adipose tissue, and umbilical cord.

11. The method of claim 10, wherein the umbilical cord MSC is harvested from human umbilical cord perivascular tissue.

12. The method of claim 1, wherein the recombinant therapeutic agent is a recombinant anti-tumor gene.

13. The method of claim 1, wherein the recombinant therapeutic agent is an oncolytic virus.

14. The method of claim 13, wherein the oncolytic virus is engineered to express a recombinant anti-tumor gene.

15. The method of claim 12, wherein the recombinant anti-tumor gene is selected from the group consisting of an interferon, an interleukin, a chemokine, a suicide gene, and any combination thereof.

16. The method of claim 15, wherein the anti-tumor gene is selected from the group consisting of interferon α, interferon ρ, interleukin 1, interleukin 12, CX3CL1, thymidine kinase, IL-12, IFN-gamma, TNF-alpha, or any combination thereof.

17. The method of claim 1, wherein the MSC further comprises a recombinant AMF receptor.

18. The method of claim 2, wherein the administration is systemic.

19. The method of claim 2, wherein the administration is to an intra-hepatic artery.

* * * * *

UNITED STATES PATENT AND TRADEMARK OFFICE
CERTIFICATE OF CORRECTION

PATENT NO. : 11,173,180 B2
APPLICATION NO. : 15/892680
DATED : November 16, 2021
INVENTOR(S) : Mazzolini et al.

Page 1 of 1

It is certified that error appears in the above-identified patent and that said Letters Patent is hereby corrected as shown below:

On the Title Page

Column 1, Item (73), in "Assignee", Line 1, delete "National" and insert -- Nacional --, therefor.

In the Claims

In Column 103, Claim 1, Line 3, delete "comprising" and insert -- comprising: --, therefor.

In Column 103, Claim 1, Line 11, delete "the" and insert -- the in --, therefor.

In Column 103, Claim 2, Line 15, delete "comprising" and insert -- comprising: --, therefor.

In Column 104, Claim 16, Line 25, delete "ρ," and insert -- β, --, therefor.

Signed and Sealed this
First Day of March, 2022

Drew Hirshfeld
*Performing the Functions and Duties of the*
*Under Secretary of Commerce for Intellectual Property and*
*Director of the United States Patent and Trademark Office*